US007666863B2

(12) United States Patent
Saha et al.

(10) Patent No.: US 7,666,863 B2
(45) Date of Patent: Feb. 23, 2010

(54) BENZOFURAN COMPOUNDS, COMPOSITIONS AND METHODS FOR TREATMENT AND PROPHYLAXIS OF HEPATITIS C VIRAL INFECTIONS AND ASSOCIATED DISEASES

(75) Inventors: Ashis K. Saha, Harleysville, PA (US); Christopher J Burns, Malvern, PA (US); Alfred M. Del Vecchio, West Chester, PA (US); Thomas R. Bailey, Phoenixville, PA (US); Jason A. Reinhardt, Audubon, PA (US); Bheemashankar A. Kulkarni, Exton, PA (US); Thomas H. Faitg, Exton, PA (US); Hao Feng, Aston, PA (US); Susan R. Rippin, Wilmington, DE (US); Charles W. Blackledge, Spring City, PA (US); David J. Rys, Philadelphia, PA (US); Thomas A. Lessen, Langhorne, PA (US); John Swestock, Reading, PA (US); Yijun Deng, Dresher, PA (US); Theodore J. Nitz, Pottstown, PA (US)

(73) Assignees: ViroPharma Incorporated, Exton, PA (US); WYETH, Madison, NJ (US)

( * ) Notice: Subject to any disclaimer, the term of this patent is extended or adjusted under 35 U.S.C. 154(b) by 121 days.

(21) Appl. No.: 11/753,145

(22) Filed: May 24, 2007

(65) Prior Publication Data
US 2007/0231318 A1 Oct. 4, 2007

Related U.S. Application Data

(62) Division of application No. 10/699,336, filed on Oct. 31, 2003, now Pat. No. 7,265,152.

(60) Provisional application No. 60/423,291, filed on Nov. 1, 2002, provisional application No. 60/461,077, filed on Apr. 8, 2003, provisional application No. 60/489,060, filed on Jul. 21, 2003, provisional application No. 60/515,944, filed on Oct. 30, 2003.

(51) Int. Cl.
*A61K 31/54* (2006.01)
*A61K 31/53* (2006.01)
*C07D 307/00* (2006.01)
*C07D 401/00* (2006.01)
*C07D 417/00* (2006.01)

(52) U.S. Cl. .............. 514/222.2; 514/226.5; 514/228.8; 514/241; 514/252.01; 514/279; 514/337; 514/359; 514/365; 514/383; 514/408; 514/444; 514/468; 514/469; 549/469; 548/146; 548/215; 548/256; 548/311.1; 544/60; 544/66; 544/111; 544/152; 544/153; 544/179

(58) Field of Classification Search ................. 549/469; 546/268.1, 284.1; 548/146, 215, 256, 311.4; 544/60, 66, 111, 152, 153, 179; 514/222.2, 514/226.5, 228.8, 241, 252.01, 279, 337, 514/359, 365, 383, 408, 444, 468, 469
See application file for complete search history.

(56) References Cited

U.S. PATENT DOCUMENTS

| 4,988,727 A | 1/1991 | Clemence et al. |
| 5,721,233 A | 2/1998 | Grisar et al. |
| 6,653,346 B1 | 11/2003 | Wang et al. |
| 7,265,152 B2 | 9/2007 | Saha et al. |

OTHER PUBLICATIONS

Ambinter Stock Screening Collection Catalog, Ambinter, Paris, France; Chemical Name: 3-Benzofurancarboxamide, 5-methoxy-N-methyl-2-phenyl- (Jan. 1, 2004).
TimTec Microplates Catalog, TimTec, Inc., Newark, DE; Chemical Name: 3-Benzofurancarboxamide, 5-methoxy-N-methyl-2-phenyl- (Jan. 19, 2004).
AKos Samples Catalog, AKos Consulting and Solutions, GmbH Basel, Switzerland; Chemical Name: 3-Benzofurancarboxamide, 5-methoxy-N-methyl-2-phenyl- (Jan. 19, 2004).
TimTec Stock Library Catalog, TimTec, Inc., Newark, DE; Chemical Name: 3-Benzofurancarboxamide, 5-methoxy-N-methyl-2-phenyl- (Jan. 19, 2004).
Interchim Intermediates Catalog, Interchim, Montlucon, France; Chemical Name: 3-Benzofurancarboxamide, 5-methoxy-N-methyl-2-phenyl- (Jul. 9, 2002).
ChemBridge Product List, ChemBridge Corp., San Diego, CA; Chemical Name: 3-Benzofurancarboxamide, 5-methoxy-N-methyl-2-phenyl- (Jan. 17, 2002).
Screening Collection Catalog, Zelinsky Inst. of Organic Chemistry, Moscow, Russia; Chemical Name: 3-Benzofurancarboxamide, 5-methoxy-N-methyl-2-phenyl- (Aug. 11, 2003).
Chemical Block Stock Library Catalog, Chemical Block, Ltd., Moscow, Russia; Chemical Name: 3-Benzofurancarboxamide, 5-methoxy-N-methyl-2-phenyl- (Feb. 2, 2004).
AsInEx Express Gold Collection Catalog, AsInEx, Moscow, Russia; Chemical Name: 3-Benzofurancarboxamide, 5-methoxy-N-methyl-2-phenyl- (Apr. 23, 2003).
Interbioscreen Compound Library Catalog, Interbioscreen Ltd., Moscow, Russia; Chemical Name: 3-Benzofurancarboxamide, 5-methoxy-N-methyl-2-phenyl- (May 9, 2003).

(Continued)

*Primary Examiner*—Janet L. Andres
*Assistant Examiner*—Raymond Covington
(74) *Attorney, Agent, or Firm*—Dann, Dorfman, Herrell and Skillman; Patrick J. Hagan

(57) ABSTRACT

The present invention relates to benzofuran derivatives and analogs, as well as compositions containing the same and to the use thereof for the treatment or prophylaxis of viral infections and diseases associated therewith, particularly those viral infections and associated diseases caused by the hepatitis C virus.

49 Claims, No Drawings

OTHER PUBLICATIONS

Otava Stock Chemicals Catalog, Otava, Kyiv, Ukraine; Chemical Name: 3-Benzofurancarboxamide, 5-methoxy-N-methyl-2-phenyl- (Nov. 26, 2003).

Ambinter Stock Screening Collection Catalog, Ambinter, Paris, France; Chemical Name: 3-Benzofurancarboxamide, 5-hydroxy-N-methyl-2-phenyl- (Jan. 1, 2004).

AKos Samples Catalog, AKos Consulting and Solutions GmbH Basel, Switzerland; Chemical Name: 3-Benzofurancarboxamide, 5-hydroxy-N-methyl-2-phenyl- (Feb. 9, 2004).

Interchim Interemdiates Catalog, Interchim, Montlucan, France; Chemical Name: 3-Benzofurancarboxamide, 5-hydroxy-N-methyl-2-phenyl- (Jul. 9, 2002).

ChemBridge Product List, ChemBridge Corp. San Diego, CA; Chemical Name: 3-Benzofurancarboxamide, 5-hydroxy-N-methyl-2-phenyl- (Jan. 17, 2002).

Interbioscreen Compound Library Catalog, Interbioscreen Ltd., Moscow, Russia; Chemical Name: 3-Benzofurancarboxamide, 5-hydroxy-N-methyl-2-phenyl- (May 9, 2003).

Otava Stock Chemicals Catalog, Otava, Kyiv, Ukraine; Chemical Name: 3-Benzofurancarboxamide, 5-hydroxy-N-methyl-2-phenyl- (Nov. 26, 2003).

Structural formulas from "Screening Compound Database" of Pharmeks Ltd., Moscow Russia, including Pharmeks ID Nos. PHAR000844 (Mol. Formula C24H18BrNO6), PHAR023049 (Mol. Formula C23H23BrO5) and PHAR 023900 (Mol. Formula C18H15BrO5) (1 page); Sep. 2002.

BENZOFURAN COMPOUNDS, COMPOSITIONS AND METHODS FOR TREATMENT AND PROPHYLAXIS OF HEPATITIS C VIRAL INFECTIONS AND ASSOCIATED DISEASES

This application is a divisional of U.S. patent application Ser. No. 10/699,336, filed Oct. 31, 2003 now U.S. Pat. No. 7,265,152 which claims the benefit of U.S. Provisional Application No. 60/423,291, filed Nov. 1, 2002; U.S. Provisional Application No. 60/461,077, filed Apr. 8, 2003; U.S. Provisional Application No. 60/489,060, filed Jul. 21, 2003; and U.S. Provisional Application No. 60/515,944, filed Oct. 30, 2003. These applications are hereby incorporated by reference in their entirety.

FIELD OF THE INVENTION

The present invention relates to novel benzofuran derivatives and analogs, as well as compositions containing the same and to the use thereof for the treatment or prophylaxis of viral infections and diseases associated therewith, particularly those viral infections and associated diseases caused by the hepatitis C virus.

BACKGROUND OF THE INVENTION

Hepatitis C is a common infection that can lead to chronic hepatitis, cirrhosis, liver failure, and hepatocellular carcinoma. Infection with the hepatitis C virus (HCV) leads to chronic hepatitis in at least 85% of cases. It is the leading reason for liver transplantation, and is responsible for at least 10,000 deaths annually in the United States (Hepatology, 1997, 26 (Suppl. 1), 2S-10S).

Interferon and interferon in combination with ribavirin are used in the U.S. for hepatitis due to HCV. These treatments are associated with improved serum enzyme response in some patients. The remainder are non-responsive to treatment. For responders, a sustained clinical improvement is seen in only a small percentage of patients; the majority of patients relapse upon cessation of treatment. Thus, the effectiveness of therapy for chronic hepatitis C is variable and its cure rate remains low. Moreover, therapy is often associated with considerable side effects.

New therapies and preventatives are clearly needed for infections and diseases caused by the hepatitis C virus.

The hepatitis C virus is a member of the Flaviviridae family. The genome of HCV is positive strand, single stranded linear RNA (Hepatology, 1997, 26 (Suppl. 1), 11S-14S). HCV displays extensive genetic heterogeneity; at least six genotypes and more than 50 subtypes have been identified.

Following infection by HCV, the viral RNA is translated into a polyprotein. This approximately 3,000 residue polyprotein is subsequently cleaved into individual proteins by host peptidases, as well as virally encoded proteases. The HCV genome encodes structural proteins (required for virus assembly) and nonstructural proteins (required for replication). Some of the nonstructural proteins include: NS2, NS3, NS4A, NS4B, NS5A, and NS5B (J. General Virology, 2000, 81, 1631-1648). NS5B is a RNA-dependent RNA polymerase that is essential for viral replication. In positive stranded RNA viruses, such as HCV, RNA is the sole genetic material. Since mammalian host cells ordinarily lack RNA-dependent RNA polymerase activity, the positive stranded RNA viruses encode their own replicative polymerase (NS5B in the case of HCV), which is essential for the production of virion progeny. The inhibition of NS5B activity, therefore, provides an attractive target for HCV drug design.

SUMMARY OF THE INVENTION

In accordance with one aspect, the present invention provides compounds and compositions for the treatment and prophylaxis of viral infections, as well as diseases associated with viral infections in living hosts. The compounds of the invention are of the following general formula:

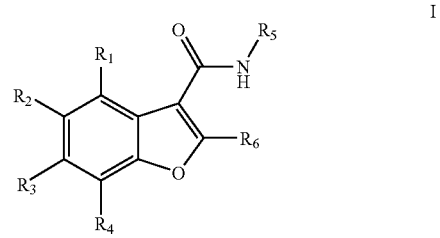

wherein:

$R_1$ represents a radical selected from the group consisting of hydrogen, alkyl, halogen, and cyano;

$R_2$ represents a radical selected from the group consisting of hydrogen, a substituted or unsubstituted alkyl radical, a substituted or unsubstituted alkoxy group, hydroxy, cycloalkyl, cycloalkyloxy, polyfluoroalkyl, polyfluoroalkoxy, halogen, amino, monoalkylamino, dialkylamino, cyano, a substituted or unsubstituted benzyloxy group, and a substituted or unsubstituted heterocyclic radical;

$R_3$ represents a radical selected from the group consisting of hydrogen, a substituted or unsubstituted alkyl radical, a substituted or unsubstituted alkoxy group, alkenyl, halogen, hydroxy, polyfluoroalkyl, polyfluoroalkoxy, formyl, carboxyl, alkylcarbonyl, alkoxycarbonyl, hydroxyalkylcarbonyl, amino, a substituted or unsubstituted monoalkylamino, dialkylamino, cyano, amido, alkoxyamido, a substituted or unsubstituted heteroarylamino, acetylsulfonylamino, ureido, carboxamide, sulfonamide, a substituted sulfonamide, a substituted or unsubstituted heterocyclosulfonyl, alkylthio, alkylsulfinyl, alkylsulfonyl, alkylsulfonic acid, a substituted or unsubstituted heterocyclic radical, and —O(CH$_2$)—C(=O)—R$_7$;

$R_4$ represents a radical selected from the group consisting of hydrogen, alkyl, halogen, and alkoxy;

$R_5$ represents a radical selected from the group consisting of an alkyl (C$_1$-C$_6$) group, cycloalkyl, and cycloalkylalkyl;

$R_6$ represents a radical selected from the group consisting of a substituted or unsubstituted aryl group and a substituted or unsubstituted heteroaryl group;

$R_7$ represents a radical selected from the group consisting of dialkylamino, a substituted or unsubstituted arylamino, a substituted or unsubstituted heteroarylamino, and a substituted or unsubstituted aryl group, said monoalkylamino substituents being one or more radical(s) independently selected from the group consisting of cycloalkyl, hydroxy, alkoxy, and a substituted or unsubstituted heterocyclic radical;

said arylamino substituents and said heteroarylamino substituents being one or more radical(s) independently selected from an alkyl group and an alkoxycarbonyl;

said sulfonamide substituents being one or more radical(s) independently selected from the group consisting of alkenyl, cycloalkyl, alkoxy, hydroxy, halogen, polyfluoroalkyl, polyfluoroalkoxy, carboxyl, alkylcarbonyl, alkoxycarbonyl, carboxamide, a substituted or unsubstituted aryl group, and a substituted or unsubstituted heterocyclic radical;

said heterocyclosulfonyl substituents being one or more radical(s) independently selected from the group consisting of alkoxy and hydroxy;

said alkyl radical substituents and said alkoxy group substituents being one or more radical(s) independently selected from the group consisting of alkenyl, amino, monoalkylamino, dialkylamino, alkoxy, cycloalkyl, hydroxy, carboxyl, halogen, cyano, polyfluoroalkyl, polyfluoroalkoxy, sulfonamide, carboxamide, alkylsulfonyl, alkylcarbonyl, alkoxycarbonyl, mercapto, 2,2-dimethyl-4-oxo-4H-benzo[1,3]dioxinyl, a substituted or unsubstituted aryl group, and a substituted or unsubstituted heterocyclic radical;

said heterocyclic radical substituents being one or more radical(s) independently selected from the group consisting of alkyl, amino, amido, monoalkylamino, cycloalkyl-alkylamino, dialkylamino, alkoxy, alkoxyalkyl, hydroxy, hydroxyalkyl, cycloalkyl, cycloalkylalkyl, carboxyl, carboxamide, halogen, haloalkyl, cyano, polyfluoroalkyl, polyfluoroalkoxy, alkylsulfonyl, alkylcarbonyl, cycloalkylcarbonyl, alkoxycarbonyl, mercapto, oxo, a substituted or unsubstituted aryl group, arylalkyl, and a substituted or unsubstituted heteroaryl group;

said heteroaryl group substituents being one or more radical(s) independently selected from the group consisting of alkyl, amino, alkoxy, alkoxyalkyl, hydroxy, hydroxyalkyl, cycloalkyl, carboxyl, carboxamide, halogen, polyfluoroalkyl, polyfluoroalkoxy, alkylsulfonyl, mercapto, and oxo;

said benzyloxy group substituents being one or more radical(s) independently selected from the group consisting of alkyl, alkoxy, polyfluoroalkyl, polyfluoroalkoxy, hydroxy, carboxyl, alkoxycarbonyl, halogen, cyano, alkylsulfonyl, and phenyl;

said aryl group substituents being one or more radical(s) independently selected from the group consisting of alkyl, acetylenyl, alkoxy, hydroxy, halogen, polyfluoroalkyl, polyfluoroalkoxy, cyano, amino, monoalkylamino, dialkylamino, aminoalkyl, alkoxyalkoxy, amido, amidoalkyl, carboxyl, alkylsulfonyl, alkylcarbonyl, alkoxycarbonyl, mercapto, and a heterocyclic radical; and pharmaceutically acceptable salts thereof;

with the proviso that said formula does not include the compounds selected from the group consisting of 5-methoxy-2-phenyl-benzofuran-3-carboxylic acid methylamide and 5-hydroxy-2-phenyl-benzofuran-3-carboxylic acid methylamide.

The invention also relates to pharmaceutical compositions containing the antiviral compounds of Formula I and the corresponding methods of use for treating and preventing infections caused by hepatitis C virus, as well as the intermediate compounds and related methods of preparing the antiviral compounds described herein.

DETAILED DESCRIPTION OF THE INVENTION

In one aspect, the instant invention provides compounds of Formula I:

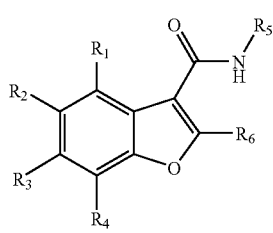

I wherein $R_1$, $R_2$, $R_3$, $R_4$, $R_5$, and $R_6$ are as defined above.

In a second aspect, the instant invention provides compounds having the formula:

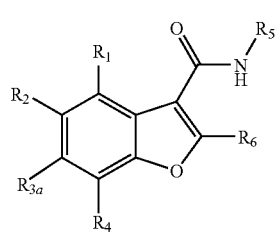

Ia wherein:
$R_1$ represents a radical selected from the group consisting of hydrogen, alkyl, halogen, and cyano;

$R_2$ represents a radical selected from the group consisting of hydrogen, a substituted or unsubstituted alkyl radical, a substituted or unsubstituted alkoxy group, hydroxy, cycloalkyl, cycloalkyloxy, polyfluoroalkyl, polyfluoroalkoxy, halogen, amino, monoalkylamino, dialkylamino, cyano, a substituted or unsubstituted benzyloxy group, and a substituted or unsubstituted heterocyclic radical;

$R_{3a}$ represents a radical selected from the group consisting of a substituted or unsubstituted alkyl radical, a substituted or unsubstituted alkoxy group, alkenyl, halogen, hydroxy, polyfluoroalkyl, polyfluoroalkoxy, formyl, carboxyl, alkylcarbonyl, alkoxycarbonyl, hydroxyalkylcarbonyl, amino, a substituted or unsubstituted monoalkylamino, dialkylamino, cyano, amido, alkoxyamido, a substituted or unsubstituted heteroarylamino, acetylsulfonylamino, ureido, carboxamide, sulfonamide, a substituted sulfonamide, a substituted or unsubstituted heterocyclosulfonyl, alkylthio, alkylsulfinyl, alkylsulfonyl, alkylsulfonic acid, a substituted or unsubstituted heterocyclic radical, and —O(CH$_2$)—C(=O)—R$_7$;

$R_4$ represents a radical selected from the group consisting of hydrogen, alkyl, halogen, and alkoxy;

$R_5$ represents a radical selected from the group consisting of an alkyl ($C_1$-$C_6$) group, cycloalkyl, and cycloalkylalkyl;

$R_6$ represents a radical selected from the group consisting of a substituted or unsubstituted aryl group and a substituted or unsubstituted heteroaryl group;

$R_7$ represents a radical selected from the group consisting of dialkylamino, a substituted or unsubstituted arylamino, a substituted or unsubstituted heteroarylamino, and a substituted or unsubstituted aryl group, said monoalkylamino substituents being one or more radical(s) independently selected from the group consisting of cycloalkyl, hydroxy, alkoxy, and a substituted or unsubstituted heterocyclic radical;

said arylamino substituents and said heteroarylamino substituents being one or more radical(s) independently selected from an alkyl group and an alkoxycarbonyl;

said sulfonamide substituents being one or more radical(s) independently selected from the group consisting of alkenyl, cycloalkyl, alkoxy, hydroxy, halogen, polyfluoroalkyl, polyfluoroalkoxy, carboxyl, alkylcarbonyl, alkoxycarbonyl, carboxamide, a substituted or unsubstituted aryl group, and a substituted or unsubstituted heterocyclic radical;

said heterocyclosulfonyl substituents being one or more radical(s) independently selected from the group consisting of alkoxy and hydroxy;

said alkyl radical substituents and said alkoxy group substituents being one or more radical(s) independently selected from the group consisting of alkenyl, amino, monoalkylamino, dialkylamino, alkoxy, cycloalkyl, hydroxy, carboxyl, halogen, cyano, polyfluoroalkyl, polyfluoroalkoxy, sulfonamide, carboxamide, alkylsulfonyl, alkylcarbonyl, alkoxycarbonyl, mercapto, 2,2-dimethyl-4-oxo-4H-benzo[1,3]dioxinyl, a substituted or unsubstituted aryl group, and a substituted or unsubstituted heterocyclic radical;

said heterocyclic radical substituents being one or more radical(s) independently selected from the group consisting of alkyl, amino, amido, monoalkylamino, cycloalkyl-alkylamino, dialkylamino, alkoxy, alkoxyalkyl, hydroxy, hydroxyalkyl, cycloalkyl, cycloalkylalkyl, carboxyl, carboxamide, halogen, haloalkyl, cyano, polyfluoroalkyl, polyfluoroalkoxy, alkylsulfonyl, alkylcarbonyl, cycloalkylcarbonyl, alkoxycarbonyl, mercapto, oxo, a substituted or unsubstituted aryl group, arylalkyl, and a substituted or unsubstituted heteroaryl group;

said heteroaryl group substituents being one or more radical(s) independently selected from the group consisting of alkyl, amino, alkoxy, alkoxyalkyl, hydroxy, hydroxyalkyl, cycloalkyl, carboxyl, carboxamide, halogen, polyfluoroalkyl, polyfluoroalkoxy, alkylsulfonyl, mercapto, and oxo;

said benzyloxy group substituents being one or more radical(s) independently selected from the group consisting of alkyl, alkoxy, polyfluoroalkyl, polyfluoroalkoxy, hydroxy, carboxyl, alkoxycarbonyl, halogen, cyano, alkylsulfonyl, and phenyl;

said aryl group substituents being one or more radical(s) independently selected from the group consisting of alkyl, acetylenyl, alkoxy, hydroxy, halogen, polyfluoroalkyl, polyfluoroalkoxy, cyano, amino, monoalkylamino, dialkylamino, aminoalkyl, alkoxyalkoxy, amido, amidoalkyl, carboxyl, alkylsulfonyl, alkylcarbonyl, alkoxycarbonyl, mercapto, and a heterocyclic radical; and pharmaceutically acceptable salts thereof.

In a third aspect, the instant invention provides compounds of the formula:

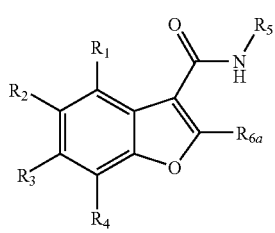

Ib wherein:

$R_1$ represents a radical selected from the group consisting of hydrogen, alkyl, halogen, and cyano;

$R_2$ represents a radical selected from the group consisting of hydrogen, a substituted or unsubstituted alkyl radical, a substituted or unsubstituted alkoxy group, hydroxy, cycloalkyl, cycloalkyloxy, polyfluoroalkyl, polyfluoroalkoxy, halogen, amino, monoalkylamino, dialkylamino, cyano, a substituted or unsubstituted benzyloxy group, and a substituted or unsubstituted heterocyclic radical;

$R_3$ represents a radical selected from the group consisting of hydrogen, a substituted or unsubstituted alkyl radical, a substituted or unsubstituted alkoxy group, alkenyl, halogen, hydroxy, polyfluoroalkyl, polyfluoroalkoxy, formyl, carboxyl, alkylcarbonyl, alkoxycarbonyl, hydroxyalkylcarbonyl, amino, a substituted or unsubstituted monoalkylamino, dialkylamino, cyano, amido, alkoxyamido, a substituted or unsubstituted heteroarylamino, acetylsulfonylamino, ureido, carboxamide, sulfonamide, a substituted sulfonamide, a substituted or unsubstituted heterocyclosulfonyl, alkylthio, alkylsulfinyl, alkylsulfonyl, alkylsulfonic acid, a substituted or unsubstituted heterocyclic radical, and —O(CH$_2$)—C(=O)—R$_7$;

$R_4$ represents a radical selected from the group consisting of hydrogen, alkyl, halogen, and alkoxy;

$R_5$ represents a radical selected from the group consisting of an alkyl ($C_1$-$C_6$) group, cycloalkyl, and cycloalkylalkyl;

$R_{6a}$ represents a radical selected from the group consisting of a substituted aryl group and a substituted or unsubstituted heteroaryl group;

$R_7$ represents a radical selected from the group consisting of dialkylamino, a substituted or unsubstituted arylamino, a substituted or unsubstituted heteroarylamino, and a substituted or unsubstituted aryl group, said monoalkylamino substituents being one or more radical(s) independently selected from the group consisting of cycloalkyl, hydroxy, alkoxy, and a substituted or unsubstituted heterocyclic radical;

said arylamino substituents and said heteroarylamino substituents being one or more radical(s) independently selected from an alkyl group and an alkoxycarbonyl;

said sulfonamide substituents being one or more radical(s) independently selected from the group consisting of alkenyl, cycloalkyl, alkoxy, hydroxy, halogen, polyfluoroalkyl, polyfluoroalkoxy, carboxyl, alkylcarbonyl, alkoxycarbonyl, carboxamide, a substituted or unsubstituted aryl group, and a substituted or unsubstituted heterocyclic radical;

said heterocyclosulfonyl substituents being one or more radical(s) independently selected from the group consisting of alkoxy and hydroxy;

said alkyl radical substituents and said alkoxy group substituents being one or more radical(s) independently selected from the group consisting of alkenyl, amino, monoalkylamino, dialkylamino, alkoxy, cycloalkyl, hydroxy, carboxyl, halogen, cyano, polyfluoroalkyl, polyfluoroalkoxy, sulfonamide, carboxamide, alkylsulfonyl, alkylcarbonyl, alkoxycarbonyl, mercapto, 2,2-dimethyl-4-oxo-4H-benzo[1,3]dioxinyl, a substituted or unsubstituted aryl group, and a substituted or unsubstituted heterocyclic radical;

said heterocyclic radical substituents being one or more radical(s) independently selected from the group consisting of alkyl, amino, amido, monoalkylamino, cycloalkyl-alkylamino, dialkylamino, alkoxy, alkoxyalkyl, hydroxy, hydroxyalkyl, cycloalkyl, cycloalkylalkyl, carboxyl, carboxamide, halogen, haloalkyl, cyano, polyfluoroalkyl, polyfluoroalkoxy, alkylsulfonyl, alkylcarbonyl, cycloalkylcarbonyl, alkoxycarbonyl, mercapto, oxo, a substituted or unsubstituted aryl group, arylalkyl, and a substituted or unsubstituted heteroaryl group;

said heteroaryl group substituents being one or more radical(s) independently selected from the group consisting of alkyl, amino, alkoxy, alkoxyalkyl, hydroxy, hydroxyalkyl, cycloalkyl, carboxyl, carboxamide, halogen, polyfluoroalkyl, polyfluoroalkoxy, alkylsulfonyl, mercapto, and oxo;

said benzyloxy group substituents being one or more radical(s) independently selected from the group consisting of alkyl, alkoxy, polyfluoroalkyl, polyfluoroalkoxy, hydroxy, carboxyl, alkoxycarbonyl, halogen, cyano, alkylsulfonyl, and phenyl;

said aryl group substituents being one or more radical(s) independently selected from the group consisting of alkyl, acetylenyl, alkoxy, hydroxy, halogen, polyfluoroalkyl, polyfluoroalkoxy, cyano, amino, monoalkylamino, dialkylamino, aminoalkyl, alkoxyalkoxy, amido, amidoalkyl, carboxyl, alkylsulfonyl, alkylcarbonyl, alkoxycarbonyl, mercapto, and a heterocyclic radical; and pharmaceutically acceptable salts thereof.

In a fourth aspect, the instant invention provides compounds of the formula:

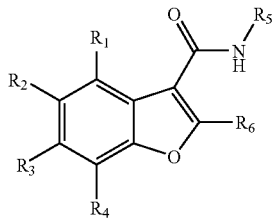

wherein:

R$_1$ represents a radical selected from the group consisting of hydrogen, methyl, and chloro;

R$_2$ represents a radical selected from the group consisting of hydrogen, methyl, ethyl, isopropyl, t-butyl, cyclopropyl, hydroxy, hydroxymethyl, methoxymethyl, methoxy, trifluoromethoxy, difluoromethoxy, cyclopropylmethoxy, carboxymethoxy, cyanomethoxy, cyano-methyl-methoxy, 1-hydroxymethyl-cyclopropylmethoxy, carbamoylmethoxy, methylcarbamoylmethoxy, diethylcarbamoylmethoxy, (4-ethoxycarbonyl-phenylcarbamoyl)-methoxy, tert-butoxycarbonylmethoxy, ethoxy, 2-methoxy-ethoxy, 2-chloro-ethoxy, 2-carboxyethoxy, 2,2,2-trifluoroethoxy, 1-(4-fluoro-phenyl)-ethoxy, 2-(4-fluoro-phenyl)-2-oxo-ethoxy, 2-(4-methoxy-phenyl)-2-oxo-ethoxy, propoxy, isopropoxy, 2-oxo-propoxy, 2-hydroxy-propoxy, 3-hydroxy-propoxy, 2-hydroxy-2-methyl-propoxy, 3-bromo-propoxy, 3-ethoxypropoxy, butoxy, 2-hydroxy-2-methyl-butoxy, cyclopentyloxy, allyloxy, cyano, chloro, fluoro, methanesulfonic acid, benzyloxy, 2-phenylbenzyloxy, 2-difluoromethoxy-benzyloxy, 3-methoxy-benzyloxy, 3-methoxycarbonyl-benzyloxy, 3-carboxy-benzyloxy, 3-cyano-benzyloxy, 4-methoxy-benzyloxy, 4-fluoro-benzyloxy, 4-cyano-benzyloxy, 4-methoxycarbonyl-benzyloxy, 4-carboxy-benzyloxy, 4-carboxy-3-hydroxy-benzyloxy, 4-methanesulfonyl-benzyloxy, 3,4-difluoro-benzyloxy, 3,5-dimethoxy-benzyloxy, 2,2-dimethyl-4-oxo-4H-benzo[1,3]dioxin-5-ylmethoxy, 2,2-dimethyl-4-oxo-4H-benzo[1,3]dioxin-7-ylmethoxy, 2,2-dimethyl-4-oxo-4H-benzo[1,3]dioxin-6-ylmethoxy, 3-chloromethyl-[1,2,4]thiadiazol-5-yloxy, 5-chloro-[1,2,4]thiadiazol-3-ylmethoxy, 5-chloro-[1,2,3]thiadiazol-4-ylmethoxy, 5-p-tolyl-[1,3,4]oxadiazol-2-ylmethoxy, 5-(3,5-dimethyl-isoxazol-4-yl)-[1,2,4]oxadiazol-3-ylmethoxy, 5-(cyclopropylmethyl-amino)-[1,2,4]thiadiazol-3-ylmethoxy, 5-tert-butyl-[1,2,4]oxadiazol-3-ylmethoxy, 5-(4-methoxy-phenyl)-[1,2,4]oxadiazol-3-ylmethoxy, 5-diethylamino-[1,2,4]thiadiazol-3-ylmethoxy, [1,3,4]thiadiazol-2-ylcarbamoylmethoxy, 3,5-dimethyl-isoxazol-4-yl, isoxazol-3-ylmethoxy, 3,5-dimethyl-isoxazol-4-ylmethoxy, 5-methyl-isoxazol-3-ylmethoxy, thiazol-2-ylmethoxy, thiazol-4-ylmethoxy, 2-methyl-thiazol-4-ylmethoxy, 1-thiazol-2-yl-ethoxy, thiazol-2-ylcarbamoylmethoxy, (4,5-dimethyl-thiazol-2-ylcarbamoyl)-methoxy, 4-chloro-1-methyl-1H-pyrazol-3-ylmethoxy, 2-pyrazol-1-yl-ethoxy, 2-(3,5-dimethyl-pyrazol-1-yl)-ethoxy, 4-ethoxycarbonyl-thiazol-2-ylmethoxy, 4-carboxy-thiazol-2-ylmethoxy, 5-amino-4H-[1,2,4]triazol-3-ylmethoxy, thiophen-2-yl, furan-2-yl, 2-morpholin-4-yl-ethoxy, 3-piperidin-1-yl-propoxy, tetrahydro-furan-2-yl, 1-methyl-1H-tetrazol-5-ylmethoxy, 1-methyl-1H-imidazol-2-ylmethoxy, 1-benzyl-1H-imidazol-2-ylmethoxy, 3H-imidazol-4-ylmethoxy, pyridine-4-ylmethoxy, 6-bromomethyl-pyridin-2-ylmethoxy, and 2-(4-cyano-piperidin-1-yl)-ethoxy;

R$_3$ represents a radical selected from the group consisting of hydrogen, methyl, methoxy, hydroxy, hydroxymethyl, 1-hydroxy-ethyl, 1-hydroxy-2-methyl-propyl, 1-hydroxy-1-methyl-ethyl, formyl, ureido, vinyl, bromo, chloro, cyano, acetyl, 2-hydroxy-acetyl, carboxy, azetidin-1-yl, carboxylic acid amide, amino, methylamino, dimethylamino, ethylamino, diethylamino, isopropylamino, tert-butylamino, ethyl-methyl-amino, 2-methoxy-ethylamino, cyclopropylmethyl-amino, 2,3-dihydroxy-propylamino, 1-methylaminoethyl, dimethylaminomethyl, 1-amino-1-methyl-ethyl, 2-amino-1-hydroxy-1-methyl-ethyl, acetylamino, 1-acetylamino-1-methyl-ethyl, (2-methoxy-ethyl)-methyl-amino, ethyl-(2-methoxyacetyl)-amino, 3-chloro-propane-1-sulfonylamino, methanesulfonylamino, ethyl-methanesulfonyl-amino, isopropyl-methanesulfonyl-amino, isobutyl-methanesulfonyl-amino, cyclobutyl-methanesulfonyl-amino, cyclopentyl-methanesulfonyl-amino, cyclopropylmethyl-methanesulfonyl-amino, (2-hydroxy-ethyl)-methanesulfonyl-amino, (2-hydroxy-propyl)-methanesulfonyl-amino, (2-fluoro-ethyl)-methanesulfonyl-amino, 2-(4-fluoro-phenyl)-2-hydroxy-ethyl]-methanesulfonyl-amino, (1-hydroxymethyl-cyclopropylmethyl)-methanesulfonyl-amino, (4-carboxy-benzyl)-methanesulfonyl-amino, allyl-methanesulfonyl-amino, acetyl-methanesulfonyl-amino, benzyl-methanesulfonyl-amino, carboxymethyl-methanesulfonyl-amino, methanesulfonylamino-methyl, 1-methanesulfonylamino-1-methyl-ethyl, methanesulfonyl-methyl-amino, 1-(methanesulfonyl-methyl-amino)-ethyl, methanesulfonyl-propyl-amino, methanesulfonyl-(2-methoxy-ethyl)-amino, methanesulfonyl(2,2,2-trifluoro-ethyl)-amino, methanesulfonyl-(2-oxo-propyl)-amino, methanesulfonyl-(2-trifluoromethoxy-ethyl)-amino, methanesulfonyl-(4-methoxy-benzyl)-amino, methanesulfonyl(4-methoxycarbonyl-benzyl)-amino, methanesulfonyl-methoxymethyl-amino, methanesulfonyl-methylcarbamoyl-methyl-amino, (methanesulfonyl-methyl-amino)-methyl, sulfamoyl, methylsulfamoyl, dimethylsulfamoyl, ethylsulfamoyl, cyclopropylsulfamoyl, cyclobutylsulfamoyl, 3-methanesulfonyl-phenyl, 4-methanesulfonyl-phenyl, benzyloxy, 1H-pyrazol-4-yl, 2H-pyrazol-3-yl, 1-methyl-1H-pyrazol-3-yl, 2-methyl-2H-pyrazol-3-yl, 5-methyl-1H-pyrazol-4-yl, 5-methyl-2H-pyrazol-3-yl, 1,5-dimethyl-1H-pyrazol-3-yl, 2,5-dimethyl-2H-pyrazol-3-yl, 2,5-dimethyl-2H-pyrazol-3-ylamino, 3,5-dimethyl-1H-pyrazol-4-yl, 1,3,5-trimethyl-1H-pyrazol-4-yl, isoxazol-3-yl, 5-methyl-isoxazol-3-yl, 3-cyclopropyl-isoxazol-5-yl, 5-cyclopropyl-isoxazol-3-yl, 3,5-dimethyl-isoxazol-4-yl, 3,5-dimethyl-isoxazol-4-ylamino, 5-methoxymethyl-isoxazol-3-yl, 5-ethoxymethyl-isoxazol-3-yl, 5-isopropoxymethyl-isoxazol-3-yl, 5-hydroxymethyl-isoxazol-3-yl, 4-(2-hydroxy-ethyl)-isoxazol-3-yl, 3-methoxymethyl-5-methyl-isoxazol-4-yl, 5-methoxymethyl-3-methyl-isoxazol-4-yl, 5-cyclopropyl-3-methoxymethyl-isoxazol-4-yl, 3-cyclopropyl-5-methoxymethyl-isoxazol-4-yl, (3,5-dimethyl-isoxazol-4-ylmethyl)-methanesulfonyl-amino, 3-metho-xymethyl-isoxazol-5-yl), 3-methyl-isoxazol-5-yl, methanesulfonyl-(5-methyl-isoxazol-3-ylmethyl)-amino, thiazol-2-yl, thiazol-5-yl, methanesulfonyl-thiazol-2-ylmethyl-amino, methanesulfonyl-thiazol-4-ylmethyl-amino, methanesulfonyl-(2-methyl-thiazol-4-ylmethyl)-amino, (4-carboxy-thiazol-2-ylmethyl)methanesulfonyl-amino, (4-ethoxycarbonyl-thiazol-2-ylmethyl)-methanesulfonyl-amino, pyridin-3-yl, pyridin-4-yl, pyridin-4-ylamino, 6-fluoro-pyridin-3-yl, methanesulfonyl-pyridin-4-ylmethyl-amino, (6-bromomethyl-pyridin-2-ylmethyl)-methanesulfonyl-amino, pyrrolidin-1-yl, pyrrolidin-2-yl, pyrrolidine-1-sulfonyl, 3-hydroxypyrrolidin-1-yl, 3-hydroxy-pyrrolidine-1-sulfonyl, 5-oxopyrrolidin-3-yl, 1-acetyl-pyrrolidin-2-yl, 1-acetyl-pyrrolidin-3-yl, 1-carbamoylpyrrolidin-2-yl, 1-methylcarbamoyl-pyrrolidin-2-yl, 4-methylcarbamoyl-5-oxo-pyrrolidin-3-yl, 1-cyclopropanecarbonyl-pyrrolidin-2-yl, 1-methanesulfonyl-pyrrolidin-2-yl, 1-methanesulfonyl-pyrrolidin-3-yl, 3-amino-pyrrolidin-1-yl, 3-methanesulfonyl-pyrrolidin-1-yl, 1H-pyrrol-2-yl, 1H-pyrrol-3-yl, 3-cyano-4-hydroxy-2-oxo-2,5-dihydro-pyrrol-1-ylmethyl, furan-2-yl, furan-3-yl, (furan-3-ylmethyl)-amino, tetrahydro-furan-3-yl, (tetrahydro-furan-2-ylmethyl)-amino, [1,3,4]oxadiazol-2-yl, [1,2,4]oxadiazol-3-yl, 5-methyl-[1,2,4]oxadiazol-3-yl, 5-methyl-[1,3,4]oxadiazol-2-yl, 5-trifluoromethyl-[1,2,4]oxadiazol-3-yl, morpholin-4-yl, 2,6-dimethyl-morpholin-4-yl, 2-morpholin-4-yl-ethylamino, morpholine-4-sulfonyl, methanesulfonyl-(2-morpholin-4-yl-ethyl)-amino, thiomorpholin-4-yl, thiomorpholine-4-sulfonyl, 1-oxo-thiomorpholin-4-yl, 1,1-dioxido-isothiazolidin-2-yl, 2-oxo-oxazolidin-5-yl, 5-methyl-2-oxo-oxazolidin-5-yl, oxazol-5-yl, 1H-imidazol-4-yl, 1H-imidazol-2-yl, 2,5-dioxo-imidazolidin-4-yl, 4-methyl-2,5-dioxo-imidazolidin-4-yl, pyrimidin-5-yl, 2,5-dimethyl-2H-[1,2,4]triazol-3-yl, 2-methyl-2H-[1,2,4]triazol-3-yl, 4H-[1,2,4]triazol-3-yl, 5-methyl-2H-[1,2,4]triazol-3-yl, 1H-tetrazol-5-yl, 1-methyl-1H-tetrazol-5-ylmethoxy, methanesulfonyl-(1-methyl-1H-tetrazol-5-ylmethyl)-amino, piperidin-1-yl, 4-fluoro-piperidin-1-yl, 4,4-difluoro-piperidin-1-yl, 3-hydroxy-piperidin-1-yl, 4-hydroxy-piperidin-1-yl, 4-hydroxy-piperidine-1-sulfonyl, 4-carbamoyl-piperazin-1-yl, 4-methyl-piperazin-1-yl, and 5-chloro-[1,2,4]thiadiazol-3-ylmethyl;

$R_4$ represents a radical selected from the group consisting of hydrogen and methyl;

$R_5$ represents a radical selected from the group consisting of methyl, ethyl, isopropyl, and cyclopropyl; and $R_6$ represents a radical selected from the group consisting of phenyl, 4-methyl-phenyl, 4-ethyl-phenyl, 4-methoxy-phenyl, 4-hydroxy-phenyl, 4-bromo-phenyl, 2-chloro-phenyl, 2-fluoro-phenyl, 4-fluoro-phenyl, 2,4-difluoro-phenyl, 3,4-difluoro-phenyl, 4-bromo-3-fluoro-phenyl, 3-chloro-4-fluoro-phenyl, 4-chloro-3-fluoro-phenyl, 2,4,5-trifluoro-phenyl, 3-fluoro-4-methyl-phenyl, 4-fluoro-3-methyl-phenyl, 4-fluoro-3-hydroxy-phenyl, 2-ethoxy-4-fluoro-phenyl, 3-trifluoromethyl-phenyl, 4-trifluoromethyl-phenyl, 4-cyanophenyl, 4-amino-phenyl, 4-(acetylamino-methyl)-phenyl, 4-morpholin-4-yl-phenyl, 4-pyrrolidin-1-yl-phenyl, furan-2-yl, furan-3-yl, 3-methyl-furan-2-yl, thiophen-2-yl, 5-chlorothiophen-2-yl, pyridin-4-yl, and pyridin-3-yl;

with the proviso that said formula does not include the compounds selected from the group consisting of 5-methoxy-2-phenyl-benzofuran-3-carboxylic acid methylamide and 5-hydroxy-2-phenyl-benzofuran-3-carboxylic acid methylamide.

Preferred compounds of Formula I include the compounds wherein $R_2$ is —OCH$_3$ or —O(CH)(CH$_3$)$_2$, —CH$_2$CH$_3$, and

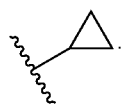

Other preferred compounds of Formula I include the compounds wherein $R_5$ is methyl.

A preferred aspect of the invention includes the compound of Formula I wherein the aryl group represented by $R_6$ is a substituted phenyl, said phenyl substituents being one or more radical(s) independently selected from the group consisting of fluoro, chloro, bromo, methoxy, and cyano.

Another preferred aspect of the invention includes the compound of the Formula Ic:

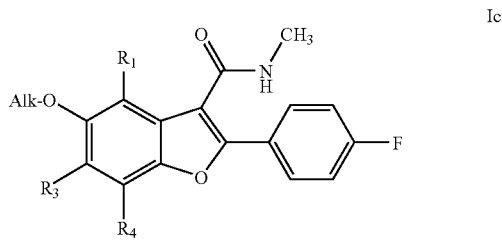

wherein Alk is an alkyl group and $R_1$, $R_3$, and $R_4$ are as defined above in reference to Formula I; and pharmaceutically acceptable salts thereof.

Preferred compounds of the invention include 2-(4-fluoro-phenyl)-5-methoxy-6-morpholin-4-yl-benzofuran-3-carboxylic acid methylamide, 2-(4-fluoro-phenyl)-5-isopropoxy-6-morpholin-4-yl-benzofuran-3-carboxylic acid methylamide, 2-(4-fluoro-phenyl)-5-isopropoxy-6-methanesulfonylamino-benzofuran-3-carboxylic acid methylamide, 2-(4-fluoro-phenyl)-5-isopropoxy-6-[(2-methoxy-ethyl)-methyl-amino]-benzofuran-3-carboxylic acid methylamide, 5-benzyloxy-2-(4-fluoro-phenyl)-6-morpholin-4-yl-benzofuran-3-carboxylic acid methylamide, 2-(4-fluoro-phenyl)-6-[(furan-3-ylmethyl)-amino]-5-isopropoxy-benzofuran-3-carboxylic acid methylamide, 6-(3,5-dimethyl-isoxazol-4-yl)-2-(4-fluoro-phenyl)-5-methoxy-benzofuran-3-carboxylic acid methylamide, 5-cyclopropyl-2-(4-fluoro-phenyl)-6-[(2-hydroxy-ethyl)-methanesulfonyl-amino]-benzofuran-3-carboxylic acid methylamide, 6-(3,5-dimethyl-isoxazol-4-yl)-2-(4-fluoro-phenyl)-5-(3-hydroxy-propoxy)-benzofuran-3-carboxylic acid methylamide, 5-ethoxy-2-(4-fluoro-phenyl)-6-(methanesulfonyl-methyl-amino)-benzofuran-3-carboxylic acid methylamide, 2-(4-fluoro-phenyl)-6-[(2-hydroxy-ethyl)-methanesulfonyl-amino]-5-methoxy-benzofuran-3-carboxylic acid methylamide, 5-ethyl-2-(4-fluoro-phenyl)-6-[(2-hydroxy-ethyl)methanesulfonyl-amino]-benzofuran-3-carboxylic acid methylamide, 2-(4-fluoro-phenyl)-6-[4-(2-hydroxy-ethyl)-isoxazol-3-yl]-5-methoxy-benzofuran-3-carboxylic acid methylamide, and pharmaceutically acceptable salts thereof.

According to another aspect, the present invention provides pharmaceutical compositions comprising one or more compounds of Formula I in combination with a pharmaceutically acceptable carrier medium. Preferred pharmaceutical compositions comprise one or more compounds listed in Table 1 below, and pharmaceutically acceptable salts thereof, in combination with a pharmaceutically acceptable carrier medium In accordance with yet another aspect, the present invention provides methods for the prophylaxis or treatment of hepatitis C infections and diseases associated with such infections in a living host, for example, a mammal including a human, comprising the step of administering a therapeutically effective amount of the compounds Formula I to a host susceptible to, or suffering from such infection.

Another aspect of the invention provides methods for the prophylaxis or treatment of hepatitis C infections and diseases associated with such infections in a living host, for example, a mammal including a human. This method comprises administering a therapeutically effective amount of a compound selected from the group consisting of 5-methoxy-2-phenyl-benzofuran-3-carboxylic acid methylamide and 5-hydroxy-2-phenyl-benzofuran-3-carboxylic acid methylamide to a host susceptible to, or suffering from such infection.

The compounds of Formula I above, their isomers and pharmaceutically acceptable salts exhibit antiviral activity. The compounds of the invention are particularly effective against hepatitis C virus and are useful in the prophylaxis and/or treatment of infections and diseases associated with this virus in living hosts.

In vitro studies (cell-based and biochemical) have been performed which demonstrate the usefulness of compounds described herein as antiviral agents. For example, antiviral activity of representative compounds was evaluated in a human liver derived cell line containing an HCV replicon. Also, antiviral activity was measured by the inhibitory activity of the compounds against the viral RdRp in an enzymological assay for RNA synthesis.

As used herein, the term "compounds of the invention" means, collectively, the compounds of Formula I, pharmaceutically acceptable salts thereof, and mixtures thereof. The compounds of the invention are identified herein by their chemical structure and/or chemical name.

The term "alkyl" as used herein refers to straight or branched chain aliphatic hydrocarbon radicals of up to 10 carbon atoms, preferably up to 6 carbon atoms and more preferably 1 to 4 carbon atoms. Similarly, the term "alkyl" or any variation thereof, used in combination form to name substituents, such as alkoxy (—O-alkyl), cycloalkylalkyl (-alkyl-cycloalkyl), arylalkyl (-alkyl-aryl), hydroxyalkyl (-alkyl-OH), monoalkylamino (—NH-alkyl), aminoalkyl (-alkyl-NH$_2$), alkylthio (—S-alkyl), alkylsulfinyl (—S(=O)-alkyl), alkylsulfonyl (—S(O)$_2$-alkyl), alkylsulfonic acid (—O—S(O)$_2$-alkyl), or the like also refers to straight or branched chain aliphatic hydrocarbon radicals of up to 10 carbon atoms, preferably 1 to 6 carbon atoms, and more preferably of 1 to 4 carbon atoms. Also "alk" in a structural formula herein denotes an alkyl group, unless divalency is indicated, in which case the "alk" denotes the corresponding alkylene group(s). Additionally, the term "alkyl (C$_1$-C$_6$)" denotes an alkyl group having one to six carbon atoms.

The term "alkenyl" as used herein refers to straight or branched chain aliphatic hydrocarbon radicals of 2 to 7 carbon atoms containing at least one double bond. Such alkenyl moieties may exist in the E or Z configurations; the compounds of this invention include both configurations. The term "alkynyl" as used herein refers to straight or branched chain aliphatic hydrocarbon radicals containing 2 to 7 carbon atoms having at least one triple bond.

The term "phenyl" as used herein refers to a

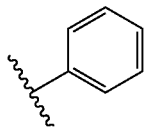

group. A "substituted phenyl" refers to a phenyl group that is substituted with the indicated substituents.

As used herein, the term "aryl", when used as such, or in combination form, for example "aralkyl," refers to an aromatic carbocyclic group, having 6 to 10 carbon atoms including, without limitation, phenyl and napthyl.

The term "heteroaryl," as used herein, refers to a 5- or 6-membered aromatic cyclic group having at least one carbon atom and one or more oxygen, nitrogen or sulfur atoms in the ring, as for example furyl, thienyl, pyridyl, pyrrolyl, oxazolyl, thiazolyl, imidazolyl, pyrazolyl, isoxazolyl, isothiazolyl, 1,2,3-oxadiazolyl, 1,2,4-oxadiazolyl, 1,2,3-triazolyl, 1,2,4-triazolyl, 1-3-oxathiolanly, thiadiazolyl, tetrazolyl, and the like.

As used herein, the term "cycloalkyl" refers to non-aromatic carbocyclic groups, having 3 to 7 carbon atoms, as for example cyclopropyl, cyclobutyl, cyclopentyl, cyclohexyl and the like.

The term "cycloalkyloxy," as used herein, refers to a radical or substituent of the formula —O-cycloalkyl, wherein cycloalkyl is as defined above.

The term "polyfluoroalkyl," as used herein, refers to an alkyl radical or substituent having one or more fluoro substituents and includes perfluoroalkyl groups. Examples include trifluoromethyl and trifluoroethyl. The term "polyfluoroalkoxy," as used herein, refers to an alkoxy radical or substituent having one or more fluoro substituents and includes perfluoroalkoxy groups. Examples include trifluoromethoxy and trifluoroethoxy.

The term "heterocyclic," as used herein, refers to an aromatic or non-aromatic cyclic group having in the ring at least one carbon atom and one to four heteroatoms independently selected from oxygen, nitrogen or sulfur atoms. The point of attachment of heterocyclic radicals can either be through a carbon atom or a heteroatom. Heterocyclic radicals preferably have 3 to 10 members, and more preferably 4, 5, or 6 members in the ring. Examples of heterocyclic radicals include azetidinyl, furyl, tetrahydrofuranyl, thienyl, pyridyl, pyrrolyl, pyrrolinyl, pyrrolidinyl, piperidinyl, piperazinyl, pyrimidinyl, oxazolyl, oxazolidinyl, thiazolyl, imidazolyl, imidazolidinyl, pyrazolyl, 2-pyrazolinyl, isoxazolyl, isothiazolyl, morpholinyl, thiomorpholinyl, 1,2,3-oxadiazolyl, 1,3,4-oxadiazolyl, 1,2,4-oxadiazolyl, 1,2,3-triazolyl, 1,2,4-triazolyl, 1-3-oxathiolanly, thiadiazolyl, tetrazolyl, and the like.

The term "amido," as used herein, refers to a radical or substituent of the formula —NR"C(=O)R"', wherein R" and R"' independently represent hydrogen, alkyl, or cycloalkyl. Similarly, the term "amidoalkyl," as used herein, refers to a radical or substituent of the formula -alkyl-NR"C(=O)R"', wherein R" and R"' are as previously defined.

The term "alkoxyamido," as used herein, refers to a radical or substituent of the formula —NR"C(=O)-alkyl-alkoxy, wherein R", alkyl, and alkoxy are as previously defined.

The term "carboxamide," as used herein, refers to a radical or substituent of the formula —C(=O)—NR"R"', wherein R" and R"' are as previously defined.

The term "ureido," as used herein, refers to a radical or substituent of the formula —NR'C(=O)—NR"R"', wherein R' represents hydrogen or alkyl and R" and R"' are as previously defined.

The term "sulfonamide," as used herein, refers to a radical or substituent of the formula —SO$_2$NR"R"' or —NR"SO$_2$R"', wherein R" and R"' are as previously defined. A substituted sulfonamide, as used herein, refers to a radical or substituent of the formula —N(alkyl)-SO$_2$(alkyl) in which at least one alkyl group is further substituted with the indicated substituents.

The term "acetylsulfonylamino," as used herein, refers to a radical or substituent of the formula —N(SO$_2$—R")—(C(=O)CH$_3$), wherein R" is as previously defined.

The term "heterocyclosulfonyl," as used herein, refers to a radical or substituent of the formula —SO$_2$—HET, wherein HET is a heterocyclic group as defined above. Preferred heterocyclosulfonyl groups include pyrrolidinylsulfonyl, piperidinylsulfonyl, morpholinylsulfonyl, and thiomorpholinylsulfonyl.

The term "arylamino," as used herein, refers to a radical or substituent of the formula —N(R")-aryl, wherein R" and aryl are as previously defined. A substituted arylamino, as used herein, refers to an arylamino radical or substituent in which the aryl group is further substituted with the indicated substituents.

The term "heteroarylamino," as used herein, refers to a radical or substituent of the formula —N(R")-heteroaryl, wherein R" and heteroaryl are as previously defined. A substituted heteroarylamino, as used herein, refers to a heteroarylamino radical or substituent in which the heteroaryl group is further substituted with the indicated substituents.

A substituted monoalkylamino, as used herein, refers to a radical or substituent of the formula —NH-alkyl in which the alkyl group is further substituted with the indicated substituents. Similarly, the term "cycloalkyl-alkylamino," as used herein, refers to a monoalkylamino radical or substituent, as defined above, in which the alkyl group is further substituted with a cycloalkyl group as defined above.

The term "carboxyl," as used herein, refers to a radical or substituent of the formula —C(=O)OH.

The term "carbonyl", whether used alone or with other terms, such as "alkoxycarbonyl", denotes —C(=O)—.

The term "alkylcarbonyl," as used herein, refers to a radical or substituent of the formula —C(=O)-alkyl, and includes, for example, methylcarbonyl, ethylcarbonyl, propylcarbonyl, butylcarbonyl, and pentylcarbonyl. Similarly, the term "cycloalkylcarbonyl," as used herein, refers to a radical or substituent of the formula —C(=O)-cycloalkyl.

The term "hydroxyalkylcarbonyl," as used herein, refers to a compound of the formula —C(=O)-alkyl-OH.

The term "alkoxycarbonyl," as used herein, refers to a radical or substituent —C(=O)—O-alkyl, and includes, for example, methoxycarbonyl, ethoxycarbonyl, propoxycarbonyl, butoxycarbonyl, and pentoxycarbonyl.

The term "formyl," as used herein, refers to a radical or substituent of the formula —C(=O)—H.

The term "mercapto," as used herein, refers to a radical or substituent of the formula —SH.

The term "benzyloxy," as used herein, refers to a radical or substituent of the formula —OCH$_2$-phenyl. A substituted benzyloxy is a benzyloxy in which the phenyl group is further substituted with the indicated substituents.

The term "hexanes," as used herein, refers to a solvent mixture of straight and branched chain hexane hydrocarbons, wherein the solvent mixture contains mostly n-hexane and some minor amounts of branched hexanes.

The term "halogen," as used herein, refers to a radical or substituent selected from the group consisting of chloro, bromo, iodo, and fluoro.

The term "haloalkyl," as used herein, refers to an alkyl group as defined above that is further substituted with a halogen, as defined above.

The term "psig" refers to pounds per square inch gauge.

The term "HPLC," as used herein, refers to high-performance liquid chromatography.

The term "TLC," as used herein, refers to thin layer chromatography.

The term "tautomeric form" as used herein refers two or more isomeric structures formed by migration of a hydrogen atom.

The term "amino" as used herein refers to an —NH$_2$ group.

The term "2,2-dimethyl-4-oxo-4H-benzo[1,3]dioxinyl" as used herein refers to a radical or substituent of the formula:

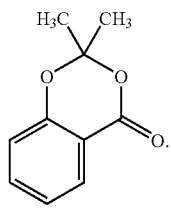

The term "living host" as used herein refers to an organism that is living and capable of being infected with a virus, such as the hepatitis C virus; for example, a mammal, which includes a human.

The compounds of the present invention and their isomeric forms and pharmaceutically acceptable salts thereof are also useful in treating and preventing viral infections, in particular hepatitis C infection, and diseases in living hosts when used in combination with each other or with other biologically active agents, including but not limited to the group consisting of interferon, a pegylated interferon, ribavirin, protease inhibitors, polymerase inhibitors, small interfering RNA compounds, anti-sense compounds, nucleotide analogs, nucleoside analogs, immunoglobulins, immunomodulators, hepatoprotectants, anti-inflammatory agents, antibiotics, antivirals, and anti-infective compounds. Such combination therapy may also comprise providing a compound of the invention either concurrently or sequentially with other medicinal agents or potentiators, such as acyclovir, famicyclovir, valgancyclovir and related compounds, ribavirin and related compounds, amantadine and related compounds, various interferons such as, for example, interferon-alpha, interferon-beta, interferon-gamma and the like, as well as alternative forms of interferons such as pegylated interferons. Additionally, combinations of, for example ribavirin and interferon, may be administered as an additional combination for a multiple combination therapy with at least one of the compounds of the present invention.

The combination therapy can be sequential, that is the treatment with one agent first and then the second agent (for example, where each treatment comprises a different compound of the invention or where one treatment comprises a compound of the invention and the other comprises one or more biologically active agent), or it can be treatment with both agents at the same time (concurrently). The sequential therapy can be within a reasonable time after the completion of the first therapy before beginning the second therapy. The treatment with both agents at the same time can be in the same daily dose or in separate doses. The dosages for both concurrent and sequential combination therapy will depend on absorption, distribution, metabolism, and excretion rates of the components of the combination therapy as well as other factors known to one of skill in the art. Dosage values will also vary with the severity of the condition to be alleviated. It is to be further understood that for any particular subject, specific dosage regimens and schedules may be adjusted over time according to the individual's need and the professional judgment of the person administering or supervising the administration of the combination therapy.

In a further embodiment, the compounds of the invention may be used for the treatment of HCV in humans in combination therapy mode with other inhibitors of the HCV polymerase.

In yet a further embodiment, the compounds of the present invention may be used for the treatment of HCV in humans in combination therapy mode with other inhibitors of the HCV life cycle such as, for example, inhibitors of HCV cell attachment or virus entry, HCV translation, HCV RNA transcription or replication, HCV maturation, assembly or virus release, or inhibitors of HCV enzyme activities such as the HCV nucleotidyl transferase, helicase, protease or polymerase.

It is intended that combination therapies of the present invention include any chemically compatible combination of a compound of this inventive group with other compounds of the inventive group or other compounds outside of the inventive group, as long as the combination does not eliminate the anti-viral activity of the compound of this inventive group or the anti-viral activity of the pharmaceutical composition itself.

The term "interferon-alpha" as used herein means the family of highly homologous species-specific proteins that inhibit viral replication and cellular proliferation and modulate immune response. Typical suitable interferon-alphas include, but are not limited to, recombinant interferon alpha-2b such as INTRON-A INTERFERON available from Schering Corporation, Kenilworth, N.J., recombinant interferon alpha-2a such as Roferon interferon available from Hoffmann-La Roche, Nutley, N.J., a recombinant interferon alpha-2C, such as BEROFOR ALPHA 2 INTERFERON available from Boehringer Ingelheim Pharmaceutical, Inc., Ridgefield, Conn., interferon alpha-n1, a purified blend of natural alpha interferons such as SUMIFERON available from Sumitomo, Japan or as Wellferon interferon alpha-n1 (INS) available from Glaxo-Wellcome Ltd., London, Great Britain, or a consensus alpha interferon such as those described in U.S. Pat. Nos. 4,897,471 and 4,695,623 (the contents of which are hereby incorporated by reference in their entireties, specifically examples 7, 8 or 9 thereof) and the specific product available from Amgen, Inc., Newbury Park, Calif., or interferon alpha-n3 a mixture of natural interferons made by Interferon Sciences and available from the Purdue Frederick Co., Norwalk, Conn., under the ALFERON trademark. The use of interferon alpha-2a or alpha 2b is preferred. Since interferon alpha 2b, among all interferons, has the broadest approval throughout the world for treating chronic hepatitis C infection, it is most preferred. The manufacture of interferon alpha 2b is described in U.S. Pat. No. 4,503,901.

The term "pegylated interferon" as used herein means polyethylene glycol modified conjugates of interferon, preferably interferon alpha-2a and alpha-2b. The preferred polyethylene-glycol-interferon alpha-2b conjugate is PEG-.sub.12000-interferon alpha 2b. The phrase "PEG.sub.12000-IFN alpha" as used herein means conjugates such as are prepared according to the methods of International Application No. WO 95/13090 and containing urethane linkages between the interferon alpha-2a or alpha-2b amino groups and polyethylene glycol having an average molecular weight of 12000.

Compounds described herein are also useful in preventing or resolving viral infections in cell, tissue or organ cultures and other in vitro applications. For example, inclusion of compounds of the invention as a supplement in cell or tissue culture growth media and cell or tissue culture components will prevent viral infections or contaminations of cultures not previously infected with viruses. Compounds described above may also be used to eliminate viruses from cultures or other biological materials infected or contaminated with viruses (for example, blood), after a suitable treatment period, under any number of treatment conditions as determined by the skilled artisan.

The compounds of the invention can form useful salts with inorganic and organic acids such as hydrochloric, sulfuric, acetic, lactic, or the like and with inorganic or organic bases such as sodium or potassium hydroxide, piperidine, ammonium hydroxide, or the like. The pharmaceutically acceptable salts of the compounds of Formula I are prepared following procedures that are familiar to those skilled in the art. For example, sodium and potassium salts can be made by dissolving an appropriate compound of the invention in ethanol and adding about 1.1 equivalents of sodium hydroxide or potassium hydroxide, and allowing salt formation. Examples of pharmaceutically acceptable salts are listed in Table 3, below.

The isomeric forms of the compounds of the invention include, without limitation, the various isomers of the heterocyclic substituents that may be present therein. The chemical structures depicted herein and therefore the compounds of the invention also encompass all of the corresponding possible tautomeric forms. Such tautomers may, in certain instances, be resolved into individual compounds by methods known to those of skill in the art.

The compounds of the present invention are useful for treating HCV in living hosts, for example, mammals including humans. When administered to a living host the compounds can be used alone, or as a pharmaceutical composition.

Pharmaceutical compositions comprising the compounds of the present invention, either alone or in combination with each other, offer a treatment against hepatitis C infection. The antiviral pharmaceutical compositions of the present invention comprise one or more of the compound(s) of Formula I above, as the active ingredient in combination with a pharmaceutically acceptable carrier medium or auxiliary agent.

The composition may be prepared in various forms for administration, including tablets, caplets, pills or dragees, or can be filled in suitable containers, such as capsules, or, in the case of suspensions, filled into bottles. As used herein, "pharmaceutically acceptable carrier medium" includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Twentieth Edition, A. R. Gennaro (William and Wilkins, Baltimore, Md., 2000) discloses various carriers used in formulating pharmaceutical compositions and known techniques for the preparation thereof. Except insofar as any conventional carrier medium is incompatible with the antiviral compounds of the invention, such as by producing any undesirable biological effect or otherwise interacting in a deleterious manner with any other component(s) of the pharmaceutical composition, its use is contemplated to be within the scope of this invention.

In the pharmaceutical compositions of the invention, the active agent may be present in an amount of at least 0.5% and generally not more than 90% by weight, based on the total weight of the composition, including carrier medium and/or auxiliary agent(s), if any. Preferably, the proportion of active agent varies between 5 to 50% by weight of the composition.

Pharmaceutical organic or inorganic solid or liquid carrier media suitable for enteral or parenteral administration can be used to make up the composition. Gelatine, lactose, starch, magnesium stearate, talc, vegetable and animal fats and oils, gum, polyalkylene glycol, or other known medicament components may all be suitable as carrier media or excipients.

The compounds of the invention may be administered using any amount and any route of administration effective for attenuating infectivity of the virus. Thus, the expression "amount effective to attenuate infectivity of virus," as used herein, refers to a nontoxic but sufficient amount of the antiviral agent to provide the desired prophylaxis and/or treatment of viral infection. The exact amount required will vary from subject to subject, depending on the species, age, and general condition of the subject, the severity of the infection, the particular antiviral agent, its mode of administration, and the like.

The antiviral compounds are preferably formulated in dosage unit form for ease of administration and uniformity of dosage. "Dosage unit form" as used herein refers to a physically discrete unit of antiviral agent appropriate for the patient to be treated. Each dosage should contain the quantity of active material calculated to produce the desired therapeutic effect either as such, or in association with the selected pharmaceutical carrier medium and/or the supplemental active agent(s), if any. Typically, the antiviral compounds of the invention will be administered in dosage units containing from about 2 mg to about 7000 mg of the antiviral agent by weight of the composition, with a range of about 10 mg to about 2000 mg being preferred.

The compounds may be administered orally, rectally, parenterally, such as by intramuscular injection, subcutaneous injection, intravenous infusion or the like, intracisternally, intravaginally, intraperitoneally, locally, such as by powders, ointments, or drops, or the like, or by inhalation, such as by aerosol or the like, taking into account the nature and severity of the infection being treated. Depending on the route of administration, the compounds of the invention may be administered at dosage levels of about 0.05 to about 100 mg/kg of subject body weight per day, one or more times a day, to obtain the desired therapeutic effect.

The compounds of the invention will typically be administered from 1 to 4 times a day so as to deliver the above-mentioned daily dosage. However, the exact regimen for administration of the compounds and compositions described herein will necessarily be dependent on the needs of the individual host or patient being treated, the type of treatment administered and the judgment of the attending medical specialist.

In view of the inhibitory effect on viral RNA synthesis produced by the compounds of the invention, it is anticipated that these compounds will be useful not only for therapeutic treatment of virus infection, but for virus infection prophylaxis, as well. The dosages may be essentially the same, whether for treatment or prophylaxis of virus infection.

The following examples are provided to describe the invention in further detail. These examples illustrate suitable methods of synthesis of representative compounds of this invention. However, the methods of synthesis are intended to illustrate and not to limit the invention to those exemplified below. The starting materials for preparing the compounds of the invention are either commercially available or can be conveniently prepared according to one of the examples set forth below or otherwise using known chemistry procedures.

EXAMPLE 1

Preparation of 2-furan-3-yl-5-methoxy-benzofuran-carboxylic acid methylamide a. Preparation of compound 1(a) (2-furan-3-yl-5-hydroxy-benzofuran-3-carboxylic acid ethyl ester). In an oven dried 25 mL 3-neck flask under argon was dissolved ethyl β-oxo-3-furanpropionate (2.22 g, 12.2 mmol) in absolute ethanol (4 mL) with magnetic stirring. Zinc chloride (anhydrous, 1.66 g, 12.2 mmol) was added, and the reaction was stirred magnetically until homogenous (20 minutes). Solid 1,4-benzoquinone (1.32 g, 12.2 mmol) was placed in a glass-wool insulated side-arm addition funnel atop the reaction flask (a cotton plug was used), capped by a cold finger. The reaction was heated in an oil bath until gently refluxing, with the hot ethanol slowly dissolving and dripping the 1,4-benzoquinone into the pot over a period of 18 hours. The reaction was cooled to room temperature and treated with water (about 100 mL). After extraction with ethyl acetate (3×75 mL), the organics were combined, dried with $Na_2SO_4$, and evaporated. The resulting oil was purified by HPLC (silica gel, ethyl acetate/hexanes) to provide 1.42 g (43%) of the product as pale yellow crystals.

b. Preparation of compound 1(b) (2-furan-3-yl-5-methoxy-benzofuran-3-carboxylic acid ethyl ester). In an oven-dried 50 mL flask under argon was combined compound 1(a) (1.42 g, 5.21 mmol), potassium carbonate (milled, 2.16 g, 15.6 mmol) and anhydrous acetonitrile (20 mL). Methyl iodide (3.25 mL, 52.2 mmol) was added to this mixture, and the reaction was heated to reflux for 18 hours. The reaction was cooled to room temperature and filtered through a pad of Celite™ 503 (diatomaceous earth) before evaporation of the solvent. The resulting solid was purified by HPLC (silica gel, ethyl acetate/hexanes) to provide 1.37 g (92%) of the desired product as pale yellow crystals.

c. Preparation of compound 1(c) (2-furan-3-yl-5-methoxy-benzofuran-3-carboxylic acid). Compound 1(b) (1.37 g, 4.78 mmol) was combined with potassium hydroxide pellets (0.4 g, 7.13 mmol) in 50% aqueous ethanol (35 mL) in a 50 mL flask. The mixture was refluxed overnight and cooled to room temperature. Evaporation of half of the solvent and acidification with 3M HCl precipitated a white solid that was filtered, washed with water, and dried under vacuum at 60° C. to provide 1.21 g (97%) of the desired product.

d. Preparation of 2-furan-3-yl-5-methoxy-benzofuran-carboxylic acid methylamide. Compound 1(c) (0.05 g, 0.19 mmol) was dissolved in anhydrous tetrahydrofuran (THF) (3 mL) in an oven-dried 10 mL flask under argon. 1,1'-Carbonyldiimidazole (0.05 g, 0.31 mmol) was added with magnetic stirring, and the resulting mixture was gently heated to about 50° C. for 30 minutes to drive off $CO_2$. Excess methylamine (2.0M in THF, 2 mL) was added, and heating continued for 4 hours. The reaction was cooled to room temperature, and the solvent was evaporated yielding an oil, which was purified by HPLC (reverse-phase C18, acetonitrile/water). After lypholization, 0.021 g (39%) of the desired product was isolated as a white solid.

EXAMPLE 2

Preparation of 2-phenyl-5-trifluoromethoxy-benzofuran-3-carboxylic acid methylamide a. Preparation of compound 2(a) (5-hydroxy-2-phenyl-benzofuran-3-carboxylic acid ethyl ester). The intermediate compound was prepared essentially according to the general procedure described in Example 1, step a above; however, ethyl benzoylacetate was used instead of ethyl β-oxo-3-furanpropionate.

b. Preparation of compound 2(b) (5-thiomethylthiocarbonyloxy-2-phenyl-benzofuran-3-carboxylic acid ethyl ester). In a 25 mL flask open to the atmosphere, tetrabutylammonium hydrogen sulfate (0.06 g, 0.177 mmol) was added to 12M sodium hydroxide (5 mL) and carbon disulfide (5 mL) with magnetic stirring. Compound 2(a) (0.5 g, 1.77 mmol) and methyl iodide (0.12 mL, 1.93 mmol) were added, and the mixture was stirred vigorously for 1 hour at room temperature. The reaction mixture was poured into a separatory funnel, the organic layer collected, and the aqueous layer washed with carbon disulfide (3×10 mL). The organics were combined, dried with sodium sulfate, and the solvent was evaporated yielding an orange oil, which was purified by HPLC (silica gel, ethyl acetate/hexanes) to provide 0.42 g (63%) of the desired product as a clear oil.

c. Preparation of compound 2(c) (2-phenyl-5-trifluoromethoxy-benzofuran-3-carboxylic acid ethyl ester). In a 25 mL flask under argon, HF/Pyridine (70%, 2.56 mL) was added to a suspension of 1,3-dibromo-5,5-dimethylhydantoin (0.96 g, 3.36 mmol) and compound 2(b) (0.42 g, 1.13 mmol) in dichloromethane (10 mL) at −78° C. Once the addition was complete (20 minutes), the reaction was transferred to an ice bath and stirred magnetically for 1 hour at 0° C. The reaction mixture was then poured into a solution of 50:50 saturated aqueous $NaHCO_3/NaHSO_3$ (100 mL) and extracted into diethyl ether (3×40 mL). The organics were dried with sodium sulfate, and the solvent was evaporated.

The crude product was purified by HPLC (reverse-phase C18, acetonitrile/water) to provide 0.12 g (30%) of the desired product as a yellow oil.

d. Preparation of 2-phenyl-5-trifluoromethoxy-benzofuran-3-carboxylic acid methylamide. The title compound was prepared essentially according to the procedure described in Example 1, steps c and d above; however, compound 2(c) was used in step c instead of compound 1(b).

EXAMPLE 3

Preparation of 2-(3,4-difluoro-phenyl)-5-methoxy-benzofuran-3-carboxylic acid methylamide a. Preparation of compound 3(a) (3-(3,4-difluoro-phenyl)-3-oxo-propionic acid ethyl ester).

Ethyl malonate potassium salt (7.46 g, 43.8 mmol) and $MgCl_2$ (3.14 g, 33.0 mmol) were mixed in anhydrous THF (36 mL) and refluxed for 4 hours. To a separate solution of 3,4-difluorobenzoic acid (5.22 g, 33.0 mmol) in anhydrous THF (36 mL) was added 1,1'-carbonyldiimidazole (6.29 g, 38.8 mmol) in one portion, and the mixture was heated for 30 minutes. The second solution was then added to the $MgCl_2$ solution at room temperature. The reaction mixture was stirred overnight (16 hours) at room temperature. The reaction flask was cooled in an ice bath, and an HCl solution (10 mL of concentrated HCl and 20 mL of $H_2O$) was added. The resulting mixture was stirred at room temperature for 1 hour. Ethyl acetate was added to extract the product, and the combined organic layers were washed with brine and water, dried over $Na_2SO_4$, and concentrated to give an oil residue. The crude product was purified by a short flash column (silica gel, 10:90 ethyl acetate/hexanes) to provide 7.0 g (93%) of the desired product as an off-white oil product.

b. Preparation of compound 3(b) (2-(3,4-difluoro-phenyl)-5-hydroxy-benzofuran-3-carboxylic acid ethyl ester). Absolute ethanol (10 mL) was added to an oven-dried flask containing anhydrous $ZnCl_2$ (2.98 g, 21.9 mmol, pre-dried in oven for 1 hour) under argon. Compound 3(a) (5.0 g, 21.9 mmol) was then added to the above clear solution. 1,4-Benzoquinone (2.37 g, 21.9 mmol) was placed in an addition funnel with a side arm (a pad of glass wool at the bottom of funnel), and a condenser was equipped on the top of the addition funnel. The reaction mixture in the flask was slowly heated to 105° C. in an oil bath. Ethanol slowly refluxed through the side arm of the addition funnel (wrapped with glass wool and aluminum foil), and then slowly washed down the 1,4-benzoquinone overnight (18 hours). The reaction mixture was cooled to room temperature, diluted with ethyl acetate, washed with brine and water, and dried over $Na_2SO_4$. After concentration, the residue was purified by flash column chromatography (silica gel, 5 to 10% ethyl acetate in hexanes) to provide 3.60 g (52%) of the desired product as a pale yellow solid.

c. Preparation of compound 3(c) (2-(3,4-difluoro-phenyl)-5-methoxy-benzofuran-3-carboxylic acid ethyl ester). Potassium carbonate (276 mg, 2.0 mmol) was added to compound 3(b) (255 mg, 0.8 mmol) in acetonitrile (5 mL). The mixture was heated to reflux for 30 minutes, than cooled to room temperature. Methyl iodide (249 μl, 4.0 mmol) was added, and the reaction mixture was stirred overnight. The mixture was diluted with water and extracted into ethyl acetate. The organic layer washed with brine and dried. The crude product was purified by column chromatography (silica gel, 5:95 ethyl acetate/hexanes) to provide 235 mg (88%) of product as a white solid.

d. Preparation of compound 3(d) (2-(3,4-difluoro-phenyl)-5-methoxy-benzofuran-3-carboxylic acid). Sodium hydroxide (10N, 0.5 mL) was added to a hot solution of compound 3(c) (230 mg, 0.69 mmol) in absolute ethanol (8 mL). The reaction mixture was heated to 90° C. and stirred for 2 hours. After cooling to room temperature, the mixture was acidified with 10% HCl to pH 2. The resulting suspension was extracted with ethyl acetate, dried over $Na_2SO_4$ and concentrated to provide a white solid (210 mg) in quantitative yield. The product was taken directly to the next step without further purification.

e. Preparation of 2-(3,4-difluoro-phenyl)-5-methoxy-benzofuran-3-carboxylic acid methylamide. Methylamine (0.45 mL, 2.0M in THF) was added to a solution of compound 3(d) (91 mg, 0.30 mmol) in anhydrous N,N-dimethylformamide (DMF) (5 mL) under argon, followed by the addition of benzotriazol-1-yloxytrispyrrolidinophosphonium hexafluorophosphate (PyBOP) (156 mg, 0.30 mmol). The resulting reaction mixture was stirred at room temperature for 2 hours, diluted with water, extracted with ethyl acetate, dried and concentrated. The crude product was purified by chromatography (silica gel, 10:90 ethyl acetate/hexanes) to provide 72 mg (76%) of the product as a white solid.

EXAMPLE 4

Preparation of 2-[4-(acetylamino-methyl)-phenyl]-5-isopropoxy-benzofuran-3-carboxylic acid methylamide a. Preparation of compound 4(a) (3-(4-bromo-phenyl)-3-oxo-propionic acid ethyl ester). A mixture of ethyl malonate potassium salt (5.63 g, 33.08 mmol) and magnesium chloride (2.37 g, 24.87 mmol) was refluxed in THF (60 mL) under argon for 4 hours. In a second reaction vessel, 1,1'-carbonyldiimidazole (4.76 g, 29.35 mmol) was added to a solution of 4-bromobenzoic acid (5.0 g, 24.87 mmol) in THF (30 mL) under argon, and the solution was gently refluxed for 30 minutes. Both reactions were cooled to room temperature, and the second solution was added drop wise to the ethyl malonate/magnesium chloride mixture. The reaction was stirred at room temperature for 16 hours. Concentrated hydrochloric acid (10 mL) and water (20 mL) were mixed in an addition funnel and added dropwise to the reaction mixture over a 15-minute period. The organic solvents were removed by rotary evaporation, and the product was extracted several times with ethyl acetate. The organics were combined, washed with brine and concentrated. The product was purified by flash chromatography (silica gel, ethyl acetate/hexanes gradient) to provide 6.07 g (90%) of the desired product as an orange oil.

b. Preparation of compound 4(b) (2-(4-bromo-phenyl)-5-hydroxy-benzofuran-3-carboxylic acid ethyl ester). An addition funnel, flask, stir bar and zinc chloride (3.02 g, 22.13 mmol) were oven dried for an hour and cooled under argon. Compound 4(a) (6.0 g, 22.13 mmol) was dissolved in ethanol (11 mL) and added to the flask containing the zinc chloride. 1,4-Benzoquinone (2.39 g, 22.13 mmol) was added through an addition funnel (wrapped with glass wool and aluminum foil and using a cotton plug). The reaction was heated to 105° C. in an oil bath, while regulating the amount of ethanol condensing into the addition funnel to facilitate an 18-hour addition of the 1,4-benzoquinone. When the 1,4-benzoquinone was consumed, the reaction was cooled to room temperature, ethyl acetate was added, and the crude product washed with brine. The aqueous layer washed several times with ethyl acetate, and the organics were combined and concentrated. The product was purified by flash chromatography (silica gel, ethyl acetate/hexanes gradient) and sonicated in a 15% ethyl acetate in hexanes solution to provide 2.24 g (28%) of the product as an orange solid.

c. Preparation of compound 4(c) (2-(4-bromo-phenyl)-5-isopropoxy-benzofuran-3-carboxylic acid ethyl ester). Compound 4(b) (10.59 g, 29.32 mmol) and acetonitrile (100 mL) were added to an oven-dried flask containing dry potassium carbonate (10.13 g, 73.30 mmol). The mixture was refluxed for one hour then cooled to room temperature. 2-Iodopropane (8.78 mL, 87.96 mmol) was added, and the reaction mixture was heated to reflux temperature for 16 hours. The reaction mixture was cooled to room temperature, concentrated, dissolved in ethyl acetate, and filtered. The filtrate was concentrated in vacuo, and the crude product was recrystallized (ethyl acetate and hexanes) to provide 9.38 g (79%) of the desired product as a tan solid.

d. Preparation of compound 4(d) (2-(4-bromo-phenyl)-5-isopropoxy-benzofuran-3-carboxylic acid). Potassium hydroxide pellets (1.0 g, 17.82 mmol) were added to a suspension of compound 4(c) (2.02 g, 5.01 mmol) in 1:1 ethanol/water (25 mL/25 mL). The reaction was heated to reflux for 2 hours. The reaction mixture was cooled to room temperature and concentrated in vacuo. The product was extracted into ethyl acetate without acidification. The organic layer was concentrated, and the solid was recrystallized (ethyl acetate and hexanes) to provide 1.86 g (99%) of the desired product as an orange solid.

e. Preparation of compound 4(e) (2-(4-bromo-phenyl)-5-isopropoxy-benzofuran-3-carboxylic acid methylamide). 1-(3-Dimethylaminopropyl)-3-ethylcarbodiimide hydrochloride (1.40 g, 7.32 mmol), 1-hydroxybenzotriazole (0.99 g, 7.32 mmol) and methylamine (4.88 mL, 2.0M in THF, 9.75 mmol) were added to a solution of compound 4(d) (1.83 g, 4.88 mmol) in dichloromethane (35 mL). The reaction mixture was stirred for 16 hours at room temperature, then concentrated, dissolved in ethyl acetate, and washed with water. The organic layer was concentrated in vacuo, and the crude product was purified by flash chromatography (silica gel, ethyl acetate/hexanes gradient) to provide 1.24 g (66%) of the desired product as a yellow solid.

f. Preparation of compound 4(f) (2-(4-cyano-phenyl)-5-isopropoxy-benzofuran-3-carboxylic acid methylamide). Copper cyamide (1.95 g, 21.81 mmol) was added to a solution of compound 4(e) (1.21 g, 3.12 mmol) in 1-methyl-2-pyrrolidinone (NMP) (30 mL). The reaction mixture was heated to 170° C. in an oil bath. The reaction was cooled to room temperature, diluted with water and ethyl acetate, and filtered through a Celite™ plug, rinsing with ethyl acetate and water. The layers were separated, and the organic layer was concentrated in vacuo. The crude product was purified by flash chromatography (silica gel, ethyl acetate/hexanes gradient) to provide 0.68 g (65%) of the desired product.

g. Preparation of compound 4(g) (2-(4-aminomethyl-phenyl)-5-isopropoxy-benzofuran-3-carboxylic acid methylamide, HCl salt). 10% Palladium on carbon (0.10 g) was mixed with water and concentrated hydrochloric acid (0.5 mL) and added to a reaction flask containing a solution of compound 4(f) (0.68 g, 2.03 mmol) in methanol (15 mL). The reaction flask was shaken under 55 psig of hydrogen gas on a Parr shaker for 16 hours. The reaction mixture was filtered through Celite™, rinsing with ethanol. The filtrate was concentrated in vacuo, and the crude product was recrystallized (ethyl acetate) to provide 0.65 g (86%) of the desired product as a dark yellow solid.

h. Preparation of 2-[4-(acetylamino-methyl)-phenyl]-5-isopropoxy-benzofuran-3-carboxylic acid methylamide. Triethylamine (0.037 mL, 0.267 mmol) was added to a suspension of compound 4(g) (50 mg, 0.133 mmol) in dichloromethane (10 mL). Acetic anhydride (0.015 mL, 0.160 mmol) was added to the solution, and the reaction was stirred at room temperature. After 16 hours, dichloromethane (10 mL) and water (15 mL) were added to the mixture, and the layers were separated. The organics were concentrated in vacuo, and the crude product was purified by flash chromatography (silica gel, ethanol/ethyl acetate gradient) to provide 50 mg (96%) of the desired product as an off-white solid.

EXAMPLE 5

Preparation of 2-(4-hydroxy-phenyl)-5-isopropoxy-benzofuran-3-carboxylic acid methylamide a. Preparation of compound 5(a) (3-(4-benzyloxy-phenyl)-3-oxo-propionic acid ethyl ester). A mixture of ethyl malonate potassium salt (9.92 g, 58.27 mmol) and magnesium chloride (4.17 g, 43.81 mmol) was refluxed in THF (100 mL) under argon for 4 hours. In a second reaction vessel, 1,1'-carbonyldiimidazole (CDI) (8.38 g, 51.70 mmol) was added to a solution of 4-benzyloxybenzoic acid (10 g, 43.81 mmol) in THF (60 mL) under argon. The solution was gently refluxed for 30 minutes. Both reactions were cooled to room temperature, and the second solution was added dropwise to the ethyl malonate/magnesium chloride mixture. The reaction was stirred at room temperature overnight. After 16 hours, a hydrochloric acid solution (20 mL concentrated HCl and 40 mL water) was added to the reaction mixture. The organic solvents were removed in vacuo, and the crude product was extracted with ethyl acetate several times. The organics were combined, washed with brine and concentrated. The product was purified by flash chromatography (silica gel, ethyl acetate/hexanes gradient) to provide 10 g (77%) of the desired product as a pale yellow solid.

b. Preparation of compound 5(b) (2-(4-benzyloxy-phenyl)-5-hydroxy-benzofuran-3-carboxylic acid ethyl ester). Compound 5(a) (10.0 g, 33.52 mmol) was dissolved in ethanol (15 mL) and added to an oven-dried flask containing zinc chloride (oven-dried, 4.57 g, 33.52 mmol). 1,4-Benzoquinone (3.62 g, 33.52 mmol) was placed in an addition funnel (wrapped with glass wool and aluminum foil and using a cotton plug). The reaction mixture was heated to 100° C. in an oil bath, while regulating the amount of ethanol condensing into the addition funnel to facilitate an 18-hour addition of the 1,4-benzoquinone. When the 1,4-benzoquinone was consumed, the mixture was cooled to room temperature, ethyl acetate was added, and the crude product was washed with brine. The aqueous layer washed several times with ethyl acetate, and the organics were combined and concentrated in vacuo. The product was purified by flash chromatography (silica gel, ethyl acetate/hexanes gradient) and sonicated in a 15% ethyl acetate in hexanes solution to provide 4.08 g (31%) of the desired product as a solid.

c. Preparation of compound 5(c) (2-(4-benzyloxy-phenyl)-5-isopropoxy-benzofuran-3-carboxylic acid ethyl ester). Compound 5(b) (4.07 g, 10.48 mmol) and acetonitrile (60 mL) were added to an oven-dried flask containing potassium carbonate (oven-dried, 3.62 g, 26.20 mmol). The mixture was refluxed for one hour, and then cooled to room temperature. 2-Iodopropane (3.14 mL, 31.43 mmol) was added, and the mixture was again heated to reflux temperature. After 16 hours, the reaction mixture was cooled to room temperature, concentrated, dissolved in ethyl acetate, and washed with water. The organics were concentrated in vacuo and purified by flash chromatography (silica gel, ethyl acetate/hexanes gradient) to provide 4.07 g (90%) of the product as a yellow solid.

d. Preparation of compound 5(d) (2-(4-benzyloxy-phenyl)-5-isopropoxy-benzofuran-3-carboxylic acid). Potassium hydroxide pellets (0.5 g, 8.91 mmol) were added to a suspension of compound 5(c) (1.00 g, 2.32 mmol) in 1:1 ethanol/water (20 mL/20 mL). The reaction mixture was heated to reflux for 2 hours, and then cooled to room temperature. 1M Hydrochloric acid was added, and the precipitate was filtered and dried to provide 0.92 g (99%) of the product as a white solid.

e. Preparation of compound 5(e) (2-(4-benzyloxy-phenyl)-5-isopropoxy-benzofuran-3-carboxylic acid methylamide). Compound 5(d) (0.92 g, 2.48 mmol) and benzotriazole-1-yl-oxy-tris-pyrrolidino-phosphonium hexafluorophosphate (1.29 g, 2.48 mmol) were combined under argon and treated with methylamine (20 mL, 2.0M in THF). The solution was stirred at room temperature for 3 hours. The reaction mixture was concentrated, dissolved in ethyl acetate, and washed with water. The organics were concentrated and purified by flash chromatography (silica gel, ethyl acetate/hexanes gradient) to provide 0.78 g (76%) of the desired product as a white solid.

f. Preparation of 2-(4-hydroxy-phenyl)-5-isopropoxy-benzofuran-3-carboxylic acid methylamide. A mixture of 10% palladium on carbon (0.10 g) in water was added to mixture of compound 5(e) (0.78 g, 1.88 mmol) in an ethanol/ethyl acetate (20 mL/10 mL) solution. The reaction mixture was shaken under 55 psig of hydrogen gas on a Parr shaker for 6 hours. The reaction mixture was filtered through Celite™, rinsing with ethyl acetate and ethanol. The filtrate was concentrated, and the crude product was recrystallized (ethyl acetate and hexanes) to provide 0.57 g (93%) of the desired product as an off white solid.

EXAMPLE 6

Preparation of 2-(4-fluoro-phenyl)-5-isopropoxy-6-pyrrolidin-1-yl-benzofuran-3-carboxylic acid methylamide a. Preparation of compound 6(a) (3-(4-fluoro-phenyl)-3-oxo-propionic acid ethyl ester).

4-Fluorobenzoic acid (275 g, 1.96 mol) in THF (1 L) was added to a solution of 1,1'-carbonyldiimidazole (CDI) (381 g, 2.36 mol) in THF (1 L) over a one hour period. The reaction mixture was stirred at 30° C. for one hour, then at room temperature overnight. Magnesium chloride (186 g, 1.96 mol) was added over 5 minutes to a second mixture of ethyl malonate potassium salt (435 g, 2.56 mol) in THF (2 L). The resulting mixture was stirred overnight in a closed apparatus. The first mixture was added to the malonate mixture over 1½ hours. The reaction mixture was stirred for several hours at ambient temperature, than warmed to 30° C. for several hours. The reaction mixture was treated with 4N HCl (1.0 L), and the layers were separated. The aqueous layer was diluted with water (1 L), acidified with HCl (250 mL) until about pH 1, and washed with ethyl acetate (1 L). The ethyl acetate layer was concentrated to provide 65 g of the crude product. The original organic layer was concentrated to remove the THF, diluted with ethyl acetate (1 L), and rinsed with water (1 L). The organic layer was combined with the 65 g of crude product and concentrated to an oil. The oil was diluted with ethyl acetate (1 L) and rinsed with 5% aqueous $NaHCO_3$ (1 L). The organic layer was concentrated, and the crude product was vacuum distilled to provide 322 g (78%) of the desired product.

b. Preparation of compound 6(b) (2-(4-fluoro-phenyl)-5-hydroxy-benzofuran-3-carboxylic acid ethyl ester). Compound 6(a) (157 g, 0.75 mol) was added to a flask containing zinc chloride (100 g, 0.74 mol) and ethanol (250 mL), and washed in with additional ethanol (about 50 mL). 1,4-Benzoquinone (80 g, 0.74 mol) was mixed with Celite™ (40 g) and placed in an addition funnel, which was plugged lightly with glass wool. The reaction mixture was heated to 95° C., and the 1,4-benzoquinone was added at a rate of about 4 mL/min. After the 1,4-benzoquinone was consumed, the mixture was cooled to room temperature, ethyl acetate was added (2 L), and the crude product washed with water (1 L) and brine. Insoluble impurities were removed by filtration, and the filtrate was concentrated. The resulting solid was stirred in dichloromethane (500 mL) and cooled to −20° C. Additional impurities were removed by filtration. The filtrate was concentrated, and the crude product was mixed with dichloromethane (400 mL), cooled to −20° C., and filtered. The isolated solid was rinsed with dichloromethane and air-dried to provide 71.8 g (32.3%) of the desired product.

c. Preparation of compound 6(c) (2-(4-fluoro-phenyl)-5-isopropoxy-benzofuran-3-carboxylic acid ethyl ester). Cesium carbonate (111.6 g, 343 mmol) was added to compound 6(b) (73.5 g, 245 mmol) in 1-methyl-2-pyrrolidinone (250 mL). The reaction mixture was heated to 50° C. in an oil bath for 16 hours, and then cooled to room temperature. The solid impurities were removed by filtration, and the filtrate was diluted with brine and t-butylmethyl ether. The layers were separated, and the aqueous layer was rinsed several times with t-butylmethyl ether. The organic layers were combined and concentrated. The solid, which formed overnight, was isolated by filtration and rinsed with hexane to provide about 28 g of desired product. The filtrate was purified by column chromatography (silica gel, ethyl acetate/hexanes gradient) to provide an additional 47.2 g of desired product.

d. Preparation of compound 6(d) (6-bromo-2-(4-fluoro-phenyl)-5-isopropoxy-benzofuran-3-carboxylic acid ethyl ester). A solution of bromine (0.75 mL, 0.014 mol) in anhydrous dioxane (20 mL) was added dropwise over 1 hour to a solution of compound 6(c), which can be prepared according to the previous step (4.59 g, 0.014 mol) in anhydrous dioxane (50 mL). The reaction mixture was stirred for 1 hour under argon, at room temperature under a 300-watt lamp. An additional 3 drops of bromine were added, and the reaction was allowed to stir overnight. The reaction mixture was concentrated to ½ volume, diluted with water, extracted with ethyl acetate, dried with $MgSO_4$, and concentrated. The crude product was purified by HPLC (reverse phase, acetonitrile/water gradient) to provide the desired product as a white solid.

e. Preparation of compound 6(e) (2-(4-fluoro-phenyl)-5-isopropoxy-6-pyrrolidin-1-yl-benzofuran-3-carboxylic acid ethyl ester). An oven-dried flask containing cesium carbonate (dried, 0.271 g) was placed in a dry bag under argon, and compound 6(d) (0.250 g, 0.594 mmol), tris(dibenzylideneacetone)-dipalladium(0) (0.0163 g, 0.0178 mmol) and rac-2,2-bis(diphenylphosphino)-1,1'-binaphthyl (racemic mixture, 0.011 g, 0.0177 mmol) were added. The flask was removed from the dry bag, purged, and evacuated with argon (3×). Anhydrous toluene (1.0 mL), followed by pyrrolidine (0.059 mL) were added to the flask. The reaction mixture was heated to 95° C. in an oil bath overnight, and then cooled to room temperature, diluted with diethyl ether, filtered through a pad of Celite™, and washed with diethyl ether. The solvents were evaporated, and the crude product was purified by flash chromatography (silica gel, ethyl acetate/hexanes) to provide 0.117 g (49%) of the desired product as a yellow oil.

f. Preparation of compound 6(f) (2-(4-fluoro-phenyl)-5-isopropoxy-6-pyrrolidin-1-yl-benzofuran-3-carboxylic acid). Potassium hydroxide was added (1 pellet) to a solution of compound 6(e) (0.114 g, 0.277 mmol) in 2:1 ethanol/water (2.0 mL/1.0 mL). The reaction mixture was heated to reflux over a 2-hour period, and then stirred at room temperature overnight. Ethanol was removed from the mixture by evaporation. The remaining oil was dissolved in water and acidified with 3N hydrochloric acid until a solid formed (around pH 7.5). The yellow solid was filtered to provide 0.09 g (85%) of the desired product.

g. Preparation of 2-(4-fluoro-phenyl)-5-isopropoxy-6-pyrrolidin-1-yl-benzofuran-3-carboxylic acid methylamide. Benzotriazole-1-yl-oxy-tris-pyrrolidino-phosphonium hexafluorophosphate (0.107 g, 0.183 mmol) was added to a solution of compound 6(f) SBE-0628-198 (79.0 mg, 0.206 mmol) in methylamine (3.0 mL, 2.0M in THF) in an oven-dried flask under an argon atmosphere. The reaction mixture was allowed to stir at room temperature for 6 hours, then concentrated in vacuo. The resulting oil was purified by flash chromatography (silica gel, ethyl acetate/hexanes) to provide 0.045 g (63%) of the product as a yellow solid.

EXAMPLE 7

Preparation of 5-difluoromethoxy-2-(4-fluoro-phenyl)-benzofuran-3-carboxylic acid methylamide a. Preparation of compound 7(a) (5-difluoromethoxy-2-(4-fluoro-phenyl)-benzofuran-3-carboxylic acid ethyl ester). Potassium iodide (28 mg, 0.167 mmol) and potassium carbonate (0.69 g, 5.00 mmol) were added to a solution of compound 6(b), which can be prepared according to Example 6 (0.50 g, 1.67 mmol) in 2-butanone (20 mL). The reaction mixture was stirred for 10 minutes at room temperature. Ethyl chlorodifluoroacetate (0.32 mL, 2.50 mmol) was added, and the reaction was refluxed for 16 hours. The reaction was cooled to room temperature and concentrated in vacuo. The crude product was dissolved in ethyl acetate and washed with water and 1M hydrochloric acid. The product was concentrated and purified by flash chromatography (silica gel, ethyl acetate/hexanes gradient) to provide 130 mg (22%) of the desired product as a white solid.

b. Preparation of compound 7(b) (5-difluoromethoxy-2-(4-fluoro-phenyl)-benzofuran-3-carboxylic acid). Potassium hydroxide pellets (0.50 g, 8.91 mmol) were added to a suspension of compound 7(a) (0.13 g, 0.371 mmol) in 1:1 ethanol/water (7 mL/7 mL). The reaction mixture was heated to reflux for 1.5 hours. The reaction mixture was cooled to room temperature and concentrated in vacuo. 1M Hydrochloric acid was added until the solution became acidic, forming a precipitate. The solid was filtered and dried to provide 120 mg (100%) of the desired product as a white solid.

c. Preparation of 5-difluoromethoxy-2-(4-fluoro-phenyl)-benzofuran-3-carboxylic acid methylamide. 1-(3-Dimethylaminopropyl)-3-ethylcarbodiimide hydrochloride (0.11 g, 0.558 mmol), 1-hydroxybenzotriazole (75 mg, 0.558 mmol) and methylamine (2.0M in THF, 0.37 mL, 0.745 mmol) were added to a solution of compound 7(b) (0.12 g, 0.372 mmol) in dichloromethane (10 mL). The reaction mixture was stirred for 16 hours at room temperature, then concentrated, dissolved in ethyl acetate and washed with water. The organic layer was concentrated, and the crude product was purified by flash chromatography (silica gel, ethyl acetate/hexanes gradient) to provide 87 mg (70%) of the desired product as a white solid.

EXAMPLE 8

Preparation of 2-(4-fluoro-phenyl)-5-isopropoxy-6-(2-methoxy-ethylamino)-benzofuran-3-carboxylic acid methylamide The title compound (0.038 g, yellow solid) was prepared essentially according to the general procedure described in Example 6 above; however, in step e no dry bag was used and 2-methoxyethylamine was used instead of pyrrolidine. Also, the title compound was purified by reverse phase HPLC using a gradient of 60% to 90% acetonitrile in water.

EXAMPLE 9

Preparation of 5-methyl-2-phenyl-benzofuran-3-carboxylic acid methylamide a. Preparation of compound 9(a) (3-methoxy-6-methyl-2-phenylflavylium chloride). Dry HCl gas was bubbled through a solution of 2-hydroxy-5-methylbenzaldehyde (2.0 g, 14.69 mmol) and 2-methoxyacetophenone (2 mL, 14.51 mmol) in ethyl acetate (28 mL) and ethanol (7 mL) at 0° C. for one hour. The reaction was then capped and placed in the refrigerator for 56 hours. Diethyl ether was added until a precipitate formed. The solid was isolated by filtration to provide 3.73 g (88%) of the desired salt.

b. Preparation of compound 9(b) (5-methyl-2-phenyl-benzofuran-3-carboxylic acid methyl ester). Hydrogen peroxide (7.5 mL, 72.8 mmol) was added to a suspension of compound 9(a) (3.5 g, 12.20 mmol) in 50% aqueous methanol (72 mL). The reaction was heated to reflux temperature overnight, cooled to room temperature and diluted with ether. The layers were separated, and the aqueous phase was extracted with diethyl ether (2×). The organics were combined, washed with brine, dried ($MgSO_4$) and evaporated. Purification by column chromatography on silica gel using 5:1 hexane/ethyl acetate as eluant afforded 736 mg (22.6%) of the desired compound as a yellow solid.

c. Preparation of compound 9(c) (5-methyl-2-phenyl-benzofuran-3-carboxylic acid). Aqueous potassium hydroxide (4N, 12 mL) was added to a suspension of compound 9(a) (655 mg, 2.46 mmol) in methanol (r 5 mL). The reaction was stirred at an elevated temperature overnight. The mixture was cooled to room temperature and acidified with 1N hydrochloric acid to pH 2. The precipitate was collected by suction filtration, washed with water and dried to give 471 mg (76%) of the desired carboxylic acid.

d. Preparation of 5-methyl-2-phenyl-benzofuran-3-carboxylic acid methylamide. To a solution of compound 9(c) (125 mg, 0.495 mmol) in dry dichloromethane (2 mL) was added methylamine (0.495 mL of 2M solution in THF, 0.99 mmol), 1-[3-(dimethylamino)propyl]-3-ethylcarbodiimide hydrochloride (142 mg, 0.742 mmol) and hydroxybenzotriazole (100 mg, 0.742 mmol), respectively. The reaction was stirred at room temperature under argon overnight, quenched with 1N hydrochloric acid and extracted with dichloromethane. The organic layer was washed with brine, dried ($MgSO_4$) and evaporated. Purification by column chromatography on silica gel using dichloromethane as eluant afforded 49 mg (37%) of the title product as a white solid.

EXAMPLE 10

Preparation of 5-methyl-2-(4-fluoro-phenyl)-benzofuran-3-carboxylic acid methylamide a. Preparation of compound 110(a) (1-(4-fluoro-phenyl)-2-methoxy-ethanone). A solution of 4-fluorobenzoyl chloride (25.6 g, 161 mmol) in acetonitrile (60 mL) was added dropwise to a solution of trimethylsilyl diazomethane (96 mL of 2M solution, 193.2 mmol) and triethylamine (27 mL, 193.2 mmol) in anhydrous acetonitrile (250 mL) at 0° C. under an argon atmosphere. The reaction was stirred for two hours at 0° C. and then capped and placed in the refrigerator overnight. The solvent was removed via rotary evaporation, and the residue was taken up in saturated sodium bicarbonate solution and extracted with ethyl acetate. The organics were washed with water and brine, dried ($MgSO_4$) and evaporated to give 25.16 g of a yellow solid. The solid was dissolved in anhydrous methanol (200 mL), and boron trifluoride diethyl etherate (19.4 mL, 161 mmol) was added. The reaction was stiffed at room temperature for 2 hours, and the solvent was removed via rotary evaporation. The residue was dissolved in diethyl ether and washed with water and brine, dried ($MgSO_4$) and evaporated. Purification by column chromatography on silica gel using 5:1 hexanes/ethyl acetate afforded 18.77 g (69%) of the desired product as an orange solid.

b. Preparation of 5-methyl-2-(4-fluoro-phenyl)-benzofuran-3-carboxylic acid methylamide. The title compound was prepared essentially according to Example 9, steps a-b; however in step a 2-methoxy-4'-fluoroacetophenone was used instead of 2-methoxyacetophenone and compound 10(a) was used instead of 2-methoxyacetophenone.

EXAMPLE 11

Preparation of 2-phenyl-5-(2,2,2-trifluoro-ethoxy)-benzofuran-3-carboxylic acid methylamide a. Preparation of compound 11(a) (5-hydroxy-2-phenyl-benzofuran-3-carboxylic acid). Compound 11(a) was prepared essentially according to the general procedure described in Example 3, step d above; however, compound 2(a) was used instead of compound 3(c).

b. Preparation of resin 11(b).

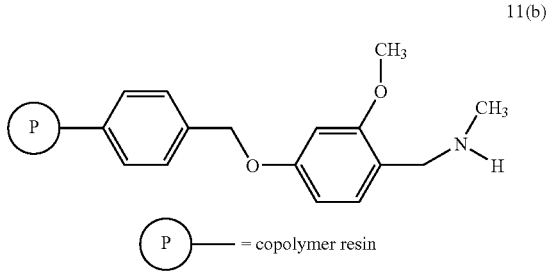

11(b)

4-Formyl-3-methoxyphenoxymethyl functionalized styrene/divinylbenzene copolymer (2 g; Aldrich, 0.9 mmol/g) was swelled in 1% acetic acid in dichloroethane (20 mL) and then drained. Addition of 1% acetic acid in dichloroethane (20 mL) was followed by methylamine (2M in THF, 4 mL), and the mixture was sonicated for 20 minutes. The resin mixture was then allowed to stand at room temperature for 16 hours. A sonicated suspension of sodium acetoxy borohydride (422 mg, 2 mmol) in 1% acetic acid in dichloroethane (5 mL) was then added followed by mild agitation at room temperature for 16 hours. Methanol (5 mL) was added, and the solvents were drained. The resin was then extensively washed in methanol and dichloromethane. The reaction was repeated to ensure complete consumption of the resin bound aldehyde. The dried resin was taken on to the next step without characterization.

c. Preparation of resin 11(c).

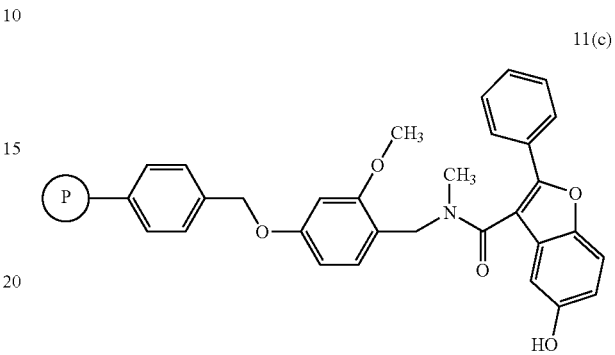

11(c)

The resin 11(b) was swelled in DMF (6 mL) and then compound 11(a) (325 mg, 1.5 mmol) was added followed by the addition of benzotriazole-1-yl-oxy-tris-pyrrolidino-phosphonium hexafluorophosphate (780 mg, 1.5 mmol; NovaBiochem), diisopropyl ethylamine (0.523 mL, 3 mmol), and DMF (4 mL). The reaction mixture was gently agitated under nitrogen for 4 hours and then drained. The resin washed extensively with DMF (6×10 mL), methanol (6×10 mL) and dichloromethane (6×10 mL) and dried under vacuo. The dried resin was continued to step d.

A small sample was subjected to treatment with 25% trifluoroacetic acid (TFA) in dichloromethane ($CH_2Cl_2$) for a qualitative assessment of resin loading. After 30 min, the TFA-$CH_2Cl_2$ mixture was filtered, and the filtrate was evaporated to dryness. Characterization by LCMS and NMR of dried product from TFA treatment revealed that the resin loading was successful.

d. Preparation of 2-phenyl-5-(2,2,2-trifluoro-ethoxy)-benzofuran-3-carboxylic acid methylamide. Cesium carbonate (325 mg, 1 mmol) was mixed with DMF (2 mL) and heated to 75° C. for 15 minutes. The resin 11(c) (150 mg, about 0.135 mmol) was added as a solid followed by 2,2,2-trifluoroethyl iodide (210 mg, 1 mmol) and DMF (2 mL). The reaction mixture was heated under nitrogen at 75° C. for 18 hours. The resin was then cooled to room temperature and washed extensively with DMF (6×10 mL), methanol (6×10 mL) and dichloromethane ($CH_2Cl_2$) (6×10 mL) and dried under vacuo. The dried resin was treated with 25% TFA in $CH_2Cl_2$ for 60 minutes. The TFA-$CH_2Cl_2$ mixture was filtered, and the filtrate was evaporated to dryness. The dried crude product was then purified by reverse phase HPLC on a Gilson HPLC-MS semi-prep system (eluting with 0.1% acetic acid in acetonitrile/water) to provide 12.7 mg (27%) of the desired product.

EXAMPLE 12

Preparation of 2-(4-fluoro-phenyl)-5-methoxy-benzofuran-3-carboxylic acid methylamide a. Preparation of compound 12(a)(i) and compound 12(a)(ii) (2-(4-fluoro-phenyl)-5-hydroxy-benzofuran-3-carboxylic acid methyl ester and 2-(4-fluoro-phenyl)-5-hydroxy-benzofuran-3-carboxylic acid ethyl ester). In an oven-dried flask under argon was placed methyl 4-fluorobenzoylacetate (4.0 g, 20.4 mmol), zinc chloride (anhydrous, 2.73 g, 20.4 mmol) and absolute ethanol (8 mL) with magnetic stirring. Solid 1,4-benzoquinone (2.21 g, 20.4 mmol) was placed in an addition funnel atop the reaction flask. The reaction was heated in an oil bath until gently refluxing, with the hot ethanol slowly dissolving and dripping the 1,4-benzoquinone into the pot over a period of 18 hours. The reaction was cooled to room temperature and diluted with ethyl acetate (40 mL) and water. After extraction with ethyl acetate (2×), the organics were combined, dried with $Na_2SO_4$, filtered through silica gel, and evaporated. The resulting residue was filtered then purified by HPLC (silica gel, 40% ethyl acetate in hexanes), and the crude product was further purified via crystallization from hot ethyl acetate/hexanes to provide 2.09 g (36%) of a mixture of compound 12(a)(i) and compound 12(a)(ii).

b. Preparation of compound 12(b)(i) and compound 12(b)(ii) (2-(4-fluoro-phenyl)-5-methoxy-benzofuran-3-carboxylic acid methyl ester and 2-(4-fluoro-phenyl)-5-methoxy-benzofuran-3-carboxylic acid ethyl ester). Methyl iodide (0.43 mL, 6.99 mmol) was added to a mixture of the compounds 12(a)(i) and 12(a)(ii) (1.00 g, 3.49 mmol), potassium carbonate (milled, 1.21 g, 8.73 mmol) and anhydrous acetonitrile (15 mL) under an argon atmosphere. The reaction mixture was heated to reflux under argon for 18 hours, and then cooled to room temperature and stirred for 24 hours. The mixture was diluted with acetonitrile (10 mL) and filtered, followed by evaporation of the solvent. The crude solid was diluted with 60:40 ethyl acetate/hexanes, refiltered, and purified by HPLC (silica gel, ethyl acetate/hexanes) to provide 0.85 g (78%) of the desired product.

c. Preparation of compound 12(c) (2-(4-fluoro-phenyl)-5-methoxy-benzofuran-3-carboxylic acid). Compound mixture 12(b) (0.85 g, 2.70 mmol) was combined with potassium hydroxide pellets (0.23 g, 4.06 mmol) in ethanol (24 mL) and water (4 mL). The mixture was gently refluxed overnight and cooled to room temperature. The solvent was removed by rotary evaporation, and the remaining solid was dissolved in water. Acidification with 3M HCl precipitated a solid that was filtered, washed with water and hexanes, and partially dried under vacuum to provide 0.84 g of the desired product.

d. Preparation of compound 12(d) (2-(4-fluoro-phenyl)-5-methoxy-benzofuran-3-carboxylic acid methylamide). 1,1'-Carbonyldiimidazole (42 mg, 0.262 mmol) was added to a solution of compound 12 (c) (50 mg, 0.175 mmol) in anhydrous THF (3 mL) under argon. The reaction mixture was gently heated for 30 minutes to drive off $CO_2$, after which ethylamine in excess (40% by weight in water, 1 mL) was added. The reaction mixture was stirred at room temperature overnight. The solvent was evaporated, and the crude product was purified by HPLC (reverse-phase C18, 1 mL dimethyl sulfoxide in acetonitrile/water, 2×). The acetonitrile was removed by rotary evaporation, and a solid was isolated by filtration and washed with water and hexanes to provide 14.3 mg (28%) of the desired product.

EXAMPLE 13

Preparation of 6-bromo-2-(4-fluoro-phenyl)-5-methoxy-benzofuran-3-carboxylic acid methylamide a. Preparation of compound 13(a) (6-bromo-2-(4-fluoro-phenyl)-5-methoxy-benzofuran-3-carboxylic acid ethyl ester). A solution of bromine (127 mg, 0.795 mmol) in anhydrous dioxane (1 mL) was added dropwise over 20 minutes to a solution of compound 12(b)(ii), prepared essentially according to Example 12, step b (250 mg, 0.795 mmol) in anhydrous dioxane (3 mL). The reaction was stirred at room temperature, under a 300-watt lamp, for 3 hours under argon. The reaction mixture was diluted with water, and the solids were filtered, washed with water and hexanes, and dried in a vacuum oven. The crude product was purified by HPLC (reverse phase, acetonitrile/water gradient) to provide 47 mg (15%) of the desired product as a white solid.

b. Preparation of 6-bromo-2-(4-fluoro-phenyl)-5-methoxy-benzofuran-3-carboxylic acid methylamide. The title compound was prepared essentially according to the general procedure described in Example 1, steps c and d, above; however compound 13(a) was used in step c instead of compound 1(b).

EXAMPLE 14

Preparation of 5-methoxy-6-methyl-2-phenyl-benzofuran-3-carboxylic acid methylamide a. Preparation of compound 14(a)(i) and compound 14(a)(ii) (5-hydroxy-6-methyl-2-phenyl-benzofuran-3-carboxylic acid ethyl ester and 5-hydroxy-7-methyl-2-phenyl-benzofuran-3-carboxylic acid ethyl ester). Absolute ethanol (30 mL) and ethyl benzoylacetate (9.9 mL, 57.3 mmol) were added to an oven-dried flask containing anhydrous $ZnCl_2$ (7.8 g, 57.3 mmol, pre-dried in oven for 1 hour) under argon. Methyl-1,4-benzoquinone (7.0 g, 57.3 mmol) was placed in an addition funnel with a side arm (a pad of glass wool at the bottom of funnel), and a condenser was equipped on the top of the addition funnel. The reaction mixture in the flask was slowly heated in oil bath. Ethanol refluxed through the side arm of the addition funnel (wrapped with glass wool and aluminum foil), and then slowly washed down the methyl-1,4-benzoquinone overnight (18 hours). The reaction mixture was cooled to room temperature, diluted with ethyl acetate (about 200 mL), washed with water (2×300 mL), and dried over $Na_2SO_4$. After concentration, the residue was purified by column chromatography (dry loading onto silica gel, ethyl acetate/hexane solvent gradient) and crystallized from hot ethyl acetate/hexanes in two crops, yielding a mixture of compound 14(a)(i) and compound 14(a)(ii), which was carried forward to the next step without further purification.

b. Preparation of compound 14(b)(i) and compound 14(b)(ii) (5-methoxy-6-methyl-2-phenyl-benzofuran-3-carboxylic acid ethyl ester and 5-methoxy-7-methyl-2-phenyl-benzofuran-3-carboxylic acid ethyl ester). In an oven-dried 50 mL flask under argon was combined compound mixture 14(a) (1.00 g, 3.37 mmol), potassium carbonate (milled, 1.16 g, 8.42 mmol) and anhydrous acetonitrile (20 mL). Methyl iodide (0.42 mL, 6.75 mmol) was added to this mixture, and the reaction was heated to reflux under argon for 3 hours. The reaction mixture was cooled to room temperature, and the solvent was removed by rotary evaporation. The residue was diluted with ethyl acetate and filtered, followed by evaporation of the solvent. The resulting oil was diluted with hexanes, and a solid was isolated by filtration. The crude product was purified by HPLC (silica gel, ethyl acetate/hexanes) to provide 0.135 g of compound 14(b)(i) and 0.432 g of compound 14(b)(ii).

c. Preparation of 5-methoxy-6-methyl-2-phenyl-benzofuran-3-carboxylic acid methylamide. The title compound was prepared essentially according to the general procedure described in Example 12, steps c and d above; however, compound 14(b)(i) was used in step c instead of compound 12(b).

EXAMPLE 15

Preparation of 6-(3-amino-pyrrolidin-1-yl)-2-(4-fluoro-phenyl)-5-isopropoxy-2,3-dihydro-benzofuran-3-carboxylic acid methylamide a. Preparation of compound 15(a) (6-(3-tert-butoxycarbonylamino-pyrrolidin-1-yl)-2-(4-fluoro-phenyl)-5-isopropoxy-benzofuran-3-carboxylic acid ethyl ester). Anhydrous cesium carbonate (270 mg, 0.830 mmol), bis(dibenzylideneacetone)-dipalladium(0) (11 mg, 0.0119 mmol), rac-2,2-bis(diphenylphosphino)-1,1-binaphthyl (11 mg, 0.0178 mmol), 3-(tert)butoxycarbonylamino)pyrrolidine (0.132 g, 0.712 mmol) and compound 6(d), which can be prepared according to Example 6 (250 mg, 0.593 mmol) were placed in an oven dried 2-neck flask, which was degassed and purged several times with argon. Anhydrous toluene (2 mL) was syringed into the reaction mixture, and the reaction flask was purged with argon. The reaction was stirred under argon for 18 hours at 80° C., then cooled to room temperature, diluted with diethyl ether (8 mL), and filtered through a pad of silica gel. The solvent was evaporated, and the resulting oil was purified by HPLC (reverse phase, acetonitrile/water gradient) to provide the desired product.

b. Preparation of compound 15(b) (6-(3-amino-pyrrolidin-1-yl)-2-(4-fluoro-phenyl)-5-isopropoxy-benzofuran-3-carboxylic acid). Compound 15(a) was combined with three potassium hydroxide pellets (approximately 0.4 g) in ethanol (30 mL) and water. The mixture was gently refluxed overnight and cooled to room temperature. The mixture was acidified with 6M acetic acid to about pH 6 and treated with saturated aqueous sodium bicarbonate until a precipitate formed. The solid was filtered, rinsed with water and hexanes, and dried in vacuo, to provide 86 mg of the desired product.

c. Preparation of 6-(3-amino-pyrrolidin-1-yl)-2-(4-fluoro-phenyl)-5-isopropoxy-2,3-dihydro-benzofuran-3-carboxylic acid methylamide. Benzotriazol-1-yloxytrispyrrolidinophosphonium hexafluorophosphate (PyBOP) (123 mg, 0.216 mmol) was added to a mixture of methylamine (10 mL, 2.0M in THF) and compound 15(b) (86 mg, 0.216 mmol) in anhydrous DMF (5 mL) under argon. The resulting reaction mixture was stirred at room temperature for 30 minutes, and concentrated on a rotary evaporator. The crude solid was sonicated and dissolved in ethyl acetate. The solution washed with water, dried, and concentrated. The crude product was purified by prep HPLC (reverse phase C18, acetonitrile/water, with 4 drops of dimethyl sulfoxide to solubilize the product) to provide 20 mg of the title product.

EXAMPLE 16

Preparation of 6-amino-2-(4-fluoro-phenyl)-5-isopropoxy-benzofuran-3-carboxylic acid methylamide a. Preparation of compound 16(a) (2-(4-fluoro-phenyl)-5-isopropoxy-benzofuran-3-carboxylic acid). Compound 6(c), which can be prepared according to Example 6 (18.5 g, 5.4 mmol) was added to a stirred solution of potassium hydroxide (9.1 g, 0.612 mol) in 1:1 ethanol/water (200 mL). After stirring for 12 hours at reflux temperature, the solvent was removed, and the remaining slurry was dissolved in water and extracted with t-butylmethylether. The organic layer was discarded, and the aqueous was acidified with 3N HCl. A solid was isolated by filtration, rinsed with water and hexanes, and dried in a vacuum oven at 60° C. to provide 15.0 g (88%) of the desired product.

b. Preparation of compound 16(b) (2-(4-fluoro-phenyl)-5-isopropoxy-6-nitro-benzofuran-3-carboxylic acid). In a 500 mL 3-neck flask fitted with a thermometer, a mechanical stirrer, and an addition funnel for solid, was poured a (4:1) mixture of concentrated (70%) nitric acid (200 mL) and glacial acetic acid (50 mL). The solution was cooled to −10° C. with an ethanol/dry ice bath. Compound 16(a), which can be prepared according to the preceding step, (10.0 g, 31.8 mmol) was added portionwise over a 15-minute period. The reaction was stirred at −10° C. for one hour, than allowed to warm up to 11° C. for 4 additional hours. The suspension was poured carefully into ice-cold water, and the precipitate was collected by filtration, washed thoroughly with water, then air-dried. The yellow powder was a mixture 16:84 of the 4- and 6-nitro isomers. The isomers were separated via a recrystallization (150 mL of ethyl acetate with 2 mL of hexanes added dropwise until cloudy) to provide 8.2 g (72%) of the desired product as a yellow powder.

c. Preparation of compound 16(c) (2-(4-fluoro-phenyl)-5-isopropoxy-6-nitro-benzofuran-3-carboxylic acid methylamide). 1-Hydroxybenzotriazole (purity 98%, 2.82 g, 20.9 mmol), followed by anhydrous dichloromethane (70 mL) were added to compound 16(b) (5 g, 13.9 mmol) in a dry 100 mL flask under dry argon. 1-(3-Dimethylaminopropyl)-3-ethylcarbodiimide hydrochloride (4 g, 20.9 mmol) and was then introduced. Finally, methylamine solution (2M in THF, 13.9 mL, 27.8 mol) was added to the slurry, while stirring vigorously. The reaction mixture was stirred at room temperature overnight. The reaction mixture was diluted with dichloromethane (120 mL), then washed with water (3×) and brine (3×). The organic layer was separated, dried over magnesium sulfate, and filtered through a silica gel pad, rinsing with ethyl acetate. Concentration of the organic layers afforded 5.01 g (97%) of the desired product.

d. Preparation of 6-amino-2-(4-fluoro-phenyl)-5-isopropoxy-benzofuran-3-carboxylic acid methylamide.

To a sonicated suspension of compound 16(c), which can be prepared according to step c above, (2.0 g, 10.7 mmol) in ethyl acetate (125 mL) was added activated 10% palladium on carbon (200 mg, 10% weight). The mixture was allowed to stir under 50 psig of hydrogen gas on a Parr-shaker overnight. The reaction was then filtered through a pad of Celite™, rinsing with a 9:1 mixture of ethyl acetate/methanol. Concentration of the filtrate gave 1.78 g (97%) of pure expected compound.

EXAMPLE 17

Preparation of 6-amino-2-(4-fluoro-phenyl)-5-methoxy-benzofuran-3-carboxylic acid methylamide a. Preparation of compound 17(a) (2-(4-fluoro-phenyl)-5-methoxy-6-nitro-benzofuran-3-carboxylic acid). The intermediate compound was prepared essentially according to the general procedure described in Example 16, step b above; however, compound 12(c) was used instead of compound 16(a).

b. Preparation of compound 17(b) (2-(4-fluoro-phenyl)-5-methoxy-6-nitro-benzofuran-3-carboxylic acid methylamide). To a suspension of compound 17(a) (2.0 g, 6.04 mmol) in anhydrous dichloromethane (50 mL) was added methylamine (6 mL, 2M in THF), 1-[3-(dimethylamino)propyl]-3-ethylcarbodiimide hydrochloride (EDCl) (1.74 g, 9.06 mmol) and hydroxybenzotriazole (1.22 g, 9.06 mmol), respectively.

The mixture was allowed to stir overnight. The reaction was quenched with water (100 mL) and diluted with dichloromethane (50 mL). The layers were separated, and the aqueous phase was extracted with dichloromethane (3×). The combined organics were washed with water then brine, dried over MgSO$_4$, and concentrated. The oil was triturated under hexanes/ether (3:1) in order to afford a yellow solid, which was filtered and air-dried. This reaction yielded 2.0 g (97%) of the expected compound.

c. Preparation of 6-amino-2-(4-fluoro-phenyl)-5-methoxy-benzofuran-3-carboxylic acid methylamide. The title compound was prepared essentially according to the general procedure described in Example 16, step d above; however, compound 17(b) was used instead of compound 16(c).

EXAMPLE 18

Preparation of 6-acetylamino-2-(4-fluoro-phenyl)-5-methoxy-benzofuran-3-carboxylic acid methylamide Diisopropylethylamine (83.2 µL, 477 µmol), followed by acetic anhydride (239 µmol) were added to a solution of 6-amino-2-(4-fluoro-phenyl)-5-methoxy-benzofuran-3-carboxylic acid methylamide, prepared according to Example 17 (75 mg, 239 µmol) in dry trichloromethane (3 mL). After one hour, the reaction was quenched with water (3 mL). After concentration to dryness, the crude oil was purified by HPLC (reverse phase, C18, acetonitrile/water with 0.1% acetic acid) to provide 73 mg (87%) of the title compound.

EXAMPLE 19

Preparation of 2-(4-fluoro-phenyl)-5-isopropoxy-6-methylamino-benzofuran-3-carboxylic acid methylamide 6-Amino-2-(4-fluoro-phenyl)-5-isopropoxy-benzofuran-3-carboxylic acid methylamide, prepared according to Example 16 (55 mg, 161 µmol) was dissolved in anhydrous diethyl ether (2 mL). Triethylamine (25 µL, 193 µmol) was added to the reaction mixture, followed by the slow addition of dimethylsulfate (17 µL, 177 µmol). Water (1 mL) was added after 2 hours. The reaction was concentrated to dryness, and the crude product was purified on HPLC (reverse phase) to provide 32 mg (56%) of pure product.

EXAMPLE 20

Preparation of 6-dimethylamino-2-(4-fluoro-phenyl)-5-isopropoxy-benzofuran-3-carboxylic acid methylamide The title compound (35 mg, 59%) was prepared essentially according to the general procedure in Example 19, however the equivalents of triethylamine and dimethylsulfate were doubled.

EXAMPLE 21

Preparation of 2-(4-fluoro-phenyl)-5-isopropoxy-6-methanesulfonylamino-benzofuran-3-carboxylic acid methylamide 6-Amino-2-(4-fluoro-phenyl)-5-isopropoxy-benzofuran-3-carboxylic acid methylamide, prepared according to Example 16 (100 mg, 292 µmol) was dissolved in dry dichloromethane (3 mL) under an argon atmosphere. The reaction was cooled down to 0° C. with an ice bath. Pyridine (16.83 µL, 321 µmol) and methanesulfonyl chloride (22.61 µL, 292 µmol) were mixed together under argon, and then added dropwise to the first aniline solution. The reaction mixture was allowed to warm to room temperature for 1 hour. The reaction mixture was diluted with water (20 mL) and extracted with dichloromethane (3×10 mL). The combined organic layers were washed with a 1N HCl solution, water, a saturated aqueous bicarbonate solution and brine and concentrated in vacuo. The crude product was purified by column chromatography (silica gel, 20 to 50% ethyl acetate in hexanes gradient) to provide 68 mg (56%) of the product.

An alternative method for preparing 2-(4-fluoro-phenyl)-5-isopropoxy-6-methanesulfonylamino-benzofuran-3-carboxylic acid methylamide is as follows:

a. Preparation of compound 21(a) (3-(4-fluoro-phenyl)-3-oxo-propionic acid ethyl ester). A slurry of ethyl malonate, potassium salt (1.58 kg, 9.28 mol) in THF (8.0 L) was treated with magnesium chloride (0.68 kg, 7.14 mol) in one portion. The exothermic reaction was stirred for 6 hours at 65-70° C., then at ambient temperature overnight. Meanwhile, a solution of fluorobenzoic acid (1.00 kg, 7.14 mol) in THF (3.7 L) was slowly added to a mixture of 1,1'-carbonyldiimidazole (1.39 kg, 8.56 mol) in THF (3.7 L) and stirred at 30° C. for 2 hours. The solution was added to the ethyl malonate mixture over a 1¼-hour period at 20-30° C. and stirred overnight at 30° C.

The mixture was cooled to 20° C. and neutralized with dilute HCl (4N, 7.0 L), and the aqueous layer was removed. The solution was concentrated, and the product was collected by hi-vac distillation. The resulting solution was dissolved in ethyl acetate and rinsed with 5% sodium bicarbonate. The organic layer was concentrated, and the product was collected by distillation to provide 1.36 kg of the desired product as a colorless oil.

Compound 21(a) can also be prepared according to the following procedure:

Toluene (7.20 kg) was added to a flask containing potassium-t-butoxide (2.60 kg, 23.17 mol) under a nitrogen atmosphere. The mixture was agitated, and then diethyl carbonate (6.61 kg, 55.96 mol) was added over a 20-minute period. The reaction was heated to >78° C. for over an hour. The reaction was cooled to about 70° C., and 4-fluoroacetophenone (2.00 kg, 14.91 mol) was added over a 1-hour period, rinsing with toluene (0.3 kg). The reaction was stirred for an additional hour at about 70-75° C. The reaction was cooled to room temperature, and stirred overnight. A solution of hydrochloric acid and water (3.3 L concentrated HCL in 8.7 kg water) was added, and the reaction was mixed for 10 minutes. The layers were separated, and the aqueous layer was rinsed with water (2.0 L) and 5% sodium bicarbonate (0.1 kg). The product was isolated by vacuum distillation, to provide 2.44 kg (80%) of the desired product.

b. Preparation of compound 21(b) (2-(4-fluoro-phenyl)-5-hydroxy-benzofuran-3-carboxylic acid ethyl ester). A solution of p-benzoquinone (617 g, 5.71 mol) in THF (3.6 L) was added over 6 hours to a solution of anhydrous zinc chloride (778-810 g, about 5.7 mol) and compound 21 (a) (1200 g, 5.71 mol) in ethanol (2 L) at 105° C., distilling off THF to maintain this temperature. After one hour, the reaction was quenched in water/ethyl acetate (6 L/8 L). The insoluble materials were removed by filtration, and the organic layer washed with water (3 L) and concentrated to dryness. The solids were slurried in dichloromethane (2 L) and filtered. The isolated solids were suspended in ethanol (2 L), stirred, and cooled to <0° C. The solids were collected by filtration to obtain 1012 g of the desired product as a white solid.

¹H NMR in CDCl₃ (300 MHz): 8.02 (m, 2H); 7.51 (d, 1H, J=2.90 Hz); 7.38 (d, 1H); 7.16 (m, 2H); 6.88 (dd, 1H, J-8.70, 2.79); 5.09 (s, 1H); 4.40 (q, 2H, J=7.2 Hz); 1.40 (t, 3H, J=7.20 Hz). Mass Spec: (M+1)=301.

c. Preparation of compound 21(c) (2-(4-fluoro-phenyl)-5-isopropoxy-benzofuran-3-carboxylic acid ethyl ester). A solution of compound 21(b) (2.35 kg, 7.83 mol) in 1-methyl-2-pyrrolidinone (8.3 L) was treated with cesium carbonate (5.10 kg. 15.65 mol) over a ten-minute period. 2-Bromopropane (2.98 kg, 24.26 mol) was added, then the mixture was heated overnight at 50° C. The reaction was added to dilute ammonium hydroxide (1.8 L) and agitated for 30 minutes. The mixture was diluted with water (11.8 L) and extracted with heptane (14.7 L). The layers were separated, and the organic layer was rinsed with water. And concentrated by rotary evaporation to provide an oil which solidified to give the product in quantitative yield.

¹H NMR in CDCl₃ (300 MHz) 8.02(m, 2H); 7.56 (d, 1H, J=2.34 Hz); 7.40 (d, 1H, J=8.79 Hz); 7.16 (t, 2H, J=8.79 Hz); 6.95 (dd, 1H, J-8.79 Hz), 4.59 (m, 1H), 4.41 (q, 2H, J=7.03 Hz) and 1.39 (m, 9H). Mass Spec: (M+1)=343.

d. Preparation of compound 21(d) (2-(4-fluoro-phenyl)-5-isopropoxy-6-nitro-benzofuran-3-carboxylic acid ethyl ester). A solution of compound 21(c) (2.68 kg, 7.83 mol) in chloroform was added slowly to a cooled mixture of chloroform (13.4 kg, ethanol can also be used) and 70% nitric acid (6.7 kg), at a temperature of about 20° C. After one hour, the mixture was allowed to come to room temperature and diluted with water (8.6 L). The organic layer was separated, washed and concentrated to a solid. The crude product was mixed with t-butylmethyl ether and agitated for one hour. The solid was collected by filtration, rinsed with heptane, and dried to afford 2.43 kg (80%) of desired product.

¹H NMR in CDCl₃ (300 MHz): 8.05 (m, 2H); 8.00 (s, 1H), 7.76 (s, 1H), 7.20 (m, 2H), 4.71 (septuplet, 1H, J=6.00 Hz); 4.42 (q, 2H, J=7.20 Hz); 1.45 (d, 6H, J=6.00 Hz); 1.41 (t, 3H, J=7.20 Hz). Mass Spec: (M+1)=388.

e. Preparation of compound 21(e) (6-amino-2-(4-fluoro-phenyl)-5-isopropoxy-benzofuran-3-carboxylic acid ethyl ester). Compound 21(d) (285.10 g, 0.736 mol) was combined with isopropyl acetate (1 L) in a heavy-walled Parr bottle. 10% Palladium on carbon (16.51 g) was carefully wet with isopropyl acetate (1200 mL) and washed into the Parr bottle. The reaction mixture was hydrogenated at 0-50 psig of hydrogen pressure on a Parr shaker until hydrogen uptake ceased. The mixture was filtered through Celite™ and rinsed with isopropyl acetate (1 L). The filtrate was concentrated by rotary evaporation, and the remaining wet solid was isolated.

The above reaction was repeated using 287.52 g (0.74 mol) of compound 21(d), 16.67 g of 10% palladium on carbon and 1200 mL of isopropyl acetate, and the products were combined and used directly in the next step.

f. Preparation of compound 21(f) (2-(4-fluoro-phenyl)-5-isopropoxy-6-methanesulfonylamino-benzofuran-3-carboxylic acid ethyl ester). Compound 21(e) (about 1.48 mol) was dissolved in dichloromethane (5.6 L) and cooled in an ice/ethanol bath. Methane sulfonyl chloride (186.27 g, 1.63 mol) was added in one portion, followed by the dropwise addition of diisopropylethylamine (210.16 g, 1.63 mol) over a 25-minute period. The reaction was allowed to warm to room temperature, and was stirred for about 36 hours under nitrogen gas. The reaction was partitioned with water (2 L), the layers separated, and the organic layer was rinsed with water (3×2 L). The combined aqueous layers were back-extracted with dichloromethane (500 mL), and the organic layers were combined. The organics were concentrated by rotary evaporation. Ethanol was slowly added during the concentration, after the product began to precipitate. After the dichloromethane was removed, the mixture was diluted with t-butylmethyl ether (500 mL). The product was isolated by filtration and air-dried to provide 603.1 g of a mixture of product (90.8%) and disubstituted amine (8.9%).

¹H NMR in DMSO (300 MHz): 9.00 (s, 1H); 8.05 (m, 3H); 7.60 (s, 1H); 7.53 (s, 1H); 7.39 (dd, J=8.8 & 8.8 Hz, 2H); 4.73 (septet, J=5.9 Hz, 1H); 4.32 (q, J=7.0 Hz, 2H); 3.00 (s, 3H); 1.37 (d, J=5.9 Hz, 6H); 1.32 (t, J=7.0 Hz, 3H), g. Preparation of compound 21(g) (2-(4-fluoro-phenyl)-5-isopropoxy-6-methanesulfonylamino-benzofuran-3-carboxylic acid). Compound 21(f) (570 g) was added to a solution of ethanol (6 L) and 1N NaOH (6 L). The solution was heated slowly to about 73° C. for several hours. Heat was then removed, and when the mixture reached about 50° C., 6N HCl was added until approximately pH2 was obtained. The mixture was stirred for 15-minutes, and the solids were quickly isolated by filtration and rinsed with 50/50 ethanol/water (500 mL), and then water (500 mL). The solid was dried in a vacuum oven to provide 513 g of the desired product.

¹H NMR in DMSO (300 MHz) of compound 21(g), prepared essentially as above: 8.97 (s, 1H); 8.05 (m, 2H); 7.58 (s, 1H); 7.54 (s, 1H); 7.38 (dd, J=8.8 & 8.8 Hz, 2H); 4.69 (septet, J=5.9 Hz, 1H); 2.99 (s, 3H); 1.35 (d, J=5.9 Hz, 6H).

h. Preparation of compound 21(h) (2-(4-fluoro-phenyl)-5-isopropoxy-6-methanesulfonylamino-benzofuran-3-carboxylic acid methylamide). Compound 21(g) (1.39 kg, 3.4 mol, which can be prepared according to the previous step) was mixed with dichloromethane (18.9 kg), and stirred under nitrogen, gas. The mixture was cooled to below 20° C., and 1,1'-carbonyldiimidazole (714 g, 4.40 mol) was added in portions over about 15 to 30 minutes. The mixture was warmed to about 30° and stirred for at least ninety minutes. Methylamine (2M in THF, 72.9 kg, 6.8 mol) was added to the reaction over an about 45-minute period, maintaining the temperature below 40° C. The reaction was allowed to stir at about 30° C. to 40° C. for three hours. The reaction was cooled to 20° C. and was quenched with water (6.8 kg). The mixture was stirred and the layers were separated. The aqueous layer was rinsed with dichloromethane (4.5 kg), and the first organic layer washed with water (2×6.8 kg). The aqueous layers were combined and back extracted with the second organic layer. The organic layers were filtered, combined, and concentrated by atmospheric distillation of the volatiles. Ethanol (3.4 L) was added and the mixture was cooled to less than 30° C. The solid was isolated by filtration, rinsed with ethanol (3.4 L, 190 proof), and dried to provide 1.35 kg (94%) of desired product.

EXAMPLE 22 AND EXAMPLE 23

Preparation of 6-ethylamino-2-(4-fluoro-phenyl)-5-isopropoxy-benzofuran-3-carboxylic acid methylamide and 6-diethylamino-2-(4-fluoro-phenyl)-5-isopropoxy-benzofuran-3-carboxylic acid methylamide Diisopropylethylamine (407 μL, 2.34 mmol) and ethyl iodine (187 μL, 2.34 mmol) were added to a solution of 6-amino-2-(4-fluoro-phenyl)-5-isopropoxy-benzofuran-3-carboxylic acid methylamide, prepared according to Example 16 (200 mg, 584 μmol) in dry acetonitrile (8 mL). The reaction was monitored under analytical LC/MS conditions and quenched by addition of water (4 mL). After concentration to dryness, the crude product was purified by preparative HPLC (reverse phase C18, acetonitrile/water plus 0.1% acetic acid), affording 97 mg (45%) of the 6-ethylamino-2-(4-fluoro-phenyl)-5-isopropoxy-benzofuran-3-carboxylic acid methylamide and 63 mg (27%) of 6-diethylamino-2-(4-fluoro-phenyl)-5-isopropoxy-benzofuran-3-carboxylic acid methylamide.

EXAMPLE 24

Preparation of 2-(4-fluoro-phenyl)-5-isopropoxy-6-morpholin-4-yl-benzofuran-3-carboxylic acid methylamide a. Preparation of compound 24(a) (6-bromo-2-(4-fluoro-phenyl)-5-isopropoxy-benzofuran-3-carboxylic acid). Bromine (neat, 1.1 mL, 20.70 mmol) was added dropwise over 30 minutes to a stirred solution of compound 16(a) (5.0 g, 0.016 mol) in 1,4-dioxane (160 mL) in the presence of a 300-watt light. After stirring for an additional 20 minutes, the reaction mixture was mixed with water and extracted with ethyl acetate. The organic phase washed with water and brine, dried over $MgSO_4$, and concentrated under reduced pressure to yield a yellow solid. The product was triturated with 30% ethyl acetate in hexanes to yield 4.1 g (66%) of the desired product as a white solid.

b. Preparation of compound 24(b) (6-bromo-2-(4-fluoro-phenyl)-5-isopropoxy-benzofuran-3-carboxylic acid methylamide). Benzotriazol-1-yloxytrispyrrolidinophosphonium hexafluorophosphate (PyBop) (10.79 g, 20.76 mmol) and methylamine (43.0 mL, 86 mmol) (2.0M solution in THF) were added to a solution of compound 24(a), which can be prepared according to the preceding step, (6.8 g, 17.3 mmol) in DMF (10.0 mL) under an argon atmosphere. After stirring at room temperature for 12 hours, the reaction mixture was treated with water and extracted with ethyl acetate. The organic layer washed with water and brine, dried over $MgSO_4$, and concentrated under reduced pressure. The crude product was purified by column chromatography (silica gel, 50 to 100% ethyl acetate in hexanes) to yield desired product 6.5 g (92%) as a white solid.

c. Preparation of 2-(4-fluoro-phenyl)-5-isopropoxy-6-morpholin-4-yl-benzofuran-3-carboxylic acid methylamide. Compound 24(b) (120 mg, 0.30 mmol), tris(dibenzylideneacetone)dipalladium (5.4 mg, 0.0059 mmol), and (2-dicyclohexylphosphino-2'-N,N-dimethylamino)-biphenyl (3.0 mg 2.4 mol %) were added to an oven-dried 100 mL round bottomed flask. The flask was sealed with a rubber septum, degassed and purged with argon. Morpholine (31 µl, 0.35 mmol) and lithium bis(trimethylsilyl amide) (650 µl, 0.65 mmol, 1M solution in THF) were added to the reaction mixture. The septum was quickly removed, and a reflux condenser was placed on the flask. The reaction flask was degassed again and purged with argon. The reaction mixture was then heated to 65° C. for 12 hours and cooled to room temperature. 1M Hydrochloric acid (600 µl) was added, and the reaction mixture was stirred for 5 minutes, followed by passage through a small pad of Celite™. The filtrate was diluted with water and extracted with ethyl acetate. The organic layer washed with water and brine, dried over $MgSO_4$, and concentrated under reduced pressure. The crude product was purified by column chromatography (silica gel, 20 to 40% ethyl acetate in hexanes) to provide 70 mg (57%) of the desired product as a white solid.

EXAMPLE 25

Preparation of 5-methoxy-4-methyl-2-phenyl-benzofuran-3-carboxylic acid methylamide a. Preparation of compound 25(a) (4-bromo-5-hydroxy-2-phenyl-benzofuran-3-carboxylic acid ethyl ester). Compound 2(a), which can be prepared according to Example 2 (450 mg, 1.595 mmol) was dissolved in a mixture of $CS_2$: $CH_3CN$ (3:1) (8.0 mL) under argon. The solution was cooled to 0° C., and N-bromosuccinimide (312 mg, 1.755 mmol) was added in one portion. The reaction was stirred for 4 hours at 0° C., and then warmed to room temperature. The solvent was evaporated, and the residue was dissolved in ethyl acetate, washed with water and brine, dried over $MgSO_4$, and concentrated under reduced pressure. The crude product was purified by HPLC (silica gel, eluting with 10 to 100% ethyl acetate in hexanes to provide 396 mg (69%) of the desired product.

b. Preparation of compound 25(b) (4-bromo-5-methoxy-2-phenyl-benzofuran-3-carboxylic acid ethyl ester). Potassium carbonate (365 mg, 2.638 mmol) and methyl iodide (1.3 mL, 21.1 mmol) were added to a solution of compound 25(a) (380 mg, 1.055 mmol) dissolved in acetonitrile (5.0 mL), under an argon atmosphere. After stirring under reflux conditions for 4 hours, the reaction mixture was cooled to room temperature, diluted with water, and extracted with ethyl acetate. The organic layer washed with water and brine, dried over $MgSO_4$, and concentrated under reduced pressure to provide 385 mg (98%) of the desired product.

c. Preparation of compound 25(c) (5-methoxy-4-methyl-2-phenyl-benzofuran-3-carboxylic acid ethyl ester). Compound 25(b) (30 mg, 0.082 mmol) was mixed with $Ag_2O$ (46.5 mg, 0.201 mmol), methyl boronic acid (6.0 mg, 0.0884 mmol), $K_2CO_3$ (34.0 mg, 0.246 mmol), 1,1-bis(diphenylphosphinoferrocene)dichloropalladium(II) complex with dichloromethane (1:1) (Pd(dppf)Cl$_2$) (6.0 mg, 10 mol %), and THF (degassed, 1.0 mL) under argon atmosphere in a tube. The pressure tube was sealed, and the reaction mixture was stirred at 80° C. for 12 hours, cooled to room temperature, and quenched with a mixture of 30% $H_2O_2$ (5 mL) and 10% NaOH. The reaction mixture was diluted with water and extracted with ethyl acetate. The organic phase washed with water and brine, dried over $MgSO_4$, and concentrated under reduced pressure. The crude product was purified by reverse phase HPLC to provide 16.9 mg (64%) of the desired product.

d. Preparation of compound 25(d) (5-methoxy-4-methyl-2-phenyl-benzofuran-3-carboxylic acid). Compound 25(c) (16.9 mg, 0.0545 mmol) was dissolved in ethanol (2.0 mL) and 12M NaOH (200 µl) was added. The reaction mixture was heated to 100° C. for 6 hours and cooled to room temperature. The solvent was evaporated under reduced pressure. The residue was dissolved in water, acidified with 10% aqueous HCl, and extracted with ethyl acetate. The organic layer washed with water and brine, dried over $MgSO_4$, and concentrated under reduced pressure to provide 13.5 mg, (87%) of the desired product.

e. Preparation of 5-methoxy-4-methyl-2-phenyl-benzofuran-3-carboxylic acid methylamide. Bromo-tris-pyrrolidinophosphonium hexafluorophosphate (PyBrop) (25.0 mg, 0.0526 mmol) and methylamine (0.5 mL, 2.0 M solution in THF) were added to a solution of compound 25(d) (13.5 mg, 0.479 mmol) dissolved in DMF (1.0 mL) under an argon atmosphere. After stirring at room temperature for 12 hours, the reaction mixture was treated with water and extracted with ethyl acetate. The organic layer washed with water and brine, dried over $MgSO_4$, and concentrated under reduced pressure. The crude product was purified by column chromatography (silica gel, ethyl acetate/hexanes) to provide 9.0 mg (64%) of the title compound.

EXAMPLE 26

Preparation of
5-cyano-2-phenyl-benzofuran-3-carboxylic acid
methylamide a. Preparation of compound 26(a) (acetic acid 4-cyano-2-phenylethynyl-phenyl ester).

1,4-Dioxane (2.5 mL, dry) was added to a stirred suspension of CuI (8.0 mg, 2 mol %) and dichlorobis(benzonitrile) palladium (II) (24 mg, 3 mol %) in a dry septum-capped flask with constant purging of argon. Tri-t-butylphosphine (542 µl, 0.25M solution in 1,4-dioxane), diisopropyl amine (350 µl, 4.17 mmol), acetic acid 2-bromo-4-cyano-phenyl ester (500 mg, 2.08 mmol), and phenyl acetylene (254 mg, 2.71 mmol) were added with syringes to the stirred reaction mixture. The reaction mixture was stirred for 6 hours, and then diluted with ethyl acetate and passed through small pad of silica gel. The filtrate was concentrated, and the crude product was purified by column chromatography (silica gel, 5 to 20% ethyl acetate in hexanes) to provide 390 mg (72%) of the desired product.

b. Preparation of compound 26(b) (4-hydroxy-3-phenylethynyl-benzonitrile). Potassium carbonate (309 mg, 2.24 mmol) was added to a solution of compound 26(a) (390 mg, 1.49 mmol) in methanol (10.0 mL). The reaction mixture was stirred at room temperature overnight, and then the solvent was evaporated under reduced pressure. The residue was treated with water and extracted with ethyl acetate. The organic layer washed with water and brine, dried over $MgSO_4$, and concentrated under reduced pressure. The crude product was purified by column chromatography (silica gel, eluting with 5 to 25% ethyl acetate in hexanes) to provide 180 mg (55%) of the desired product.

c. Preparation of compound 26(c) (5-cyano-2-phenyl-benzofuran-3-carboxylic acid methyl ester). Compound 26(b) (100 mg, 0.4566 mmol) was mixed with thiourea (2.0 mg, 5 mol %), $CBr_4$ (378.5 mg, 1.141 mmol), cesium carbonate (445 mg, 1.367 mmol), $PdI_2$ (8.2 mg, of 5 mol %) and methanol (2 mL). The reaction mixture was treated with a stream of carbon monoxide gas at room temperature for five minutes and at 45° C. for 10 minutes. Stirring was continued at 45° C. under a carbon monoxide atmosphere (balloon) overnight. The reaction mixture was then passed through a small pad of silica gel, rinsing with ethyl acetate. The filtrate was concentrated, and the crude product was purified by column chromatography (silica gel, eluting with 5-10% ethyl acetate in hexanes) to provide 74 mg of a 60:40 mixture of compound 26(c)(i) and 2-phenyl-benzofuran-5-carbonitrile.

d. Preparation of compound 26(d) (5-cyano-2-phenyl-benzofuran-3-carboxylic acid). The above mixture of compound 26(c) and 2-phenyl-benzofuran-5-carbonitrile (74 mg) was dissolved in ethanol (2.0 mL) and treated with 12M NaOH (200 µl). The reaction mixture was heated to 50° C. for 6 hours, then cooled to room temperature, and the solvent was concentrated under reduced pressure. The residue was dissolved in water, acidified with 10% HCl, and extracted with ethyl acetate. The organic layer washed with water and brine, dried over $MgSO_4$, and concentrated under reduced pressure. The crude product was purified by column chromatography (silica gel, eluting with 30 to 40% ethyl acetate/hexanes) to yield acid 30 mg (25% yield from steps c-d) of the desired product.

e. Preparation of 5-cyano-2-phenyl-benzofuran-3-carboxylic acid methylamide. The target product (16.0 mg, 51%) was prepared essentially according to the general procedure described in Example 25, step e; however, compound 26(d) was used instead of compound 25(d).

EXAMPLE 27

Preparation of 5-isopropoxy-2-pyridin-4-yl-benzofuran-3-carboxylic acid methylamide a. Preparation of compound 27(a) (4-isopropoxy-phenol). 2-Iodopropane (27.22 mL, 0.27 mol) was added to a stirred mixture of hydroquinone (30 g, 0.27 mol) in ethanol (30 mL), and the reaction mixture was heated to 60° C. Potassium hydroxide (15.3 g, 0.27 mol) was dissolved in water (50 mL) and added dropwise to the reaction mixture over a one-hour period. After stirring at 60° C. for five hours, the mixture was cooled to room temperature, and the solvent was removed under reduced pressure. The residue was acidified with 6N HCl and extracted with ether. The organic layer washed with water and brine, dried with $MgSO_4$, and concentrated. The crude product was purified by column chromatography (silica gel, eluting with 10 to 30% ethyl acetate/hexanes) to yield 20.3 g (49%) of the desired product.

b. Preparation of compound 27(b) (2-bromo-4-isopropoxy-phenol). N-Bromosuccinimide (5.85 g, 0.033 mol) was added to a stirred solution of compound 27(a) (5.0 g, 0.033 mol) in carbon disulfide (132 mL). The reaction mixture was stirred at room temperature for 2 hours, and then the solvent was evaporated under reduced pressure to dryness. The residue was treated with water and extracted with ethyl acetate. The organic layer washed with water and brine, dried with $MgSO_4$ and concentrated. The crude product was purified by column chromatography (silica gel, eluting with 5 to 10% ethyl acetate/hexanes) to yield 4.65 g (61%) of the desired product.

c. Preparation of compound 27(c) (acetic acid 2-bromo-4-isopropoxy-phenyl ester). 4-Dimethylaminopyridine (catalytic) and triethyl amine (6.9 mL, 0.050 mol) were added to a stirred solution of compound 27(b) (4.6 g, 0.02 mol) in dichloromethane (20 mL). The reaction mixture was stirred for 10 minutes, and then acetic anhydride (4.5 mL, 0.48 mol) was added. After stirring for 4 hours, water was added to the reaction mixture. The mixture was extracted with ethyl acetate, and the organic layer washed with water and brine, dried with $MgSO_4$, and concentrated. The crude product was purified by column chromatography (silica gel, eluting with 0 to 10% ethyl acetate/hexanes) to yield 4.75 g (87%) of the desired product.

d. Preparation of compound 27(d) (4-trimethylsilanylethynyl-pyridine). Compound 27(d) (2.4 g, 53%) was prepared essentially according to the general procedure described in Example 26, step a; however 4-bromopyridine hydrochloride salt and (trimethylsilyl)acetylene were used instead of acetic acid 2-bromo-4-cyano-phenyl ester and phenyl acetylene.

e. Preparation of compound 27(e) (4-ethynyl-pyridine). Potassium hydroxide (21.0 mg, 3.0 mol %) was added to a stirred solution of compound 27(d) (2.2 g, 0.0126 mmol) in degassed methanol (8.0 mL). After stirring for 30 minutes, water was added, and the mixture was extracted with dichloromethane. The organic layer washed with water and brine, dried with $MgSO_4$, and concentrated to yield 640 m g (53%) of the desired product.

f. Preparation of compound 27(f) (acetic acid 4-isopropoxy-2-pyridin-4-ylethynyl-phenyl ester). Compound 27(f) (564 mg, 61%) was prepared essentially according to the general procedure described in Example 26, step a; however compound 27(c) and compound 27(e) were used instead of 2-bromo-4-cyano-phenyl ester and phenyl acetylene.

g. Preparation of compound 27(e) (4-isopropoxy-2-pyridin-4-ylethynyl-phenol). Hydrazine (9.5 mL, 0.5 M in THF) was added to a stirred solution of compound 27(f) (564 mg, 1.91 mmol) in THF (3.0 mL). After stirring for 30 minutes, water was added, and the product was extracted with ethyl acetate. The organic layer washed with water (3×100 mL) and brine, dried with MgSO$_4$, and concentrated to provide 470 mg (97%) of the desired product as a white solid.

h. Preparation of compound 27(h) (5-isopropoxy-2-pyridin-4-yl-benzofuran-3-carboxylic acid methyl ester). The intermediate compound (430 mg, 74%) was prepared essentially according to the general procedure described in Example 26, step c; however compound 27(g) was used instead of compound 26(b).

i. Preparation of 5-isopropoxy-2-pyridin-4-yl-benzofuran-3-carboxylic acid methylamide. Lithium hydroxide (540 mg) and water (1.0 mL) were added to compound 27(g) (200 mg, 0.644 mmol) dissolved in 1,4-dioxane (5.0 mL). The reaction mixture was stirred at 80° C. for 12 hours. The mixture was cooled to room temperature, and the solvent was concentrated under reduced pressure. The residue was dissolved in water, brought to pH 7.0 with 10% HCl, and extracted with ethyl acetate. The organic layer washed with water and brine, dried over MgSO$_4$, and concentrated under reduced pressure to provide 130 mg (68%) of the acid.

The above acid (65 mg, 0.22 mmol), benzotriazol-1-yloxytrispyrrolidinophosphonium hexafluorophosphate (PyBOP) (148 mg, 0.284 mmol) was dissolved in DMF (0.5 mL) and methylamine (2.2 mL, 2.0M solution in THF). After stirring for 12 hours, water was added, and the crude product was extracted with ethyl acetate. The organic layer washed with water and brine, dried over MgSO$_4$, and concentrated. The crude product was purified by column chromatography (silica gel, eluting with 0 to 5% methanol/ethyl acetate) to provide 65 mg (96%) of the title compound.

EXAMPLE 28

Preparation of 6-(3,5-dimethyl-isoxazol-4-yl)-2-(4-fluoro-phenyl)-5-methoxy-benzofuran-3-carboxylic acid methylamide a. Preparation of compound 28(a) (2-(4-fluorophenyl)-5-methoxybenzofuran-3-carboxylic acid ethyl ester). Compound 21(b) (50.0 g, 0.167 mol, which can be prepared according to the general procedure described in Example 21) was dissolved in anhydrous 1-methyl-2-pyrrolidinone (176 mL) under argon with mechanical stirring. Once homogeneous, cesium carbonate (108.8 g, 0.334 mol) was added portion wise over 15 minutes. Methyl iodide (32.2 mL, 0.516 mol) was added over 5 minutes. The reaction was heated to 50° C. for 18 hours, then cooled to room temperature, diluted with concentrated ammonium hydroxide (39 mL), and stirred for 30 minutes. The mixture was diluted with heptane (1000 mL) and washed with water (3×1000 mL). The combined organics were dried with magnesium sulfate and evaporated to dryness. The resulting solid was stirred in hexanes for 18 hours, filtered, and dried. Since the reaction was incomplete (by proton NMR), the isolated solid was resubjected to anhydrous 1-methyl-2-pyrrolidinone (176 mL). Once homogeneous, cesium carbonate (40.0 g, 0.123 mol) and methyl iodide (20.0 mL, 0.321 mol) were added. The reaction was again heated to 50° C. for 18 hours, cooled to room temperature, diluted with ammonium hydroxide (24 mL), and stirred for 30 minutes. The mixture was diluted with water (1000 mL) and extracted with t-butylmethyl ether (3×300 mL). The combined organics were washed with water (300 mL) and dried with magnesium sulfate. After the solvent was evaporated, the product was crystallized from hot n-heptane, to provide 32.1 g (61%) of the desired product as a tan solid.

b. Preparation of compound 28(b) (2-(4-fluorophenyl)-5-methoxybenzofuran-3-carboxylic acid). Compound 28(a) (32 g, 0.102 mol) and potassium hydroxide (6.3 g, 0.112 mol) were combined in ethanol (80 mL) and water (80 mL). The reaction mixture was gently refluxed overnight. TLC analysis showed reaction to be incomplete, so an additional amount of potassium hydroxide (2.0 g, 0.035 mol) was added. After one hour, the solvent was evaporated to half volume. The solution was diluted with water (400 mL) and extracted with ethyl acetate (2×300 mL). The aqueous solution was acidified with 3M HCl, and the resulting precipitate was filtered, washed with water, and dried to provide 28.9 g (99%) of the product as a white solid.

c. Preparation of compound 28(c) (6-bromo-2-(4-fluorophenyl)-5-methoxybenzofuran-3-carboxylic acid). Compound 28(b) (28.9 g, 0.101 mol) was dissolved in anhydrous 1,4-dioxane (725 mL) under argon. The resulting solution was degassed with argon through a gas dispersion tube for 10 minutes. Bromine (8.8 mL, 0.170 mol) was added dropwise via syringe over 45 minutes. Once addition was complete, the reaction was stirred at room temperature for 30 minutes. An additional amount of bromine (0.5 mL, 0.01 mol) was added dropwise over 5 minutes. The mixture was diluted with ethyl acetate (1800 mL), washed with water (5×350 mL), and dried with magnesium sulfate. The solvent was evaporated, and the remaining solid was dissolved in ethyl acetate (250 mL). The solvent was again removed by evaporation. The process of dissolving in ethyl acetate, followed by evaporation was repeated until the solvent was free of color. The resulting solid was sonicated in a 80/20 mixture of hexane/ethyl acetate (500 mL), and the crude product was isolated via filtration. The filtrate was concentrated, and the resulting solids were sonicated in an 80/20 mixture of hexane/ethyl acetate (300 mL). The solid was isolated via filtration and combined with the crude product. The solids were washed with a 95/5 mixture of hexane/ethyl acetate (100 mL) and then with hexanes. The solid was dried under vacuum dry, to provide 28.4 g (77%) of the desired product as a tan solid.

d. Preparation of compound 28(d) (6-bromo-2-(4-fluorophenyl)-5-methoxybenzofuran-3-carboxylic acid methyl ester). Milled potassium carbonate (40.6 g, 0.294 mol) and methyl iodide (92.0 mL, 1.47 mol) were added to a stirring solution of compound 28(c) (53.6 g, 0.147 mol, which can be prepared according to the previous step) dissolved in 1-methyl-2-pyrrolidinone (1000 mL). The reaction mixture was stirred at 50° C. for 18 hours. Upon cooling, the reaction was diluted with water (2200 mL) and extracted with ethyl acetate (5×600 mL). The organics were combined, washed with water (3×1000 mL), and dried with magnesium sulfate. The solvent was evaporated, and the crude product was purified by sonicating in a 90/10 mixture of hexane/ethyl acetate for 1 hour. The solid was removed by filtration, washed with hexanes and dried under vacuum, to provide 47.4 g (125 mol, 85%) of the desired product as a white solid.

e. Preparation of compound 28(e) (6-(3,5-dimethylisoxazol-4-yl)-2-(4-fluorophenyl)-5-methoxybenzofuran-3-carboxylic acid methyl ester). Compound 28(d) (12.0 g, 0.0316 mol) was dissolved in toluene (900 mL), ethanol (420 mL), and water (24 mL), under argon. The resulting solution was degassed with argon through a gas dispersion tube for 10 minutes. Sodium carbonate (8.37 g, 79.0 mmol), 3,5-dimethylisoxazole-4-boronic acid (6.69 g, 47.5 mmol), and tetrakistriphenylphosphine-palladium(0) (1.83 g, 1.58 mmol) were added, and the reaction was gently refluxed for 21 hours. The solvent was evaporated, and the reaction was diluted with ethyl acetate (500 mL) and water (300 mL). The layers were separated, and the organic phase washed with water (2×500 mL). The aqueous washings were combined and extracted with ethyl acetate (300 mL). The organics were combined, washed with brine, and dried with magnesium sulfate. The solvent was evaporated, and the crude product was purified by flash chromatography (silica gel, ethyl acetate/hexane gradient) providing 10.4 g (83%) of the desired product as an off-white solid.

f. Preparation of compound 28(f) (6-(3,5-dimethylisoxazol-4-yl)-2-(4-fluorophenyl)-5-methoxybenzofuran-3-carboxylic acid). Compound 28(e) (10.4 g, 26.3 mmol) and potassium hydroxide (5.90 g, 105 mmol) were combined in ethanol (500 mL) and water (500 mL) and gently refluxed for 4 hours. After cooling, two-thirds of the solvent was evaporated, and the solution was diluted with water (300 mL). The solution was filtered through a pad of Celite™ 503 to remove a small amount of palladium residue from the previous step. The solution was acidified with 6M HCl, and the precipitate was filtered, washed with water and hexanes, and partially dried under vacuum to provide the desired product as a white solid. The unpurified product was used directly in the next step.

g. Preparation of 6-(3,5-dimethylisoxazol-4-yl)-2-(4-fluorophenyl)-5-methoxybenzofuran-3-carboxylic acid methylamide. Compound 28(f) (10.0 g, 0.0262 mol), benzotriazol-1-yloxytrispyrrolidinophosphonium hexafluorophosphate (PyBOP) (16.4 g, 0.0315 mol), and methylamine (131 mL, 2M in THF, 0.262 mol) were combined with DMF (16 mL). The reaction was stirred at room temperature under argon for 18 hours. The solvent was evaporated, and the resulting solids were dissolved in ethyl acetate (250 mL) and water (300 mL). The layers were separated, and the aqueous phase was extracted with ethyl acetate (4×200 mL). The organics were combined, washed with water (3×150 mL) and brine (300 mL), and dried with magnesium sulfate. The solvent was evaporated, and the crude product was mixed with a 90/10 mixture of hexane/ethyl acetate (100 mL). The mixture was filtered, and the solids were washed with hexane and dried under vacuum to provide the desired product 8.16 g (79%) as a white solid.

The crude product was later purified via crystallization (hot ethanol and water) after being combined with several other batches of compound, to provide the title compound as white needles.

EXAMPLE 29

Preparation of 2-(4-fluoro-phenyl)-6-(methanesulfonyl-methyl-amino)-5-methoxy-benzofuran-3-carboxylic acid methylamide a. Preparation of compound 29(a) (2-(4-fluoro-phenyl)-5-hydroxy-6-methanesulfonylamino-benzofuran-3-carboxylic acid methylamide). Boron trichloride (60 mL of 1M dichloromethane) was added for 10 minutes to 2-(4-fluoro-phenyl)-5-isopropoxy-6-methanesulfonylamino-benzofuran-3-carboxylic acid methylamide (7.10 g, 16.9 mmol, which can be prepared according to one of the procedures described in Example 21), in dichloromethane (200 mL). The mixture was stirred for 20 hours, and then carefully quenched with 1N HCl (10 mL). An additional amount of 4N HCl (100 mL) was added, and the reaction mixture was stirred for 24 hours. The precipitated solid was filtered off, washed with water, dried, and triturated with ethyl acetate/hexanes to provide 6.39 g (100%) of the desired product as a white solid.

b. Preparation of 2-(4-fluoro-phenyl)-6-(methanesulfonyl-methyl-amino)-5-methoxy-benzofuran-3-carboxylic acid methylamide. Potassium carbonate (0.30 g, 2.17 mmol) and iodomethane (0.10 mL, 1.61 mmol) were added to a solution of compound 29(a) (0.11 g, 0.291 mmol, which can be prepared according the previous step) in 2-butanone (20 mL). The reaction mixture was refluxed for 1-2 hours and then cooled to room temperature and concentrated. The crude product was dissolved in ethyl acetate and washed with 1M hydrochloric acid. The organic layer was concentrated, and the product was purified by flash chromatography (silica gel, ethyl acetate/hexanes gradient) to provide 73 mg (62%) of the desired product as a white solid.

EXAMPLE 30

Preparation of 2-(4-fluoro-phenyl)-5-(4-methoxy-benzyloxy)-6-morpholin-4-yl-benzofuran-3-carboxylic acid methylamide a. Preparation of compound 30 (a) (2-(4-fluoro-phenyl)-5-hydroxy-6-morpholin-4-yl-benzofuran-3-carboxylic acid methylamide). Boron trichloride (1M solution in xylenes, 5.0 mL, 5.0 mmol) was added to a solution of 2-(4-fluoro-phenyl)-5-isopropoxy-6-morpholin-4-yl-benzofuran-3-carboxylic acid methylamide (0.71 g, 1.7 mmol, which can be prepared according to Example 24, above), dissolved in dichloromethane (30 mL). The reaction mixture was refluxed for 30 minutes, cooled to room temperature, quenched with 1M hydrochloric acid (10 mL) and stirred for 1 hour. The organics were removed by evaporation, and a saturated solution of sodium bicarbonate was added until pH=8-9. The product was extracted with ethyl acetate and purified via column chromatography (dry loading onto silica gel, ethyl acetate/hexanes gradient) to provide 0.53 g (84%) of the desired product.

b. Preparation of 2-(4-fluoro-phenyl)-5-(4-methoxy-benzyloxy)-6-morpholin-4-yl-benzofuran-3-carboxylic acid methylamide. Potassium carbonate (0.40 g, 2.89 mmol) and 4-methoxybenzyl chloride (0.20 mL, 1.47 mmol) were added to compound 30(a) (0.311 g, 0.840 mmol) dissolved in acetonitrile (20 mL). The reaction mixture was refluxed for 12 hours, cooled to room temperature and concentrated. The crude product was dissolved in ethyl acetate and washed with 1M hydrochloric acid. The organic layer was concentrated, and the product was purified by flash chromatography (silica gel, ethyl acetate/hexanes gradient) to provide 296 mg (72%) of the desired product as a white solid.

EXAMPLE 31

Preparation of 2-(4-fluoro-phenyl)-6-[methanesulfonyl-(4-methoxy-benzyl)-amino]-5-(4-methoxy-benzyloxy)-benzofuran-3-carboxylic acid methylamide Potassium carbonate (0.040 g, 0.285 mmol) and 4-methoxybenzyl chloride (0.026 mL, 0.190 mmol) were added to a solution of compound 29(a) (0.036 g, 0.095 mmol, which can be prepared according to Example 29, step a above), dissolved in 2-butanone (10 mL). The reaction was stirred at 20° C. for 72 hours. The reaction mixture was concentrated, and the crude product was dissolved in ethyl acetate and washed with 1M hydrochloric acid. The organic layer was concentrated, and the product was purified by flash chromatography (silica gel, ethyl acetate/hexanes gradient) to provide 34 mg (58%) of the desired product as a white solid.

EXAMPLE 32

Preparation of 5-ethoxy-6-(ethyl-methanesulfonyl-amino)-2-(4-fluoro-phenyl)-benzofuran-3-carboxylic acid methylamide Potassium carbonate (0.10 g, 0.72 mmol) and iodoethane (0.10 mL, 1.25 mmol) were added to a solution of compound 29(a) (0.036 g, 0.095 mmol, which can be prepared according to Example 29 step a, above), dissolved in 2-butanone (15 mL), and the reaction mixture was stirred at 20° C. for 72 hours. The reaction mixture was concentrated, and the crude product was dissolved in ethyl acetate and washed with 1M hydrochloric acid. The organic layer was concentrated, and the product was purified by flash chromatography (silica gel, ethyl acetate/hexanes gradient) to provide 25 mg (61%) of the title compound as a white solid.

EXAMPLE 33

Preparation of 2-(4-fluoro-phenyl)-6-morpholin-4-yl-5-(thiazol-2-ylmethoxy)-benzofuran-3-carboxylic acid methylamide a. Preparation of (2-chloromethyl-thiazole). Thionyl chloride (2 mL, 27.4 mmol) was added to 2-hydroxymethyl thiazole (0.15 g, 1.30 mmol) dissolved in dichloromethane (2 mL). The reaction mixture was heated to reflux for 3 seconds and then cooled and stirred for 20 minutes at room temperature. The reaction was concentrated, dried on high vacuum pump and used immediately in the following step.

b. Preparation of 2-(4-fluoro-phenyl)-6-morpholin-4-yl-5-(thiazol-2-ylmethoxy)-benzofuran-3-carboxylic acid methylamide. Potassium carbonate (0.10 g, 0.72 mmol) and 2-chloromethyl-thiazole (0.021 g, 0.157 mmol) were added to a solution of compound 30(a) (0.050 g, 0.135 mmol, which can be prepared according to Example 30, step (a) above) dissolved in acetonitrile (15 mL). The reaction was refluxed for 2 hours and then warmed at 60° C. for 16 hours. The reaction was cooled and concentrated, and crude product was dissolved in ethyl acetate and washed with 1M hydrochloric acid. The organic layer was concentrated, and the product was purified by flash chromatography (silica gel, ethyl acetate/hexanes gradient) to give 37 mg (59%) of the desired product as a white solid.

EXAMPLE 34

Preparation of 2-(4-fluoro-phenyl)-5-isopropoxy-6-[methanesulfonyl-(2-oxo-propyl)-amino]-benzofuran-3-carboxylic acid methylamide 2-(4-Fluoro-phenyl)-5-isopropoxy-6-methanesulfonylamino-benzofuran-3-carboxylic acid methylamide (0.093 g, 0.221 mmol, which can be prepared according to one of the procedures described in Example 21) was dissolved in 2-butanone (20 mL). Potassium carbonate (0.20 g, 1.45 mmol) and chloroacetone (0.10 mL, 1.25 mmol) were added at 20° C. The reaction mixture was refluxed for 2 hours, cooled to room temperature and concentrated. The crude product was dissolved in ethyl acetate and washed with 1M hydrochloric acid. The organic layer was concentrated, and the product was purified by flash chromatography (silica gel, ethyl acetate/hexanes gradient) to provide 99 mg (94%) of the title compound as a white solid

EXAMPLE 35

Preparation of 2-(4-fluoro-phenyl)-6-morpholin-4-yl-5-(thiazol-4-ylmethoxy)-benzofuran-3-carboxylic acid methylamide Potassium carbonate (0.200 g, 1.45 mmol) and 4-(chloromethyl)thiazole hydrochloride (0.100 g, 0.588 mmol) were added to a solution of compound 30(a) (0.100 g, 0.270 mmol, which can be prepared according to Example 30, step a above) dissolved in 2-butanone (15 mL). The reaction was refluxed for 16 hours and then cooled to room temperature. The mixture was concentrated, and the residue was dissolved in ethyl acetate and washed with water. The organic layer was concentrated, and the product was purified via column chromatography (dry loading onto silica gel, ethyl acetate/hexanes gradient, followed by 1% methanol/ethyl acetate) to provide the crude product. The solid was triturated with ethyl acetate, filtered, and dried on high vacuum pump to provide 45 mg (36%) of the title compound as a white solid.

EXAMPLE 36

Preparation of 2-(4-fluoro-phenyl)-5-isopropoxy-6-(methanesulfonyl-thiazol-4-ylmethyl-amino)-benzofuran-3-carboxylic acid methylamide Potassium carbonate (0.050 g, 0.357 mmol) followed by 4-(chloromethyl)thiazole hydrochloride (0.041 g, 0.238 mmol) were added to a solution of 2-(4-fluoro-phenyl)-5-isopropoxy-6-methanesulfonylamino-benzofuran-3-carboxylic acid methylamide (0.050 g, 0.119 mmol, which can be prepared according to one of the procedures described in Example 21 above), dissolved in acetonitrile (10 mL). The reaction was refluxed for 1 hour with no visible product formation observed by TLC, so potassium iodide (0.020 g, 0.120 mmol) was added to the reaction. The mixture was refluxed for an additional 2 hours, and then cooled to room temperature. The reaction mixture was concentrated, and the residue was dissolved in ethyl acetate and washed with water. The product was concentrated and purified by flash chromatography (silica gel, ethyl acetate/hexanes gradient) to provide 30 mg (48%) of the desired product as a white solid.

EXAMPLE 37

Preparation of 2-(4-fluoro-phenyl)-6-(5-hydroxymethyl-isoxazol-3-yl)-5-isopropoxy-benzofuran-3-carboxylic acid methylamide a. Preparation of compound 37(a) (2-(4-fluoro-phenyl)-6-formyl-5-isopropoxy-benzofuran-3-carboxylic acid ethyl ester). Hexamethylenetetramine (3.07 g, 21.9 mmol) and compound 6(c) (5.0 g, 14.6 mmol, which can be prepared according to Example 6, step c above), were dissolved in trifluoroacetic acid (10 mL). The reaction mixture was heated to 80° C. until the reaction appeared to be 80% complete by TLC. The reaction mixture was cooled to room temperature, concentrated in vacuo, and partitioned between ethyl acetate and water. The aqueous phase was washed with ethyl acetate, and then the combined organic layers were washed with brine, dried (MgSO$_4$), and concentrated in vacuo. Purification by column chromatography (silica gel, ethyl acetate/hexanes gradient) provided 2.39 g (44%) of the desired product as a white solid.

b. Preparation of compound 37(b) (2-(4-fluoro-phenyl)-6-(hydroxyimino-methyl)-5-isopropoxy-benzofuran-3-carboxylic acid ethyl ester). To a solution of compound 37(a) (1.23 g, 3.32 mmol) in ethanol (10 mL) and THF (25 mL) was added sodium acetate trihydrate (0.497 g, 3.65 mmol) in water (10 mL), followed by hydroxylamine hydrochloride (0.254 g, 3.65 mmol). The reaction mixture was gently warmed in a hot water bath, then allowed to cool slowly to ambient temperature. The reaction was concentrated in vacuo and partitioned between ethyl acetate and water. The aqueous phase washed with ethyl acetate, and then the combined organic layers were washed with brine, dried (MgSO$_4$) and concentrated in vacuo to provide 1.44 g (>100%) of the desired product. The product was taken on to the next step without further purification.

c. Preparation of compound 37(c) (2-(4-fluoro-phenyl)-5-isopropoxy-6-[5-(tetrahydropyran-2-yloxymethyl)-isoxazol-3-yl]-benzofuran-3-carboxylic acid ethyl ester). Compound 37(b) (0.300 g, 0.778 mmol) in chloroform (7 mL) was added dropwise to a solution of N-chlorosuccinimide (0.104 g, 0.778 mmol) and pyridine (catalytic) in chloroform (3 mL). The reaction mixture was heated to 50° C. for 4 hours then cooled to ambient temperature. Triethylamine (0.219 mL, 1.55 mmol), and then tetrahydro-2-(2-propynloxy)-2H-pyran (0.108 mL, 0.778 mmol) were added. The reaction was warmed to 70° C. for 16 hours, cooled to ambient temperature, diluted with dichloromethane, and washed with 1 M HCl and brine, dried (MgSO$_4$) and concentrated in vacuo. Purification by column chromatography (silica gel, ethyl acetate/hexanes gradient) provided 0.22 g (54%) of the desired product as a white solid.

d. Preparation of compound 37(d) (2-(4-fluoro-phenyl)-6-(5-hydroxymethyl-isoxazol-3-yl)-5-isopropoxy-benzofuran-3-carboxylic acid ethyl ester). Pyridinium p-toluenenesulfonate (7 mg, 0.028 mmol) was added to a solution of compound 27(c) (0.15 g, 0.28 mmol) in ethanol (5 mL) and THF (5 mL). After stirring at room temperature for 4 days, a 1/1 mixture of ethanol/THF (10 mL) and an additional amount of pyridinium p-toluenenesulfonate (7 mg, 0.028 mmol) were added. The reaction mixture was warmed to 50° C. for 30 minutes, then cooled to room temperature and concentrated in vacuo. The residue was partitioned between ethyl acetate and water. The aqueous phase washed with ethyl acetate, and the combined organic layers were washed with brine, dried (MgSO$_4$) and concentrated in vacuo to provide 0.13 g (100%) of the desired product.

e. Preparation of compound 37(e) (2-(4-fluoro-phenyl)-6-(5-hydroxymethyl-isoxazol-3-yl)-5-isopropoxy-benzofuran-3-carboxylic acid). Potassium hydroxide solution (4N, 0.18 mL, 0.74 mmol) was added to a suspension of compound 37(d) (0.13 g, 0.29 mmol) in ethanol (1 mL). The reaction mixture was stirred for 16 hours at room temperature, warmed to reflux for ½ hour, then cooled to room temperature. The mixture was neutralized with 4M HCl$_{(aq)}$ (0.18 mL, 0.74 mmol), filtered, and washed with ethanol/water (1/1, 2 mL). The mother liquor was extracted with ethyl acetate (2×), washed with brine, dried (MgSO$_4$) and concentrated in vacuo. Both residues were combined and purified by column chromatography (silica gel, 99/1 ethyl acetate/acetic acid) to provide 0.078 g (65%) of the desired product.

f. Preparation of 2-(4-fluoro-phenyl)-6-(5-hydroxymethyl-isoxazol-3-yl)-5-isopropoxy-benzofuran-3-carboxylic acid methylamide. 4-Methylmorpholine (23 µL, 0.210 mmol) followed by isobutylchloroformate (27 µL, in 2 mL THF, 0.210 mmol) were added to an ice cooled solution of compound 27(e) (0.078 g, 0.190 mmol) in THF (5 mL). The reaction mixture was stirred for 5 minutes, then methyl amine (2.0M in THF, 0.19 mL, 0.38 mmol) was added. The reaction was allowed to come to room temperature and stirred for 16 hours. The mixture was then partitioned between ethyl acetate and water. The layers were separated, and the aqueous layer washed with ethyl acetate (2×). The combined organic layers were washed with brine, dried (MgSO$_4$) and concentrated in vacuo. Crystallization from ethyl acetate provided 10 mg (12%) of the title compound.

EXAMPLE 38

Preparation of 5-ethoxy-2-(4-fluoro-phenyl)-6-(methanesulfonyl-methyl-amino)-benzofuran-3-carboxylic acid methylamide a. Preparation of compound 38(a) (5-(tert-butyl-dimethylsilanyloxy)-2-(4-fluorophenyl)-6-methanesulfonylamino-benzofuran-3-carboxylic acid methylamide). A mixture of compound 29(a) (6.39 g, 16.9 mmol, which can be prepared according to Example 29, step a above), imidazole (5.00 g, 73.5 mmol) and tert butyldimethylsilyl chloride (5.00 g, 33.2 mmol) in acetonitrile (70 mL) was stirred for 20 hours. The solvent was removed in vacuo, and the crude product was dissolved in 1N HCl and extracted with ethyl acetate. The combined organic layers were concentrated in vacuo, then purified by column chromatography (silica gel, ethyl acetate) to provide 7.20 g (87%) of the desired product as a white solid.

b. Preparation of compound 38(b) (5-(tert-butyl-dimethylsilanyloxy)-2-(4-fluorophenyl)-6-(methanesulfonyl-methyl-amino)-benzofuran-3-carboxylic acid methylamide). A solution compound 38(a) (5.50 g, 11.2 mmol), potassium carbonate (8.0 g, 58 mmol), and iodomethane (17 g, 0.12 mol) in acetonitrile (120 mL) was stirred at 20° C. for 20 hours, then poured into 1N HCl (100 mL). The organic solvents were removed in vacuo, and the aqueous residue was extracted with ethyl acetate. The combined organic layers were concentrated in vacuo, and the resulting solid was triturated with ethyl acetate/hexanes to give 5.60 g (99%) of the desired product as a white solid.

c. Preparation of compound 38(c) (2-(4-fluoro-phenyl)-5-hydroxy-6-(methanesulfonyl-methyl-amino)-benzofuran-3-carboxylic acid methylamide). A solution of compound 38(b) (7.80 g, 15.4 mmol, which can be prepared according to the previous step) in THF (100 mL) was treated with a 1M solution of tetrabutylammonium fluoride (16 mL, 16 mmol) in THF. After 1 hour the solvent was removed in vacuo, and the crude product was dissolved in 1N HCl and extracted with ethyl acetate. The combined organic layers were concentrated in vacuo, and the resulting solid was triturated with ethyl acetate/hexanes to give 5.61 g (99%) of the desired product as a white solid.

d. Preparation of 5-ethoxy-2-(4-fluoro-phenyl)-6-(methanesulfonyl-methyl-amino)-benzofuran-3-carboxylic acid methylamide. A solution of compound 38(c) (0.600 g, 1.53 mmol), potassium carbonate (0.58 g, 4.2 mmol) and iodoethane (1.00 g, 6.41 mmol) in acetonitrile (30 mL) was stirred at reflux for 3 hours. The solvent was removed in vacuo, and the crude product was dissolved in 1N HCl and extracted with ethyl acetate. The combined organic layers were concentrated in vacuo, and the resulting solid was recrystallized from absolute ethanol. The precipitated solid was filtered and dried to provide 0.54 g (84%) of the title compound as a white solid.

EXAMPLE 39

Preparation of 4-[2-(4-fluoro-phenyl)-6-(methanesulfonyl-methyl-amino)-3-methylcarbamoyl-benzofuran-5-yloxymethyl]-2-hydroxy-benzoic acid a. Preparation of compound 39(a) (2,2,7-trimethyl-benzo[1,3]dioxin-4-one). 4-(Dimethylamino)pyridine (DMAP) (0.40 g, 3.29 mmol) and acetone (6.27 mL, 85.44 mmol) were added to a solution of 4-methylsalicylic acid (10.0 g, 65.72 mmol) in 1,2-dimethoxyethane (DME) (50 mL). Thionyl chloride (6.7 mL, 92.01 mmol) was dissolved in DME (5 mL) and added slowly to the reaction mixture. The reaction was stirred at room temperature for 36 hours. The mixture was concentrated, and the crude product was dissolved in ethyl acetate and washed with water. The organics were concentrated, and the product was purified by flash chromatography (silica gel, ethyl acetate/hexanes gradient) to provide 1.40 g (11%) of the desired product as a yellow solid.

b. Preparation of compound 39(b) (7-bromomethyl-2,2-dimethyl-benzo[1,3]dioxin-4-one). To a solution of compound 39(a) (0.67 g, 3.49 mmol, which can be prepared according to the previous step), in carbon tetrachloride (15 mL) was added N-bromosuccinimide (0.74 g, 4.18 mmol)

and benzoyl peroxide (0.068 g, 0.279 mmol). The reaction was refluxed and irradiated with a heat lamp for 5 hours. The reaction was then cooled, and a solid was filtered away. The filtrate was concentrated, dissolved in ethyl acetate and washed with water. The organic layer was concentrated, and the product was purified by flash chromatography (silica gel, ethyl acetate/hexane gradient) to provide 175 mg (19%) of the desired product as a white solid.

c. Preparation of compound 39(c) (5-(2,2-dimethyl-4-oxo-4H-benzo[1,3]dioxin-7-ylmethoxy)-2-(4-fluoro-phenyl)-6-(methanesulfonyl-methyl-amino)-benzofuran-3-carboxylic acid methylamide). Potassium carbonate (0.19 g, 1.38 mmol) and compound 39(b) (0.25 g, 0.917 mmol) were added to a solution of compound 38(d) (0.18 g, 0.459 mmol, which can be prepared according to Example 38 step d above), in acetonitrile (15 mL). The reaction mixture was refluxed for 4 hours and then concentrated in vacuo. The crude product was dissolved in ethyl acetate and washed with water. The organic layer was concentrated to a solid, which was triturated in 20% ethyl acetate/hexanes, filtered, and dried to provide 240 mg (90%) of the desired product as an off-white solid.

d. Preparation of 4-[2-(4-fluoro-phenyl)-6-(methanesulfonyl-methyl-amino)-3-methylcarbamoyl-benzofuran-5-yloxymethyl]-2-hydroxy-benzoic acid. LiOH monohydrate (0.015 g, 0.343 mmol) was added to a suspension of compound 39(c) (0.10 g, 0.172 mmol) in water/THF (10 mL/10 mL). The reaction was stirred at room temperature for 4 hours. The THF was removed by rotary evaporation, and 1M HCl was added until an acidic pH was reached. The precipitate was filtered and dried to provide 65 mg (70%) of the title compound as an off-white solid.

EXAMPLE 40

Preparation of 2-(4-fluoro-phenyl)-6-(5-hydroxymethyl-isoxazol-3-yl)-5-methoxy-benzofuran-3-carboxylic acid methylamide a. Preparation of compound 40(a). ((2,5-dihydroxy-phenyl)-acetic acid methyl ester). A solution of 5-hydroxy-3H-benzofuran-2-one (10.8 g, 71.9 mmol) and Amberlyst®-15 (8.00 g) in dry methanol (25 mL) was stirred at 22° C. for 72 hours. The reaction mixture was filtered through a pad of Celite™ 503 before evaporation of the solvent. The resulting solid was purified by flash column chromatography (silica gel, 20:80 ethyl acetate/hexanes) to provide 12.84 g (98%) of the desired product as a white solid.

b. Preparation of compound 40(b).

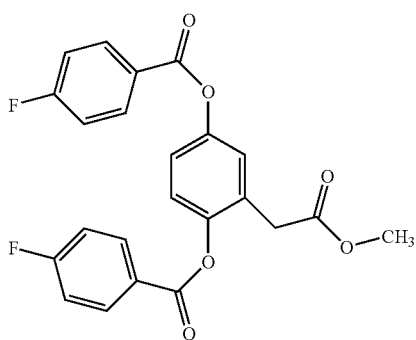

40(b)

A solution of 4-fluoro-benzoyl chloride (4.20 mL, 35.7 mmol) in dichloromethane (01 mL) was added dropwise to a solution of compound 125(a) (3.00 g, 16.5 mmol) and triethylamine (5.00 mL, 35.9 mmol) in dichloromethane (70 mL) at 0° C. over 15 minutes. The reaction mixture was stirred for 18 hours at 22° C., and then concentrated, diluted with 1N HCl (100 mL) and extracted with ethyl acetate. The organic layer was concentrated to a crude oil, which was purified by flash column chromatography (silica gel, ethyl acetate/hexanes gradient) to provide 6.81 g (97%) of the desired compound as a white solid.

c. Preparation of compound 40(c) (3-(4-fluoro-benzoyl)-5-hydroxy-3H-benzofuran-2-one).

Sodium hydride (95% in oil, 0.123 g, 5.13 mmol) was suspended in dry THF (0 mL) at 0° C., and compound 125(f) (1.05 g, 2.46 mmol) was added in one portion. The reaction mixture was stirred at 22° C. for 24 hours. After carefully quenching with water, the reaction mixture was diluted with ethyl acetate and extracted with 1N HCl and brine, then concentrated to give a dark oil. The crude oil was purified by flash column chromatography (silica gel, 60% ethyl acetate/hexanes) to provide 0.74 g (1100%) of the desired compound.

d. Preparation of compound 40(d) (2-(4-fluoro-phenyl)-5-hydroxy-benzofuran-3-carboxylic acid ethyl ester). A solution of compound 40(c) (0.74 g, 2.46 mmol) in dry methanol (50 mL) was treated with concentrated sulfuric acid (0.2 mL), and the mixture was refluxed for 25 hours. The reaction mixture was concentrated, and the resulting solid was purified by flash column chromatography (silica gel, 10% ethyl acetate/hexanes) to provide 0.580 g (78%) of the desired product as a white solid.

e. Preparation of compound 40(e) (2-(4-fluoro-phenyl)-5-methoxy-benzofuran-3-carboxylic acid ethyl ester). The intermediate compound was prepared essentially according to the general procedure described in Example 12, step b above; however, compound 40(d) was used instead of the mixture of compounds 12(a)(i) and 12(a)(ii).

f. Preparation of compound 40(f) (2-(4-fluoro-phenyl)-6-formyl-5-meth oxy-benzofuran-3-carboxylic acid ethyl ester). Titanium tetrachloride, 99% (15.4 mL, 140 mmol) was added to a solution of a,a-dichloromethylmethyl ether (6.45 mL, 71.0 mmol) in dichloromethane (100 mL) at 0° C. under an argon atmosphere. After the addition was complete, compound 40(e) (20.0, 63.6 mmol) dissolved in dichloromethane (75 mL) was added dropwise to the solution. One half hour after the addition was complete, the reaction was cooled in an ice-bath, and water (100 mL) was added dropwise. The reaction was diluted with dichloromethane until homogenous. The layers were separated, and the organic layer washed with 3M HCl (1×100 mL) and brine (1×100 mL), dried over MgSO$_4$, filtered and concentrated in vacuo. The residue was dissolved in ethyl acetate (1.3 L) and enough chloroform to bring everything into solution. The solution was filtered through a plug of Florisil®, concentrated in vacuo, and purified via crystallization from ethyl acetate to provide 5.90 g (27%) of the desired product.

g. Preparation of compound 40(g) (2-(4-fluoro-phenyl)-6-(hydroxyimino-methyl)-5-methoxy benzofuran-3-carboxylic acid ethyl ester). To a suspension of compound 40(f) (3.29 g, 9.61 mmol) in THF (200 mL) was added sodium acetate trihydrate (1.44 g, 10.6 mmol) in water (20 mL), then hydroxylamine hydrochloride (0.73 g, 10.6 mmol). After 1 hour, the reaction was concentrated in vacuo, and the residue was suspended in water. The solid was filtered to yield 3.20 g (93%) of the desired product. The product was taken on to the next step without further purification.

h. Preparation of compound 40(h) (2-(4-fluoro-phenyl)-5-methoxy-6-[5-(tetrahydropyran-2-yloxymethyl)-isoxazol-3-yl]-benzofuran-3-carboxylic acid ethyl ester). Compound 40(g) (3.20 g, 8.95 mmol) in DMF (120 mL) was added dropwise to a solution of N-chlorosuccinimide (1.19 g, 8.95 mmol) and pyridine (catalytic) in DMF (60 mL). The reaction mixture was warmed to 60° C. for 20 hours at which time an additional amount of N-chlorosuccinimide (0.238 g, 1.79 mmol) was added to the reaction. After compound 40(b) was consumed (monitored by TLC), the reaction was cooled to ambient temperature. Triethylamine (1.26 mL, 8.95 mmol) followed by tetrahydro-2-(2-propynloxy)-2H-pyran (2.51 mL, 17.9 mmol) were added. The reaction was warmed to 60° C. for 2 hours, cooled to ambient temperature, and extracted with ethyl acetate (2×100 mL). The combined organic layers were washed with ice cold water (several times) and brine, dried (MgSO$_4$) and concentrated in vacuo. Purification by column chromatography (silica gel, ethyl acetate/hexanes gradient) provided 2.05 g (46%) of the desired product as a white solid.

i. Preparation of compound 40(i) (2-(4-fluoro-phenyl)-5-methoxy-6-[5-(tetrahydropyran-2-yloxymethyl)-isoxazol-3-yl]-benzofuran-3-carboxylic acid). Potassium Hydroxide solution (4N, 1.34 mL, 5.35 mmol) was added to a suspension of compound 40(h) (1.06 g, 2.14 mmol) in ethanol (10 mL). The reaction mixture was warmed to reflux for 2 hours, then cooled to room temperature. The reaction mixture was neutralized with 4M HCl$_{(aq)}$ (1.34 mL, 5.35 mmol), filtered, air dried, and dried under vacuum to provide 0.95 g (95%) of the desired product.

j. Preparation of compound 40(i) (2-(4-fluoro-phenyl)-5-methoxy-6-[5-(tetrahydropyran-2-yloxymethyl)-isoxazol-3-yl]-benzofuran-3-carboxylic acid methylamide). Carbonyldiimidazole (0.401 g, 2.47 mmol) was added to a suspension of compound 40(i) (0.958 g, 2.06 mmol) in dichloromethane. The resulting solution was stirred for 1 hour at ambient temperature. N-methyl amine (2.0M in THF, 1.55 mL, 3.09 mmol) was added, and the reaction was allowed to stir for 20 hours at ambient temperature. The mixture was then refluxed for 1 hour, cooled to ambient temperature and partitioned between water and dichloromethane. The aqueous layer washed with ethyl acetate, and the combined organic layers were washed with brine, dried (MgSO$_4$), filtered and concentrated in vacuo. Purification by column chromatography (silica gel, ethyl acetate/hexanes gradient) provided 0.46 g (46%) of the desired product.

k. Preparation of 2-(4-fluoro-phenyl)-6-(5-hydroxymethyl-isoxazol-3-yl)-5-methoxybenzofuran-3-carboxylic acid methylamide. Pyridinium p-toluenenesulfonate (7 mg, 0.028 mmol) was added to a solution of compound 40(e) (0.135 g, 0.281 mmol) in ethanol (10 mL), THF (3 mL), and water. The reaction mixture was stirred for 20 hours at room temperature. The reaction mixture was then warmed to 95° C. for 4 hours, cooled to room temperature, and concentrated in vacuo. The residue was partitioned between ethyl acetate and water. The organic layer washed with brine, dried (MgSO$_4$) and concentrated in vacuo. Purification by column chromatography (silica gel, ethyl acetate/hexanes gradient) and crystallization from ethyl acetate provided 50 mg (45%) of the title compound.

EXAMPLE 41

Preparation of 2-(4-fluoro-phenyl)-6-[4-(2-hydroxy-ethyl)-isoxazol-3-yl]

a. Preparation of compound 41(a) (2-(4-fluoro-phenyl)-5-methoxy-6-(3a,4,5,6a-tetrahydro-furo[3,2-d]isoxazol-3-yl)-benzofuran-3-carboxylic acid ethyl ester). N-Chlorosuccinimide (0.747 g, 5.59 mmol) and pyridine (catalytic) were added to a solution of compound 40(g) (2.00 g 5.59 mmol, which can be prepared according to Example 40, step g above), in DMF (100 mL). The reaction mixture was warmed to 60° C. for 20 hours. Triethylamine (0.78 mL, 5.59 mmol) followed by 2,3-dihydrofuran (0.85 mL, 11.2 mmol) were added. The reaction was warmed to 60° C. for 1 hour, cooled to ambient temperature, diluted with water to 500 mL, and extracted with ethyl acetate (3×75 mL). The combined organic layers were washed several times with ice cold water, once with brine, then dried (MgSO$_4$) and concentrated in vacuo to provide 2.27 g (95%) of the desired product.

b. Preparation of compound 41(b) (2-(4-fluoro-phenyl)-5-methoxy-6-(3a,4,5,6a-tetrahydro-furo[3,2-d]isoxazol-3-yl)-benzofuran-3-carboxylic acid). Potassium hydroxide solution (4N, 0.73 mL, 2.93 mmol) was added to a suspension of compound 41 (a) (0.500 g, 1.17 mmol) in ethanol (7 mL) and water (2 mL). The reaction mixture was warmed to reflux for 1.5 hours, then cooled to room temperature. The reaction mixture was neutralized with 4M HCl$_{(aq)}$ (0.73 mL, 2.93 mmol), filtered, air dried, and dried under vacuum to provide 0.502 g (quantitative) of the desired product, which was taken on to the next step without further purification.

c. Preparation of compound 41(c) (2-(4-fluoro-phenyl)-5-methoxy-6-(3a,4,5,6a-tetrahydro-furo[3,2-d]isoxazol-3-yl)-benzofuran-3-carboxylic acid methylamide). Carbonyldiimidazole (0.20 g, 1.27 mmol) was added to a suspension of compound 41(b) (0.42 g, 1.05 mmol) in dichloromethane. The resulting solution was stirred for 2 hours at ambient temperature. N-methyl amine (2.0M in THF, 0.79 mL, 1.58 mmol) was added, and the reaction was refluxed for 3 hours, cooled to ambient temperature and partitioned between water and ethyl acetate. The aqueous layer washed with ethyl acetate, then the combined organic layers were washed with brine, dried (MgSO$_4$), filtered, and concentrated in vacuo. The product was purified by column chromatography (silica gel, ethyl acetate/hexanes gradient) to provide 0.30 g (70%) of the desired compound.

d. Preparation of 2-(4-fluoro-phenyl)-6-[4-(2-hydroxy-ethyl)-isoxazol-3-yl]-5-methoxy-benzofuran-3-carboxylic acid methylamide. Compound 41(c) (0.160 g, 0.38 mmol) was suspended in ethanol (15 mL) and concentrated HCl (3 drops). The reaction was warmed to reflux for 50 hours, cooled to ambient temperature, and partitioned between ethyl acetate and water. The layers were separated, and the organic layer washed with brine, dried (MgSO$_4$), filtered, and concentrated in vacuo. Purification by column chromatography (silica gel, ethyl acetate/hexanes gradient) and crystallization from ethyl acetate provided 50 mg (31%) of the title compound.

EXAMPLE 42

Preparation of 2-(4-fluoro-phenyl)-6-[(2-hydroxy-ethyl)-methanesulfonyl-amino]-5-methoxy-benzofuran-3-carboxylic acid methylamide a. Preparation of compound 42(a) (2-(4-fluoro-phenyl)-5-hydroxy-6-nitro-benzofuran-3-carboxylic acid ethyl ester). Boron trichloride (106 mL, 0.106 mol) was added to dropwise to a solution of compound 21 (d) (20.5 g, 0.053 mol, which can be prepared according to Example 21, steps a-d, above) in anhydrous dichloromethane (264 mL), under argon. The reaction mixture was stirred at ambient temperature overnight. The reaction was quenched with ice water and extracted with dichloromethane (3×). The organic layers were combined, dried over magnesium sulfate, filtered, and evaporated. The resulting solid was sonicated in hexanes, filtered and dried to provide 17.82 g (99%) of the product as a yellow solid.

b. Preparation of compound 42(b) (2-(4-fluoro-phenyl)-5-methoxy-6-nitro-benzofuran-3-carboxylic acid ethyl ester). Cesium carbonate (33.04 g, 0.101 mol) and methyl iodide (31.6 mL, 0.507 mol) were added to a solution of compound 42(a) (17.5 g, 0.053 mol) in 1-methyl-2-pyrrolidinone (250 mL). The reaction mixture was heated to 50° C. overnight, quenched with water, extracted with ethyl acetate (3×), and a portion of insoluble product was filtered. The organic layers were combined, dried (MgSO$_4$), and concentrated. The resulting solid was combined with the previously isolated solid to provide 14.91 g (82%) of the product as a yellow solid.

c. Preparation of compound 42(c) (6-amino-2-(4-fluoro-phenyl)-5-methoxy-benzofuran-3-carboxylic acid ethyl ester). 10% Palladium on carbon (0.900 g) was added to mixture of compound 42(b) (7.0 g, 0.0195 mol) in isopropyl acetate (32.0 mL). The reaction mixture was shaken under 50 psig of hydrogen gas on a Parr shaker overnight. The reaction mixture was filtered through Celite™, rinsing with ethyl acetate and methanol. The filtrate was concentrated in vacuo. This reaction was repeated using the same quantities of solvents reactants, and the products of both reactions were combined to provide a total of 12.8 g (99%) of the desired product as a solid.

d. Preparation of compound 42(d) (2-(4-fluoro-phenyl)-6-methanesulfonylamino-5-methoxy-benzofuran-3-carboxylic acid ethyl ester). Methanesulfonyl chloride (0.64 mL, 85.6 mmol) was added to a chilled solution (0° C., ice/water bath) of compound 42(c) (12.8 g, 12.8 mmol) in anhydrous dichloromethane (130 mL), under argon. The reaction mixture was then cooled using an ethanol/ice bath, and N,N-diisopropylethylamine (16.93 mL, 97.2 mmol) was added. The reaction mixture was stirred at ambient temperature overnight. The reaction mixture was diluted with water and extracted with dichloromethane (3×). The organic layers were combined, dried over magnesium sulfate, and evaporated to afford 18.7 g (99%) of the desired product as a solid.

e. Preparation of compound 42(e) (2-(4-fluoro-phenyl)-6-methanesulfonylamino-5-methoxy-benzofuran-3-carboxylic acid). Potassium hydroxide (51.5 g, 0.918 mol) was added to a mixture of compound 42(d) (18.7 g, 0.0459 mol) in ethanol (200 mL) and water (100 mL) under argon. The reaction mixture was heated to reflux for about 7 hours, then stirred at ambient temperature overnight. The reaction mixture was concentrated, and the residue was dissolved in water. The water mixture was acidified with 6N HCl until a solid precipitated. The solid was filtered, washed with water and dried to afford 15.0 g (86%) of the desired product as a tan solid.

f. Preparation of compound 42(f) (2-(4-fluoro-phenyl)-6-methanesulfonylamino-5-methoxy-benzofuran-3-carboxylic acid methylamide). 1,1-Carbonyldiimidazole (8.66 g, 53.3 mmol), followed by methylamine (2.0M in THF, 30.0 mL, 59.3 mmol) were added to a suspension of compound 42 (e) (15 g, 39.5 mmol) in dichloromethane (155 mL) under argon. The reaction mixture was stirred at ambient temperature overnight, diluted with water, extracted with dichloromethane (3×), and a portion of insoluble product was filtered and set aside. The organic layers were combined, dried over magnesium sulfate, and evaporated. The resulting solid was sonicated in water, filtered, and combined with previously isolated product to provide a total of 14.42 g (92%) of the desired product.

g. Preparation of 2-(4-fluoro-phenyl)-6-[(2-hydroxy-ethyl)-methanesulfonyl-amino]-5-methoxy-benzofuran-3-carboxylic acid methylamide. Potassium iodide (80 mg, 0.48 mmol), potassium carbonate (2.82 g, 20.4 mmol), and 2-bromoethanol (3.62 mL, 51 mmol) were added to a solution of compound 42(f) (4.0 g, 10.2 mmol) dissolved in anhydrous DMF (100 mL) under argon. The mixture was heated to 50° C. for 7 hours, and then additional amounts of potassium iodide (80 mg, 0.48 mmol) and 2-bromoethanol (1.81 mL, 25.5 mmol) were added. The mixture was stirred at 50° C. overnight, and then an additional amount of potassium carbonate (19.73 g) was added. The reaction mixture was stirred at 85° C. for about 4 hours, diluted with water, and extracted with ethyl acetate (3×). The organic layers were combined and evaporated. The remaining solid was diluted with water, sonicated and filtered. After several water washings, the solid was dried to afford 3.14 g of crude product, which was subsequently crystallized from hot ethanol.

EXAMPLE 43

Preparation of 5-cyclopropyl-2-(4-fluoro-phenyl)-6-[(2-hydroxy-ethyl)-methanesulfonyl-amino]-benzofuran-3-carboxylic acid methylamide a. Preparation of cyclopropylboronic acid. Cyclopropylboronic acid was prepared from cyclopropylmagnesium bromide, according to the literature procedure: Wallace, D. J., Chen, C., *Tetrahedron Lett.* 2002, 43, 6987-6990, on a 4 g scale (56% yield).

b. Preparation of compound 43(b) (2-(4-fluoro-phenyl)-6-nitro-5-trifluoromethanesulfonyloxy-benzofuran-3-carboxylic acid ethyl ester). N,N-Diisopropylethylamine (8.8 mL, 56 mmol) and 4-(dimethylamino)pyridine (0.618 g, 5.06 mmol) were added to a suspension of compound 42(a) (17.5 g, 50.6 mmol, which can be prepared according to Example 42, step a above), in anhydrous dichloromethane (300 mL) under argon. The reaction mixture was cooled to 0° C. in an ice/water bath, and then trifluoromethanesulfonic anhydride (9.34 mL, 56 mmol) was added. The reaction was stirred at ambient temperature for about 5 hours, and then additional amounts of N,N-diisopropylethylamine (4.4 mL, 28 mmol) and trifluoromethanesulfonic anhydride (4.67 mL, 28 mmol) were added. The reaction was stirred at room temperature overnight, diluted with water and extracted with dichloromethane (3×). The organic layers were washed with water (3×) and 1N HCl (1×), combined, dried over magnesium sulfate, and evaporated. The residue was recrystallized from t-butylmethyl ether to provide a total of 20.36 g (84%) of the desired product as a yellow solid.

c. Preparation of compound 43(c) (5-cyclopropyl-2-(4-fluoro-phenyl)-6-nitro-benzofuran-3-carboxylic acid ethyl ester). Anhydrous toluene (10.0 mL) was added to a mixture of cyclopropylboronic acid (0.271 g, 3.14 mmol), potassium fluoride dihydrate (0.652 g, 6.92 mmol), sodium bromide (0.216 g, 2.16 mmol), tetrakis(triphenylphosphine)palladium (0) (0.073 g, 0.0629 mmol), and compound 43(b) (1.0 g, 2.09 mmol). The resulting solution was degassed with argon through a gas dispersion tube for 10 minutes. The reaction mixture was heated to reflux overnight, diluted with water, and extracted with ethyl acetate (3×). The organic layers were combined, dried over magnesium sulfate, and evaporated. The crude product was purified by column chromatography (silica gel, dry loading, hexane/ethyl acetate gradient) to afford 0.670 g (86%) of the desired product as a solid.

d. Preparation of compound 43(d) (6-amino-5-cyclopropyl-2-(4-fluoro-phenyl)-benzofuran-3-carboxylic acid ethyl ester). 10% Palladium on carbon (0.150 g) and 1N HCl (7 drops) were added to a solution of compound 43(c) (0.665 g, 1.8 mmol) in ethyl acetate (70.0 mL). The reaction mixture was shaken under 50 psig of hydrogen gas on a Parr shaker overnight. The reaction mixture was filtered through Celite™, rinsing with ethyl acetate and methanol. The filtrate was concentrated in vacuo to afford 0.540 g (88%) of the desired product as a solid.

e. Preparation of compound 43(e) (5-cyclopropyl-2-(4-fluoro-phenyl)-6-methanesulfonylamino-benzofuran-3-carboxylic acid). Methanesulfonylchloride (0.270 mL, 3.48 mmol) was added to chilled solution (0° C., ice/water bath) of compound 43(d) (0.535 g, 1.58 mmol) dissolved in dichloromethane (6 mL). The reaction mixture was cooled further in an ethanol/ice bath, and then N,N-diisopropylethylamine (0.688 mL, 3.95 mmol) was added. The reaction was stirred at room temperature overnight, diluted with water, and extracted with dichloromethane (3×). The organic layers were combined, dried over magnesium sulfate, and evaporated to afford 0.653 g (86%) of the bis(sulfonylated) intermediate.

Potassium hydroxide (1.52 g, 27 mmol) was added to a solution of the bis(sulfonylated) intermediate (0.670 g, 1.35 mmol) dissolved in ethanol (10.0 mL) and water (5.0 mL) under argon. The reaction was heated to reflux overnight, and then concentrated in vacuo. The remaining solid was dissolved in water, and the solution was acidified with 1N HCL until a precipitate formed. The solid was filtered and dried to afford 0.532 g (99%) of the desired product.

f. Preparation of compound 43(f) (5-cyclopropyl-2-(4-fluoro-phenyl)-6-methanesulfonylamino-benzofuran-3-carboxylic acid methylamide). Benzotriazol-1-yloxytrispyrrolidinophosphonium hexafluorophosphate (PyBop) (1.02 g, 1.97 mmol) was added to a mixture of methylamine (12.0 mL, 16.3 mmol, 2.0M in THF), DMF (1.0 mL), and compound 43(e) (0.530 g, 1.36 mmol) under argon. The reaction was stirred at room temperature overnight and then concentrated in vacuo. The residue was diluted with water and extracted with ethyl acetate (3×). The organic layers were combined, washed with water, dried over magnesium sulfate, and air-dried to afford 0.347 g (63%) of crude product. A portion of the crude product (100 mg) was purified by reverse phase HPLC (acetonitrile/water gradient) to afford 0.050 g of the desired product.

g. Preparation of compound 43(g) (6-[(2-benzyloxy-ethyl)-methanesulfonyl-amino]-5-cyclopropyl-2-(4-fluoro-phenyl)-benzofuran-3-carboxylic acid methylamide). Potassium carbonate (0.125 g, 0.91 mmol) and benzyl 2-bromoethyl ether (0.105 mL, 0.67 mol) were added to a solution of compound 43(g) (0.120 g, 0.0003 mol), dissolved in acetonitrile (1.5 mL) under argon. The reaction mixture was heated to reflux overnight, diluted with water, and extracted with dichloromethane (3×). The organic layers were combined, dried over magnesium sulfate, and evaporated. The crude product was purified by reprecipitating out of ethyl acetate/hexanes, and the isolated solid was taken on to the next step without further purification.

h. Preparation of (5-cyclopropyl-2-(4-fluoro-phenyl)-6-[(2-hydroxy-ethyl)-methanesulfonyl-amino]-benzofuran-3-carboxylic acid methylamide). 10% Palladium on carbon (0.100 g) was added to mixture of compound 43(g) (0.162 g, 0.41 mmol) in ethyl acetate (20 mL). The reaction mixture was shaken under 50 psig of hydrogen gas on a Parr shaker overnight. The reaction mixture was filtered through Celite™, rinsing with ethyl acetate and methanol. The filtrate was concentrated in vacuo, and the crude product was dissolved in ethyl acetate and precipitated with hexanes. The solid was isolated by filtration to afford 0.083 g of desired product as a tan solid.

EXAMPLE 44

Preparation of 5-ethyl-2-(4-fluoro-phenyl)-6-methanesulfonylamino-benzofuran-3-carboxylic acid methylamide a. Preparation of compound 44(a) (trifluoro-methanesulfonic acid 2-(4-fluoro-phenyl)-6-methanesulfonylamino-3-methylcarbamoyl-benzofuran-5-yl ester). A solution of N-phenyltriflimide (14.2 g, 39.68 mmol) in anhydrous dichloromethane (20 mL) followed by triethylamine (5.4 mL, 52.9 mmol) were introduced to a suspension of compound 38(a) (10 g, 26.45 mmol, which can be prepared according to Example 38 step a above), in anhydrous dichloromethane (110 mL) at 0° C. under argon. The reaction mixture was stirred at room temperature overnight. The reaction mixture was poured into water (150 mL), and the layers were separated. The aqueous layer was extracted with dichloromethane (3×100 mL). The combined organic layers were dried (MgSO$_4$) and concentrated under vacuum. The crude product was purified by recrystallization (1:1 ethyl acetate/hexanes) to provide 12.7 g (94%) of the desired product as light orange crystals.

b. Preparation of compound 44(b) (2-(4-fluoro-phenyl)-6-methanesulfonylamino-5-vinyl-benzofuran-3-carboxylic acid methylamide). Lithium chloride (498 mg, 11.75 mmol), tetrakistriphenylphosphinepalladium(0) (90 mg, 0.08 mmol), triphenylphosphine (83 mg, 0.31 mmol) and 2,6-di-tert-butyl-4-methylphenol (about 16 mg, 0.08 mmol) were added to a solution of compound 44(a) (2.0 g, 3.92 mmol) in anhydrous 1,4-dioxane (17.6 mL) under argon. The reaction was degassed with argon for 15 minutes. Tri-n-butylethyl-stannane (1.17 mL) was introduced via syringe, and the reaction was then heated to 100° C. for 18 hours. The reaction mixture was poured into a saturated aqueous solution of potassium fluoride (50 mL) and vigorously stirred for 4 hours. The layers were separated, and the aqueous layer was extracted with dichloromethane (3×50 mL). The combined organic layers were washed with 10% ammonium hydroxide solution (3×50 mL). The latter aqueous layers were extracted with of dichloromethane (50 mL). All organic layers were combined, dried (MgSO$_4$), and concentrated. The residue was purified by flash chromatography (silica gel, hexane, then dichloromethane/hexanes gradient) and recrystallization (ethyl acetate) to provide 1.10 g (72%) of the desired product.

c. Preparation of 5-ethyl-2-(4-fluoro-phenyl)-6-methanesulfonylamino-benzofuran-3-carboxylic acid methylamide. 10% Palladium on carbon (50 mg) was added to mixture of compound 44(b) (500 mg, 1.29 mmol) in ethyl acetate (50 mL). The reaction mixture was shaken under 50 psig of hydrogen gas on a Parr shaker for 2 days. The reaction mixture was filtered through Celite™, rinsing with ethyl acetate and ethanol, and the product was purified by HPLC (reverse phase, acetonitrile/water gradient with 0.1% of acetic acid) affording 342 mg (74%) of desired product.

EXAMPLE 45

Preparation of 5-ethyl-2-(4-fluoro-phenyl)-6-(methanesulfonyl-methyl-amino)-benzofuran-3-carboxylic acid methylamide The title compound was prepared essentially according to the general procedure described in Example 38, step b above;

however, 5-ethyl-2-(4-fluoro-phenyl)-6-methanesulfonylamino-benzofuran-3-carboxylic acid methylamide (which can be prepared according Example 44) was used instead of compound 38(a). The crude product was purified via HPLC to provide the product in a 64% yield.

EXAMPLE 46

Preparation of 5-ethyl-2-(4-fluoro-phenyl)-6-[(2-hydroxy-ethyl)-methanesulfonyl-amino]-benzofuran-3-carboxylic acid methylamide a. Preparation of compound 46(a) (6-[(2-benzyloxy-ethyl)-methanesulfonyl-amino]-2-(4-fluorophenyl)-5-vinyl-benzofuran-3-carboxylic acid methylamide). Benzyl-2-bromoethyl ether (448 uL, 2.82 mmol) was added to a suspension of compound 44(b) (500 mg, 1.28 mmol), which can be prepared according to Example 44 steps a-b above, and potassium carbonate (534 mg, 3.86 mmol) in anhydrous acetonitrile (6.4 mL), under argon. The mixture was heated to reflux for 12 hours, poured over water (100 mL), and extracted with dichloromethane (3×100 mL). The organic layers were combined, washed with brine (100 mL), dried over $MgSO_4$, and concentrated. The crude product was purified via flash chromatography (silica gel, dichloromethane/methanol gradient) to afford 650 mg (97%) of the desired product.

b. Preparation of 5-ethyl-2-(4-fluoro-phenyl)-6-[(2-hydroxy-ethyl)-methanesulfonyl-amino]-benzofuran-3-carboxylic acid methylamide. 10% Palladium on carbon (3 additions of 50 mg/day, 150 mg total) was added to mixture of compound 46(a) (650 mg, 1.28 mmol) in ethyl acetate (65 mL). The reaction mixture was shaken under 50 psig of hydrogen gas on a Parr shaker for 4 days. The reaction mixture was filtered through Celite™, rinsing with ethyl acetate. The filtrate was concentrated in vacuo, and a solid was isolated. The crude product was purified by HPLC (reverse phase, acetonitrile/water gradient with 0.1% of acetic acid), to afford 398 mg (78%) of the titled compound.

EXAMPLE 47

Preparation of 6-(1-acetyl-pyrrolidin-2-yl)-2-(4-fluoro-phenyl)-5-methoxy-benzofuran-3-carboxylic acid methylamide a. Preparation of compound 47(a) (6-bromo-2-(4-fluoro-phenyl)-5-methoxy-benzofuran-3-carboxylic acid methylamide). The intermediate compound was prepared essentially according to the general procedure described in Example 28, step g above; however, compound 28(c) was used instead of compound 28(f).

b. Preparation of compound 47(b) (2-[2-(4-fluoro-phenyl)-5-methoxy-3-methylcarbamoyl-benzofuran-6-yl]-pyrrole-1-carboxylic acid tert-butyl ester). To a mixture of compound 47(a) (527 mg, 1.40 mmol, which can be prepared according to the general procedures described in the previous step), 1-(t-butoxycarbonyl)pyrrole-2-boronic acid (445 mg, 2.10 mmol) in a degassed solvent of toluene/ethanol/water (20 mL/10 mL/0.5 mL) was added solid $Na_2CO_3$ (371 mg, 3.5 mmol) and tetrakis-triphenylphosphine-palladium(0) (81 mg, 0.07 mmol) at room temperature. After stirring for 20 hours at 85° C. under argon atmosphere, the reaction was quenched with water and extracted with ethyl acetate. The organic phase was washed with water and brine, dried over $MgSO_4$, and concentrated under reduced pressure. The crude product was purified by column chromatography (silica gel, 20% ethyl acetate in hexanes) to yield desired product 550 mg (85%) as a light yellow solid.

c. Preparation of compound 47(c) (2-[2-(4-fluoro-phenyl)-5-methoxy-3-methylcarbamoyl-benzofuran-6-yl]-pyrrolidine-1-carboxylic acid tert-butyl ester). To a solution of compound 47(b) (500 mg, 1.08 mmol) in 4:1 ethyl acetate:ethanol was added activated 10% palladium on carbon (200 mg, 10% weight). The mixture was allowed to stir under 50 psig of hydrogen gas on a Parr-shaker overnight at room temperature. Another portion of activated 10% palladium on carbon (200 mg, 10% weight) was added. The mixture was agitated for another 24 hours under 50 psig of hydrogen gas on a Parr-shaker at room temperature. The reaction was then filtered through a pad of Celite™, rinsing with ethyl acetate. Concentration of the filtrate gave 480 mg (95%) of pure expected compound as a white solid.

d. Preparation of compound 47(d) (2-(4-fluoro-phenyl)-5-methoxy-6-pyrrolidine-2-yl-benzofuran-3-carboxylic acid methylamide). Compound 47(c) (450 mg, 0.96 mmol) in a solution of 20% (vol.) trifluoroacetic acid in dichloromethane was stirred at room temperature for one hour. The solvent was then removed under reduced pressure, and the residue was dissolved in dichloromethane and treated with excess triethylamine for 30 minutes. The solvent was in vacuo, and the residue was used in the next step without further purification.

e. Preparation of compound 6-(1-acetyl-pyrrolidin-2-yl)-2-(4-fluoro-phenyl)-5-methoxy-benzofuran-3-carboxylic acid methylamide. Acetic anhydride (18 μL, 0.186 mmol) was added dropwise to a solution of compound 47(c) (45 mg, 0.124 mmol) in dichloromethane at 0° C. The resulting mixture was stirred at 0° C. to room temperature for 24 hours. The reaction was quenched with water and extracted into ethyl ether. The organic layer washed with $NaHCO_3$ and brine, dried over $Na_2SO_4$, and evaporated under reduced pressure. The crude material was purified by column chromatography (silica gel, 10% methanol in ethyl acetate) to provide 40 mg (80%) of the desired product as a white solid.

EXAMPLE 48

Preparation of 2-(4-fluoro-phenyl)-5-methoxy-6-(2-oxo-oxazolidin-5-yl)-benzofuran-3-carboxylic acid methylamide a. Preparation of compound 48(a) (2-(4-fluoro-phenyl)-6-formyl-5-methoxy-benzofuran-3-carboxylic acid methylamide). $TiCl_4$ (276 μL, 3.0 mmol) was slowly added to a solution of a,a-dichloromethyl methylether (107 μL, 1.20 mmol) in dichloromethane (1 mL) at 0° C., followed by addition of a suspension of compound 47(a)(300 mg, 1 mmol, which can be prepared according to Example 47, step a above) in dichloromethane (6 mL). After the addition was complete, the ice-bath was removed. The mixture was stirred for 1.5 hours at room temperature, then poured into ice water and extracted with ethyl acetate. The organic phase washed with water and brine, dried over $MgSO_4$, and concentrated under reduced pressure. The crude product was purified by column chromatography (silica gel, 30-50% ethyl acetate in hexanes) to yield the desired product 196 mg (60%) as a white solid.

b. Preparation of compound 48(b) (6-(cyano-trimethylsilanyloxy-methyl)-2-[2-(4-fluoro-phenyl)-5-methoxy-benzofuran-3-carboxylic acid methylamide). To a mixture of compound 48(a) (80 mg, 0.25 mmol) and trimethylsilyl cyamide (40 μL, 0.3 mmol) in dichloromethane (1 mL) at 0° C. was added $ZnI_2$ (catalytic amount). After stirred for 30 minutes at 0° C., another portion of trimethylsilyl cyamide (30 μL) was added. The resulting mixture was stirred for one hour at 0° C. and two hours at room temperature. The reaction was quenched with water and extracted with dichloromethane. The organic phase washed with water and brine, dried over MgSO$_4$, and concentrated under reduced pressure. The crude product (90 mg) was taken on to the next step without further purification.

c. Preparation of compound 48(c) (6-(2-amino-1-hydroxy-ethyl)-2-(4-fluoro-phenyl)-5-methoxy-benzofuran-3-carboxylic acid methylamide). To a solution of compound 48(c) (90 mg in 10:1 ethanol/acetic acid) was added activated 10% palladium on carbon (20 mg). The mixture was allowed to stir under 50 psig of hydrogen gas on a Parr-shaker for 48 hours at room temperature. The reaction mixture was filtered through a pad of Celite™, rinsing with ethyl acetate. Concentration of the filtrate under reduced pressure provided 60 mg of the product (90% purity by LC/MS).

d. Preparation of 2-(4-fluoro-phenyl)-5-methoxy-6-(2-oxo-oxazolidin-5yl)-benzofuran-3-carboxylic acid methylamide. To a mixture of compound 48(c) (60 mg, 0.15 mmol, 90% purity) and triethylamine (63 µL, 0.45 mmol) in dichloromethane (1 mL) was added phosgene (12 µL, 20% solution in toluene) at 0° C. The resulting mixture was stirred for one hour at 0° C. and for one hour at room temperature. The solvent was removed under reduced pressure. The residue was purified by HPLC (reverse phase) to provide 35 mg (67%) of the title compound as a white solid.

EXAMPLE 49

Preparation of 2-(4-fluoro-phenyl)-6-(1-hydroxy-1-methyl-ethyl)-5-methoxy-benzofuran-3-carboxylic acid methylamide a. Preparation of compound 49(a) (6-acetyl-2-(4-fluoro-phenyl)-5-isopropoxy-benzofuran-3-carboxylic acid methylamide). A sealed tube was charged with magnetic stirrer, compound 24(b) (1.22 g, 3.0 mmol, which can be prepared according to Example 24, step b above), palladium(II) acetate (34 mg, 0.015 mmol), [1,1'-bis(diphenylphosphino)propane] (DPPP) (136 mg, 0.33 mmol), butyl vinyl ether (1.92 mL, 15 mmol), and K$_2$CO$_3$ (622 mg, 4.5 mmol) in DMF (5 mL). The tube was flushed with argon, sealed, and heated to 100° C. for 24 hours, then cooled to room temperature. 5% HCl (20 mL) was added dropwise over 20 minutes, and the mixture with extracted with ethyl acetate. The organic layer washed with water and brine, dried over MgSO$_4$, and concentrated under reduced pressure. The crude material was purified by column chromatography (silica gel, 20% ethyl acetate in hexanes) to yield 0.94 g (85%) of the desired product.

b. Preparation of compound 49(b) (6-acetyl-2-(4-fluoro-phenyl)-5-hydroxy-benzofuran-3-carboxylic acid methylamide). Boron trichloride (27.1 mL, 1.0M in dichloromethane) was slowly added to a solution of compound 49(a) (5.0 g, 13.6 mmol) in dichloromethane (58 mL) at 0° C. under argon. The mixture was stirred at 0° C. to room temperature for 1 hour. The mixture was poured into ice water (250 mL) and extracted with ethyl acetate. The organic layer washed with saturated NaHCO$_3$ and brine, dried over MgSO$_4$, and concentrated under reduced pressure. The crude material was purified by column chromatography (silica gel, 30% ethyl acetate in hexanes) to yield 3.85 g (87%) of the desired product.

c. Preparation of compound 49(c) (6-acetyl-2-(4-fluoro-phenyl)-5-methoxy-benzofuran-3-carboxylic acid methylamide). To a mixture of compound 49(b) (1.35 g, 4.1 mmol) and cesium carbonate (2.7 g, 8.3 mmol) in NMP (2 mL) was added methyl iodide (0.65 mL, 10.2 mmol). The resulting mixture was stirred at room temperature for 24 hours. The reaction was quenched with water (50 mL) and extracted with ethyl acetate. The organic layer washed with water and brine, dried over MgSO$_4$, and concentrated under reduced pressure. The crude product was purified by column chromatography (silica gel, 35% ethyl acetate in hexanes) to yield 1.17 g (83%) of the desired product.

d. Preparation of 2-(4-fluoro-phenyl)-6-(1-hydroxy-1-methyl-ethyl)-5-methoxy-benzofuran-3-carboxylic acid methylamide. To a stirred solution of methylmagnesium bromide (1.4M in toluene/THF, 2.6 mL, 3.6 mmol) at 0° C. was added compound 49(c) (500 mg, 1.5 mmol) in THF (1 mL). The resulting mixture was stirred at 0° C. to room temperature for 1 hour. The reaction was quenched with saturated NH$_4$Cl (1 mL) and extracted with ethyl acetate. The organic layer washed with water and brine, dried over MgSO$_4$, and concentrated under reduced pressure. The crude material was purified by column chromatography (silica gel, 50% ethyl acetate in hexanes) to provide 361 mg (70%) of the desired product.

EXAMPLE 50

Preparation of 2-(4-fluoro-phenyl)-5-methoxy-6-(5-methyl-[1,2,4]oxadiazol-3-yl)-benzofuran-3-carboxylic acid methylamide a. Preparation of compound 50(a) (6-cyano-2-(4-fluoro-phenyl)-5-methoxy-benzofuran-3-carboxylic acid methyl ester). Anhydrous 1-methyl-2-pyrrolidinone (60 mL) was added to a mixture of compound 28(d) (2.2 g, 5.80 mmol, which can be prepared according to Example 28, steps a-d, above) and copper(I) cyanide (1.04 g, 11.61 mmol) and heated to 170° C. After stirring for 16 hours under argon, the reaction mixture was cooled to room temperature. Water (200 mL) and ethyl acetate (300 mL) were added, and the solution was filtered though Celite™, rinsing with ethyl acetate. The organic layer was separated and washed with water (3×100 mL) and brine, dried over MgSO$_4$, and concentrated under reduced pressure. The crude product was purified by column chromatography (silica gel 20-40% ethyl acetate in hexanes) to yield 1.5 g (79%) of the desired product.

b. Preparation of compound 50(b) (2-(4-fluoro-phenyl)-6-(N-hydroxycarbamimidoyl)-5-methoxy-benzofuran-3-carboxylic acid methyl ester). To a stirred suspension of compound 50(a) (340 mg, 1.046 mmol) in ethanol (5.0 mL) and triethylamine (393 µL, 2.824 mmol) was added hydroxylamine hydrochloride (182 mg, 2.62 mmol). The reaction mixture was stirred at 75° C. for 12 hours, cooled to room temperature, diluted with water (100 mL) and filtered. The isolated solid washed with water and hexanes and dried in a vacuum oven to yield 300 mg (80%) of the desired compound.

c. Preparation of compound 50(c) (2-(4-fluoro-phenyl)-5-methoxy-6-(5-methyl-[1,2,4]oxadiazol-3-yl)-benzofuran-3-carboxylic acid methyl ester). Pyridine (65 mg, 3.3519 mmol) followed by acetic anhydride (237 µL, 2.55 mmol) were added to a solution of compound 50(b) (300 mg, 0.838 mmol) dissolved in 1,2-dichloroethane (10 mL). After refluxing for 12 hours under argon, the reaction mixture was cooled to room temperature, diluted with water, and extracted with dichloromethane. The organic layer washed with water and brine, dried over MgSO$_4$, and concentrated. The crude product was purified by column chromatography (silica gel, 10-30% ethyl acetate in hexanes) to provide 80 mg (50%) of the desired product.

d. Preparation of 2-(4-fluoro-phenyl)-5-methoxy-6-(5-methyl-[1,2,4]oxadiazol-3-yl)-benzofuran-3-carboxylic acid methylamide. The title compound (55 mg) was prepared essentially according to the general procedures described in Example 15, steps b and c, above; however in step b compound 50(c) was used instead of compound 15(a).

EXAMPLE 51

Preparation of 6-(3,5-dimethyl-isoxazol-4-yl)-2-(4-fluoro-phenyl)-5-(3-hydroxy-propoxy)-benzofuran-3-carboxylic acid methylamide a. Preparation of compound 51(a) (6-(3,5-dimethyl-isoxazol-4-yl)-2-(4-fluoro-phenyl)-5-hydroxy-benzofuran-3-carboxylic acid methylamide). The intermediate compound 51(a) was prepared essentially according to the general procedure described in Example 29, step a above; however, 6-(3, 5-dimethyl-isoxazol-4-yl)-2-(4-fluoro-phenyl)-5-methoxy-benzofuran-3-carboxylic acid methylamide (which can be prepared according to Example 28, above) was used instead of 2-(4-fluoro-phenyl)-5-isopropoxy-6-methanesulfonylamino-benzofuran-3-carboxylic acid methylamide.

b. Preparation of 6-(3,5-dimethyl-isoxazol-4-yl)-2-(4-fluoro-phenyl)-5-(3-hydroxypropoxy)-benzofuran-3-carboxylic acid methylamide. Compound 51(a) (0.250 g, 0.657 mmol), 3-bromo-1-propanol (0.12 mL, 1.33 mmol), potassium carbonate (0.227 g, 1.64 mmol) and potassium iodide (0.011 g, 0.066 mmol) were combined with anhydrous acetonitrile (4 mL) in an oven-dried flask under argon. The reaction was refluxed with stirring for 4 hours, cooled to room temperature, and diluted with water (5 mL). The resulting precipitate was filtered, washed with water and hexanes, and dried to provide 0.241 g (84%) of the title compound as a white solid.

By appropriate selection of suitable starting materials, other compounds of the invention may be prepared according to the procedures described in the foregoing examples. Representative examples of further benzofuran derivatives and analogues thus prepared are set forth in Table 1 below.

TABLE 1

| Example Number | Name | NMR data* | Mass Spec | HCV pol-BB7 $IC_{50}(\mu M)$ A=$\leq$0.5$\mu$M B=0.5 to $\leq$5.0$\mu$M C=5.0 to $\leq$30$\mu$M D=>30$\mu$M | Replicon ($\mu$M) |
|---|---|---|---|---|---|
| 1. | 2-Furan-3-yl-5-methoxy-benzofuran-3-carboxylic acid methylamide | *** | $(M+H)^+$=272 | B | <30 |
| 2. | 2-Phenyl-5-trifluoromethoxy-benzofuran-3-carboxylic acid methylamide | $^1$H NMR in Dimethyl-d$_6$ Sulfoxide(DMSO): 8.47-8.49(d, J=4.69Hz, H); 7.88-7.91(dd, J=1.76Hz, 8.21Hz, 2H); 7.80-7.83(d, J=9.38Hz, 1H); 7.50-7.57(m, 3H); 7.38-7.41(d, J=8.79Hz, 1H); 2.83-2.84(d, J=4.69Hz, 3H) | $(M+H)^+$=336 | B | *** |
| 3. | 2-(3,4-Difluoro-phenyl)-5-methoxy-benzofuran-3-carboxylic acid methylamide | $^1$H NMR in DMSO: 8.44(s, 1H); 7.98(m, 1H); 7.74(m, 1H); 7.60(m, 2H); 7.12(m, 1H); 7.03(m, 1H); 3.82(s, 3H); 2.85(d, J=4.2Hz, 3H) | $(M+H)^+$=318 | A | <10 |
| 4. | 2-[4-(Acetylamino-methyl)-phenyl]-5-isopropoxy-benzofuran-3-carboxylic acid methylamide | $^1$H NMR in DMSO: 8.35(brm, 2H); 7.78(d, 2H, J=8.21); 7.52(d, 1H, J=8.79); 7.36(d, 2H, J=7.03); 7.04(d, 1H, J=2.34); 6.93(dd, 1H, J=8.79, 2.34); 4.59(m, 1H); 4.28(d, 2H, J=5.86); 2.80(d, 3H, J=4.69); 1.87(s, 3H); 1.26(d, 6H, J=5.86) | $(M+H)^+$=381 | B | <30 |
| 5. | 2-(4-Hydroxy-phenyl)-5-isopropoxy-benzofuran-3-carboxylic acid methylamide | $^1$H NMR in DMSO: 9.91(s, 1H); 8.20(d, 1H, J=4.69); 7.70(d, 2H, J=8.79); 7.47(d, 1H, J=8.79); 7.02(d, 1H, J=2.34); 6.86(m, 3H); 4.57(m, 1H); 2.79(d, 3H, J=4.69); 1.26(d, 6H, J=5.86) | $(M-H)^-$=324 | B | <10 |
| 6. | 2-(4-Fluoro-phenyl)-5-isopropoxy-6-pyrrolidin-1-yl-benzofuran-3-carboxylic acid methylamide | $^1$H NMR in DMSO: 8.26(d, J=4.84, 1H); 7.89-7.84(m, 2H); 7.31(t, J=8.79, 2H); 6.98(s, 1H); 6.90(s, 1H); 4.56(septet, J=6.15, 1H); 3.33-3.29(m, 4H); 2.81(d, J=4.40, 3H); 1.90-1.86(m, 4H); 1.29(d, J=6.15, 6H) | $(M+H)^+$=397 | A | <1 |
| 7. | 5-Difluoromethoxy-2-(4-fluoro-phenyl)-benzofuran-3-carboxylic acid methylamide | $^1$H NMR in Trichloromethane-d(CDCl$_3$): 7.92(m, 2H); 7.61(d, 1H, J=2.93); 7.48(d, 1H, J=8.79); 7.22-7.13(m, 3H); 6.54(t, 1H, J=74); 5.80(brs, 1H); 3.00(d, 3H, J=5.27) | $(M+H)^+$=336 | B | <10 |

TABLE 1-continued

| Example Number | Name | NMR data* | Mass Spec | HCV pol-BB7 IC$_{50}$(μM) A=≦0.5μM B=0.5 to ≦5.0μM C=5.0 to ≦30μM D=>30μM | Replicon (μM) |
|---|---|---|---|---|---|
| 8. | 2-(4-Fluoro-phenyl)-5-isopropoxy-6-(2-methoxy-ethylamino)-benzofuran-3-carboxylic acid methylamide | $^1$H NMR in DMSO: 8.25(d, J=4.69, 1H); 7.88-7.83(m, 2H); 7.31(t, J=8.79, 2H); 6.97(s, 1H); 6.83(s, 1H); 5.04(t, J=5.27, 1H); 4.62-4.50(septet, J=5.27, 1H); 3.56(t, J=5.27, 2H); 3.33-3.30(m, 5H); 2.82(d, J=4.69, 3H); 1.31(d, J=5.86, 6H) | (M+H)$^+$=401 | A | <1 |
| 9. | 5-Methyl-2-phenyl-benzofuran-3-carboxylic acid methylamide | $^1$H NMR in CDCl$_3$: 7.91-7.86(m, 2H); 7.66(s, 1H); 7.52-7.37(m, 4H); 7.14(d, J=8.8Hz, 1H); 5.81(brs, 1H); 2.97(d, J=4.7Hz, 3H); 2.46(s, 3H) | (M+H)$^+$=266 | B | <10 |
| 10. | 5-Methyl-2-(4-fluoro-phenyl)benzofuran-3-carboxylic acid methylamide | $^1$H NMR in CDCl$_3$: 7.97-7.93(m, 2H); 7.59(s, 1H); 7.39(d, J=8.2Hz, 1H); 7.19-7.14(m, 3H); 5.81(br s, 1H); 3.02(d, J=5.3Hz, 3H); 2.47(s, 3H) | (M+H)$^+$=284 | B | <10 |
| 11. | 2-Phenyl-5-(2,2,2-trifluoro-ethoxy)-benzofuran-3-carboxylic acid methylamide | $^1$H NMR in CDCl$_3$: 7.87(dd, 2H); 7.65(dd, 1H); 7.47-7.54(m, 4H); 7.08(dd, 1H); 5.8(s, br, 1H); 3.93(s, 2H); 2.97(d, 3H) | (M+H)$^+$=350 | D | <30 |
| 12. | 2-(4-Fluoro-phenyl)-5-methoxy-benzofuran-3-carboxylic acid methylamide | $^1$H NMR in DMSO: 8.37(br.s, 1H); 7.91-7.96(m, 2H); 7.56-7.58(d, J=8.79Hz 1H); 7.34-7.40(t, J=8.79Hz, 2H); 7.09-7.10(d, J=2.35Hz, 1H); 6.97-7.00(dd, J=2.35Hz, 8.79Hz, 1H); 3.82(s, 3H); 2.83-2.8(d, J=4.69Hz, 3H) | (M+H)$^+$=299.9 | A | <10 |
| 13. | 6-Bromo-2-(4-fluoro-phenyl)-5-methoxy-benzofuran-3-carboxylic acid methylamide | $^1$H NMR in DMSO: 8.42(d, J=4.69Hz, 1H); 8.01(s, 1H); 7.90-7.94(m, 2H); 7.35-7.41(t, J=8.79Hz, 2H); 7.23(s, 1H); 3.91(s, 3H); 2.83-2.85(d, J=4.69Hz, 3H) | *** | A | <1 |
| 14. | 5-Methoxy-6-methyl-2-phenyl-benzofuran-3-carboxylic acid methylamide | $^1$H NMR in DMSO: 8.34-8.36(d, J=4.69Hz, 1H); 7.83-7.86(dd, J=1.76Hz, 8.79Hz, 2H); 7.43-7.53(m, 4H); 7.04(s, 1H); 3.85(s, 3H); 2.83-2.84(d, J=4.69Hz, 3H); 2.28(s, 3H) | (M+H)$^+$=296 | A | <1 |
| 15. | 6-(3-Amino-pyrrolidin-1-yl)-2-(4-fluoro-phenyl)-5-isopropoxy-2,3-dihydro-benzofuran-3-carboxylic acid methylamide | *** | (M+H)$^+$=412 | C | <30 |
| 16. | 6-Amino-2-(4-fluoro-phenyl)-5-isopropoxy-benzofuran-3-carboxylic acid methylamide | $^1$H NMR in CDCl$_3$: 7.82(dd, 2H, J=5.5 and 8.7Hz); 7.22(s, 1H); 7.18(t, 2H, J=8.7Hz); 6.84(s, 1H); 5.76(brs, 1H); 4.61(heptuplet, J=6.1Hz); 2.96(d, J=4.9Hz, 3H); 1.92(brs, 2H); 1.40(d, J=6.1Hz, 6H) | (M+H)$^+$=343 | A | <10 |
| 17. | 6-Amino-2-(4-fluoro-phenyl)-5-methoxy-benzofuran-3-carboxylic acid methylamide | $^1$H NMR in methanol-d$_4$(CD$_3$OD): 7.81(m, 2H); 7.20(m, 2H); 7.02(s, 1H); 6.91(s, 1H); 4.72(s, 1H); 3.91(s, 3H); 2.93(s, 3H) | (M+H)$^+$=315 | B | <10 |
| 18. | 6-Acetylamino-2-(4-fluoro-phenyl)-5-methoxy-benzofuran-3-carboxylic acid methylamide | $^1$H NMR in CDCl$_3$: 7.95(brs, 1H); 7.83(m, 2H); 7.46(m, 1H); 7.38(s, 1H); 7.28(m, 2H); 5.76(brs, 1H); 3.96(s, 3H); 2.98(s, 3H); 2.21(s, 3H) | (M+H)$^+$=357 | A | <1 |
| 19. | 2-(4-Fluoro-phenyl)-5-isopropoxy-6- | $^1$H NMR in CDCl$_3$: 7.81(dd, J=8.7 & 5.1Hz, 2H); | (M+H)$^+$=357 | A | <1 |

TABLE 1-continued

| Example Number | Name | NMR data* | Mass Spec | HCV pol-BB7 IC$_{50}$(μM) A=≦0.5μM B=0.5 to ≦5.0μM C=5.0 to ≦30μM D=>30μM | Replicon (μM) |
|---|---|---|---|---|---|
| | methylamino-benzofuran-3-carboxylic acid methylamide | 7.25(s, 1H); 7.14(t, J=9.3Hz, 2H); 6.66(s, 1H); 5.78(brs, 1H); 4.63(septuplet, J=6.3Hz, 1H); 4.55(brs, 1H); 2.97(d, J=4.8Hz, 3H); 2.91(s, 3H); 1.37(d, J=6.3Hz, 6H) | | | |
| 20. | 6-Dimethylamino-2-(4-fluoro-phenyl)-5-isopropoxy-benzofuran-3-carboxylic acid methylamide | $^1$H NMR in CDCl$_3$: 7.51(dd, J=8.7 & 5.1Hz, 2H); 7.28(s, 1H); 7.26(m, 3H); 5.80(brs, 1H); 4.70(septuplet, J=6.3Hz, 1H); 2.98(d, J=4.9Hz, 3H); 2.91(s, 6H); 1.42(d, J=6.3Hz, 6H) | (M+H)$^+$=371 | A | <1 |
| 21. | 2-(4-Fluoro-phenyl)-5-isopropoxy-6-methanesulfonylamino-benzofuran-3-carboxylic acid methylamide | $^1$H NMR in CDCl$_3$: 7.81(dd, J=8.7 & 4.1Hz, 2H); 7.73(s, 1H); 7.42(s, 1H); 7.19(t, J=8.7Hz, 2H); 6.90(s, 1H); 5.81(brs, 1H); 4.75(septuplet, J=6.3Hz, 1H); 2.98(s, 3H); 2.95(d, J=2.6Hz, 3H); 1.40(d, J=6.3Hz, 6H) | (M+H)$^+$=421 | A | <1 |
| 22. | 6-Ethylamino-2-(4-fluoro-phenyl)-5-isopropoxy-benzofuran-3-carboxylic acid methylamide | $^1$H NMR in CDCl$_3$: 7.81(dd, J=8.8, 5.3Hz, 2H); 7.18(s, 1H); 7.16(t, J=8.8Hz, 2H); 6.67(s, 1H); 5.76(brs, 1H); 4.61(heptuplet, J=6.2Hz, 1H,); 3.20(quadruplet, J=7.0Hz, 2H); 2.97(d, J=4.8Hz, 3H); 1.38(d, J=6.2Hz, 6H); 1.32(t, J=7.0Hz, 3H) | (M+H)$^+$=371 | A | <1 |
| 23. | 6-Diethylamino-2-(4-fluoro-phenyl)-5-isopropoxy-benzofuran-3-carboxylic acid methylamide | $^1$H NMR in CDCl$_3$: 7.83(dd, J=8.8, 5.3Hz, 2H); 7.26(s, 1H); 7.15(d, J=8.8Hz, 2H); 7.05(s, 1H); 5.78(brs, 1H,); 4.17(heptuplet, J=6.1Hz, 1H); 3.18(m, 4H); 2.95(d, 5.0Hz, 3H); 1.38(d, J=6.1Hz, 6H); 1.32(t, J=7.0Hz, 6H) | (M+H)$^+$=399 | A | <1 |
| 24. | 2-(4-Fluoro-phenyl)-5-isopropoxy-6-morpholin-4-yl-benzofuran-3-carboxylic acid methylamide | $^1$H NMR in DMSO: 8.30-8.31(d, J=4.69Hz, 1H); 7.88-7.93(m, 2H); 7.31-7.37(t, J=8.79Hz, 2H); 7.19(s, 1H); 7.07(s, 1H); 4.58-4.66(septet, J=6.45Hz, 1H); 3.75-3.77(m, 4H); 3.02-3.05(m, 4H); 2.82-2.83(d, J=4.69Hz, 3H); 1.29-1.31(d, J=6.45Hz, 6H) | (M+H)$^+$=413 | A | <1 |
| 25. | 5-Methoxy-4-methyl-2-phenyl-benzofuran-3-carboxylic acid methylamide | $^1$H NMR in CDCl$_3$: 7.84-7.81(m, 2H); 7.48-7.40(m, 3H); 7.30-7.26(m, 1H); 6.93(d, J=8.7Hz, 1H); 3.86(s, 3H); 3.01(d, J=4.8Hz, 3H); 2.40(s, 3H) | (M+H)$^+$=296 | D | >30 |
| 26. | 5-Cyano-2-phenyl-benzofuran-3-carboxylic acid methylamide | $^1$H NMR in CDCl$_3$: 8.32(s, 1H); 7.89-7.85(m, 2H); 7.62-7.47(m, 5H); 5.80(s, 1H); 2.98(d, J=5.1Hz, 3H); | (M−H)$^-$=275 | C | <30 |
| 27. | 5-Isopropoxy-2-pyridin-4-yl-benzofuran-3-carboxylic acid methylamide | $^1$H NMR in CDCl$_3$: 8.70(d, J=5.4Hz, 2H); 7.84(dd, J=1.2Hz, 4.2HZ, 2H); 7.43(d, J=8.7Hz, 1H); 7.21(d, J=2.7Hz, 1H); 7.00(dd, J=2.1Hz, 8.7Hz, 1H); 5.91(brs, 1H); 4.54(m, 1H); 3.07(d, J=5.1Hz, 3H); 1.36(d, J=5.7Hz, 3H) | (M+H)$^+$=311 | C | >30 |
| 28. | 6-(3,5-Dimethyl-isoxazol-4-yl)-2-(4-fluoro-phenyl)-5-methoxy-benzofuran-3-carboxylic acid methylamide | $^1$H NMR in CDCl$_3$: 7.85-7.89(m, 2H); 7.43(s, 1H); 7.25(s, 1H); 7.18-7.23(t, J=8.79Hz, 2H); 5.79(brs, 1H); 3.86(s, 3H); 3.00-3.02(d, J=5.28Hz, 3H); 2.32(s, 3H); 2.18(s, 3H) | (M+H)$^+$=395 | A | <1 |

TABLE 1-continued

| Example Number | Name | NMR data* | Mass Spec | HCV pol-BB7 IC$_{50}$(μM) A=≤0.5μM B=0.5 to ≤5.0μM C=5.0 to ≤30μM D=>30μM | Replicon (μM) |
|---|---|---|---|---|---|
| 29. | 2-(4-Fluoro-phenyl)-6-(methanesulfonyl-methyl-amino)-5-methoxy-benzofuran-3-carboxylic acid methylamide | $^1$H NMR in CDCl$_3$: 7.86(m, 2H); 7.56(s, 1H); 7.45(s, 1H); 7.28(t, 8.3Hz, 2H); 5.77(brs, 1H); 3.98(s, 3H); 3.33(s, 3H); 2.98(d, J=5.2Hz, 3H); 2.96(s, 3H) | (M+H)$^+$=407 | A | <1 |
| 30. | 2-(4-Fluoro-phenyl)-5-(4-methoxy-benzyloxy)-6-morpholin-4-yl-benzofuran-3-carboxylic acid methylamide | $^1$H NMR in CDCl$_3$: 7.84(dd, J=8.4, 5.2Hz, 2H); 7.40(d, J=8.3Hz, 2H); 7.37(s, 1H); 7.15(t, J=8.4Hz, 2H); 7.06(s, 1H); 6.93(d, J=8.8Hz, 2H); 5.82(d, J=3.9Hz, 1H); 5.09(s, 2H); 3.85(t, J=4.4Hz, 4H); 3.82(s, 3H); 3.11(t, J=4.4Hz, 4H); 2.97(d, J=4.8Hz, 3H) | (M+H)$^+$=491 | A | <1 |
| 31. | 2-(4-Fluoro-phenyl)-6-[methanesulfonyl-(4 methoxy-benzyl)-amino]-5-(4-methoxy-benzyloxy)-benzofuran-3-carboxylic acid methylamide | $^1$H NMR in DMSO: 8.38(d, J=4.1Hz, 1H); 7.88(dd, J=8.4, 5.2Hz, 2H); 7.48(d, J=8.8Hz, 2H); 7.34(t, J=8.8Hz, 2H); 7.29(s, 1H); 7.28(s, 1H); 7.12(d, J=8.8Hz, 2H); 7.00(d, J=8.2Hz, 2H); 6.79(d, J=8.8Hz, 2H); 5.13(s, 2H); 4.60(br m, 2H); 3.77(s, 3H); 3.66(s, 3H); 2.94(s, 3H); 2.80(d, J=4.7Hz, 3H) | (M+H)$^+$=619 | A | <1 |
| 32. | 5-Ethoxy-6-(ethyl-methanesulfonyl-amino)-2-(4-fluoro-phenyl)-benzofuran-3-carboxylic acid methylamide | $^1$H NMR in DMSO: 8.41(d, J=4.1Hz, 1H); 7.94(dd, J=8.2, 5.3Hz, 2H); 7.55(s, 1H); 7.36(t, J=8.2Hz, 2H); 7.16(s, 1H); 4.14(q, J=7.0Hz, 2H); 3.62(q, J=7.0Hz, 2H); 3.01(s, 3H); 2.82(d, J=4.7Hz, 3H); 1.38(t, J=7.0Hz, 3H); 1.05(t, J=7.0Hz, 3H) | (M+H)$^+$=435 | A | <1 |
| 33. | 2-(4-Fluoro-phenyl)-6-morpholin-4-yl-5-(thiazol-2-ylmethoxy)-benzofuran-3-carboxylic acid methylamide | $^1$H NMR in DMSO: 8.35(d, J=4.4Hz, 1H); 7.95-7.80(m, 4H); 7.35-7.25(m, 4H); 5.49(s, 2H); 3.78(m, 4H); 3.06(m, 4H); 2.83(d, J=4.4Hz, 3H) | (M+H)$^+$=468 | A | <1 |
| 34. | 2-(4-Fluoro-phenyl)-5-isopropoxy-6-[methanesulfonyl-(2-oxo-propyl)-amino]-benzofuran-3-carboxylic acid methylamide | $^1$H NMR in DMSO: 8.38(d, J=4.8Hz, 1H); 7.94(dd, J=8.4, 5.3Hz, 2H); 7.71(s, 1H); 7.36(t, J=8.8Hz, 2H); 7.15(s, 1H); 4.77(septet, J=6.1Hz, 1H); 4.04(s, 2H); 3.04(s, 3H); 2.81(d, J=4.4Hz, 3H); 2.11(s, 3H); 1.36(d, J=6.1Hz, 6H) | (M+H)$^+$=477 | A | <1 |
| 35. | 2-(4-Fluoro-phenyl)-6-morpholin-4-yl-5-(thiazol-4-ylmethoxy)-benzofuran-3-carboxylic acid methylamide | $^1$H NMR in CDCl$_3$: 8.84(d, 1H, J=1.76); 7.88(m, 2H); 7.44(s, 2H); 7.17(t, 2H, J=8.79); 7.10(s, 1H); 5.77(brs, 1H); 5.37(s, 2H); 3.89(m, 4H); 3.16(m, 4H); 3.00(d, 3H, J=4.69) | (M+H)$^+$=468 | A | <1 |
| 36. | 2-(4-Fluoro-phenyl)-5-isopropoxy-6-(methanesulfonyl-thiazol-4-ylmethyl-amino)-benzofuran-3-carboxylic acid methylamide | $^1$H NMR in CDCl$_3$: 8.69(d, 1H, J=2.20Hz); 7.77(m, 2H); 7.40(s, 1H); 7.37(s, 1H); 7.30(d, 1H, J=2.20Hz); 7.18(t, 2H, J=8.79Hz); 5.67(brs, 1H); 5.03(brs, 2H); 4.79(m, 1H); 3.07(s, 3H); 2.95(d, 3H, J=4.84Hz); 1.44(d, 6H, J=5.72Hz) | (M+H)$^+$=518 | A | <1 |
| 37. | 2-(4-Fluoro-phenyl)-6-(5-hydroxymethyl-isoxazol-3-yl)-5-isopropoxy-benzofuran-3-carboxylic acid methylamide | $^1$H NMR in CD$_3$OD: 7.94(s, 1H); 7.92(dd, J=9.2, 5.3Hz, 2H); 7.32(s, 1H); 7.25(apparent triplet, J=8.8Hz, 2H); 6.87(s, 1H); 4.75(m, 1H); 4.72(s, 2H); 2.95(s, 3H); 1.39(d, J=5.7Hz, 6H) | (M+H)+=425 | A | <1 |

TABLE 1-continued

| Example Number | Name | NMR data* | Mass Spec | HCV pol-BB7 IC$_{50}$(μM) A=≤0.5μM B=0.5 to ≤5.0μM C=5.0 to ≤30μM D=>30μM | Replicon (μM) |
|---|---|---|---|---|---|
| 38. | 5-Ethoxy-2-(4-fluoro-phenyl)-6-(methanesulfonyl-methyl-amino)-benzofuran-3-carboxylic acid methylamide | $^1$H NMR in DMSO: 8.39(d, J=4.0Hz, 1H); 7.92(dd, J=8.8, 5.3Hz, 2H); 7.59(s, 1H); 7.36(t, J=8.8Hz, 2H); 7.17(s, 1H); 4.16(q, J=7.0Hz, 2H); 3.19(s, 3H); 3.01(s, 3H); 2.81(d, J=4.4Hz, 3H); 1.40(t, J=7.0Hz, 3H) | (M+H)$^+$=421 | A | <1 |
| 39. | 4-[2-(4-Fluoro-phenyl)-6-(methanesulfonyl-methyl-amino)-3-methylcarbamoyl-benzofuran-5-yloxymethyl]-2-hydroxy-benzoic acid | $^1$H NMR in DMSO: 8.39(brd, 1H, J=4.69Hz); 7.93(m, 2H); 7.84(d, 1H, J=8.21Hz); 7.72(s, 1H); 7.39(t, 2H, J=8.79Hz); 7.30(s, 1H); 7.12(m, 2H); 5.27(s, 2H); 3.24(s, 3H); 3.00(s, 3H); 2.83(d, 3H, J=4.69Hz) | (M−H)$^−$=541 | A | <10 |
| 40. | 2-(4-Fluoro-phenyl)-6-(5-hydroxymethyl-isoxazol-3-yl)-5-methoxy-benzofuran-3-carboxylic acid methylamide | $^1$H NMR in DMSO: 8.44(brq, J=4.83Hz, 1H); 7.97(m, 3H); 7.39(t, J=8.79Hz, 2H); 7.29(s, 1H); 6.80(d, J=0.879Hz, 1H); 5.66(t, J=6.15 & 5.71Hz, 1H); 4.63(d, J=6.15Hz, 2H); 3.93(s, 3H); 2.86(d, J=4.39Hz, 3H) | (M+H)$^+$=397.0 | A | <1 |
| 41. | 2-(4-Fluoro-phenyl)-6-[4-(2-hydroxy-ethyl)-isoxazol-3-yl]-5-methoxy-benzofuran-3-carboxylic acid methylamide | $^1$H NMR in CDCl$_3$: 8.40(s, 1H); 7.86(dd, J=5.27, 8.79Hz, 2H); 7.52(s, 1H); 7.45(s, 1H); 7.20(t, J=8.35, 8.79Hz, 2H); 5.81(brs, 1H); 3.87(s, 3H); 3.69(q, J=6.15Hz, 2H); 3.00(d, J=4.83Hz, 3H); 2.64(t, J=6.15Hz, 2H); 1.45(t, J=5.27, 5.71Hz, 1H). | (M+H)$^+$=411 | A | <1 |
| 42. | 2-(4-Fluoro-phenyl)-6-[(2-hydroxy-ethyl)-methanesulfonyl-amino]-5-methoxy-benzofuran-3-carboxylic acid methylamide | $^1$H NMR in DMSO: 8.49(d, J=4.84Hz, 1H); 7.96-7.90(m, 2H); 7.66(s, 1H); 7.41(t, J=7.03Hz, 2H); 7.2(s, 1H); 4.75(t, J=5.71Hz, 2H); 3.91(s, 3H); 3.44(brs, 1H); 3.41(d, J=5.27Hz, 2H); 3.05(s, 3H); 2.84(d, J=4.39Hz, 3H) | (M+H)$^+$=437 | A | <1 |
| 43. | 5-Cyclopropyl-2-(4-fluoro-phenyl)-6-[(2-hydroxy-ethyl)-methanesulfonyl-amino]-benzofuran-3-carboxylic acid methylamide | $^1$H NMR in CDCl$_3$: 7.90-7.85(m, 2H); 7.55(s, 1H); 7.35(s, 1H); 7.22-7.16(m, 2H); 5.74(brs, 1H); 4.09-4.03(m, 1H); 3.75(s, 3H); 3.14(s, 3H); 2.99(d, J=4.40Hz, 3H); 2.40-2.30(m, 1H); 1.95(m, 1H); 1.10-0.98(m, 2H); 0.88(m, 1H); 0.68(m, 1H) | (M+H)$^+$=447 | A | <1 |
| 44. | 5-Ethyl-2-(4-fluoro-phenyl)-6-methanesulfonylamino-benzofuran-3-carboxylic acid methylamide | $^1$H NMR in DMSO: 9.20(brs, 1H); 8.61(m, 1H); 7.93(dd, J=5.3 & 8.8Hz, 2H); 7.60(s, 1H); 7.48(s, 1H); 7.37(t, J=8.8Hz, 2H); 3.05(s, 3H); 2.83(d, J=4.7Hz, 3H); 2.81(q, J=7.7Hz, 2H); 1.21(t, J=7.7Hz, 3H) | (M+H)$^+$=391 | A | <10 |
| 45. | 5-Ethyl-2-(4-fluoro-phenyl)-6-(methanesulfonyl-methyl-amino)-benzofuran-3-carboxylic acid methylamide | $^1$H NMR in DMSO: 8.50(m, 1H); 7.94(dd, J=5.3 & 8.8Hz, 2H); 7.89(s, 1H); 7.54(s, 1H); 7.60(t, J=8.8Hz, 2H); 3.29(q, J=7.0Hz, 2H); 3.21(s, 3H); 3.13(s, 3H); 2.83(d, J=4.7Hz, 3H); 1.21(t, J=7.0Hz, 3H) | (M+H)$^+$=405 | A | <1 |
| 46. | 5-Ethyl-2-(4-fluoro-phenyl)-6-[(2-hydroxy-ethyl)-methanesulfonyl-amino]-benzofuran-3-carboxylic acid methylamide | $^1$H NMR in DMSO: 8.45(m, 1H); 7.94(dd, J=5.3 & 9.4Hz, 2H); 7.81(s, 1H); 7.55(s, 1H); 7.39(t, J=8.8Hz, 2H); 3.72(m, 1H); 3.58(m, 1H); 3.4(m, 3H); 3.15(s, 3H); 2.84(d, | (M+H)$^+$=435 | A | <1 |

TABLE 1-continued

| Example Number | Name | NMR data* | Mass Spec | HCV pol-BB7 IC$_{50}$(μM) A=≦0.5μM B=0.5 to ≦5.0μM C=5.0 to ≦30μM D=>30μM | Replicon (μM) |
|---|---|---|---|---|---|
| | | J=4.7Hz, 3H); 2.82(q, J=7.0Hz, 2H); 1.25(t, J=7.0Hz, 3H) | | | |
| 47. | 6-(1-Acetyl-pyrrolidin-2-yl)-2-(4-fluoro-phenyl)-5-methoxy-benzofuran-3-carboxylic acid methylamide | $^1$H NMR in CDCl$_3$: 7.85(m, 2H); 7.36(s, 1H); 7.20(m, 3H); 5.78(brs, 1H); 5.40(m, 1H); 3.92(s, 3H); 3.40-3.91(m, 2H); 2.99(d, J=4.8Hz, 3H); 1.51-2.0(m, 4H); 1.85(s, 3H) | (M−H)$^−$=411.1 | A | <1 |
| 48. | 2-(4-Fluoro-phenyl)-5-methoxy-6-(2-oxo-oxazolidin-5-yl)-benzofuran-3-carboxylic acid methylamide | $^1$H NMR in(CD$_3$)$_2$CO: 8.03(m, 2H); 7.68(s, 1H); 7.40(brs, 1H); 7.20-7.31(4H); 5.14(m, 1H); 3.90(s, 3H); 3.60(m, 1H); 3.38(m, 1H); 2.94(d, J=4.8Hz, 3H) | (M+H)$^+$=385.0 | A | <10 |
| 49. | 2-(4-Fluoro-phenyl)-6-(1-hydroxy-1-methyl-ethyl)-5-methoxy-benzofuran-3-carboxylic acid methylamide | $^1$H NMR in CDCl$_3$: 7.85(m, 2H); 7.50(s, 1H); 7.39(s, 1H); 7.20(m, 2H); 5.75(brs, 1H); 4.17(s, 1H); 3.99(s, 3H); 2.98(d, J=4.8Hz, 3H); 1.66(s, 6H) | (M+H)$^+$=358.1 | A | <1 |
| 50. | 2-(4-Fluoro-phenyl)-5-methoxy-6-(5-methyl-[1,2,4]oxadiazol-3-yl)-benzofuran-3-carboxylic acid methylamide | $^1$H NMR in CDCl$_3$: 8.12(s, 1H); 7.90-7.86(m, 2H); 7.48(s, 1H); 7.24-7.18(m, 2H); 5.78(s, 1H); 4.03(s, 3H); 3.0(d, J=4.8Hz, 3H); 2.67(s, 3H) | (M+H)$^+$=382 | A | <1 |
| 51. | 6-(3,5-Dimethyl-isoxazol-4-yl)-2-(4-fluoro-phenyl)-5-(3-hydroxy-propoxy)-benzofuran-3-carboxylic acid methylamide | $^1$H NMR in DMSO: 8.41-8.43(d, J=4.69Hz, 1H), 7.92-7.97(m, 2H); 7.57(s, 1H); 7.35-7.41(t, J=8.79Hz, 2H); 7.23(s, 1H); 4.49-4.52(t, J=5.28Hz, 1H); 4.06-4.11(t, J=6.45Hz, 2H); 3.43-3.49(q, J=5.86Hz, 2H); 2.84-2.86(d, J=4.69Hz, 3H); 2.29(s, 3H) | (M+H)$^+$=439.0 | A | <1 |
| 52. | 2-(4-Fluoro-phenyl)-6-(methanesulfonyl-methyl-amino)-5-(2-morpholin-4-yl-ethoxy)-benzofuran-3-carboxylic acid methylamide | $^1$H NMR in DMSO: 8.40(brd, J=4.40Hz, 1H); 7.94(m, 2H); 7.60(s, 1H); 7.38(t, J=8.79Hz, 2H); 7.24(s, 1H); 4.21(t, J=5.28Hz, 2H); 3.57(m, 4H); 3.23(s, 3H); 3.10(s, 3H); 2.84(d, J=4.84Hz, 3H); 2.76(t, J=5.28Hz, 2H); 2.48(m, 4H). | (M+H)$^+$=506 | A | <1 |
| 53. | 5-(Biphenyl-2-ylmethoxy)-2-phenyl-benzofuran-3-carboxylic acid methylamide | $^1$H NMR in DMSO: 2.82(d, 3H); 5.0(s, 2H) 6.96(m, 1H); 7.32-7.96(m, 16H); 8.34(d, 1H) | (M+H)$^+$=434 | C | <30 |
| 54. | 5-Methoxy-2-(4-methoxy-phenyl)-benzofuran-3-carboxylic acid methylamide | $^1$H NMR in DMSO: 8.31(br s, 1H); 7.82-7.84(d, J=7.03Hz, 2H); 7.52-7.55(d, J=8.79Hz, 1H); 7.06-7.10(m, 3H); 6.93-6.96(dd, J=2.35Hz, 8.79Hz, 1H); 3.83(s, 3H); 3.81(s, 3H); 2.81-2.83(d, J=4.69Hz, 3H) | *** | B | <10 |
| 55. | 5-Methoxy-2-(3-trifluoromethyl-phenyl)-benzofuran-3-carboxylic acid methylamide | $^1$H NMR in DMSO: 8.47-8.49(d, J=4.69Hz, 1H); 8.19(s, 1H); 8.15-8.18(d, J=7.62Hz, 1H); 7.74-7.84(m, 2H); 7.61-7.64(d, J=9.38Hz, 1H); 7.13(d, J=2.34Hz, 1H); 7.01-7.05(dd, J=2.34Hz, 7.62Hz, 1H); 2.83-2.85(d, J=4.69Hz, 3H) | *** | B | <30 |
| 56. | 5-Methoxy-2-(4-trifluoromethyl-phenyl)-benzofuran-3-carboxylic acid methylamide | $^1$H NMR in DMSO: 8.48-8.49(d, J=4.69Hz, 1H); 8.06-8.09(d, J=8.21Hz, 2H); 7.88-7.90(d, J=8.21Hz, 2H); 7.61-7.64(d, J=8.79Hz, 1H); 7.12-7.13(d, J=2.93Hz, 1H); 7.02-7.06(dd, J=2.93, 8.79Hz, | *** | B | <10 |

TABLE 1-continued

| Example Number | Name | NMR data* | Mass Spec | HCV pol-BB7 IC$_{50}$(μM) A=≦0.5μM B=0.5 to ≦5.0μM C=5.0 to ≦30μM D=>30μM | Replicon (μM) |
|---|---|---|---|---|---|
| | | 1H); 3.83(s, 3H); 2.85-2.86(d, J=4.69Hz, 3H) | | | |
| 57. | 5-Ethoxy-2-phenyl-benzofuran-3-carboxylic acid methylamide | $^1$H NMR in CDCl$_3$: 7.85(dd, 2H); 7.35-7.52(m, 5H); 6.95(d, 1H); 5.8(s, br, 1H); 4.14(q, 2H); 2.97(d, 3H) 1.41(t, 3H) | (M+H)$^+$=296 | B | >30 |
| 58. | 2-(2-Fluoro-phenyl)-5-methoxy-benzofuran-3-carboxylic acid methylamide | $^1$H NMR in DMSO: 8.05-8.07(d, J=4.69Hz, 1H); 7.72-7.77(t of d, J=1.76Hz, 7.62-7.63(m, 2H); 7.52-7.63(m, 2H); 7.37-7.39(d, J=7.62Hz 1H); 7.33-7.38(m, 1H); 7.18-7.19(d, J=2.35Hz, 1H); 6.99-7.03(m, 2H); 3.83(s, 3H); 2.75-2.76(d, J=4.69Hz, 3H) | (M+H)$^+$=300 | B | <10 |
| 59. | 5-Isopropoxy-2-phenyl-benzofuran-3-carboxylic acid methylamide | $^1$H NMR in CDCl$_3$: 7.87(d, 2H); 7.52-7.37(m, 5H); 6.94(d, 1H); 5.78(s, br, 1H); 4.6(m, 1H); 2.98(d, 3H); 1.38(d, 6H) | (M+H)$^+$=310 | B | <30 |
| 60. | 5-Butoxy-2-phenyl-benzofuran-3-carboxylic acid methylamide | $^1$H NMR in CDCl$_3$: 7.87(m, 2H), 7.51-7.3(m, 5H); 6.97(d, 1H); 5.78(s, br, 1H); 4.06(m, 2H); 2.98(d, 3H); 1.83-1.54(m, 4H); 1.02(m, 3H) | (M+H)$^+$=324 | B | <30 |
| 61. | 2-Phenyl-5-propoxy-benzofuran-3-carboxylic acid methylamide | $^1$H NMR in CDCl$_3$: 7.86(m, 2H); 7.5-7.27(m, 5H); 6.96(dd, 1H); 5.76(s, br, 1H); 3.99(t, 2H); 2.98(d, 3H); 1.84(m, 2H); (t, 3H) | (M+H)$^+$=310 | B | <30 |
| 62. | 5-Methoxy-2-(2,4,5-trifluoro-phenyl)-benzofuran-3-carboxylic acid methylamide | $^1$H NMR in DMSO: 8.08-8.09(d, J=4.69Hz, 1H); 7.86-7.95(m, 1H); 7.71-7.80(m, 1H); 7.58-7.61(d, J=9.38Hz, 1H); 7.22-7.23(d, J=2.35Hz, 1H); 7.02-7.06(dd, J=2.93Hz, 9.38Hz, 1H); 3.83(s, 3H); 2.76-2.77(d, J=4.69Hz, 3H) | *** | C | <30 |
| 63. | 5-Methoxy-7-methyl-2-phenyl-benzofuran-3-carboxylic acid methylamide | $^1$H NMR in DMSO: 8.33-8.34(d, J=4.69Hz, 1H); 7.87-7.89(d, J=7.62Hz, 2H); 7.45-7.55(m, 3H); 6.89-6.90(d, J=2.34Hz, 1H); 6.83-6.84(d, J=2.34Hz, 1H); 3.80(s, 3H); 2.82-2.84(d, J=4.69Hz, 3H); 2.50(s, 3H) | (M+H)$^+$=296 | B | <10 |
| 64. | 2-(4-Fluoro-phenyl)-5-(2,2,2-trifluoro-ethoxy)-benzofuran-3-carboxylic acid methylamide | $^1$H NMR in CDCl$_3$: 8.06(dd, 1H); 7.41(dd, 2H); 7.17(m, 2H); 7.02(dd, 1H); 5.76(m, br, 1H); 4.42(q, 2H); 2.99(d, 3H) | (M+H)$^+$=368 | B | *** |
| 65. | 2-(4-Fluoro-phenyl)-5-isopropoxy-benzofuran-3-carboxylic acid methylamide | $^1$H NMR in CDCl$_3$: 7.90(dd, 2H); 7.29(dd, 2H); 7.16(dd, 1H); 6.92(dd, 1H); 5.82(s, br, 1H); 4.58(m, 1H); 2.99(d, 3H); 1.34(s, 3H) | (M+H)$^+$=328 | B | <30 |
| 66. | 2-(2-Chloro-phenyl)-5-methoxy-benzofuran-3-carboxylic acid methylamide | $^1$H NMR in DMSO: 7.85-7.86(d, J=4.69Hz, 1H); 7.47-7.69(m, 5H); 7.27-7.28(d, J=2.34Hz, 1H); 7.00-7.04(dd, J=2.93Hz, 9.38Hz, 1H); 3.84(s, 3H); 2.72-2.73(d, J=4.69Hz, 3H) | (M+H)$^+$=315.9 | C | >30 |
| 67. | 6-Methoxy-2-phenyl-benzofuran-3-carboxylic acid methylamide | $^1$H NMR in CDCl$_3$: 7.86(m, 2H); 7.73(d, J=8.87Hz, 1H); 7.51-7.42(m, 3H); 7.04(d, J=2.4Hz, 1H); 6.94(d of d, J=8.8Hz, 1H); 5.81(br s, 1H); 3.87(s, 3H); 2.98(d, J=4.7Hz, 3H) | (M+H)$^+$=282 | B | <10 |

TABLE 1-continued

| Example Number | Name | NMR data* | Mass Spec | HCV pol-BB7 IC$_{50}$(μM) A=≦0.5μM B=0.5 to ≦5.0μM C=5.0 to ≦30μM D=>30μM | Replicon (μM) |
|---|---|---|---|---|---|
| 68. | 2-Furan-2-yl-5-methoxy-benzofuran-3-carboxylic acid methylamide | $^1$H NMR in DMSO: 8.28-8.29(d, J=4.10Hz 1H); 7.92(s, 3H); 7.54-7.57(d, J=8.79Hz, 1H); 7.18-7.19(d, J=3.52Hz, 1H); 7.15-7.16(d, J=2.35Hz, 1H); 6.96-7.00(dd, J=2.35, 8.79Hz, 1H); 6.71-6.72(m, 1H); 3.82(s, 3H); 2.84-2.86(d, J=4.10Hz, 3H) | M=271 | B | <30 |
| 69. | 2-(3-Fluoro-4-methyl-phenyl)-5-methoxy-benzofuran-3-carboxylic acid methylamide | $^1$H NMR in DMSO: 8.42(s, 1H); 7.63(m, 3H); 7.43(m, 1H); 7.09(m, 1H); 7.00(m, 1H); 3.82(s, 3H); 2.84(d, J=4.8Hz, 3H); 2.30(s, 3H) | (M+H)$^+$=314 | A | <10 |
| 70. | 2-(4-Bromo-phenyl)-5-methoxy-benzofuran-3-carboxylic acid methylamide | $^1$H NMR in DMSO: 8.41(m, 1H); 7.81(d, J=7.5Hz, 2H); 7.72(d, J=8.4Hz, 2H); 7.58(d, J=9.3Hz, 1H); 7.09(s, 1H); 7.01(d, J=8.7Hz, 1H); 3.82(s, 3H); 2.83(d, J=4.2Hz, 3H) | (M+H)$^+$=361 | A | <10 |
| 71. | 2-(4-Fluoro-3-methyl-phenyl)-5-methoxy-benzofuran-3-carboxylic acid methylamide | $^1$H NMR in DMSO: 8.33(m, 1H); 7.80(dd, J=8.1, 1.8Hz, 1H); 7.75(m, 1H); 7.56(d, J=9.0Hz, 1H); 7.29(m, 1H); 7.09(d, J=2.4Hz, 1H); 6.97(dd, J=8.1, 2.1Hz, 1H); 3.81(s, 3H); 2.84(d, J=4.2Hz, 3H); 2.35(s, 3H) | (M+H)$^+$=314 | A | <30 |
| 72. | 2-(4-Fluoro-phenyl)-5-methoxy-7-methyl-benzofuran-3-carboxylic acid methylamide | $^1$H NMR in DMSO: 8.3(d, br, 1H); 7.94(dd, 2H); 7.35(dd, 2H); 6.89(d, 1H), 6.81(d, 1H); 3.83(s, 3H); 2.80(d, 3H); 2.47(s, 3H) | (M+H)$^+$=314 | A | <10 |
| 73. | 5-Chloro-2-(4-fluoro-phenyl)-benzofuran-3-carboxylic acid methylamide | $^1$H NMR in CDCl$_3$: 7.96-7.91(m, 2H); 7.81(d, J=2.4Hz, 1H); 7.42(d, J=8.7Hz, 1H); 7.30(d, d, J=2.4, 8.7Hz, 1H); 7.21-7.16(m, 2H); 5.789(s, 1H); 3.01(d, J=4.8Hz, 3H) | (M+H)$^+$=304.27, 306.13 | B | <10 |
| 74. | 5-tert-Butyl-2-phenyl-benzofuran-3-carboxylic acid methylamide | $^1$H NMR in CDCl$_3$: 7.87-7.84(m, 3H); 7.52-7.39(m, 5H); 5.79(br s, 1H); 2.99(d, J=4.7Hz, 3H); 1.39(s, 9H) | (M+H)$^+$=308 | A | <10 |
| 75. | 5-Chloro-2-p-tolyl-benzofuran-3-carboxylic acid methylamide | $^1$H NMR in CDCl$_3$: 7.90(d, J=1.8Hz, 1H); 7.75(d, J=7.8Hz, 2H); 7.43-7.40(m, 1H); 7.32-7.27(m, 3H); 2.97(d, J=4.8Hz, 3H); 2.43(s, 3H) | (M+H)$^+$=300 | A | <10 |
| 76. | 2-(3-Chloro-4-fluoro-phenyl)-5-methoxy-benzofuran-3-carboxylic acid methylamide | $^1$H NMR in CDCl$_3$: 8.62(s, 1H); 8.08(dd, J=7.2, 1.8Hz, 1H); 7.88(m, 1H); 7.58(m, 2H); 7.10(d, J=2.4Hz, 1H); 6.98(dd, J=8.1, 2.4Hz, 1H); 3.82(s, 3H); 2.84(d, J=4.8Hz, 3H) | (M+H)$^+$=334 | B | <10 |
| 77. | 2-(4-Chloro-3-fluoro-phenyl)-5-methoxy-benzofuran-3-carboxylic acid methylamide | $^1$H NMR in CDCl$_3$: 8.48(s, 1H); 7.93(d, J=1.2Hz, 1H); 7.90(m, 2H); 7.59(d, J=9.0Hz, 1H); 7.12(d, J=2.4Hz, 1H); 7.04(dd, J=9.0, 2.4Hz, 1H); 3.82(s, 3H); 2.85(d, J=4.5Hz, 3H) | (M+H)$^+$=334 | A | <10 |
| 78. | 5-Methoxymethyl-2-phenyl-benzofuran-3-carboxylic acid methylamide | $^1$H NMR in CDCl$_3$: 7.90(d of d, J=8.2Hz, 2H); 7.83(s, 1H); 7.51-7.42(m, 4H); 7.34(d, J=8.8Hz, 1H); 5.83(brs, 1H); 4.56(s, 2H); 3.41(s, 3H); 3.00(d, J=4.7Hz, 3H) | (M+H)$^+$=296 | B | <30 |
| 79. | 2-(4-Fluoro-phenyl)-5-isopropoxy-6-methyl-benzofuran-3-carboxylic acid | $^1$H NMR in CD$_3$OD: 7.85(dd, 2H); 7.31(s, 1H); 7.20(dd, 2H); 7.10(s, 1H); 4.61(m, | (M+H)$^+$=342 | A | <10 |

TABLE 1-continued

| Example Number | Name | NMR data* | Mass Spec | HCV pol-BB7 $IC_{50}(\mu M)$ A=≤0.5µM B=0.5 to ≤5.0µM C=5.0 to ≤30µM D=>30µM | Replicon (µM) |
|---|---|---|---|---|---|
| | acid methylamide | 1H); 2.92(s, 3H); 2.29(s, 3H); 1.37(d, 6H) | | | |
| 80. | 2-(4-Fluoro-phenyl)-5-isopropoxy-7-methyl-benzofuran-3-carboxylic acid methylamide | $^1$H NMR in CD$_3$OD: 7.85(dd, 2H); 7.25(d, 1H); 7.20(dd, 2H); 6.80(d, 1H); 4.61(m, 1H); 2.92(s, 3H); 2.38(s, 3H); 1.37(d, 6H) | (M+H)$^+$=342 | B | <30 |
| 81. | 2-(4-Fluoro-phenyl)-5-methoxy-6-methyl-benzofuran-3-carboxylic acid methylamide | $^1$H NMR in CDCl$_3$: 7.9(dd, 2H); 7.26(s, 1H); 7.22(s, 1H); 7.16(dd, 2H); 5.78(s, 1H, br); 3.89(s, 3H); 2.98(d, 3H); 2.33(s, 3H) | (M+H)$^+$=314 | A | <10 |
| 82. | 5-Fluoro-2-(4-fluoro-phenyl)-benzofuran-3-carboxylic acid methylamide | $^1$H NMR in CDCl$_3$: 7.93-7.88(m, 2H); 7.48(dd, J=2.7Hz, 8.4Hz, 1H); 7.41(dd, J=3.9Hz, 8.7Hz, 1H); 7.21-7.14(m, 2H); 7.06(td, J=2.7Hz, 8.7Hz, 1H); 5.86(s, 1H); 2.98(d, J=4.8Hz, 3H) | (M+H)$^+$=288 | B | <30 |
| 83. | 2-(4-Ethyl-phenyl)-5-fluoro-benzofuran-3-carboxylic acid methylamide | $^1$H NMR in CDCl$_3$: 7.77(d, J=7.8Hz, 2H); 7.59(dd, J=2.7Hz, 8.4Hz, 1H); 7.41(dd, J=4.5Hz, 8.7Hz, 1H); 7.33(d, J=8.4Hz, 2H); 7.03(td, J=2.4Hz, 8.7Hz, 1H); 5.79(s, 1H); 2.96(d, J=5.1Hz, 3H); 2.72(q, J=7.8Hz, 15.3Hz, 2H); 1.29(t, J=7.5Hz, 3H) | (M+H)$^+$=298 | A | <10 |
| 84. | 5-Ethyl-2-phenyl-benzofuran-3-carboxylic acid methylamide | $^1$H NMR in CDCl$_3$: 7.89(m, 3H); 7.70(s, 1H); 7.5-7.37(m, 3H); 7.15(m, 1H); 5.81(br s, 1H); 3.0(d, 3H); 2.76(q, 2H); 1.25(t, 3H) | (M+H)$^+$=280 | B | <30 |
| 85. | 2-(5-Chloro-thiophen-2-yl)-5-methoxy-benzofuran-3-carboxylic acid methylamide | $^1$H NMR in DMSO: 8.32(s, 1H); 7.67(d, J=4.2Hz, 1H); 7.54(d, J=9.0Hz, 1H); 7.22(d, J=4.2Hz, 1H); 7.15(s, 1H); 6.98(d, J=6.9Hz, 1H); 3.81(s, 3H); 2.84(d, J=4.5Hz, 3H) | (M+H)$^+$=322 | A | <10 |
| 86. | 5-Isopropyl-2-phenyl-benzofuran-3-carboxylic acid methylamide | $^1$H NMR in CDCl$_3$: 7.87(m, 2H); 7.74(s, 1H); 7.54-7.43(m, 4H); 7.27-7.23(m, 1H); 5.82(br s, 1H); 3.10-3.00(m+d, 4H); 1.33(d, 6H) | (2M+Na)$^+$=609.2 | A | <10 |
| 87. | 2-(5-Chloro-thiophen-2-yl)-5-ethoxy-benzofuran-3-carboxylic acid methylamide | $^1$H NMR in CDCl$_3$: 7.72(d, J=3.6Hz, 1H); 7.38(d, J=8.1Hz, 1H); 7.14(d, J=2.4Hz, 1H); 6.95(d, J=3.9Hz, 1H); 6.92(d, J=2.4Hz, 1H); 5.98(s, 1H) 4.10(q, 2H); 3.07(d, J=4.5Hz, 3H); 1.45(t, 3H) | (M+H)$^+$=336 | A | <10 |
| 88. | 5-Methoxy-2-thiophen-2-yl-benzofuran-3-carboxylic acid methylamide | $^1$H NMR in DMSO: 8.38(s, 1H), 7.83(d, J=3.3Hz, 1H); 7.76(d, J=5.4Hz, 1H); 7.55(d, J=9.0Hz, 1H); 7.21(m, 1H); 7.11(d, J=2.1Hz, 1H); 6.97(dd, J=9.0, 2.4Hz, 1H); 3.82(s, 3H); 2.86(d, J=4.5Hz, 3H) | (M+H)$^+$=288 | B | <30 |
| 89. | 5-Chloro-2-pyridin-3-yl-benzofuran-3-carboxylic acid methylamide | $^1$H NMR in CDCl$_3$: 9.15-9.14(m, 1H); 8.68-8.66(m, 1H); 8.33-8.29(m, 1H); 7.77(d, J=2.1Hz, 1H); 7.49-7.39(m, 2H); 7.34(dd, J=2.1Hz, 8.7Hz, 1H); 6.0(s, 1H); 3.04(d, J=4.8Hz, 3H) | (M+H)$^+$=286.9 | B | >30 |
| 90. | 2-(4-Bromo-3-fluoro-phenyl)-5-isopropoxy-benzofuran-3-carboxylic acid methylamide | $^1$H NMR in DMSO: 8.45(d, J=3.9Hz, 1H); 7.88(dd, J=8.4, 2.4Hz, 1H); 7.85(d, J=3.0Hz, 1H); 7.67(dd, J=9.0, 1.8Hz, 1H); 7.57(d, J=8.1Hz, 1H); 7.10(d, J=2.4Hz, 1H); 7.02(dd, J=9.3, 2.7Hz, 1H); 4.64(m, | (M+H)$^+$=406 | A | <10 |

TABLE 1-continued

| Example Number | Name | NMR data* | Mass Spec | HCV pol-BB7 IC$_{50}$(μM) A=≦0.5μM B=0.5 to ≦5.0μM C=5.0 to ≦30μM D=>30μM | Replicon (μM) |
|---|---|---|---|---|---|
| | | 1H); 2.84(d, J=4.8Hz, 3H); 1.29(d, J=6.0Hz, 6H) | | | |
| 91. | 2-(2,4-Difluoro-phenyl)-5-isopropoxy-benzofuran-3-carboxylic acid methylamide | $^1$H NMR in DMSO: 8.04(d, J=7.2Hz, 1H); 7.82(d, J=6.3Hz, 1H); 7.56(d, J=9.3Hz, 1H); 7.46(d, J=9.3Hz, 1H); 7.30(d, J=2.4Hz, 1H); 7.20(d, J=2.1Hz, 1H); 6.99(dd, J=8.1, 2.4Hz, 1H); 4.61(m, 1H); 2.75(d, J=4.8Hz, 3H); 1.30(d, J=6.0Hz, 6H) | (M+H)$^+$=345 | A | <30 |
| 92. | 6-Bromo-2-(4-fluoro-phenyl)-5-isopropoxy-benzofuran-3-carboxylic acid methylamide | *** | (M+H)$^+$=406 | A | <1 |
| 93. | 5-Methoxy-2-(4-morpholin-4-yl-phenyl)-benzofuran-3-carboxylic acid methylamide | $^1$H NMR in CDCl$_3$: 7.76(dd, J=4.8, 3.0Hz, 2H); 7.37(m, 2H); 6.97(dd, J=9.0, 1.8Hz, 2H); 6.89(dd, J=8.1, 2.1Hz, 1H); 5.84(m, 1H); 3.87(s, 3H); 3.88(t, 4H); 3.27(t, 4H); 2.96(d, J=5.4Hz, 3H) | (M+H)$^+$=367 | B | >30 |
| 94. | 5,6-Dimethoxy-2-phenyl-benzofuran-3-carboxylic acid methylamide | $^1$H NMR in CDCl$_3$: 7.79(d, 6.4Hz, 2H); 7.52-7.40(m, 3H); 7.38(s, 1H); 7.06(s, 1H); 5.78(brs, 1H); 3.96(s, 3H); 3.94(s, 3H); 2.96(d, J=4.7Hz, 3H) | (M+H)$^+$=312 | A | <1 |
| 95. | 5-Isopropoxy-2-(4-pyrrolidin-1-yl-phenyl)-benzofuran-3-carboxylic acid methylamide | $^1$H NMR in DMSO: 8.16(s, 1H); 7.71(d, J=8.1Hz, 2H); 7.45(d, J=8.1Hz, 1H); 7.01(d, J=1.8Hz, 1H); 6.85(dd, J=8.1, 2.1Hz, 1H); 6.62(d, J=8.1Hz, 2H); 4.58(m, 1H); 2.81(d, J=3.9Hz, 3H); 2.00(m, 4H); 1.38(d, J=6.0Hz, 6H) | (M+H)$^+$=379 | C | <30 |
| 96. | 5-Fluoro-2-pyridin-4-yl-benzofuran-3-carboxylic acid methylamide | $^1$H NMR in CDCl$_3$: 8.75-8.73(m, 2H); 7.87-7.84(m, 2H); 7.53-7.43(m, 2H); 7.18-7.10(m, 1H); 5.92(brs, 1H); 3.09(d, J=4.8Hz, 3H) | (M+H)$^+$=271 | B | >30 |
| 97. | 2-[2-(4-Fluoro-phenyl)-6-methyl-3-methylcarbamoyl-benzofuran-5-yloxy]-propionic acid | $^1$H NMR in acetic-d$_3$ acid-d(CD$_3$CO$_2$D): 8.75-8.73(m, 2H); 7.87-7.84(m, 2H); 7.53-7.43(m, 2H); 7.18-7.10(m, 1H); 5.92(brs, 1H); 3.09(d, J=4.8Hz, 3H) | (M+H)$^+$=371 | C | >30 |
| 98. | 6-Acetylamino-2-(4-fluoro-phenyl)-5-isopropoxy-benzofuran-3-carboxylic acid methylamide | $^1$H NMR in CDCl$_3$: 8.66(s, 1H); 7.99(s, 1H); 7.82(dd, 2H, J=5.2 & 8.7Hz); 7.37(s, 1H); 7.18(t, 2H, J=8.7Hz); 5.78(brs, 1H); 4.70(heptuplet, J=6.1Hz); 2.96(d, 3H, J=4.9Hz); 2.24(s, 3H); 1.41(d, 6H, J=6.1Hz) | (M+H)$^+$=85 | A | <10 |
| 99. | 2-(4-Amino-phenyl)-5-isopropoxy-benzofuran-3-carboxylic acid methylamide | $^1$H NMR in CDCl$_3$: 7.64-7.67(d, J=8.79Hz, 2H); 7.41-7.42(d, J=2.93Hz, 1H); 7.32-7.35(d, J=8.79Hz, 1H); 6.86-6.90(dd, J=2.33Hz, 8.79Hz, 1H); 6.74-6.77(d, J=7.03Hz, 2H); 5.84(br.s, 1H); 4.56-4.64(septet, J=6.45Hz, 1H); 2.96-2.97(d, J=4.69Hz, 3H); 1.35-1.37(d, J=6.45Hz, 6H) | (M+H)$^+$=325 | B | <30 |
| 100. | 2-(4-Fluoro-phenyl)-5-isopropoxy-6-(2-morpholin-4-yl-ethylamino)-benzofuran-3-carboxylic acid methylamide | $^1$H NMR in DMSO: 8.22-8.24(d, J=4.69Hz, 1H); 7.82-7.87(m, 2H); 7.28-7.34(t, J=8.79Hz, 2H); 6.98(s, 1H); 6.79(s, 1H); 5.28(brs, 1H); 4.56(brs, 1H); 3.60(brs, 3H); | (M+H)$^+$=456 | B | <30 |

TABLE 1-continued

| Example Number | Name | NMR data* | Mass Spec | HCV pol-BB7 IC$_{50}$(μM) A=≦0.5μM B=0.5 to ≦5.0μM C=5.0 to ≦30μM D=>30μM | Replicon (μM) |
|---|---|---|---|---|---|
| | | 3.23(brs, 3H); 2.81-2.82(d, J=4.69Hz, 3H); 2.61(brs, 1H); 2.43(brs, 3H); 1.31-1.33(d, J=5.86Hz, 6H) | | | |
| 101. | 2-(4-Fluoro-phenyl)-5-isopropoxy-6-piperidin-1-yl-benzofuran-3-carboxylic acid methylamide | $^1$H NMR in CDCl$_3$: 7.89-7.84(m, 2H); 7.23(s, 1H); 7.14(t, J=8.79, 2H); 7.04(s, 1H); 5.78(brs, 1H); 4.69-4.29(septet, J=6.15, 1H); 3.05-3.01(m, 4H); 2.98(d, J=5.27, 3H); 1.77-1.72(m, 4H); 1.60-1.59(m, 2H); 1.36(d, J=6.15, 6H) | (M+H)$^+$=411 | A | <1 |
| 102. | 2-(4-Fluoro-phenyl)-5,6-dimethoxy-benzofuran-3-carboxylic acid methylamide | $^1$H NMR in CDCl$_3$: 7.85-7.81(m, 2H); 7.32(s, 1H); 7.25-7.20(m, 2H); 7.05(s, 1H); 5.75(brs, 1H); 3.96(s, 3H); 3.947(s, 3H); 2.98(d, J=4.2Hz, 3H) | (M+H)$^+$=330 | A | <1 |
| 103. | 2-(4-Fluoro-phenyl)-5-methoxy-6-morpholin-4-yl-benzofuran-3-carboxylic acid methylamide | $^1$H NMR in CDCl$_3$: 7.85-7.81(m, 2H); 7.30(s, 1H); 7.17(t, J=8.8Hz, 2H); 7.08(s, 1H); 3.94(s, 3H); 3.94-3.91(m, 4H); 3.11-3.09(m, 4H); 2.98(d, J=4.7Hz, 3H) | (M+H)$^+$=385 | A | <1 |
| 104. | 2-(4-Bromo-phenyl)-5-isopropoxy-benzofuran-3-carboxylic acid methylamide | $^1$H NMR in CDCl$_3$: 7.80(d, 2H, J=8.79); 7.61(d, 2H, J=8.79); 7.39(d, 1H, J=8.79); 7.28(d, 1H, J=2.34); 6.94(dd, 1H, J=8.79, 2.34); 5.80(brs, 1H); 4.58(m, 1H); 3.01(d, 3H, J=4.69); 1.36(d, 6H, J=6.45) | (M+H)$^+$=288 | A | <10 |
| 105. | 2-(4-Fluoro-3-hydroxy-phenyl)-5-isopropoxy-benzofuran-3-carboxylic acid methylamide | $^1$H NMR in DMSO: 10.18(brs, 1H); 8.32(d, 1H, J=4.69); 7.50(m, 2H); 7.26(m, 2H); 7.03(d, 1H, J=2.34); 6.93(dd, 1H, J=8.79, 2.34); 4.58(m, 1H); 2.81(d, 3H, J=4.69); 1.26(d, 6H, J=5.86) | (M+H)$^+$=344 | C | <30 |
| 106. | 2-(4-Cyano-phenyl)-5-isopropoxy-benzofuran-3-carboxylic acid methylamide | $^1$H NMR in CDCl$_3$: 8.11(d, 2H, J=8.21); 7.74(d, 2H, J=8.79); 7.43(d, 1H, J=9.38); 7.20(d, 1H, J=2.34); 7.00(dd, 1H, J=8.79, 2.34); 5.88(brs, 1H); 4.58(m, 1H); 3.06(d, 3H, J=4.69); 1.36(d, 6H, J=6.45) | (M+H)$^+$=335 | B | <30 |
| 107. | 5-Methoxy-2-pyridin-4-yl-benzofuran-3-carboxylic acid methylamide | $^1$H NMR in CDCl$_3$: 8.72(d, J=5.4H3, 2H); 7.83(dd, J=1.8H3, 4.5H3, 2H); 7.45(d, J=9.0H3, 1H); 7.20(d, J=2.2H3, 1H); 7.01(dd, J=2.7H3, 8.7H3, 1H); 5.90(brs, 1H); 3.88(s, 3H); 3.08(d, J=4.8H3, 3H) | (M+H)$^+$=283 | B | <100 |
| 108. | 2-(4-Fluoro-phenyl)-5-isopropoxy-6-(3-methanesulfonyl-pyrrolidin-1-yl)-benzofuran-3-carboxylic acid methylamide | $^1$H NMR in DMSO: 7.90(dd, J=1.8, 5.3Hz, 2H); 7.33(t, J=8.8Hz, 2H); 7.07(s, 1H); 7.05(s, 1H); 4.63(p, J=6.4Hz, 1H); 3.96-3.86(m, 2H); 3.49-3.32(m, 2H); 3.03(s, 3H); 2.82(s, 3H); 2.31(m, 2H); 1.33(d, J=1.2Hz, 6H) | (M+H)$^+$=475 | A | <1 |
| 109. | 6-Azetidin-1-yl-2-(4-fluoro-phenyl)-5-isopropoxy-beazofuran-3-carboxylic acid methylamide | $^1$H NMR in CDCl$_3$: 7.82(dd, J=5.3, 8.8Hz, 2H); 7.13(s, 1H); 7.13(t, J=8.2Hz, 2H); 6.54(s, 1H); 4.60(p, J=5.9Hz, 1H); 3.96(t, J=7.6Hz, 4H); 2.97(d, J=5.3Hz, 3H); 2.29(p, J=7.0Hz, 2H); 1.36(d, J=6.4Hz, 6H) | (M+H)$^+$=383 | A | <1 |
| 110. | 2-(4-Fluoro-phenyl)-6-(3-hydroxy-pyrrolidin-1- | *** | (M+H)$^+$=413 | A | <1 |

TABLE 1-continued

| Example Number | Name | NMR data* | Mass Spec | HCV pol-BB7 IC$_{50}$(μM) A=≦0.5μM B=0.5 to ≦5.0μM C=5.0 to ≦30μM D=>30μM | Replicon (μM) |
|---|---|---|---|---|---|
| | yl)-5-isopropoxy-benzofuran-3-carboxylic acid methylamide | | | | |
| 111. | 2-(4-Fluoro-phenyl)-5-isopropoxy-6-(methanesulfonyl-methyl-amino)-benzofuran-3-carboxylic acid methylamide | $^1$H NMR in CDCl$_3$: 7.81(2H, dd, J=5.3, 8.8Hz); 7.56(1H, s) 7.42(1H, s); 7.20(2H, r, J=8.8Hz); 5.70(1H, brs); 4.80(1H, heptuplet, J=6.2Hz); 3.32(3H, s); 2.98(3H, s); 2.96(3H, s); 1.42(3H, d, J=6.2Hz) | (M+H)$^+$=435 | A | <1 |
| 112. | 2-(4-Fluoro-phenyl)-6-[(furan-3-ylmethyl)-amino]-5-isopropoxy-benzofuran-3-carboxylic acid methylamide | $^1$H NMR in CDCl$_3$: 7.76-7.81(m, 2H); 7.37(d, J=1.17, 1H); 7.17(s, 1H); 7.086-7.145(t, J=8.79, 2H); 6.746(s, 1H); 6.319-6.328(m, 1H); 6.242-6.252(d, J=2.93, 1H); 5.86(brs, 1H); 4.565-4.645(septet, J=6.45, 1H); 4.365(s, 2H); 2.940-2.955(d, J=4.69, 3H); 1.375-1.254(d, J=6.45, 6H) | (M+H)$^+$=423 | A | <1 |
| 113. | 6-(2,3-Dihydroxy-propylamino)-2-(4-fluoro-phenyl)-5-isopropoxy-benzofuran-3-carboxylic acid methylamide | $^1$H NMR in CDCl$_3$: 7.78(brs, 2H); 7.12(m, 4H); 6.72(brs, 1H); 5.84(d, J=4.7Hz, 1H); 4.60(p, J=5.9Hz, 1H); 4.01(m, 1H); 3.80(dd, J=3.52, 11.1HZ, 1H); 3.66(dd, J=5.9, 11.1Hz, 1H); 2.96(d, J=4.7Hz, 3H); 1.37(dd, J=1.8, 5.9Hz, 6H) | (M+H)$^+$=417 | B | <10 |
| 114. | 2-(4-Fluoro-phenyl)-5-isopropoxy-6-isopropylamino-benzofuran-3-carboxylic acid methylamide | $^1$H NMR in CDCl$_3$: 7.805-7.834(m, 2H); 7.151(s, 1H); 7.100-7.127(m, 2H); 6.680(s, 1H); 5.960(brs, 1H); 4.580-4.600(septet, J=5.861, 1H); 3.662-3.686(septet, J=7.033, 1H); 2.955-2.971(d, J=4.688, 3H); 2.057(s, 1H); 1.361-1.381(d, J=5.861, 6H); 1.258-1.277(d, J=5.861, 6H) | (M+H)$^+$=385 | A | <1 |
| 115. | 6-(Cyclopropylmethyl-amino)-2-(4-fluoro-phenyl)-5-isopropoxy-benzofuran-3-carboxylic acid methylamide | $^1$H NMR in CDCl$_3$: 7.780-7.866(m, 2H); 7.176(s, 1H); 7.104-7.160(m, 2H); 6.664(s, 1H); 5.781(br, 1H); 4.567-4.647(septet, J=5.861, 1H); 3.000-3.024(d, J=7.033, 2H); 2.965-2.981(d, J=4.689, 3H); 1.502-1.676(m, 1H); 1.383-1.402(m, 1H); 1.211-1.172(m, 1H); 0.557-0.619(m, 1H); 0.262-.0311(m, 1H) | (M+H)$^+$=397 | A | <1 |
| 116. | 2-(4-Fluoro-phenyl)-5-methoxy-6-pyrrolidin-1-yl-benzofuran-3-carboxylic acid methylamide | $^1$H NMR in CDCl$_3$: 8.28(d, J=4.40, 1H); 7.89-7.84(m, 2H); 7.31(t, J=8.79, 2H); 7.00(s, 1H); 6.91(s, 1H); 3.81(s, 3H); 3.29(m, 4H); 2.82(d, J=4.40, 3H); 1.88(m, 4H) | (M+H)$^+$=369 | A | <1 |
| 117. | 5-Benzyloxy-2-(4-fluoro-phenyl)-6-morpholin-4-yl-benzofuran-3-carboxylic acid methylamide | $^1$H NMR in CDCl$_3$: 7.788-7.83(m, 2H); 7.60-7.09(m, 9H); 5.71(brs, 1H); 5.19(s, 2H); 3.90-3.87(m, 4H); 3.17-3.15(m, 4H); 2.98(d, J=51.Hz, 3H) | (M+H)$^+$=461 | A | <1 |
| 118. | 5-Hydroxymethyl-2-phenyl-benzofuran-3-carboxylic acid methylamide | $^1$H NMR in CDCl$_3$: 7.98-7.87(m, 3H); 7.53-7.43(m, 4H); 7.38(d, J=7.0Hz, 1H); 5.84(br s, 1H); 4.83(d, J=6,0Hz, 2H); 2.99(d, J=5.3Hz, 3H) | (M+H)$^+$=282 | C | >100 |

TABLE 1-continued

| Example Number | Name | NMR data* | Mass Spec | HCV pol-BB7 IC$_{50}$(μM) A=≦0.5μM B=0.5 to ≦5.0μM C=5.0 to ≦30μM D=>30μM | Replicon (μM) |
|---|---|---|---|---|---|
| 119. | 2-(4-Fluoro-phenyl)-5-isopropoxy-6-[(2-methoxy-ethyl)-methyl amino]-benzofuran-3-carboxylic acid methylamide | $^1$H NMR in CDCl$_3$: 7.86-7.82(m, 2H); 7.26-7.24(m, 1H); 7.15(t, J=8.35Hz, 2H); 7.08(s, 1H); 5.76(s, 1H); 4.70-4.62(septet, J=6.15Hz, 1H); 3.59(t, J=6.15Hz, 2H); 3.37-3.35(m, 2H); 3.33(s, 1H); 2.98(d, J=4.83Hz, 3H); 2.92(s, 3H); 1.39(d, J=6.15Hz, 6H) | (M+H)$^+$=415 | A | <1 |
| 120. | 6-Amino-5-benzyloxy-2-(4-fluoro-phenyl)-benzofuran-3-carboxylic acid methylamide | $^1$H NMR in CDCl$_3$: 7.86-7.80(m, 2H); 7.45-7.33(m, 5H); 7.287(s, 1H); 7.17-7.12(m, 2H); 6.85(s, 1H); 5.71(brs, 1H); 5.15(s, 2H); 2.97(d, J=5.3Hz, 3H) | (M+H)$^+$=391 | A | <10 |
| 121. | 5-Isopropoxy-2-(3-methyl-furan-2-yl)-benzofuran-3-carboxylic acid methylamide | $^1$H NMR in CDCl$_3$: 7.664-7.674(d, J=2.931, 1H); 7.512-7.518(d, J=1.759, 1H); 7.319-7.348(d, J=8.792, 1H); 6.893-6.932(d of d, J=2.931, 5.861, 1H); 6.721(brs, 1H); 6.448-6.453(d, J=1.759, 1H); 4.584-4.664(septet, J=5.861, 1H); 3.006-3.024(d, J=5.275, 3H); 2.322(s, 3H); 1.344-1.363(d, J=5.861, 6H) | *** | B | <30 |
| 122. | 2-(4-Fluoro-phenyl)-6-methanesulfonylamino-5-methoxy-benzofuran-3-carboxylic acid methylamide | $^1$H NMR in DMSO: 8.37(m, 1H); 7.93(dd, J=5.1 & 9.1Hz, 2H); 7.56(s, 1H); 7.36(t, J=8.8Hz, 2H); 7.17(s, 1H); 3.90(s, 3H); 2.98(s, 3H); 2.83(d, J=4.9Hz, 3H) | (M+H)$^+$=393 | A | <1 |
| 123. | 2-(4-Fluoro-phenyl)-5-isopropoxy-6-[(tetrahydro-furan-2-ylmethyl)-amino]-benzofuran-3-carboxylic acid methylamide | $^1$H NMR in DMSO: 8.27(d, br, 1H); 7.88(dd, 2H); 7.31(dd, 2H); 6.92(s, 1H); 6.84(s, 1H); 4.98(m, 1H); 4.57(m, 1H); 4.11(m, 1H); 3.8-3.64(m, 2H); 3.16(m, 1H); 2.82(d, 3H); 1.84-1.42(m, 4H); 1.35(d, 6H) | (M+H)$^+$=427 | A | <10 |
| 124. | 2-(4-Fluoro-phenyl)-5-hydroxy-6-morpholin-4-yl-benzofuran-3-carboxylic acid methylamide | $^1$H NMR in CDCl$_3$: 8.00-7.95(m, 2H); 7.36-7.26(m, 2H); 7.21-7.18(m, 2H); 6.98(brs, 1H); 5.83(brs, 1H); 3.95-3.92(m, 4H); 3.04(d, J=5.1Hz, 3H); 2.97-2.96(m, 4H) | (M+H)$^+$=370 | B | <10 |
| 125. | 5-Cyclopropylmethoxy-2-(4-fluoro-phenyl)-6-morpholin-4-yl-benzofuran-3-carboxylic acid methylamide | $^1$H NMR in CDCl$_3$: 7.89-7.84(m, 2H); 7.30(s, 1H); 7.22-7.16(m, 2H); 7.08(s, 1H); 5.76(brs, 1H); 3.94-3.97(m, 6H); 3.20-3.17(m, 2H); 3.01(d, J=4.8, 2H); 0.71-0.64(m, 2H); 0.42-0.38(m, 2H) | (M+H)$^+$=425 | A | <1 |
| 126. | 6-Chloro-2-(4-fluoro-phenyl)-5-methoxy-benzofuran-3-carboxylic acid methylamide | $^1$H NMR in CDCl$_3$: 7.86-7.81(m, 2H); 7.54(s, 1H); 7.42(s, 1H); 7.23-.16(m, 2H); 5.77(brs, 1H); 3.96(S, 3H); 2.98(d, J=4.7Hz, 3H) | (M+H)$^+$=334.0 | A | <1 |
| 127. | 6-(2,5-Dimethyl-2H-pyrazol-3-ylamino)-2-(4-fluoro-phenyl)-5-isopropoxy-benzofuran-3-carboxylic acid methylamide | $^1$H NMR in CDCl$_3$: 7.782-7.826(m, 2H); 7.352(s, 1H); 7.137-7.194(m, 2H); 6.840(s, 1H); 6.069(s, 1H); 5.930(s, 1H); 5.795(brs, 1H); 4.686-4.746(septet, J=6.447, 1H); 3.695(s, 3H); 2.986-3.004(d, J=5.275, 3H); 2.287(s, 1H); 1.645(brs, 2H); 1.436-1.457(d, J=6.447, 3H) | (M+H)$^+$=437.0 | C | *** |
| 128. | 2-(4-Fluoro-phenyl)-6-morpholin-4-yl-5- | $^1$H NMR in CDCl$_3$: 8.68-8.65(m, 2H); | (M+H)$^+$=462 | A | *** |

TABLE 1-continued

| Example Number | Name | NMR data* | Mass Spec | HCV pol-BB7 IC$_{50}$(μM) A=≦0.5μM B=0.5 to ≦5.0μM C=5.0 to ≦30μM D=>30μM | Replicon (μM) |
|---|---|---|---|---|---|
|  | (pyridin-4-ylmethoxy)-benzofuran-3-carboxylic acid methylamide | 7.87-7.82(m, 2H); 7.40-7.43(m, 3H); 7.25-7.15(m, 3H); 5.70(brs, 1H); 5.23(3, 2H): 3.98-3.92(m, 4H); 3.15-3.21(m, 4H): 2.99(d, J=48Hz, 3H) |  |  |  |
| 129. | 6-Cyano-2-(4-fluoro-phenyl)-5-isopropoxy-benzofuran-3-carboxylic acid methylamide | $^1$H NMR in CDCl$_3$: 7.87-7.82(m, 2H): 7.67(s, 1H); 7.45(s, 1H); 7.26-7.19(m, 2H); 5.73(brs, 1H); 4.75-4.67(m, 1H); 2.98(d, J=4.8Hz, 3H); 1.43(d, J=6.3Hz, 6H) | (M+H)$^+$=353 | A | *** |
| 130. | 5-Methoxy-2-phenyl-benzofuran-3-carboxylic acid ethylamide | $^1$H NMR in CDCl$_3$: 7.86(dd, J=2.1, 7.4Hz, 2H); 7.47(m, 3H); 7.39(m, 2H); 5.78(brs, 1H); 3.88(s, 3H); 6.94(dd, J=2.6, 9.0Hz, 1H); 3.48(dq, J=1.3, 7.2Hz, 2H); 1.17(t, 7.2Hz, 3H) | (M+H)$^+$=295 | C | <10 |
| 131. | 2-(4-Fluoro-phenyl)-5-isopropoxy-6-(pyridin-4-ylamino)-benzofuran-3-carboxylic acid methylamide | $^1$H NMR in CDCl$_3$: 8.29-8.31(d, 2H, J=5.86Hz); 7.80-7.84(m, 2H); 7.51(s, 1H); 7.36(s, 1H); 7.13-7.19(t, 2H, J=8.21Hz); 6.95-6.98(m, 2H); 6.62(s, 1H); 6.13-6.15(d, 1H, J=4.69Hz); 4.60-4.68(septet, 1H, J=5.86Hz); 2.97-2.99(d, 3H, J=5.28Hz); 1.37-1.39(d, 6H, J=5.86Hz) | (M+H)$^+$=420 | B | <30 |
| 132. | 2-(4-Fluoro-phenyl)-5-isopropoxy-6-(4-methyl-piperazin-1-yl)-benzofuran-3-carboxylic acid methylamide | $^1$H NMR in DMSO: 7.80-7.86(m, 2H); 7.21(s, 1H); 7.09-7.15(t, 2H, J=8.79Hz); 6.99(s, 1H); 6.12-6.14(d, 1H, J=4.69Hz); 4.58-4.66(septet, 9H, J=6.45Hz); 3.10(brs, 4H); 2.95-2.96(d, 3H, J=4.69Hz); 2.58(brs, 4H); 2.34(s, 3H); 1.34-1.36(d, 6H, J=6.45Hz) | (M+H)$^+$=426 | C | >30 |
| 133. | 6-(3-Chloro-propane-1-sulfonylamino)-2-(4-fluoro-phenyl)-5-isopropoxy-benzofuran-3-carboxylic acid methylamide | $^1$H NMR in DMSO: 9.11(s, 1H); 8.37(m, 1H); 7.92(dd, J=8.8 & 5.7Hz, 2H); 7.56(s, 1H); 7.36(t, J=8.8Hz, 2H); 7.16(s, 1H); 4.74(heptuplet, J=5.7Hz, 1H); 3.74(t, J=6.6Hz, 2H); 3.21(m, 2H); 2.82(d, J=4.8Hz, 3H); 2.21(m, 2H); 1.35(d, J=5.7Hz, 6H) | (M−H)$^-$=481; 483 | B | <1 |
| 134. | 6-(1,1-Dioxido-isothiazolidin-2-yl)-2-(4 fluoro-phenyl)-5-isopropoxy-benzofuran-3-carboxylic acid methylamide | $^1$H NMR in DMSO: 8.40(m, 1H); 7.92(dd, J=5.5 d 9.2Hz, 2H); 7.60(s, 1H); 7.37(t, J=9.2Hz, 2H); 7.19(s, 1H); 4.69(heptuplet, J=5.9Hz, 1H); 3.75(t, J=7.0Hz, 2H); 3.37(m, 2H); 2.82(d, J=4.9Hz, 3H); 2.43(p, J=7.0Hz, 2H); 1.34(d, J=5.9Hz, 6H) | (M+H)$^+$=447 | B | <10 |
| 135. | 2-(4-Fluoro-phenyl)-5-isopropoxy-6-ureido-benzofuran-3-carboxylic acid methylamide | $^1$H NMR in DMSO: 8.38(s, 1H); 8.28(m, 1H); 7.87(dd, J=5.3 & 9.2Hz, 2H); 7.30(t, J=8.8Hz, 2H); 7.09(s, 1H); 6.39(brs, 2H); 4.62(heptuplet, J=6.1Hz, 1H); 2.80(d, J=4.8Hz, 3H); 1.88(s, 1H); 1.32(d, J=5.7Hz, 6H) | (M+H)$^+$=486 | A | <10 |
| 136. | 2-(4-Fluoro-phenyl)-5-isopropoxy-6-(isopropyl-methanesulfonyl-amino)-benzofuran-3-carboxylic acid methylamide | $^1$H NMR in DMSO: 8.40(m, 1H); 7.90(dd, J=5.3 & 8.84Hz, 2H); 7.69(s, 1H); 7.36(t, J=8.8Hz, 2H); 7.11(s, 1H); 4.75(heptuplet, J=6.6Hz, 2H); 4.22(heptuplet, J=7.1Hz, 1H); 3.06(s, 3H); 2.80(d, J=7.1Hz, 3H); 1.32(t, J=6.6Hz, 6H); | (M+H)$^+$=463 | A | <1 |

TABLE 1-continued

| Example Number | Name | NMR data* | Mass Spec | HCV pol-BB7 IC$_{50}$(µM) A=≦0.5µM B=0.5 to ≦5.0µM C=5.0 to ≦30µM D=>30µM | Replicon (µM) |
|---|---|---|---|---|---|
| | | 1.20(d, J=7.1Hz, 3H); 1.05(d, J=7.1Hz, 3H) | | | |
| 137. | 6-(Cyclopropylmethyl-methanesulfonyl-amino)-2-(4-fluoro-phenyl)-5-isopropoxy-benzofuran-3-carboxylic acid methylamide | $^1$H NMR in DMSO: 8.44(m, 1H); 7.94(dd, J=5.1 & 9.1Hz, 2H); 7.57(s, 1H); 7.38(t, J=8.8Hz, 2H); 7.16(s, 1H); 6.78(heptuplet, J=5.7Hz, 1H); 3.01(s, 3H); 2.83(d, J=4.4Hz, 3H); 1.33(d, J=5.7Hz, 6H); 0.85(m, 1H); 0.37(m, 2H) | (M+H)$^+$=475 | A | <1 |
| 138. | 6-(2,6-Dimethyl-morpholin-4-yl)-2-(4-fluoro-phenyl)-5-isopropoxy-benzofuran-3-carboxylic acid methylamide | $^1$H NMR in CDCl$_3$: 7.89-7.84(m, 2H); 7.28(d, J=8.79Hz, 2H); 7.17(T, J=8.79Hz, 2H); 7.04(s, 1H); 5.77(s, 1H); 4.69-4.61(septet, J=6.15Hz, 1H); 3.95-3.89(m, 2H); 3.46(d, J=11.43Hz, 2H); 2.98(d, J=4.84Hz, 3H); 2.37(T, J=10.55Hz, 2H); 1.37(d, J=6.15Hz, 6H); 1.25(d, J=6.15Hz, 6H) | (M+H)$^+$=441 | B | <10 |
| 139. | 2-(4-Fluoro-phenyl)-5-isopropoxy-6-(1H-tetrazol-5-yl)-benzofuran-3-carboxylic acid methylamide | $^1$H NMR in CDCl$_3$: 8.547(s, 1H); 7.89-7.84(m, 2H); 7.61(s, 1H); 7.60-7.20(m, 2H); 5.8(brs, 1H); 5.0-4.92(m, 1H); 3.26(brs, 1H); 2.99(d, J=5.1Hz, 3H); 1.52(d, J=6.0Hz, 6H) | (M+H)$^+$=396 | B | >30 |
| 140. | 2-(4-Fluoro-phenyl)-6-(4-hydroxy-piperidin-1-yl)-5-isopropoxy-benzofuran-3-carboxylic acid methylamide | $^1$H NMR in DMSO: 8.28(d, J=4.84Hz, 1H); 7.92-7.86(m, 2H); 7.33(t, J=8.79Hz, 2H); 7.16(s, 1H); 7.03(s, 1H); 4.64-4.56(m, 2H); 3.61(m, 1H); 3.35(m, 2H); 2.82(d, J=4.40Hz, 3H); 2.74-2.67(m, 2H); 1.88-1.85(m, 2H); 1.62-1.52(m, 2H); 1.29(d, J=5.72Hz, 6H) | (M+H)$^+$=427 | B | <10 |
| 141. | 2-(4-Fluoro-phenyl)-6-(3-hydroxy-piperidin-1-yl)-5-isopropoxy-benzofuran-3-carboxylic acid methylamide | $^1$H NMR in DMSO: 8.29(d, J=4.84Hz, 1H); 7.92-7.87(m, 2H); 7.33(t, J=8.79Hz, 2H); 7.14(s, 1H); 7.03(s, 1H); 4.73(d, J=4.84Hz, 1H); 4.63-4.55(septet, J=6.15Hz, 1H); 3.67-3.65(m, 1H); 3.49(d, J=8.79Hz, 2H); 2.82(d, J=4.40Hz, 3H); 2.5(m, 1H); 2.33(t, J=9.67Hz, 1H); 1.95-1.91(m, 1H); 1.74(m, 1H); 1.62-1.58(m, 2H); 1.29(d, J=6.15Hz, 3H); 1.28(d, J=5.71, 3H) | (M+H)$^+$=427 | B | <10 |
| 142. | 2-(4-Fluoro-phenyl)-5-isopropoxy-6-(morpholine-4-sulfonyl)-benzofuran-3-carboxylic acid methylamide | $^1$H NMR in DMSO: 8.48-8.47(d, J=4.69Hz, 1H); 8.01(s, 1H); 8.00-7.95(m, 2H); 7.44-7.38(t, J=8.79Hz, 2H); 7.34(s, 1H); 4.91-4.83(septet, J=5.86Hz, 1H); 3.62-3.59(m, 4H); 3.16-3.13(m, 4H); 2.85-2.84(d, J=4.69Hz, 3H); 1.37-1.35(d, J=5.86Hz, 6H) | (M+H)$^+$=477 | A | <10 |
| 143. | 2-(4-Fluoro-phenyl)-5-isopropoxy-6-methylsulfamoyl-benzofuran-3-carboxylic acid methylamide | $^1$H NMR in DMSO: 8.46-8.45(d, J=4.10Hz, 1H); 7.99-7.95(m, 2H); 7.95(s, 1H); 7.43-7.37(t, J=8.79Hz, 2H); 7.32(s, 1H); 6.64(d, J=4.69Hz, 1H); 4.90-4.82(septet, J=5.86Hz, 1H); 2.85-2.83(d, J=4.69Hz, 3H); 2.48-2.46(d, J=4.69Hz, 3H); 1.38-1.36(d, J=5.86Hz, 6H) | (M+H)$^+$=421 | A | >30 |
| 144. | 6-Dimethylsulfamoyl-2-(4-fluoro-phenyl)-5-isopropoxy-benzofuran-3-carboxylic acid | $^1$H NMR in DMSO: 8.461=8.451(d, J=4.689Hz, 1H); 8.016-7.949(m, 3H); 7.436-7.377(t, J=8.791Hz, 2H); | (M+H)$^+$=435 | A | <30 |

TABLE 1-continued

| Example Number | Name | NMR data* | Mass Spec | HCV pol-BB7 IC$_{50}$(μM) A=≤0.5μM B=0.5 to ≤5.0μM C=5.0 to ≤30μM D=>30μM | Replicon (μM) |
|---|---|---|---|---|---|
| | methylamide | 7.323(s, 1H); 4.904-4.823(septet, J=5.861Hz, 1H); 2.848-2.832(d, J=4.689Hz, 3H); 2.775(s, 6H); 1.365-1.344(d, J=6.447Hz, 6H) | | | |
| 145. | 2-(4-Fluoro-phenyl)-5-isopropoxy-6-(propane-2-sulfonylamino)-benzofuran-3-carboxylic acid methylamide | $^1$H NMR in DMSO: 8.85(s, 1H); 8.36(m, 1H); 7.91(dd, J=9.2, 5.3Hz, 2H); 7.59(s, 1H); 7.36(t, J=8.8Hz, 2H); 7.13(s, 1H); 4.75(heptuplet, J=5.6Hz, 1H); 3.21(heptuplet, J=5.5Hz, 1H); 2.82(d, J=4.9Hz, 3H); 1.36(d, J=5.5Hz, 6H); 1.28(d, J=5.6Hz, 6H) | (M+H)$^+$=449 | B | <10 |
| 146. | 2-(4-Fluoro-phenyl)-5-isopropoxy-benzofuran-3,6-dicarboxylic acid 6-amide 3-methylamide | $^1$H NMR in CDCl$_3$: 8.33(s, 1H); 8.10(brs, 1H); 7.88-7.84(m, 2H); 7.48(s, 1H); 7.25-7.18(m, 2H); 5.88(brs, 1H); 5.75(brs, 1H); 4.88-4.80(m, 1H); 2.99(d, J=5.4Hz, 3H); 1.46(d, J=6.3Hz, 6H) | (M+H)$^+$=371 | B | >30 |
| 147. | 2-(4-Fluoro-phenyl)-5-isopropoxy-6-pyrimidin-5-yl-benzofuran-3-carboxylic acid methylamide | $^1$H NMR in DMSO: 9.13(s, 1H); 8.99(s, 2H); 8.41(q, br, 1H); 7.92(m, 2H); 7.82(s, 1H); 7.36(m, 2H); 7.27(s, 1H); 4.64(m, 1H); 2.83(d, 3H); 1.23(d, 6H) | (M+H)$^+$=406 | A | <10 |
| 148. | 6-tert-Butylamino-2-(4-fluoro-phenyl)-5-isopropoxy-benzofuran-3-carboxylic acid methylamide | $^1$H NMR in CDCl$_3$: 7.85-7.80(m, 2H); 7.18(s, 1H); 7.14(t, J=8.79Hz, 2H); 6.98(s, 1H); 5.74(brs, 1H); 4.60-4.52(septet, J=6.15Hz, 1H); 4.57(s, 1H); 2.97(d, J=4.84Hz, 3H); 1.41(s, 9H); 1.37(d, J=6.15Hz, 6H) | (M+H)$^+$=399 | A | <10 |
| 149. | 2-(4-Fluoro-phenyl)-5-isopropoxy-6-sulfamoyl-benzofuran-3-carboxylic acid methylamide | $^1$H NMR in DMSO: 8.39-8.37(d, J=4.69Hz, 1H); 7.97-7.93(m, 2H); 7.91(s, 1H); 7.39-7.33(t, J=8.79Hz, 2H); 7.07(s, 1H); 4.66(septet, J=6.45Hz, 1H); 2.84-2.82(d, J=4.69Hz, 3H); 1.30-1.28(d, J=6.45Hz, 6H) | (M−H)$^-$=406.0 | C | >30 |
| 150. | 6-Cyclobutylsulfamoyl-2-(4-fluoro-phenyl)-5-isopropoxy-benzofuran-3-carboxylic acid methylamide | $^1$H NMR in CDCl$_3$: 8.057(s, 1H); 7.869-7.823(m, 2H); 7.522(s, 1H); 7.248-7.205(m, 2H); 5.766(brs, 1H); 5.156-5.125(d, J=9.377Hz, 1H); 4.895-4.813(septet, J=5.862Hz, 1H); 3.787-3.707(sextet, J=8.206Hz, 1H); 2.984-2.969(d, J=4.689Hz, 3H); 2.063-1.967(m, 2H); 1.828-1.734(m, 2H); 1.580-1.512(m, 2H); 1.494-1.475(d, J=5.862Hz, 6H) | (M+H)$^+$=461.0 | B | <30 |
| 151. | 2-(4-Fluoro-phenyl)-6-furan-2-yl-5-isopropoxy-benzofuran-3-carboxylic acid methylamide | $^1$H NMR in CDCl$_3$: 7.96(s, 1H); 7.88(m, 2H); 7.48(d, 1H); 7.37(s, 1H); 7.17(m, 2H); 7.08(d, 1H); 6.51(d, 1H); 5.75(s, br, 1H); 4.79(m, 1H); 2.99(d, 3H); 1.45(d, 6H) | (M+H)$^+$=394 | A | <30 |
| 152. | 2-(4-Fluoro-phenyl)-6-furan-3-yl-5-isopropoxy-benzofuran-3-carboxylic acid methylamide | $^1$H NMR in CDCl$_3$: 8.12(s, 1H); 7.90(m, 2H); 7.61(s, 1H); 7.48(d, 1H); 7.38(s, 1H); 7.18(m, 2H); 6.83(d, 1H); 5.75(s, br, 1H); 4.79(m, 1H); 2.99(d, 3H); 1.45(d, 6H) | (M+H)$^+$=394 | A | <10 |
| 153. | 2-(4-Fluoro-phenyl)-5-isopropoxy-6-pyridin-3-yl-benzofuran-3-carboxylic acid methylamide | $^1$H NMR in CDCl$_3$: 8.80(d, 1H); 8.57(dd, 2H); 7.92(m, 3H); 7.45(s, 2H); 7.33(dd, 1H); 7.20(m, 2H); 5.80(s, br, 1H); 4.56(m, 1H); 2.99(d, 3H); 1.28(d, 6H) | (M+H)$^+$=405 | A | <10 |

TABLE 1-continued

| Example Number | Name | NMR data* | Mass Spec | HCV pol-BB7 IC$_{50}$(μM) A=≦0.5μM B=0.5 to ≦5.0μM C=5.0 to ≦30μM D=>30μM | Replicon (μM) |
|---|---|---|---|---|---|
| 154. | 2-(4-Fluoro-phenyl)-5-isopropoxy-6-(pyrrolidine-1-sulfonyl)-benzofuran-3-carboxylic acid methylamide | $^1$H NMR in DMSO: 8.455-8.471(m, 1H); 8.028(s, 1H), 7.996-7.949(m, 2H); 7.436-7.375(m, 2H); 7.321(s, 1H); 4.918-4.838(septet, J=5.861Hz, 1H); 2.846-2.832(d, J=4.103, 3H); 2.512-2.486(pentet, J=1.758Hz, 4H); 1.779-1.736(t, J=6.447Hz, 4H); 1.371-1.350(d, J=6.447Hz, 6H) | (M+H)$^+$=461.0 | A | <10 |
| 155. | 6-Cyclopropylsulfamoyl-2-(4-fluoro-phenyl)-5-isopropoxy-benzofuran-3-carboxylic acid methylamide | $^1$H NMR in DMSO: 8.47-8.46(d, J=41.0Hz, 1H); 8.03(s, 1H); 8.00-7.94(m, 2H); 7.44-7.38(t, J=8.79Hz, 2H); 7.32(s, 1H); 7.21(s, 1H); 4.89-4.85(septet, J=5.86Hz, 1H); 2.85-2.83(d, J=4.69Hz, 3H); 2.17(m, 1H); 1.38-1.36(d, J=5.86Hz, 6H); 0.44(m, 4H) | (M+H)$^+$=447.0 | A | <10 |
| 156. | 6-Ethylsulfamoyl-2-(4-fluoro-phenyl)-5-isopropoxy-benzofuran-3-carboxylic acid methylamide | $^1$H NMR in DMSO: 8.87(s, 1H); 8.36(m, 1H); 7.91(dd, J=9.0, 5.3Hz, 2H); 7.56(s, 1H); 7.36(t, J=8.8Hz, 2H); 7.14(s, 1H); 4.75(heptuplet, J=6.1Hz, 1H); 3.05(quadruplet, J=7.5Hz, 2H); 2.82(d, J=4.8Hz, 3H); 1.33(d, J=6.1Hz, 6H); 1.26(t, J=7.5Hz, 3H) | (M+H)$^+$=435 | A | <10 |
| 157. | 2-(4-Fluoro-phenyl)-5-isopropoxy-6-vinyl-benzofuran-3-carboxylic acid methylamide | $^1$H NMR in DMSO: 8.39(q, br, 1H); 7.91(dd, 2H); 7.82(s, 1H); 7.35(dd, 2H); 7.12(s, 1H); 7.05(dd, 1H); 6.89(d, 1H); 5.27(d, 1H); 4.60(m, 1H); 2.81(d, 3H); 1.31(d, 6H) | (M+H)$^+$=354 | A | <10 |
| 158. | 2-(4-Fluoro-phenyl)-5-isopropoxy-6-methoxy-benzofuran-3-carboxylic acid methylamide | $^1$H NMR in CDCl$_3$: 7.86(m, 2H); 7.34(s, 1H); 7.16(t, J=8.79Hz, 2H); 7.05(s, 1H); 5.75(brs, 1H); 4.55(m, 1H); 3.91(s, 3H); 2.99(d, J=4.69Hz, 3H); 1.39(d, J=5.86Hz, 6H) | (M+H)$^+$=358 | A | <10 |
| 159. | 6-(3,5-Dimethyl-isoxazol-4-yl)-2-(4-fluoro-phenyl)-5-isopropoxy-benzofuran-3-carboxylic acid methylamide | $^1$H NMR in CDCl$_3$: 7.90-7.85(m, 2H); 7.63(s, 2H); 7.23-7.17(m, 3H); 5.78(brs, 1H); 4.52-4.48(m, 1H); 3.0(d, J=4.8Hz, 3H); 2.32(s, 3H); 2.20(s, 3H); 1.24(d, J=6.3Hz, 6H) | (M+H)$^+$=423 | A | <1 |
| 160. | 2-(4-Fluoro-phenyl)-6-formyl-5-isopropoxy-benzofuran-3-carboxylic acid methylamide | $^1$H NMR in CDCl$_3$: 10.524(s, 1H); 7.93(s, 1H); 7.90-7.85(m, 2H); 7.44(s, 1H); 7.25-7.19(m, 2H); 5.78(br, 1H); 4.76(pent, 1H); 2.98(d, 3H); 1.43(d, 6H) | (M+H)$^+$=355.9 | A | <30 |
| 161. | 2-(4-Fluoro-phenyl)-6-(6-fluoro-pyridin-3-yl)-5-isopropoxy-benzofuran-3-carboxylic acid methylamide | $^1$H NMR in CDCl$_3$: 8.52(s, 1H); 8.45(d, 1H); 7.88(dd, 2H); 7.45(s, 1H); 7.38(m, 1H); 7.26(s, 1H); 7.20(dd, 2H); 5.77(s, br, 1H); 4.55(m, 1H); 2.99(d, 3H); 1.24(d, 6H) | (M+H)$^+$=423 | A | <10 |
| 162. | 2-(4-Fluoro-phenyl)-5-isopropoxy-6-(methanesulfonylamino-methyl)-benzofuran-3-carboxylic acid methylamide | $^1$H NMR in CDCl$_3$: 7.85-7.81(m, 2H); 7.44(s, 1H); 7.41(s, 1H), 7.23-7.17(m, 2H), 5.73(s, 1H); 4.98(t, J=5.4Hz, 1H); 4.78-4.71(m, 1H); 4.39(d, J=6.6Hz, 3H); 2.97(d, J=4.8Hz, 3H); 2.74(s, 3H); 1.40(d, J=5.7Hz, 6H) | (M+H)$^+$=435 | B | <10 |
| 163. | 6-(Cyclopentyl-methanesulfonylamino)-2-(4-fluoro-phenyl)-5-isopropoxy-benzofuran-3-carboxylic acid | $^1$H NMR in DMSO: 8.42(m, 1H); 7.94(dd, J=6.2 & 8.8Hz, 2H); 7.53(s, 1H); 7.38(t, J=8.8Hz, 2H); 7.13(s, 1H); 4.76(heptuplet, J=5.7Hz, 1H); 4.28(quintuplet, J=8.8Hz, 1H); | (M+H)$^+$=489 | A | <1 |

TABLE 1-continued

| Example Number | Name | NMR data* | Mass Spec | HCV pol-BB7 IC$_{50}$(μM) A=≦0.5μM B=0.5 to ≦5.0μM C=5.0 to ≦30μM D=>30μM | Replicon (μM) |
|---|---|---|---|---|---|
| | methylamide | 3.11(s, 3H); 2.83(m, 3H); 1.93(m, 2H); 1.45(m, 2H); 1.34(m, 4H) | | | |
| 164. | 2-(4-Fluoro-phenyl)-6-[(2-hydroxy-ethyl)-methanesulfonylamino]-5-isopropoxy-benzofuran-3-carboxylic acid methylamide | $^1$H NMR in DMSO: 8.41(m, 1H); 7.93(dd, J=5.2Hz, 2H); 7.60(s, 1H); 7.38(t, J=8.8Hz, 2H); 7.16(s, 1H); 4.78(heptuplet, J=5.8Hz, 1H); 4.67(t, J=5.7Hz, 1H); 3.60(brs, 1H); 3.04(s, 3H); 2.83(d, J=4.8Hz, 3H); 1.34(d, J=5.7Hz, 6H) | (M+H)$^+$=465 | A | <10 |
| 165. | 2-(4-Fluoro-phenyl)-5-hydroxy-6-methoxy-benzofuran-3-carboxylic acid methylamide | $^1$H NMR in CDCl$_3$: 7.94(m, 2H); 7.28(s, 1H); 7.15(t, 2H, J=8.79Hz); 7.04(s, 1H); 5.82(brs, 1H); 5.59(s, 1H); 3.97(s, 3H); 3.01(d, 3H, J=5.28Hz) | (M+H)$^+$=316 | C | >30 |
| 166. | 5-Ethoxy-2-(4-fluoro-phenyl)-6-morpholin-4-yl-benzofuran-3-carboxylic acid methylamide | $^1$H NMR in DMSO: 8.30(m, 1H); 7.88(m, 2H); 7.32(t, 2H, J=8.79Hz); 7.16(s, 1H); 7.04(s, 1H); 4.06(q, 2H, J=7.03Hz); 3.74(brm, 4H); 3.02(brm, 4H); 2.80(d, 3H, J=4.69Hz); 1.36(t, 3H, J=7.03Hz) | (M+H)$^+$=399 | B | <10 |
| 167. | 5-(4-Fluoro-benzyloxy)-2-(4-fluoro-phenyl)-6-morpholin-4-yl-benzofuran-3-carboxylic acid methylamide | $^1$H NMR in DMSO: 8.30(m, 1H); 7.88(m, 2H); 7.55(m, 2H); 7.33(t, 2H, J=8.79Hz); 7.27-7.20(m, 4H); 5.14(s, 2H); 3.72(brm, 4H); 3.03(brm, 4H); 2.82(d, 3H, J=4.69) | (M+H)$^+$=479 | B | <1 |
| 168. | 2-(4-Fluoro-phenyl)-5-isopropoxy-6-oxazol-5-yl-benzofuran-3-carboxylic acid methylamide | $^1$H NMR in CDCl$_3$: 7.91-7.83(m, 4H); 7.69(s, 1H); 7.41(s, 1H); 7.22-7.14(m, 2H); 5.79(brs, 1H); 4.86-4.78(m, 1H); 2.99(d, J=4.8Hz, 2H); 1.46(d, J=6.3Hz, 6H) | (M+H)$^+$=395 | A | <10 |
| 169. | 2-(4-Fluoro-phenyl)-6-(4-hydroxy-piperidine-1-sulfonyl)-5-isopropoxy-benzofuran-3-carboxylic acid methylamide | $^1$H NMR in DMSO: 8.47-8.49(d, 1H, J=4.69Hz); 8.01(s, 1H); 7.95-8.00(m, 2H); 7.38-7.44(t, 2H, J=8.79Hz); 7.32(s, 1H); 4.82-4.90(septet, 1H, J=5.86Hz); 4.67-4.69(d, 1H, J=4.10Hz); 3.58-3.59(m, 1H); 3.35-3.45(m, 2H); 3.24-3.30(m, 1H); 2.92-3.00(m, 2H); 2.84-2.85(d, 3H, J=4.69Hz); 1.69-1.73(m, 2H); 1.36-1.41(m, 1H); 1.34-1.36(d, 6H, J=5.86Hz) | (M+H)$^+$=491 | A | <1 |
| 170. | 6-(4,4-Difluoro-piperidin-1-yl)-2-(4-fluoro-phenyl)-5-isopropoxy-benzofuran-3-carboxylic acid methylamide | $^1$H NMR in CDCl$_3$: 7.87(m, 2H); 7.31(s, 1H); 7.17(t, J=8.35Hz, 2H); 7.07(s, 1H); 5.74(s, 1H); 4.69-4.61(septet, J=6.16Hz, 1H); 3.23-3.19(m, 4H); 2.98(d, J=5.27Hz, 3H); 2.24-2.11(m, 4H); 1.39(d, J=6.16Hz, 6H) | (M+H)$^+$=447 | C | <1 |
| 171. | 2-(4-Fluoro-phenyl)-6-(4-fluoro-piperidin-1-yl)-5-isopropoxy-benzofuran-3-carboxylic acid methylamide | $^1$H NMR in CDCl$_3$: 7.89-7.83(m, 2H); 7.28(s, 1H); 7.16(t, J=8.79Hz, 2H); 7.07(s, 1H); 5.76(s, 1H); 4.92-4.72(m, 1H); 4.69-4.61(septet, J=6.16Hz, 1H); 3.24-3.22(m, 2H); 3.08-3.01(m, 2H); 2.98(d, J=4.84Hz, 3H); 2.18-2.02(m, 4H); 1.38(d, J=5.71Hz, 6H) | (M+H)$^+$=429 | B | <1 |
| 172. | 5-Difluoromethoxy-2-(4-fluoro-phenyl)-6-morpholin-4-yl-benzofuran-3-carboxylic acid methylamide | $^1$H NMR in CDCl$_3$: 7.87(dd, J=8.8, 5.7Hz, 2H); 7.54(s, 1H); 7.16(t, J=8.8Hz, 2H); 7.11(s, 1H); 6.57(t, J=75.6Hz, 1H); 5.92(d, J=4.7Hz, 1H); 3.87(t, J=4.0Hz, 4H); 3.08(t, J=4.0Hz, 4H); 2.98(d, J=4.9Hz, 3H) | (M+H)$^+$=421 | A | <1 |

TABLE 1-continued

| Example Number | Name | NMR data* | Mass Spec | HCV pol-BB7 IC$_{50}$(μM) A=≦0.5μM B=0.5 to ≦5.0μM C=5.0 to ≦30μM D=>30μM | Replicon (μM) |
|---|---|---|---|---|---|
| 173. | 5-Cyclopentyloxy-2-(4-fluoro-phenyl)-6-morpholin-4-yl-benzofuran-3-carboxylic acid methylamide | $^1$H NMR in CDCl$_3$: 7.86(dd, J=9.4, 5.3Hz, 2H); 7.28(s, 1H); 7.16(t, J=9.4Hz, 2H); 7.04(s, 1H); 5.74(brs, 1H); 4.90(m, 1H); 3.90(t, J=4.7Hz, 4H); 3.11(t, J=4.7Hz, 1H); 2.98(d, J=4.7Hz, 3H); 1.95(m, 4H); 1.80(m, 2H); 1.70(m, 2H) | (M−H)$^-$=437 | A | <1 |
| 174. | 2-(4-Fluoro-phenyl)-5-hydroxy-6-methanesulfonylamino-benzofuran-3-carboxylic acid methylamide | $^1$H NMR in DMSO: 8.36(d, J=14.7Hz, 1H); 7.91(dd, J=8.8, 3.0Hz, 2H); 7.48(s, 1H); 7.36(t, J=8.8Hz, 2H); 7.08(s, 1H); 2.98(s, 1H); 2.82(d, J=4.7Hz, 3H) | (M+H)$^+$=379 | B | <30 |
| 175. | 2-(4-Fluoro-phenyl)-5-isopropoxy-6-(thiomorpholine-4-sulfonyl)-benzofuran-3-carboxylic acid methylamide | $^1$H NMR in DMSO: 8.47-8.48(d, 1H J+4.10Hz); 8.03(s 1H); 7.95-8.00(m, 2H); 7.38-7.44(t, 2H, J=8.79Hz); 7.33(s, 1H); 4.84-4.92(septet, 1H, J=6.45Hz); 3.42-3.46(m, 4H); 2.83-2.85(d, 3H, J=4.69Hz); 2.62-2.65(m, 4H); 1.35-1.37(d, 6H, J=5.86Hz) | (M+H)$^+$=493 | A | <1 |
| 176. | 2-(4-Fluoro-phenyl)-6-(3-hydroxy-pyrrolidine-1-sulfonyl)-5-isopropoxy-benzofuran-3-carboxylic acid methylamide | $^1$H NMR in DMSO: 8.46-8.48(d, 1H, J=4.69Hz); 8.03(s, 1H); 7.95-7.99(m, 2H); 7.38-7.43(t, 2H, J=8.79Hz); 7.31(s, 1H); 4.99(br.s, 1H); 4.82-4.80(septet, 1H, J=5.86Hz); 4.24(br.s, 1H); 3.38-3.46(m, 4H); 3.07-3.11(dd, 1H, J=2.35Hz, 9.96Hz); 2.83-2.84(d, 3H, J=4.69Hz); 1.79-1.86(m, 1H); 1.68-1.77(m, 1H); 1.35-1.37(d, 6H, J=5.86Hz) | (M+H)$^+$=477 | A | <1 |
| 177. | 2-(4-Fluoro-phenyl)-5-isopropoxy-6-pyridin-4-yl-benzofuran-3-carboxylic acid methylamide | $^1$H NMR in DMSO: 8.61(m, 2H); 8.42(s, 1H); 7.94(dd, 2H); 7.72(s, 1H); 7.60(d, 2H); 7.36(dd, 2H); 7.25(s, 1H); 4.6(m, 1H); 2.84(d, 3H); 1.22(d, 6H) | (M+H)$^+$=405 | A | <10 |
| 178. | 2-(4-Fluoro-phenyl)-5-isopropoxy-6-(3-methanesulfonyl-phenyl)-benzofuran-3-carboxylic acid methylamide | $^1$H NMR in DMSO: 8.42(m, 1H); 8.16(m, 1H); 7.98-7.88(m, 4H); 7.72(s, 1H); 7.69(t, 1H); 7.39(dd, 2H); 7.27(s, 1H); 4.60(m, 1H); 3.26(s, 3H); 2.86(d, 3H); 1.29(d, 6H) | (M+H)$^+$=482 | A | <10 |
| 179. | 2-(4-Fluoro-phenyl)-5-isopropoxy-6-(4-methanesulfonyl-phenyl)-benzofuran-3-carboxylic acid methylamide | $^1$H NMR in DMSO: 8.43(m, 1H); 7.99-7.94(m, 4H); 7.84(d, 2H); 7.70(s, 1H); 7.41(dd, 2H); 7.27(s, 1H); 4.62(m, 1H); 3.28(s, 3H); 2.85(d, 3H); 1.24(d, 6H) | (M+H)$^+$=482 | A | <10 |
| 180. | 5-(2-Chloro-ethoxy)-2-(4-fluoro-phenyl)-6-morpholin-4-yl-benzofuran-3-carboxylic acid methylamide | $^1$H NMR in CDCl$_3$: 7.85-7.80(m, 2H); 7.32(s, 1H); 7.20-7.15(m, 2H); 7.08(s, 2H); 5.75(brs, 2H); 4.37-4.33(m, 2H); 4.94-4.89(m, 6H); 3.17-3.14(m, 4H); 2.97(d, J=5.4Hz, 3H) | (M+H)$^+$=433 | A | >30 |
| 181. | 6-Benzyloxy-2-(4-fluoro-phenyl)-5-methoxy-benzofuran-3-carboxylic acid methylamide | $^1$H NMR in DMSO: 7.80(dd, J=8.8, 5.3Hz, 2H); 7.50(m, 2H), 7.40(m, 3H), 7.34(s, 1H); 7.16(t, J=8.8Hz, 2H); 7.05(s, 1H); 5.75(br d, J=4.7Hz, 1H); 5.22(s, 3H); 3.96(s, 3H); 2.99(d, J=4.7Hz, 3H) | (M+H)$^+$=406 | A | <10 |
| 182. | 6-Amino-2-(4-fluoro-phenyl)-5-hydroxy-benzofuran-3-carboxylic acid | $^1$H NMR in DMSO: 10.55(br s, 1H); 8.40(d, J=4.7Hz, 1H); 7.90(dd, J=8.8, 5.3Hz, 2H); 7.61(s, 1H); 7.34(t, | (M+H)$^+$=301 | B | <30 |

TABLE 1-continued

| Example Number | Name | NMR data* | Mass Spec | HCV pol-BB7 IC$_{50}$(μM) A=≦0.5μM B=0.5 to ≦5.0μM C=5.0 to ≦30μM D=>30μM | Replicon (μM) |
|---|---|---|---|---|---|
| | methylamide | J=8.8Hz, 2H); 7.16(s, 1H); 2.79(d, J=4.7Hz, 3H) | | | |
| 183. | 5,6-Bis-benzyloxy-2-(4-fluoro-phenyl)-benzofuran-3-carboxylic acid methylamide | $^1$H NMR in DMSO: 8.29(m, 1H); 7.86(m, 2H); 7.49-7.30(m, 13H); 7.23(s, 1H); 5.22(s, 2H); 5.14(s, 2H); 2.80(d, 3H, J=4.10) | (M+H)$^+$=482 | D | <10 |
| 184. | 2-(4-Fluoro-phenyl)-5-isopropoxy-6-(5-trifluoromethyl-[1,2,4]oxadiazol-3-yl)-benzofuran-3-carboxylic acid methylamide | $^1$H NMR in CDCl$_3$: 8.17(s, 1H); 7.91-7.86(m, 2H); 7.54(s, 1H); 7.25-7.19(m, 2H); 5.77(brs, 1H); 4.81-4.73(m, 1H); 3.0(d, J=4.8Hz, 3H); 1.44(d, J=6.3Hz, 6H) | (M+H)$^+$=464 | B | <30 |
| 185. | [2-(4-Fluoro-phenyl)-5-isopropoxy-3-methylcarbamoyl-benzofuran-6-yl]-piperazine-1-carboxylic acid amide | $^1$H NMR in CDCl$_3$: 7.87-7.81(m, 2H); 7.31(s, 1H); 7.16(t, J=8.35Hz, 2H); 7.03(s, 1H); 5.80(s, 1H); 4.69-4.61(septet, J=6.15Hz, 1H); 4.53(s, 2H); 3.60-3.57(m, 4H); 3.12-3.09(m, 4H); 2.98(d, J=5.27Hz, 3H); 1.38(d, J=6.15Hz, 6H) | (M+H)$^+$=455 | C | <10 |
| 186. | 2-(4-Fluoro-phenyl)-5-isopropoxy-6-thiomorpholin-4-yl-benzofuran-3-carboxylic acid methylamide | $^1$H NMR in CDCl$_3$: 7.87-7.83(m, 2H); 7.29(s, 1H); 7.16(t, J=8.35Hz, 2H); 7.05(s, 1H); 5.73(s, 1H); 4.65-4.62(septet, J=5.71Hz, 1H); 3.34(m, 4H); 2.98(d, J=4.84Hz, 3H); 2.84(m, 4H); 1.37(d, J=6.15Hz, 6H) | (M+H)$^+$=429 | A | <1 |
| 187. | 2-(4-Fluoro-phenyl)-5-isopropoxy-3-methylcarbamoyl-benzofuran-6-carboxylic acid | $^1$H NMR in CDCl$_3$: 8.41-8.42(d, 1H, J=4.69Hz); 7.93-7.97(m, 2H); 7.80(s, 1H); 7.35-7.41(t, 2H, J=8.79Hz); 7.20(s, 1H); 4.58-4.66(septet, 1H, J=5.86Hz); 2.83-2.84(d, 3H, J=4.69Hz); 1.28-1.30(d, 6H, J=5.86Hz) | (M−H)$^−$=370 | C | <10 |
| 188. | 2-(4-Fluoro-phenyl)-5-isopropoxy-6-(1-oxo-thiomorpholin-4-yl)-benzofuran-3-carboxylic acid methylamide | $^1$H NMR in CDCl$_3$: 7.84-7.82(m, 2H); 7.34(s, 1H); 7.18(t, J=8.35, 2H); 7.13(s, 1H); 5.76(s, 1H); 4.69-4.65(septet, J=5.71Hz, 1H); 3.75-3.68(m, 2H); 3.39-3.35(m, 2H); 3.10(s, 4H); 2.99(d, J=4.40Hz, 3H); 1.41(d, J=6.15Hz, 6H) | (M+H)$^+$=445 | C | <10 |
| 189. | {[2-(4-Fluoro-phenyl)-5-isopropoxy-3-methylcarbamoyl-benzofuran-6-yl]-methanesulfonyl-amino}-acetic acid | $^1$H NMR in DMSO: 10.9(s, 1H); 8.43(m, 1H); 7.96(m, 2H); 7.66(s, 1H); 7.38(m, 2H); 7.17(s, 1H); 4.79(heptuplet, J=6.1Hz, 1H); 4.28(s, 2H); 3.08(s, 3H); 2.83(d, J=4.8Hz, 3H); 1.35(d, J=6.1Hz, 6H) | (M+H)$^+$=479 | B | <1 |
| 190. | 6-(Cyclobutyl-methanesulfonyl-amino)-2-(4-fluoro-phenyl)-5-isopropoxy-benzofuran-3-carboxylic acid methylamide | $^1$H NMR in DMSO: 8.43(m, 1H); 7.93(dd, J=3.1 & 6.6Hz, 2H); 7.57(s, 1H); 7.39(t, J=8.8Hz, 2H); 7.15(s, 1H); 4.78(heptuplet, J=6.1Hz, 1H); 3.2(m, 1H); 3.02(s, 3H); 2.83(d, J=5.8Hz, 3H); 2.46(m, 6H); 2.38(d, 6.1Hz, 6H) | (M+H)$^+$=475 | A | <1 |
| 191. | 2-(4-Fluoro-phenyl)-5-isopropoxy-6-[methanesulfonyl-(2-morpholin-4-yl-ethyl)-amino]-benzofuran-3-carboxylic acid methylamide | $^1$H NMR in DMSO: 8.42(d, J=4.7Hz, 1H); 7.93(dd, J=7.0 & 9.4Hz, 2H); 7.58(s, 1H); 7.38(t, J=8.8Hz, 2H); 7.16(s, 1H); 4.79(heptuplet, J=5.8Hz, 1H); 3.50(t, J=4.6Hz, 4H); 3.16(m, 2H); 3.06(s, 3H); 2.83(d, J=4.6Hz, 3H) | (M+H)$^+$=534 | A | <1 |
| 192. | 2-(4-Fluoro-phenyl)-5,6-dihydroxy- | $^1$H NMR in DMSO: 8.25(brs, 1H); 7.83(m, 2H); | (M+H)$^+$=302 | C | >30 |

TABLE 1-continued

| Example Number | Name | NMR data* | Mass Spec | HCV pol-BB7 IC$_{50}$(μM) A=≦0.5μM B=0.5 to ≦5.0μM C=5.0 to ≦30μM D=>30μM | Replicon (μM) |
|---|---|---|---|---|---|
| | benzofuran-3-carboxylic acid methylamide | 7.28(m, 2H); 6.96(d, 1H, J=2.34Hz); 6.90(d, 1H, J=2.34Hz); 2.77(brd, 3H, J=6.45Hz) | | | |
| 193. | 2-(4-Fluoro-phenyl)-5-isopropoxy-6-[methanesulfonyl-(2-methoxy-ethyl)-amino]-benzofuran-3-carboxylic acid methylamide | $^1$H NMR in DMSO: 8.48(m, 1H); 7.95(dd, J=5.2 & 8.7Hz, 2H); 7.53(s, 1H); 7.39(t, J=8.8Hz, 2H); 7.17(s, 1H); 4.79(heptuplet, J=5.9Hz, 1H); 3.34(m, 6H); 3.18(s 3H); 3.05(s, 3H); 2.83(d, J=4.7Hz, 3H); 1.34(d, J=5.8Hz, 6H) | (M+H)$^+$=479 | A | <1 |
| 194. | 6-Benzyloxy-2-(4-fluoro-phenyl)-5-isopropoxy-benzofuran-3-carboxylic acid methylamide | $^1$H NMR in CDCl$_3$: 7.85(m, 2H); 7.47(m, 2H); 7.41-7.31(m, 4H); 7.15(t, 2H, J=8.79Hz); 7.08(s, 1H); 5.75(brs, 1H); 5.17(s, 2H); 4.55(m, 1H); 2.99(d, 3H, J=5.28Hz); 1.38(d, 6H, J=6.45Hz) | (M+H)$^+$=434 | B | *** |
| 195. | 6-(Allyl-methanesulfonyl-amino)-2-(4-fluoro-phenyl)-5-isopropoxy-benzofuran-3-carboxylic acid methylamide | $^1$H NMR in DMSO: 8.41(m, 1H); 7.93(dd, J=5.3 & 8.8Hz, 2H); 7.38(s, 1H); 7.34(t, J=8.8Hz, 2H); 5.81(m, 1H); 5.10(dd, J=1.8 & 17Hz, 1H); 5.02(dd, J=1.1 & 10Hz, 1H); 4.79(heptuplet, J=6.4Hz, 1H); 4.22(m, 2H); 3.06(s, 3H); 2.82(d, J=4.7Hz, 3H) | (M+H)$^+$=461 | A | <1 |
| 196. | 6-Acetyl-2-(4-fluoro-phenyl)-5-isopropoxy-benzofuran-3-carboxylic acid methylamide | $^1$H NMR in CDCl$_3$: 7.88(s, 1H); 7.86(m, 2H); 7.41(s, 1H); 7.18(m, 2H); 5.77(brs, 1H); 4.79(m, 1H); 3.00(d, J=4.8Hz, 3H); 2.69(s, 3H); 1.44(d, J=6.0Hz, 6H) | (M+H)$^+$=370.0 | A | <1 |
| 197. | 2-(4-Fluoro-phenyl)-5-isopropoxy-6-methanesulfonylamino-benzofuran-3-carboxylic acid isopropylamide | $^1$H NMR in CDCl$_3$: 7.85-7.80(m, 2H); 7.74(s, 1H); 7.43(s, 1H); 7.19(t, J=8.79Hz, 2H); 6.95(s, 1H); 5.53-5.50(m, 1H); 4.78-4.70(septet, J=6.15Hz, 1H); 4.38-4.26(septet, J=7.03Hz, 1H); 2.95(s, 3H); 1.40(d, J=5.44Hz, 6H); 1.18(d, J=6.49Hz, 6H) | (M+H)$^+$=449 | C | <10 |
| 198. | 2-(4-Fluoro-phenyl)-5-isopropoxy-6-(5-methyl-[1,2,4]oxadiazol-3-yl)-benzofuran-3-carboxylic acid methylamide | $^1$H NMR in CDCl$_3$: 8.07(s, 1H); 7.92-7.87(m, 1H); 7.49(s, 1H); 7.23-7.17(m, 2H); 5.80(brs, 1H); 4.70-4.64(s, 1H); 3.00(d, J=4.8Hz, 3H); 2.65(s, 3H); 1.41(d, J=6.3Hz, 6H) | (M+H)$^+$=410 | A | <1 |
| 199. | 2-(4-Fluoro-phenyl)-5-isopropoxy-6-methanesulfonylamino-benzofuran-3-carboxylic acid cyclopropylamide | $^1$H NMR in CDCl$_3$: 7.79-7.74(m, 2H); 7.73(s, 1H); 7.47(s, 1H); 7.20(T, J=8.79Hz, 2H); 6.95(s, 1H); 5.8(s, 1H); 4.78-4.70(septet, J=6.15Hz, 1H); 2.95(s, 3H); 2.90-2.86(m, 1H); 1.40(d, J=6.15Hz, 6H); 0.89-0.82(m, 2H); 0.53-0.48(m, 2H) | (M+H)$^+$=447 | A | <1 |
| 200. | 2-(4-Fluoro-phenyl)-5-isopropoxy-6-methanesulfonylamino-benzofuran-3-carboxylic acid ethylamide | $^1$H NMR in CDCl$_3$: 7.85-7.79(m, 2H); 7.74(s, 1H); 7.44(s, 1H); 7.19(t, J=8.35Hz, 2H); 6.95(s, 1H); 5.7(s, 1H); 4.80-4.68(septet, J=6.15Hz, 1H); 3.52-3.43(m, 2H); 2.95(s, 3H); 1.39(d, J=5.71, 6H); 1.17(T, J=7.47, 3H) | (M+H)$^+$=435 | A | <1 |
| 201. | 2-(4-Fluoro-phenyl)-5-(2-methyl-thiazol-4-ylmethoxy)-6-morpholin-4-yl-benzofuran-3- | $^1$H NMR in CDCl$_3$: 7.89(m, 2H); 7.41(s, 1H); 7.16(m, 3H); 7.10(s, 1H); 5.78(brs, 1H); 5.25(s, 2H); 3.90(m, 4H); 3.16(m, 4H); 3.00(d, 3H, | (M+H)$^+$=482 | A | <1 |

TABLE 1-continued

| Example Number | Name | NMR data* | Mass Spec | HCV pol-BB7 IC$_{50}$(μM) A=≦0.5μM B=0.5 to ≦5.0μM C=5.0 to ≦30μM D=>30μM | Replicon (μM) |
|---|---|---|---|---|---|
| | carboxylic acid methylamide | J=4.69Hz); 2.74(s, 3H) | | | |
| 202. | 2-(4-Fluoro-phenyl)-6-(1-hydroxy-1-methyl-ethyl)-5-isopropoxy-benzofuran-3-carboxylic acid methylamide | $^1$H NMR in CDCl$_3$: 7.84(m, 2H); 7.49(s, 1H); 7.39(s, 1H); 7.19(m, 2H); 5.73(brs, 1H); 3.56(m, 1H); 2.99(d, J=4.8Hz, 3H); 1.38(d, J=6.1Hz, 6H) | (M+H)$^+$=386.1 | A | <1 |
| 203. | 5-[5-(3,5-Dimethyl-isoxazol-4-yl)-[1,2,4]oxadiazol-3-ylmethoxy]-2-(4-fluoro-phenyl)-6-morpholin-4-yl-benzofuran-3-carboxylic acid methylamide | $^1$H NMR in CDCl$_3$: 7.86(m, 2H); 7.52(s, 1H); 7.18(t, 2H, J=8.79Hz); 7.12(s, 1H); 5.75(brs, 1H); 5.36(s, 2H); 3.92(m, 4H); 3.19(m, 4H); 2.98(d, 3H, J=4.69Hz); 2.81(s, 3H); 2.59(s, 3H) | (M+H)$^+$=548 | B | <10 |
| 204. | 5-(5-tert-Butyl-[1,2,4]oxadiazol-3-ylmethoxy)-2-(4-fluoro-phenyl)-6-morpholin-4-yl-benzofuran-3-carboxylic acid methylamide | $^1$H NMR in DMSO: 8.28(br m, 1H); 7.90(m, 2H); 7.33(t, 2H, J=8.79Hz); 7.24(s, 1H); 7.22(s, 1H); 5.28(s, 2H); 3.74(m, 4H); 3.06(m, 4H); 2.81(d, 3H, J=4.69); 1.40(s, 9H) | (M+H)$^+$=509 | A | <1 |
| 205. | 2-(4-Fluoro-phenyl)-5-isopropoxy-6-[1,2,4]oxadiazol-3-yl-benzofuran-3-carboxylic acid methylamide | $^1$H NMR in CDCl$_3$: 8.75(s, 1H); 8.14(s, 1H); 7.93-7.88(m, 2H); 7.53(s, 1H); 7.24-7.17(m, 2H); 5.78(brs, 1H); 4.70-4.68(m, 1H); 3.0(d, J=4.8Hz, 3H); 1.42(d, J=5.7Hz, 6H) | (M+H)$^+$=396 | A | <1 |
| 206. | 5-(5-Chloro-[1,2,4]thiadiazol-3-ylmethoxy)-2-(4-fluoro-phenyl)-6-morpholin-4-yl-benzofuran-3-carboxylic acid methylamide | $^1$H NMR in DMSO: 8.38(brd, 1H, J=4.69Hz); 7.95(m, 2H); 7.76(s, 1H); 7.58(s, 1H); 7.38(t, 2H, J=8.79Hz); 4.75(s, 2H); 3.52(m, 4H); 2.98(m, 4H); 2.80(d, 3H, J=4.69Hz) | (M+H)$^+$=504 | B | <1 |
| 207. | 2-(4-Fluoro-phenyl)-6-morpholin-4-yl-5-(5-p-tolyl-[1,3,4]oxadiazol-2-ylmethoxy)-benzofuran-3-carboxylic acid methylamide | $^1$H NMR in DMSO: 8.31(brd, 1H, J=4.69Hz); 7.90(m, 4H); 7.43(d, 2H, J=7.62Hz); 7.34(m, 3H); 7.25(s, 1H); 5.48(s, 2H); 3.69(m, 4H); 3.02(m, 4H); 2.81(d, 3H, J=4.69Hz); 2.40(s, 3H) | (M+H)$^+$=543 | C | <10 |
| 208. | 2-(4-Fluoro-phenyl)-6-hydroxy-5-methoxy-benzofuran-3-carboxylic acid methylamide | $^1$H NMR in DMSO: 9.33(s, 1H); 8.28(d, J=4.4Hz, 1H); 7.85(dd, J=8.8, 5.3Hz, 2H); 7.30(t, J=8.8Hz, 2H); 7.06(s, 1H); 7.02(s, 1H); 3.81(s, 3H); 2.80(d, J=4.4Hz, 3H) | (M+H)$^+$=316 | B | <30 |
| 209. | 2-(4-Fluoro-phenyl)-5-(1-methyl-1H-tetrazol-5-ylmethoxy)-6-morpholin-4-yl-benzofuran-3-carboxylic acid methylamide | $^1$H NMR in DMSO: 8.31(d, J=4.4Hz, 1H); 7.88(dd, J=8.8, 5.3Hz, 2H); 7.36(t, J=8.8Hz, 2H); 7.33(s, 1H); 7.25(s, 1H); 5.54(s, 2H); 4.14(s, 3H); 3.68(t, J=4.4Hz, 4H); 2.98(t, J=4.4Hz, 4H); 2.81(d, J=4.4Hz, 3H)) | (M+H)$^+$=467 | B | <10 |
| 210. | 2-(4-Fluoro-phenyl)-5-(3-methoxy-benzyloxy)-6-morpholin-4-yl-benzofuran-3-carboxylic acid methylamide | $^1$H NMR in DMSO: 8.30(d, J=4.4Hz, 1H); 7.88(dd, J=8.8, 5.3Hz, 2H); 7.32(m, 3H); 7.22(s, 1H); 7.19(s, 1H); 7.07(m, 2H); 6.87(m, 1H); 5.13(s, 2H); 3.76(s, 3H); 3.73(brs, 4H); 3.05(brs, 4H); 2.81(d, J=4.4Hz, 3H) | (M+H)$^+$=491 | A | <1 |
| 211. | 2-(4-Fluoro-phenyl)-5-methoxy-6-(1-methyl-1H-tetrazol-5-ylmethoxy)-benzofuran-3-carboxylic acid | $^1$H NMR in DMSO: 8.32(d, J=4.4Hz, 1H); 7.87(dd, J=8.3, 5.7Hz, 2H); 7.55(s, 1H); 7.33(t, J=8.8Hz, 2H); 7.11(s, 1H); 5.56(s, 2H); 4.15(s, 3H); | (M+H)$^+$=412 | A | <1 |

TABLE 1-continued

| Example Number | Name | NMR data* | Mass Spec | HCV pol-BB7 IC$_{50}$(μM) A=≦0.5μM B=0.5 to ≦5.0μM C=5.0 to ≦30μM D=>30μM | Replicon (μM) |
|---|---|---|---|---|---|
| | methylamide | 3.81(s, 3H); 2.80(d, J=4.4Hz, 3H)) | | | |
| 212. | 2-(4-Fluoro-phenyl)-5-[1-(4-fluoro-phenyl)-ethoxy]-6-morpholin-4-yl-benzofuran-3-carboxylic acid methylamide | $^1$H NMR in CDCl$_3$: 7.86(dd, J=8.8, 5.3Hz, 2H); 7.38(dd, J=8.8, 5.3Hz, 2H); 7.12(t, J=8.8Hz, 2H); 7.03(t, J=8.8Hz, 2H); 5.62(d, J=4.9Hz, 1H); 5.37(q, J=6.1Hz, 1H); 3.88(m, 4H); 3.14(m, 4H); 2.92(d, J=4.9Hz, 3H); 1.65(d, J=6.1Hz, 3H) | (M+H)$^+$=493 | A | <1 |
| 213. | 5-(4-Cyano-benzyloxy)-2-(4-fluoro-phenyl)-6-morpholin-4-yl-benzofuran-3-carboxylic acid methylamide | $^1$H NMR in DMSO: 8.28(d, J=4.4Hz, 1H); 7.88(m, 4H); 7.70(d, J=8.0Hz, 2H); 7.33(t, J=8.8Hz, 2H); 7.24(s, 1H); 7.20(s, 1H); 5.27(s, 1H); 3.74(m, 4H); 3.04(m, 4H); 2.81(d, J=4.4Hz, 3H) | (M+H)$^+$=486 | B | <10 |
| 214. | 2-(4-Fluoro-phenyl)-5-[5-(4-methoxy-phenyl)-[1,2,4]oxadiazol-3-ylmethoxy]-6-morpholin-4-yl-benzofuran-3-carboxylic acid methylamide | $^1$H NMR in DMSO: 8.35(d, J=4.4Hz, 1H); 7.92(m, 4H); 7.37(m, 3H); 7.25(s, 1H); 7.17(d, J=8.8Hz, 2H); 5.47(s, 2H); 3.84(s, 3H); 3.69(s, 4H); 3.02(s, 4H); 2.80(d, J=4.4Hz, 3H) | (M+H)$^+$=559 | B | <1 |
| 215. | 2-(4-Fluoro-phenyl)-6-morpholin-4-yl-5-(2-oxo-propoxy)-benzofuran-3-carboxylic acid methylamide | $^1$H NMR in DMSO: 8.26(d, J=4.4Hz, 1H); 7.87(dd, J=8.3, 5.7Hz, 2H); 7.32(t, J=8.8Hz, 2H); 7.20(s, 1H); 7.00(s, 1H); 4.80(s, 2H); 3.76(t, J=4.7Hz, 4H); 3.06(t, J=4.7Hz, 4H); 2.80(d, J=4.8Hz, 3H); 2.21(s, 3H) | (M+H)$^+$=427 | B | <10 |
| 216. | 5-(1-Benzyl-1H-imidazol-2-ylmethoxy)-2-(4-fluoro-phenyl)-6-morpholin-4-yl-benzofuran-3-carboxylic acid methylamide | $^1$H NMR in DMSO: 8.26(brd, 1H, J=4.69Hz); 7.90(m, 2H); 7.35-7.16(m, 10H); 6.94(m, 1H); 5.37(s, 2H); 5.17(s, 2H); 3.66(m, 4H); 2.95(m, 4H); 2.82(d, 3H, J=4.69Hz) | (M+H)$^+$=541 | A | <1 |
| 217. | 5-(3,5-Dimethyl-isoxazol-4-ylmethoxy)-2-(4-fluoro-phenyl)-6-morpholin-4-yl-benzofuran-3-carboxylic acid methylamide | $^1$H NMR in DMSO: 8.30(d, 1H, J=4.39); 7.82(m, 2H); 7.33(t, 2H, J=8.79); 7.20(m, 2H); 5.00(s, 2H); 3.69(m, 4H); 2.98(m, 4H); 2.82(d, 3H, J=4.39Hz); 2.39(s, 3H); 2.26(s, 3H) | (M+H)$^+$=480 | B | <10 |
| 218. | 2-(4-Fluoro-phenyl)-5-(5-methyl-isoxazol-3-ylmethoxy)-6-morpholin-4-yl-benzofuran-3-carboxylic acid methylamide | $^1$H NMR in DMSO: 8.28(brd, 1H, J=4.39Hz); 7.90(m, 2H); 7.33(t, 2H, J=8.79); 7.22(m, 2H); 6.34(s, 1H); 5.18(s, 2H); 3.73(m, 4H); 3.03(m, 4H); 2.82(d, 3H, J=4.39Hz); 2.42(s, 3H) | (M+H)$^+$=466 | A | <1 |
| 219. | 2-(4-Fluoro-phenyl)-5-isopropoxy-6-thiazol-2-yl-benzofuran-3-carboxylic acid methylamide | $^1$H NMR in DMSO: 8.50(s, 1H); 8.46-8.47(d, J=4.69Hz, 1H); 7.97-8.02(m, 3H); 7.80-7.81(d, J=3.5Hz, 1H); 7.38-7.44(t, J=8.79Hz, 2H); 7.36(s, 1H); 4.97-5.06(septet, J=6.45Hz, 1H); 2.84-2.86(d, J=5.27Hz, 3H); 1.47-1.49(d, J=5.86Hz, 6H) | (M+H)$^+$=410.9 | A | <10 |
| 220. | 2-(4-Fluoro-phenyl)-5-isopropoxy-6-(1H-pyrrol-2-yl)-benzofuran-3-carboxylic acid methylamide | $^1$H NMR in CDCl$_3$: 7.90-7.86(m, 2H); 7.77(s, 1H); 7.43(s, 1H); 7.26-7.17(m, 3H); 6.90(s, 1H); 6.67(s, 1H); 6.31(s, 1H); 5.8(s, 1H, br); 4.78(m, 1H); 3.0(d, 3H); 1.46(d, 6H) | (M+H)$^+$=393 | A | <10 |
| 221. | 2-(4-Fluoro-phenyl)-6-(isopropyl-methanesulfonyl- | $^1$H NMR in DMSO: 8.44(m, 1H); 7.94(dd, 2H, J=5.28, 8.8Hz); 7.556(s, 1H); | (M+H)$^+$=435 | A | <1 |

TABLE 1-continued

| Example Number | Name | NMR data* | Mass Spec | HCV pol-BB7 IC$_{50}$(μM) A=≦0.5μM B=0.5 to ≦5.0μM C=5.0 to ≦30μM D=>30μM | Replicon (μM) |
|---|---|---|---|---|---|
| | amino)-5-methoxy-benzofuran-3-carboxylic acid methylamide | 7.39(t, J=8.8Hz, 2H); 7.20(s, 1H); 4.27(heptuplet, J=6.4Hz, 1H); 3.86(s, 3H); 3.09(s, 3H); 2.84(d, J=4.7Hz, 3H); 1.21(d, J=7.1Hz, 3H); 1.01(d, J=6.5Hz, 3H) | | | |
| 222. | 2-(4-Fluoro-phenyl)-6-(1-hydroxy-ethyl)-5-isopropoxy-benzofuran-3-carboxylic acid methylamide | $^1$H NMR in CDCl$_3$: 7.87-7.83(m, 2H); 7.50(s, 1H); 7.34(s, 1H); 7.21-7.16(m, 2H); 5.72(bs, 1H); 5.19-5.13(m, 1H); 4.78-4.69(m, 1H); 2.98(d, J=5.1Hz, 3H); 2.78(d, J=5.1Hz, 1H); 1.55(d, J=6.6Hz, 3H); 1.41(dd, J=3.6Hz, 6.0Hz, 6H) | (M+H)$^+$=372 | A | <1 |
| 223. | 2-(4-Fluoro-phenyl)-5-isopropoxy-6-morpholin-4-ylmethyl-benzofuran-3-carboxylic acid methylamide | $^1$H NMR in CDCl$_3$: 7.89-7.84(m, 2H); 7.57(s, 1H); 7.31(s, 1H); 7.20-7.16(m, 2H); 5.74(brs, 1H); 4.64-4.60(m, 1H); 3.75-3.72(m, 4H); 3.64(s, 2H); 2.98(d, J=5.1Hz, 3H); 2.55-2.52(m, 4H); 1.36(d, J=6.3Hz, 3H) | (M+H)$^+$=427 | C | <10 |
| 224. | 2-(4-Fluoro-phenyl)-6-hydroxymethyl-5-isopropoxy-benzofuran-3-carboxylic acid methylamide | 1HNMR CDCl$_3$: 7.87-7.83(m, 2H); 7.43(s, 1H); 7.35(s, 1H); 7.21-7.15(m, 2H); 5.73(brs, 1H;, 4.76-4.68(m, 3H); 2.98(d, J=5.1Hz, 3H); 2.52-2.50(m, 1H); 1.40(d, J=6.0Hz, 6H) | (M+H)$^+$=358 | A | <10 |
| 225. | 2-(4-Fluoro-phenyl)-5-(3H-imidazol-4-ylmethoxy)-6-morpholin-4-yl-benzofuran-3-carboxylic acid methylamide | $^1$H NMR in DMSO: 8.27(brd, 1H, J=4.39Hz); 7.89(m, 2H); 7.33(t, 2H, J=8.79Hz); 7.28(s, 1H); 7.19(s, 1H); 7.15(brs, 1H); 6.90(brs, 1H); 5.10(s, 2H); 3.69(m, 4H); 3.02(m, 4H); 2.83(d, 3H, J=4.39Hz) | (M+H)$^+$=451 | A | <10 |
| 226. | 2-(4-Fluoro-phenyl)-5-(2-methoxy-ethoxy)-6-morpholin-4-yl-benzofuran-3-carboxylic acid methylamide | $^1$H NMR in DMSO: 8.28(d, 1H, J=4.69Hz); 7.89(m, 2H); 7.32(t, 2H, J=8.79Hz); 7.16(s, 1H); 7.06(s, 1H); 4.13(m, 2H); 3.72(m, 6H); 3.33(s, 3H); 3.04(m, 4H); 2.81(d, 3H, J=4.69Hz) | (M+H)$^+$=429 | A | <1 |
| 227. | 2-(4-Fluoro-phenyl)-5-isopropoxy-6-thiazol-5-yl-benzofuran-3-carboxylic acid methylamide | $^1$H NMR in DMSO: 9.07(s, 1H); 8.53(s, 1H); 8.41-8.42(d, J=4.69Hz, 1H); 8.19(s, 1H); 7.93-7.98(m, 2H); 7.36-7.42(t, J=8.79Hz, 2H); 7.28(s, 1H); 4.82-4.90(septet, J=5.86Hz, 1H); 2.84-2.86(d, J=4.69Hz, 3H); 1.38-1.40(d, J=5.86Hz, 6H) | (M+H)$^+$=411 | A | <1 |
| 228. | 5-(4-Chloro-1-methyl-1H-pyrazol-3-ylmethoxy)-2-(4-fluoro-phenyl)-6-morpholin-4-yl-benzofuran-3-carboxylic acid methylamide | $^1$H NMR in CDCl$_3$: 7.93(m, 2H); 7.47(s, 1H); 7.39(s, 1H); 7.17(t, 2H, J=8.79Hz); 7.08(s, 1H); 5.86(brs, 1H); 5.17(s, 2H); 3.89(m, 7H); 3.16(m, 4H); 3.04(d, 3H, J=4.84Hz) | (M+H)$^+$=499 | A | <1 |
| 229. | 5-(Cyano-methyl-methoxy)-2-(4-fluoro-phenyl)-6-morpholin-4-yl-benzofuran-3-carboxylic acid methylamide | $^1$H NMR in CDCl$_3$: 7.90(m, 2H); 7.52(s, 1H); 7.17(m, 3H); 5.84(brs, 1H); 5.17(q, 1H, J=7.03Hz); 3.89(t, 4H, J=4.69Hz); 3.20(m, 2H); 3.00(m, 5H); 1.80(d, 3H, J=6.45Hz) | (M+H)$^+$=424 | A | <10 |
| 230. | 2-(4-Fluoro-phenyl)-5-isopropoxy-6-(2H-pyrazol-3-yl)-benzofuran-3-carboxylic acid methylamide | $^1$H NMR in CDCl$_3$: 7.87(m, 2H); 7.80(s, 1H); 7.62(d, J=2.4Hz, 1H); 7.49(s, 1H); 7.24(m, 2H); 6.69(d, J=2.4Hz, 1H); 5.77(brs, 1H); 4.83(m, 1H); 2.99(d, J=5.4Hz, 3H); 1.48(d, J=5.7Hz, 6H) | (M+H)$^+$=394.1 | A | <10 |

TABLE 1-continued

| Example Number | Name | NMR data* | Mass Spec | HCV pol-BB7 IC$_{50}$(μM) A=≦0.5μM B=0.5 to ≦5.0μM C=5.0 to ≦30μM D=>30μM | Replicon (μM) |
|---|---|---|---|---|---|
| 231. | 2-(4-Fluoro-phenyl)-5-isopropoxy-6-(2-methyl-2H-pyrazol-3-yl)-benzofuran-3-carboxylic acid methylamide | $^1$H NMR in CDCl$_3$: 7.88(m, 2H); 7.52(d, J=1.8Hz, 1H); 7.45(s, 1H); 7.39(s, 1H); 7.22(m, 2H); 6.26(d, J=1.8Hz, 1H); 5.87(brs, 1H); 4.48(m, 1H); 3.76(s, 3H); 3.00(d, J=4.8Hz, 3H); 1.23(d, J=5.7Hz, 6H) | (M+H)$^+$=408.1 | A | <1 |
| 232. | 2-(4-Fluoro-phenyl)-5-isopropoxy-6-(1-methyl-1H-pyrazol-3-yl)-benzofuran-3-carboxylic acid methylamide | $^1$H NMR in CDCl$_3$: 8.10(s, 1H); 7.87(m, 2H); 7.37(d, J=2.1Hz, 1H); 7.36(s, 1H); 7.18(m, 2H); 6.91(d, J=2.1Hz, 1H); 5.82(brs, 1H); 4.67(m, 1H); 3.96(s, 3H); 2.99(d, J=4.8Hz, 3H); 1.39(d, J=6.0Hz, 6H) | (M+H)$^+$=408.1 | B | <10 |
| 233. | 2-(4-Fluoro-phenyl)-5-isopropoxy-6-(3-methyl-isoxazol-5-yl)-benzofuran-3-carboxylic acid methylamide | $^1$H NMR in DMSO: 8.42(d, J=4.8Hz, 1H); 8.03(s, 1H); 7.95(dd, J=5.7, 5.2, 8.8Hz, 2H); 7.37(apparent triplet, J=8.8Hz, 2H); 7.28(s, 1H); 6.79(s, 1H); 4.84(m, 1H); 2.83(d, J=4.4Hz, 3H); 2.30(s, 3H); 1.38(d, J=5.7Hz, 6H) | (M+H)$^+$=409.21 | B | <30 |
| 234. | 6-[(5-Chloro-[1,2,4]thiadiazol-3-ylmethyl)-methanesulfonyl-amino]-2-(4-fluoro-phenyl)-5-isopropoxy-benzofuran-3-carboxylic acid methylamide | $^1$H NMR in CDCl$_3$: 7.81(m, 2H); 7.69(s, 1H); 7.40(s, 1H); 7.19(t, 2H, J=8.79Hz); 5.69(brs, 1H); 5.09(brs, 2H); 4.78(m, 1H); 3.09(s, 3H); 2.95(d, 3H, J=4.84Hz); 1.42(d, 6H, J=6.15Hz) | (M+H)$^+$=553 | A | <10 |
| 235. | 6-(3,5-Dimethyl-isoxazol-4-ylamino)-2-(4-fluoro-phenyl)-5-isopropoxy-benzofuran-3-carboxylic acid methylamide | $^1$H NMR in CDCl$_3$: 7.79-7.74(m, 2H); 7.32(s, 1H); 7.14(t, J=8.79Hz, 2H); 6.43(s, 1H); 5.73(s, 1H); 5.50(s, 1H); 4.73-4.67(septet, J=6.15Hz, 1H); 2.97(d, J=5.27, 3H); 2.32(s, 3H); 2.13(s, 3H); 1.43(d, J=6.15Hz, 6H) | (M+H)$^+$=438 | C | >30 |
| 236. | 2-(4-Fluoro-phenyl)-5-methoxy-6-pyridin-3-yl-benzofuran-3-carboxylic acid methylamide | $^1$H NMR in DMSO: 8.75(s, 1H); 8.55(s, 1H, br); 8.43(d, 1H); 7.98-7.93(m, 2H); 7.68(s, 1H); 7.49-7.35(m, 3H); 7.26(s, 1H); 3.84(s, 3H); 2.84(d, 3H) | (M+H)$^+$=377 | A | <1 |
| 237. | 6-Dimethylaminomethyl-2-(4-fluoro-phenyl)-5-isopropoxy-benzofuran-3-carboxylic acid methylamide | $^1$H NMR in CDCl$_3$: 7.89-7.84(m, 2H); 7.54(s, 1H); 7.31(s, 1H); 7.21-7.15(m, 2H); 5.55(brs, 1H); 4.66-4.60(m, 1H); 3.64(s, 2H); 2.99(d, J=5.1Hz, 3H); 2.34(s, 6H); 1.37(d, J=5.7Hz, 6H) | (M+H)$^+$=385 | C | <30 |
| 238. | 2-(4-Fluoro-phenyl)-6-(1-hydroxy-2-methyl-propyl)-5-isopropoxy-benzofuran-3-carboxylic acid methylamide | $^1$H NMR in CDCl$_3$: 7.89-7.84(m, 2H); 7.43(s, 1H); 7.32(s, 1H), 7.22-7.16(m, 2H); 5.76(brs; 1H); 4.74-4.60(m, 2H); 2.99(d, J=4.8Hz, 3H); 2.61(d, J=6.5Hz, 1H); 2.14-2.09(m, 1H); 1.40(dd, J=11.7, 6.0Hz, 6H), 1.04(d, J=6.6Hz, 3H); 0.85(d, J=6.9Hz, 3H) | (M+H)$^+$=400 | A | <1 |
| 239. | 2-(4-Fluoro-phenyl)-5-isopropoxy-6-(1H-pyrazol-4-yl)-benzofuran-3-carboxylic acid methylamide | $^1$H NMR in CDCl$_3$: 8.10(s, 2H); 7.87(m, 2H); 7.65(s, 1H); 7.39(s, 2H); 7.18(m, 2H); 5.79(brs, 1H); 4.72(m, 1H); 3.00(d, J=5.1Hz, 3H); 1.41(d, J=6.0Hz, 6H) | (M+H)$^+$=394.1 | C | <10 |
| 240. | 2-(4-Fluoro-phenyl)-6-[methanesulfonyl-(2-methoxy-ethyl)-amino]- | $^1$H NMR in DMSO: 8.49(m, 1H); 8.00(dd, J=5.1 & 8.8Hz, 2H); 7.63(s, 1H); | (M+H)$^+$=451.1 | A | <1 |

TABLE 1-continued

| Example Number | Name | NMR data* | Mass Spec | HCV pol-BB7 IC$_{50}$(μM) A=≤0.5μM B=0.5 to ≤5.0μM C=5.0 to ≤30μM D=>30μM | Replicon (μM) |
|---|---|---|---|---|---|
| | 5-methoxy-benzofuran-3-carboxylic acid methylamide | 7.42(t, J=8.8Hz, 2H); 7.26(s, 1H); 3.97(s, 3H); 3.78(m, 1H); 3.35(m, 6H); 3.25(s, 3H); 3.11(s, 3H); 2.90(d, J=3.3Hz, 3H) | | | |
| 241. | 6-(3-Cyclopropyl-isoxazol-5-yl)-2-(4-fluoro-phenyl)-5-isopropoxy-benzofuran-3-carboxylic acid methylamide | $^1$H NMR in DMSO: 8.44(broad quartet, J=4.4Hz, 1H); 8.02(s, 1H); 7.96(dd, J=5.7, 5.3, 9.2Hz, 2H); 7.39(apparent triplet; J=8.8, 9.2Hz, 2H); 7.29(s, 1H); 6.64(s, 1H); 4.84(m, 1H); 2.85(d, J=4.8Hz, 3H); 2.08(m, 1H); 1.39(d, J=5.7Hz, 6H); 1.05(m, 2H); 0.84(m, 2H) | (M+H)$^+$=435 | B | <10 |
| 242. | 2-(4-Fluoro-phenyl)-5-isopropoxy-6-(3-methoxymethyl-isoxazol-5-yl)-benzofuran-3-carboxylic acid methylamide | $^1$H NMR in DMSO: 8.45(broad quartet, J=4.8Hz, 1H); 8.10(s, 1H); 7.97(dd, J=5.7, 8.8Hz, 2H); 7.40(t, J=8.8Hz, 2H); 7.32(s, 1H); 6.92(s, 1H); 4.88(quintet, J=6.1Hz, 1H); 4.55(s, 2H); 3.29(s, 3H); 2.85(d, J=4.4Hz, 3H); 1.40(d, J=6.1Hz, 6H) | (M+H)$^+$=439 | B | 30 |
| 243. | 2-(4-Fluoro-phenyl)-6-methanesulfonylamino-benzofuran-3-carboxylic acid methylamide | $^1$H NMR in DMSO: 8.37(m, 1H); 7.93(dd, J=5.7 & 8.8Hz, 2H); 7.53(d, J=8.8Hz, 1H); 7.45(d, J=1.7Hz, 1H); 7.36(t, J=8.8Hz, 2H); 7.14(dd, J=1.7 & 8.8Hz, 1H); 4.17(brs, 1H); 2.96(s, 3H); 2.82(d, J=4.8Hz, 3H) | (M+H)$^+$=363 | B | <10 |
| 244. | 2-(4-Fluoro-phenyl)-6-(1H-imidazol-2-yl)-5-isopropoxy-benzofuran-3-carboxylic acid methylamide | $^1$H NMR in CDCl$_3$: 10.70(s, 1H); 8.43(s, 1H); 7.86-7.81(m, 2H); 7.48(s, 1H); 7.21-7.15(m, 3H); 7.12(s, 1H); 5.96(s, 1H); 4.91-4.83(m, 1H); 2.99(d, J=4.8Hz, 3H); 1.49(d, J=6.0Hz, 6H) | (M+H)$^+$=394 | A | <1 |
| 245. | 6-(2,5-Dimethyl-2H-pyrazol-3-yl)-2-(4-fluoro-phenyl)-5-isopropoxy-benzofuran-3-carboxylic acid methylamide | $^1$H NMR in CDCl$_3$: 8.08(s, 1H); 7.88(m, 2H); 7.35(s, 1H); 7.19(m, 2H); 6.67(s, 1H); 5.78(brs, 1H); 4.67(m, 1H); 3.84(s, 3H); 3.00(d, J=4.8Hz, 3H); 2.33(s, 3H); 1.39(d, J=6.0Hz, 6H) | (M+H)$^+$=422.1 | B | <10 |
| 246. | 6-(3,5-Dimethyl-1H-pyrazol-4-yl)-2-(4-fluoro-phenyl)-5-isopropoxy-benzofuran-3-carboxylic acid methylamide | $^1$H NMR in CDCl$_3$: 7.91(m, 2H); 7.40(s, 1H); 7.28(s, 1H); 7.18(m, 2H); 5.80(brs, 1H); 4.36(m, 1H); 3.00(d, J=5.4Hz, 3H); 2.21(s, 6H); 1.20(d, J=5.7Hz, 6H) | (M+H)$^+$=422.1 | A | <1 |
| 247. | 2-(4-Fluoro-phenyl)-5-isopropoxy-6-(5-methyl-2H-pyrazol-3-yl)-benzofuran-3-carboxylic acid methylamide | $^1$H NMR in CDCl$_3$: 7.87(m, 2H); 7.75(s, 1H); 7.47(s, 1H); 7.20(m, 2H); 6.47(s, 1H); 5.75(brs, 1H); 4.82(m, 1H); 2.99(d, J=5.1Hz, 3H); 2.36(s, 3H); 1.46(d, J=6.0Hz, 6H) | (M+H)$^+$=408.1 | B | <10 |
| 248. | 6-(1,5-Dimethyl-1H-pyrazol-3-yl)-2-(4-fluoro-phenyl)-5-isopropoxy-benzofuran-3-carboxylic acid methylamide | $^1$H NMR in CDCl$_3$: 7.88(m, 2H); 7.44(s, 1H); 7.38(s, 1H); 7.20(m, 2H); 6.04(s, 1H); 5.68(brs, 1H); 4.44(m, 1H); 3.68(s, 3H); 3.00(d, J=4.8Hz, 3H); 2.32(s, 3H); 1.25(d, J=6.3Hz, 6H) | (M+H)$^+$=422.1 | B | <10 |
| 249. | 2-(4-Fluoro-phenyl)-5-isopropoxy-6-[(methanesulfonyl-methyl-amino)-methyl]-benzofuran-3-carboxylic acid methylamide | $^1$H NMR in CDCl$_3$: 7.86-7.83(m, 2H); 7.58(s, 1H); 7.37(s, 1H); 7.22-7.17(m, 2H); 5.75(s, 1H); 4.74-4.66(m, 1H); 4.47(s, 2H); 2.99(d, J=5.1Hz, 3H); 2.87(d, J=5.7Hz, 6H); 1.39(d, J=6.3Hz, 6H) | (M+H)$^+$=449 | A | <10 |

TABLE 1-continued

| Example Number | Name | NMR data* | Mass Spec | HCV pol-BB7 IC$_{50}$(μM) A=≦0.5μM B=0.5 to ≦5.0μM C=5.0 to ≦30μM D=>30μM | Replicon (μM) |
|---|---|---|---|---|---|
| 250. | 2-(4-Fluoro-phenyl)-5-(2-hydroxy-2-methyl-propoxy)-6-morpholin-4-yl-benzofuran-3-carboxylic acid methylamide | $^1$H NMR in CDCl$_3$: 7.87(dd, J=8.8 & 5.3Hz, 2H); 7.40(s, 1H); 7.20(t, J=8.8Hz, 2H); 7.12(s, 1H); 5.80(brs, 1H); 3.98(s, 2H); 3.92(t, J=4.4Hz, 4H); 3.10(t, J=4.4Hz, 4H); 2.96(d, J=4.4Hz, 3H); 1.35(s, 6H) | (M+H)$^+$=443 | B | <10 |
| 251. | 2-(4-Fluoro-phenyl)-5-(2-hydroxy-2-methyl-butoxy)-6-morpholin-4-yl-benzofuran-3-carboxylic acid methylamide | $^1$H NMR in CDCl$_3$: 7.86(dd, J=8.8, 5.3Hz, 2H); 7.40(s, 2H), 7.22(t, J=8.8Hz, 2H); 7.12(s, 1H); 5.90(brs, 1H); 4.00(m, 2H); 3.95(t, J=4.4Hz, 4H); 3.10(t, J=4.4Hz, 4H); 2.95(d, J=4.4Hz, 3H); 2.30(brs, 1H); 1.70(m, 2H); 1.24(s, 3H); 0.95(t, J=7.0Hz, 3H) | (M+H)$^+$=457 | B | <10 |
| 252. | 2-(4-Fluoro-phenyl)-5-(2-hydroxy-propoxy)-6-morpholin-4-yl-benzofuran-3-carboxylic acid methylamide | $^1$H NMR in DMSO: 8.28(d, J=4.4Hz, 1H); 7.88(dd, J=5.3 & 8.8Hz, 2H); 7.32(t, J=8.8Hz, 2H); 7.16(s, 1H); 7.06(s, 1H); 4.82(d, J=4.7Hz, 1H); 4.00-3.90(m, 3H); 3.74(brs, 4H); 3.04(brs, 4H); 2.81(d, J=4.0Hz, 3H); 1.19(d, J=4.7Hz, 3H) | (M+H)$^+$=429 | B | <10 |
| 253. | 2-(4-Fluoro-phenyl)-6-[(2-hydroxy-propyl)-methanesulfonyl-amino]-5-isopropoxy-benzofuran-3-carboxylic acid methylamide | $^1$H NMR in DMSO: 8.40(d, J=4.4Hz, 1H); 7.94(dd, J=8.8 & 5.3Hz, 2H); 7.63(brs, 1H); 7.36(t, J=8.8Hz, 2H); 7.14(s, 1H); 4.77(septet, J=6.1Hz, 1H); 4.62(brs, 1H); 3.60-3.40(m, 3H); 3.00(s, 3H); 2.81(d, J=4.4Hz, 3H); 1.33(d, J=6.1Hz | (M+H)$^+$=479 | A | <1 |
| 254. | 2-(4-Fluoro-phenyl)-6-morpholin-4-yl-5-(1-thiazol-2-yl-ethoxy)-benzofuran-3-carboxylic acid methylamide | $^1$H NMR in CDCl$_3$: 7.88(dd, J=8.8, 5.3Hz, 2H); 7.76(d, J=3.1Hz, 1H); 7.33(brs, 2H); 7.14(t, J=8.8Hz, 2H); 7.08(s, 1H); 5.82(q, J=6.6Hz, 1H); 5.79(brs, 1H); 3.83(m, 4H); 3.15(m, 4H); 2.97(d, J=4.9Hz, 3H); 1.78(d, J=6.1Hz, 3H) | (M+H)$^+$=482 | A | <1 |
| 255. | 6-(Ethyl-methanesulfonyl-amino)-2-(4-fluoro-phenyl)-5-isopropoxy-benzofuran-3-carboxylic acid methylamide | $^1$H NMR in CDCl$_3$: 7.83(dd, J=8.3, 3.1Hz, 2H); 7.51(s, 1H); 7.40(s, 1H); 7.20(t, J=8.3Hz, 2H); 5.72(brs, 1H); 4.78(septet, J=6.1Hz, 1H); 3.72(brs, 2H); 2.97(d, J=4.4Hz, 3H); 2.96(s, 3H); 1.40(d, J=6.1Hz, 6H); 1.13(t, J=7.0Hz, 3H) | (M+H)$^+$=449 | A | <1 |
| 256. | 6-(3,5-Dimethyl-1H-pyrazol-4-yl)-2-(4-fluoro-phenyl)-5-methoxy-benzofuran-3-carboxylic acid methylamide | $^1$H NMR in CDCl$_3$: 7.88(m, 2H); 7.39(s, 1H); 7.26(s, 1H); 7.19(m, 2H); 5.78(brd, 1H); 3.86(s, 3H); 3.01(d, J=4.8Hz, 3H); 2.25(s, 6H) | (M+H)$^+$=394.1 | A | <1 |
| 257. | 2-(4-Fluoro-phenyl)-5-isopropoxy-6-(5-methyl-1H-pyrazol-4-yl)-benzofuran-3-carboxylic acid methylamide | $^1$H NMR in CDCl$_3$: 7.87(m, 2H); 7.74(s, 1H); 7.38(s, 2H); 7.18(m, 2H); 5.81(brs, 1H); 4.52(m, 1H); 3.00(d, J=5.4Hz, 3H); 2.38(s, 3H); 1.28(d, J=6.0Hz, 6H) | (M+H)$^+$=408.1 | A | <1 |
| 258. | 3-[2-(4-Fluoro-phenyl)-3-methylcarbamoyl-benzofuran-5-yloxymethyl]-benzoic acid methyl ester | $^1$H NMR in DMSO: 8.34(brd, 1H, J=4.10Hz); 8.07(s, 1H); 7.92(m, 3H); 7.76(d, 1H, J=7.62Hz); 7.56(m, 2H); 7.35(t, 2H, J=7.03Hz); 7.21(d, 1H, J=2.34Hz); 7.07(dd, 1H, J=8.79, 2.34Hz); 5.24(s, 2H); 3.86(s, 3H); 2.81(d, 3H, J=4.69Hz) | (M+H)$^+$=434 | A | >30 |
| 259. | 4-[2-(4-Fluoro-phenyl)-3-methylcarbamoyl- | $^1$H NMR in DMSO: 8.38(brd, 1H, J=4.10Hz); | (M−H)$^-$=418 | B | <30 |

TABLE 1-continued

| Example Number | Name | NMR data* | Mass Spec | HCV pol-BB7 IC$_{50}$(μM) A=≦0.5μM B=0.5 to ≦5.0μM C=5.0 to ≦30μM D=>30μM | Replicon (μM) |
|---|---|---|---|---|---|
| | benzofuran-5-yloxymethyl]-benzoic acid | 7.90(m, 4H); 7.56(d, 1H, J=8.79Hz); 7.35(m, 4H); 7.20(s, 1H); 7.05(d, 1H, J=9.38Hz); 5.13(s, 2H); 2.82(d, 3H, J=4.69Hz) | | | |
| 260. | 3-[2-(4-Fluoro-phenyl)-3-methylcarbamoyl-benzofuran-5-yloxymethyl]-benzoic acid | $^1$H NMR in DMSO: 12.98(brs, 1H); 8.34(br m, 1H); 8.05(s, 1H); 7.91(m, 3H); 7.72(d, 1H, J=6.45Hz); 7.56(m, 2H); 7.35(t, 2H, J=8.79Hz); 7.21(s, 1H); 7.08(d, 1H, J=8.79Hz); 5.23(s, 2H); 2.81(d, 3H, J=6.71Hz) | (M−H)$^−$=418 | A | >30 |
| 261. | 6-Acetyl-2-(4-fluoro-phenyl)-5-methoxy-benzofuran-3-carboxylic acid methylamide | $^1$H NMR in CDCl$_3$: 7.84(m, 2H); 7.83(s, 1H); 7.37(s, 1H); 7.19(m, 2H); 5.95(brs, 1H); 3.97(s, 3H); 3.00(d, J=4.8Hz, 3H); 2.64(s, 3H) | (M+H)$^+$=342.1 | A | <1 |
| 262. | 4-[2-(4-Fluoro-phenyl)-3-methylcarbamoyl-6-morpholin-4-yl-benzofuran-5-yloxymethyl]-benzoic acid methyl ester | $^1$H NMR in CDCl$_3$: 8.09(d, 2H, J=8.21Hz); 7.85(m, 2H); 7.57(d, 2H, J=8.21Hz); 7.42(s, 1H); 7.18(t, 2H, J=8.21); 7.12(s, 1H); 5.72(brs, 1H); 5.24(s, 2H); 3.94(s, 3H); 3.89(m, 4H); 3.16(m, 4H); 2.98(d, 3H, J=4.69Hz) | (M+H)$^+$=519 | A | <10 |
| 263. | 3-[2-(4-Fluoro-phenyl)-3-methylcarbamoyl-6-morpholin-4-yl-benzofuran-5-yloxymethyl]-benzoic acid methyl ester | $^1$H NMR in CDCl$_3$: 8.25(s, 1H), 8.05(d, 1H, J=8.21Hz); 7.87(m, 2H); 7.67(d, 1H, J=7.62Hz); 7.51(t, 1H, J=7.62Hz); 7.45(s, 1H); 7.20(t, 2H, J=8.79Hz); 7.13(s, 1H); 5.75(brs, 1H); 5.24(s, 2H); 3.97(s, 3H); 3.93(m, 4H); 3.18(m, 4H); 3.00(d, 3H, J=5.28) | (M+H)$^+$=519 | A | <10 |
| 264. | 2-(4-Fluoro-phenyl)-5-isopropoxy-6-(1,3,5-trimethyl-1H-pyrazol-4-yl)-benzofuran-3-carboxylic acid methylamide | $^1$H NMR in CDCl$_3$: 7.90(m, 2H); 7.38(s, 1H); 7.25(s, 1H); 7.18(m, 2H); 5.78(brs, 1H); 4.36(m, 1H); 3.79(s, 3H); 3.01(d, J=4.8Hz, 3H); 2.17(s, 3H); 2.14(s, 3H); 1.20(d, J=6.0Hz, 6H) | (M+H)$^+$=436.1 | B | <10 |
| 265. | 2-(4-Fluoro-phenyl)-5-isopropoxy-6-pyrrolidin-2-yl-benzofuran-3-carboxylic acid methylamide | $^1$H NMR in CDCl$_3$: 7.82(m, 2H); 7.52(s, 1H); 7.32(s, 1H); 7.18(m, 2H); 6.76(brs, 2H); 5.80(brs, 1H); 4.75(m, 1H); 4.72(m, 1H); 3.28(m, 2H); 2.97(d, J=5.4Hz, 3H); 2.28(m, 1H); 2.03(m, 3H); 1.41(d, J=6.0Hz, 6H) | (M+H)$^+$=397.1 | C | >30 |
| 266. | 6-Cyano-2-(4-fluoro-phenyl)-5-methoxy-benzofuran-3-carboxylic acid methylamide | $^1$H NMR in CDCl$_3$: 7.89-7.83(m, 2H); 7.83(s, 1H); 7.45(s, 1H); 7.25-7.20(m, 2H); 5.74(s, 1H); 3.99(s, 3H); 2.99(d, J=5.6Hz, 3H) | (M+H)$^+$=325 | A | <1 |
| 267. | 4-[2-(4-Fluoro-phenyl)-3-methylcarbamoyl-6-morpholin-4-yl-benzofuran-5-yloxymethyl]-benzoic acid | $^1$H NMR in DMSO: 8.32(brd, 1H, J=4.69Hz); 7.90(m, 4H); 7.41-7.31(m, 4H); 7.23(s, 2H); 5.16(s, 2H); 3.75(m, 4H); 3.07(m, 4H); 2.84(d, 3H, J=4.10) | (M+H)$^+$=505 | A | <10 |
| 268. | 3-[2-(4-Fluoro-phenyl)-3-methylcarbamoyl-6-morpholin-4-yl-benzofuran-5-yloxymethyl]-benzoic acid | $^1$H NMR in DMSO: 8.33(brd, 1H, J=4.69Hz); 8.02(s, 1H); 7.92(m, 2H); 7.80(d, 1H, J=7.03Hz); 7.41-7.26(m, 4H); 7.23(d, 2H, J=4.10Hz); 5.16(s, 2H); 3.76(m, 4H); 3.07(m, 4H); 2.84(d, 3H, J=4.10Hz) | (M+H)$^+$=505 | A | <10 |
| 269. | 2-(4-Fluoro-phenyl)-5-isopropoxy-6-[methanesulfonyl-(1-methyl-1H-tetrazol-5-ylmethyl)-amino]- | $^1$H NMR in DMSO: 8.43(brd, 1H, J=4.69); 7.92(m, 2H); 7.60(s, 1H); 7.37(t, 2H, J=8.79Hz); 7.14(s, 1H); 5.19(s, 2H); 4.78(m, 1H); 4.10(s, 3H); | (M+H)$^+$=517 | A | <1 |

TABLE 1-continued

| Example Number | Name | NMR data* | Mass Spec | HCV pol-BB7 IC$_{50}$(μM) A=≦0.5μM B=0.5 to ≦5.0μM C=5.0 to ≦30μM D=>30μM | Replicon (μM) |
|---|---|---|---|---|---|
| | benzofuran-3-carboxylic acid methylamide | 3.20(s, 3H); 2.82(d, 3H, J=4.69Hz); 1.35(d, 6H, J=6.45Hz) | | | |
| 270. | 4-({[2-(4-Fluoro-phenyl)-5-isopropoxy-3-methylcarbamoyl-benzofuran-6-yl]-methanesulfonyl-amino}-methyl)-benzoic acid methyl ester | $^1$H NMR in CDCl$_3$: 7.91(d, 2H, J=8.21Hz); 7.75(m, 2H); 7.41(s, 1H); 7.34(d, 2H, J=8.21Hz); 7.20-7.14(m, 3H); 5.66(brs, 1H); 4.84(br m, 3H); 3.87(s, 3H); 3.04(s, 3H); 2.94(d, 3H, J=5.27Hz); 1.48(d, 6H, J=5.86Hz) | (M+H)$^+$=569 | A | <1 |
| 271. | 2-(4-Fluoro-phenyl)-5-isopropoxy-6-[methanesulfonyl-(2-methyl-thiazol-4-ylmethyl)-amino]-benzofuran-3-carboxylic acid methylamide | $^1$H NMR in CDCl$_3$: 7.80(m, 2H); 7.43(s, 1H); 7.39(s, 1H); 7.18(t, 2H, J=8.79Hz); 7.07(s, 1H); 5.68(brs, 1H); 4.93(brs, 2H); 4.78(m, 1H); 3.06(s, 3H); 2.95(d, 3H, J=4.69Hz); 2.63(s, 3H); 1.43(d, 6H, J=6.45Hz) | (M+H)$^+$=532 | A | <10 |
| 272. | 4-({[2-(4-Fluoro-phenyl)-5-isopropoxy-3-methylcarbamoyl-benzofuran-6-yl]-methanesulfonyl-amino}-methyl)-benzoic acid | $^1$H NMR in DMSO: 8.36(brd, 1H, J=4.69Hz); 7.89-7.82(m, 4H); 7.40(m, 3H); 7.32(t, 2H, J=8.79Hz); 7.10(s, 1H); 4.80(br m, 3H); 3.13(s, 3H); 2.79(d, 3H, J=4.10Hz); 1.38(d, 6H, J=5.86Hz) | (M+H)$^+$=555 | A | ≦1.0 |
| 273. | 2-(4-Fluoro-phenyl)-5-isopropoxy-6-(5-methoxymethyl-isoxazol-3-yl)-benzofuran-3-carboxylic acid methylamide | $^1$H NMR in DMSO: 8.43(q, J=4.4Hz, 1H); 7.98(s, 1H); 7.97(dd, J=5.3, 8.8Hz, 2H); 7.39(apparent triplet, J=8.8Hz, 2H); 7.29(s, 1H); 6.93(s, 1H); 4.76(m, J=6.1, 5.7Hz, 1H); 4.62(s, 2H); 3.36(s, 3H); 2.85(d, J=4.4Hz, 3H); 1.34(d, J=6.1Hz, 6H) | (M+H)$^+$=439.05 | A | <1 |
| 274. | 6-(5-Cyclopropyl-isoxazol-3-yl)-2-(4-fluoro-phenyl)-5-isopropoxy-benzofuran-3-carboxylic acid methylamide | $^1$H NMR in DMSO: 8.42(q, J=4.4Hz, 1H); 7.96(dd, J=5.3, 8.8Hz, 2H); 7.92(s, 1H); 7.38(apparent triplet, J=8.8Hz, 2H); 7.26(s, 1H); 6.61(s, 1H); 4.72(m, J=6.15Hz, 1H); 2.84(d, J=4.4Hz, 3H); 2.22(m, 1H); 1.33(d, J=6.15Hz, 6H); 1.10(m, 2H); 0.94(m, 2H) | (M+H)$^+$=435.12 | A | <1 |
| 275. | 2-(4-Fluoro-phenyl)-5-isopropoxy-6-(1-methanesulfonyl-pyrrolidin-2-yl)-benzofuran-3-carboxylic acid methylamide | $^1$H NMR in CDCl$_3$: 7.84(m, 2H); 7.56(s, 1H); 7.30(s, 1H); 7.21(m, 2H); 5.73(brs, 1H); 5.21(dd, J=8.4Hz, 2.4Hz, 1H); 4.69(m, 1H); 3.70(m, 1H); 3.55(m, 1H); 2.97(d, J=3.9Hz, 3H); 2.84(s, 3H); 2.35(m, 1H); 1.95(m, 3H); 1.39(d, J=6.3Hz) | (M+H)$^+$=475.1 | A | <1 |
| 276. | 6-Acetyl-2-(4-fluoro-phenyl)-5-hydroxy-benzofuran-3-carboxylic acid methylamide | $^1$H NMR in CDCl$_3$: 12.16(s, 1H); 8.03(m, 2H); 7.87(s, 1H); 7.19(m, 2H); 5.86(br, 1H); 3.02(d, J=4.8Hz, 3H); 2.71(s, 3H) | (M+H)$^+$=328.0 | B | <10 |
| 277. | 6-(Ethyl-methanesulfonyl-amino)-2-(4-fluoro-phenyl)-5-methoxy-benzofuran-3-carboxylic acid methylamide | $^1$H NMR in DMSO: 8.43(d, J=4.69Hz, 1H); 7.96-7.91(m, 2H); 7.6(s, 1H); 7.38(t, J=8.79Hz, 2H); 7.21(s, 1H); 3.9(s, 3H); 3.62(q, J=7.03, 2H); 3.02(s, 3H); 2.84(d, J=4.69Hz, 3H); 1.02(t, J=7.03Hz, 3H) | (M+H)$^+$=421.1 | A | <1 |
| 278. | 4-[2-(4-Fluoro-phenyl)-5-methoxy-3-methylcarbamoyl-benzofuran-6-yl]-2-oxo-pyrrolidine-3-carboxylic acid methylamide | $^1$H NMR in DMSO: 8.36(q, 1H, br); 8.00(q, 1H, br); 7.97-7.68(m, 3H); 7.53(s, 1H); 7.77(m, 2H); 7.11(s, 1H); 4.20(q, 1H); 3.84(s, 3H); 3.57(m, 2H); 3.16(t, 1H); 2.82(d, 3H); 2.57(d, 3H) | (M+H)$^+$=440 | A | <10 |

TABLE 1-continued

| Example Number | Name | NMR data* | Mass Spec | HCV pol-BB7 IC$_{50}$(μM) A=≦0.5μM B=0.5 to ≦5.0μM C=5.0 to ≦30μM D=>30μM | Replicon (μM) |
|---|---|---|---|---|---|
| 279. | 2-(4-Fluoro-phenyl)-5-isopropoxy-6-(4H-[1,2,4]triazol-3-yl)-benzofuran-3-carboxylic acid methylamide | $^1$H NMR in CDCl$_3$: 8.47(s, 1H); 8.03(s, 1H); 7.84-7.89(m, 2H); 7.57(s, 1H); 7.19-7.25(t, 2H, J=8.79Hz); 5.80(br.s, 1H); 4.90-4.98(septet, 1H, J=5.86Hz); 2.98-3.00(d, 3H, J=4.69Hz); 1.52-1.54(d, 6H, J=6.45Hz) | (M+H)$^+$=395.0 | A | <30 |
| 280. | 2-(4-Fluoro-phenyl)-5-methoxy-6-(5-methoxymethyl-3-methyl-isoxazol-4-yl)-benzofuran-3-carboxylic acid methylamide | $^1$H NMR in CDCl$_3$: 7.86(dd, J=8.8 and 5.1Hz, 2H); 7.43(s, 1H); 7.35(s, 1H); 7.21(apparent t, J=8.8 and 8.4Hz, 2H); 5.78(brs 1H); 4.42(s, 2H); 3.86(s, 3H); 3.36(s, 3H); 3.01(d, J=5.1Hz, 3H); 2.21(s, 3H) | (M+H)$^+$=425 | A | <1 |
| 281. | 2-(4-Fluoro-phenyl)-5-isopropoxy-6-[methanesulfonyl-(4-methoxy-benzyl)-amino]-benzofuran-3-carboxylic acid methylamide | $^1$H NMR in CDCl$_3$: 7.76(m, 2H); 7.38(s, 1H); 7.20-7.12(m, 5H); 6.75(d, 2H, J=8.79Hz); 5.86(brs, 1H); 4.90-4.70(br m, 3H); 3.74(s, 3H); 3.03(s, 3H); 2.95(d, 3H, J=4.69Hz); 1.47(d, 6H, J=6.45Hz) | (M−H)$^−$=539 | A | <1 |
| 282. | 2-(4-Fluoro-phenyl)-5-isopropoxy-6-[methanesulfonyl-(5-methyl-isoxazol-3-ylmethyl)-amino]-benzofuran-3-carboxylic acid methylamide | $^1$H NMR in CDCl$_3$: 7.79(m, 2H); 7.42(s, 1H); 7.34(s, 1H); 7.19(t, 2H, J=8.79Hz); 6.21(s, 1H); 5.86(brs, 1H); 4.83(br m, 3H); 3.04(s, 3H); 2.96(d, 3H, J=4.69Hz); 2.38(s, 3H); 1.45(d, 6H, J=5.86Hz) | (M−H)$^−$=514 | A | <1 |
| 283. | 2-(4-Fluoro-phenyl)-5-isopropoxy-6-(5-methyl-isoxazol-3-yl)-benzofuran-3-carboxylic acid methylamide | $^1$H NMR in CDCl$_3$: 8.015(s, 1H); 7.87(dd, J=5.3, 8.3Hz, 2H); 7.43(s, 1H); 7.19(apparent triplet, d, J=8.3Hz, 2H); 6.58(s, 1H); 5.79(brs, 1H); 4.68(m, 1H); 2.99(d, J=4.8Hz, 3H); 2.48(s, 3H); 1.38(d, J=5.7Hz, 6H) | *** | A | <1 |
| 284. | 6-[(3,5-Dimethyl-isoxazol-4-ylmethyl)-methanesulfonyl-amino]-2-(4-fluoro-phenyl)-5-isopropoxy-benzofuran-3-carboxylic acid methylamide | $^1$H NMR in DMSO: 8.41(brd, 1H, J=4.69Hz); 7.91(m, 2H); 7.36(m, 3H); 7.12(s, 1H); 4.79(m, 1H); 4.64(br m, 2H); 3.13(s, 3H); 2.82(d, 3H, J=4.69Hz); 2.08(s, 3H); 2.05(s, 3H); 1.37(d, 6H, J=5.86Hz) | (M+H)$^+$=530 | A | <10 |
| 285. | 2-(4-Fluoro-phenyl)-5-isopropoxy-6-(methanesulfonyl-thiazol-2-ylmethyl-amino)-benzofuran-3-carboxylic acid methylamide | $^1$H NMR in DMSO: 8.42(brd, 1H, J=4.69Hz); 7.92(m, 2H); 7.67(d, 1H, J=3.52Hz); 7.65(d, 1H, J=3.52Hz); 7.45(s, 1H); 7.36(t, 2H, J=8.79Hz); 7.18(s, 1H); 5.12(brs, 2H); 4.83(m, 1H); 3.16(s, 3H); 2.82(d, 3H, J=4.69Hz); 1.39(d, 6H, J=6.45Hz) | (M+H)$^+$=518 | A | <1 |
| 286. | 2-({[2-(4-Fluoro-phenyl)-5-isopropoxy-3-methylcarbamoyl-benzofuran-6-yl]-methanesulfonyl-amino}-methyl)-thiazole-4-carboxylic acid ethyl ester | $^1$H NMR in DMSO: 8.49(s, 1H); 8.42(brd, 1H, J=4.10Hz); 7.93(m, 2H); 7.54(s, 1H); 7.37(t, 2H, J=8.79Hz); 7.20(s, 1H); 5.13(brs, 2H); 4.84(m, 1H); 4.25(q, 2H, J=7.03Hz); 3.18(s, 3H); 2.82(d, 3H, J=4.69Hz); 1.39(d, 6H, J=6.45Hz); 1.26(t, 3H, J=7.03Hz) | (M+H)$^+$=590 | A | <10 |
| 287. | 2-(4-Fluoro-phenyl)-5-hydroxy-6-(methanesulfonyl-methyl-amino)-benzofuran-3-carboxylic acid methylamide | $^1$H NMR in DMSO: 9.98(s, 1H); 8.39(d, J=4.4Hz, 1H); 7.91(m, 2H); 7.51(s, 1H); 7.35(t, J=8.8Hz, 2H); 7.09(s, 1H); 3.20(s, 3H); 3.08(s, 3H); 2.80(d, J=4.4Hz, 3H) | (M+H)$^+$=393 | A | <10 |

TABLE 1-continued

| Example Number | Name | NMR data* | Mass Spec | HCV pol-BB7 IC$_{50}$(μM) A=≦0.5μM B=0.5 to ≦5.0μM C=5.0 to ≦30μM D=>30μM | Replicon (μM) |
|---|---|---|---|---|---|
| 288. | 6-(Allyl-methanesulfonyl-amino)-5-allyloxy-2-(4-fluoro-phenyl)-benzofuran-3-carboxylic acid methylamide | $^1$H NMR in DMSO: 8.40(d, J=4.7Hz, 1H); 7.93(dd, J=9.0, 5.3Hz, 2H); 7.57(s, 1H); 7.35(t, J=9.0Hz, 2H); 7.33(s, 1H); 6.10(m, 1H); 5.80(m, 1H); 5.50(m, 1H); 5.30(m, 1H); 5.10(m, 1H); 5.00(m, 1H); 4.70(d, J=3.5Hz, 2H); 4.20(brs, 2H); 3.05(s, 3H); 2.81(d, J=4.7Hz, 3H) | (M+H)$^+$=459 | A | <1 |
| 289. | 6-(Acetyl-methanesulfonyl-amino)-2-(4-fluoro-phenyl)-5-methoxy-benzofuran-3-carboxylic acid methylamide | $^1$H NMR in DMSO: 8.48(d, J=4.39Hz, 1H); 7.96-7.91(m, 2H); 7.86(s, 1H); 7.39(t, J=8.79Hz, 2H); 7.27(s, 1H); 3.93(s, 3H); 3.49(s, 3H); 2.84(d, J=4.39, 3H); 1.89(s, 3H) | (M+H)$^+$=435.0 | A | <1 |
| 290. | 6-[(3,5-Dimethyl-isoxazol-4-ylmethyl)-methanesulfonyl-amino]-2-(4-fluoro-phenyl)-5-methoxy-benzofuran-3-carboxylic acid methylamide | $^1$H NMR in DMSO: 8.44(m, 1H); 7.94-7.90(m, 2H); 7.43-7.33(m, 3H); 7.16(s, 1H); 4.67(brs, 2H); 3.9(s, 3H); 3.13(m, 3H); 2.84-2.82(m, 3H); 2.11(d, J=3.52Hz, 3H); 2.06(d, J=3.52, 3H) | (M+H)$^+$=502.1 | A | <10 |
| 291. | 2-(4-Fluoro-phenyl)-6-(methanesulfonyl-thiazol-4-ylmethyl-amino)-5-methoxy-benzofuran-3-carboxylic acid methylamide | $^1$H NMR in DMSO: 9.01(s, 1H), 8.41(d, J=4.84Hz, 1H); 7.93-7.88(m, 2H); 7.55(m, 1H); 7.48(s, 1H); 7.36(t, J=8.35Hz, 2H); 7.17(s, 1H); 4.93(brs, 2H); 3.90(s, 3H); 3.15(s, 3H); 2.83(d, J=4.84Hz, 3H) | (M+H)$^+$ 490.0 | A | <1 |
| 292. | 2-({[2-(4-Fluoro-phenyl)-5-isopropoxy-3-methylcarbamoyl-benzofuran-6-yl]-methanesulfonyl-amino}-methyl)-thiazole-4-carboxylic acid | $^1$H NMR in DMSO: 8.42(brm, 2H); 7.93(m, 2H); 7.53(d, 1H, J=1.17Hz); 7.36(t, 2H, J=8.79Hz); 7.19(s, 1H); 5.12(brs, 2H); 4.84(m, 1H); 3.19(s, 3H); 2.82(d, 3H, J=3.52Hz); 1.39(d, 6H, J=5.28Hz) | (M+H)$^+$=562 | A | >100 |
| 293. | 5-(2,2-Dimethyl-4-oxo-4H-benzo[1,3]dioxin-5-ylmethoxy)-2-(4-fluoro-phenyl)-6-morpholin-4-yl-benzofuran-3-carboxylic acid methylamide | $^1$H NMR in DMSO: 8.32(brd, 1H, J=4.40Hz); 8.08(s, 1H); 7.90(m, 2H); 7.80(d, 1H, J=8.79Hz); 7.35(t, 2H, J=8.79Hz); 7.26-7.19(m, 3H); 5.20(s, 2H); 3.77(m, 4H); 3.06(m, 4H); 2.83(d, 3H, J=4.00Hz); 1.72(s, 6H) | (M+H)$^+$=561 | B | <10 |
| 294. | 5-(2,2-Dimethyl-4-oxo-4H-benzo[1,3]dioxin-5-ylmethoxy)-6-(ethyl-methanesulfonyl-amino)-2-(4-fluoro-phenyl)-benzofuran-3-carboxylic acid methylamide | $^1$H NMR in DMSO: 8.42(brd, 1H, J=4.40Hz); 8.05(d, 1H, J=1.76Hz); 7.93(m, 2H); 7.85(d, 1H, J=8.35Hz); 7.65(s, 1H); 7.39(t, 2H, J=8.79Hz); 7.34(s, 1H); 7.19(d, 1H, J=8.35Hz); 5.26(s, 2H); 3.63(m, 2H); 2.93(s, 3H); 2.84(d, 3H, J=4.40Hz); 1.71(s, 6H); 1.03(t, 3H, J=7.03Hz) | (M+H)$^+$=597 | A | <1 |
| 295. | 2-(4-Fluoro-phenyl)-6-(1H-imidazol-4-yl)-5-methoxy-benzofuran-3-carboxylic acid methylamide | $^1$H NMR in CDCl$_3$: 7.96-7.85(m, 3H); 7.74(s, 1H); 7.61(s, 1H); 7.45(s, 1H); 7.24-7.18(m, 2H); 5.82(s, 1H); 4.04(s, 3H); 3.0(d, J=4.8Hz, 3H) | (M+H)$^+$=466 | A | <10 |
| 296. | 2-(4-Fluoro-phenyl)-6-(1H-imidazol-2-yl)-5-methoxy-benzofuran-3-carboxylic acid methylamide | $^1$H NMR in CDCl$_3$: 10.6(s, 1H); 8.48(s, 1H); 7.88-7.84(m, 2H); 7.50(s, 1H); 7.26-7.20(m, 3H); 7.18(s, 1H); 7.13(s, 1H); 5.84(s, 1H); 4.14(s, 3H); 3.0(d, J=6.8Hz, 3H) | (M+H)$^+$=466 | A | <1 |
| 297. | 6-(Ethyl-methanesulfonyl-amino)-2-(4-fluoro-phenyl)-5-hydroxy-benzofuran-3-carboxylic acid | $^1$H NMR in DMSO: 9.96(s, 1H); 8.40(d, J=4.4Hz, 1H); 7.92(dd, J=8.8, 5.3Hz, 2H); 7.46(s, 1H); 7.37(t, J=8.8Hz, 2H); 7.09(s, 1H); | (M−H)$^−$=405 | A | <10 |

TABLE 1-continued

| Example Number | Name | NMR data* | Mass Spec | HCV pol-BB7 IC$_{50}$(μM) A=≦0.5μM B=0.5 to ≦5.0μM C=5.0 to ≦30μM D=>30μM | Replicon (μM) |
|---|---|---|---|---|---|
| | methylamide | 3.60(q, J=7.0Hz, 2H); 3.01(s, 3H); 2.80(d, J=4.4Hz, 3H); 1.00(t, J=7.0Hz, 3H) | | | |
| 298. | 5-Difluoromethoxy-2-(4-fluoro-phenyl)-6-(methanesulfonyl-methyl-amino)-benzofuran-3-carboxylic acid methylamide | $^1$H NMR in CDCl$_3$: 7.86(dd, J=8.8, 5.3Hz, 2H); 7.70(s, 1H); 7.62(s, 1H); 7.24(t, J=8.8Hz, 2H); 6.69(t, J=73.4Hz, 1H); 5.74(brs, 1H); 3.33(s, 3H); 3.03(s, 3H); 2.98(d, J=4.8Hz, 3H) | (M+H)$^+$=443 | A | <1 |
| 299. | 2-(4-Fluoro-phenyl)-6-(methanesulfonyl-pyridin-4-ylmethyl-amino)-5-methoxy-benzofuran-3-carboxylic acid methylamide | *** | (M+H)$^+$=484 | A | <1 |
| 300. | 2-(4-Fluoro-phenyl)-6-(1-hydroxy-1-methyl-ethyl)-5-methyl-benzofuran-3-carboxylic acid methylamide | $^1$H NMR in CDCl$_3$: 7.95(m, 2H); 7.69(s, 1H); 7.56(s, 1H); 7.16(m, 2H); 5.83(brs, 1H); 3.02(d, J=4.6Hz, 3H); 2.69(s, 1H); 2.64(d, J=3.9Hz, 3H); 1.72(s, 6H) | (M+H)$^+$=342.1 | A | <10 |
| 301. | 6-Acetyl-2-(4-fluoro-phenyl)-5-methyl-benzofuran-3-carboxylic acid methylamide | $^1$H NMR in CDCl$_3$: 7.94(m, 2H); 7.79(s, 1H); 7.69(s, 1H); 7.20(m, 2H); 5.83(brs, 1H); 3.02(d, J=4.8Hz, 3H); 2.64(s, 3H); 2.96(s, 3H) | (M+H)$^+$=326.1 | A | <10 |
| 302. | 5-(2,2-Dimethyl-4-oxo-4H-benzo[1,3]dioxin-7-ylmethoxy)-2-(4-fluoro-phenyl)-6-(methanesulfonyl-methyl-amino)-benzofuran-3-carboxylic acid methylamide | $^1$H NMR in DMSO: 8.39(brd, 1H, J=4.69Hz); 7.92(m, 3H); 7.74(s, 1H); 7.37(m, 3H); 7.29(d, 2H, J=1.76Hz); 5.32(brs, 2H); 3.23(s, 3H); 3.01(s, 3H); 2.82(d, 3H, J=4.10Hz); 1.71(s, 6H) | (M+H)$^+$=583 | A | <1 |
| 303. | 2-(4-Fluoro-phenyl)-6-[1-(methanesulfonyl-methyl-amino)-ethyl]-5-methoxy-benzofuran-3-carboxylic acid methylamide | $^1$H NMR in CDCl$_3$: 7.89-7.84(m, 2H); 7.50(s, 1H); 7.39(s, 1H); 7.27-7.19(m, 2H); 5.76(s, 1H); 5.63-5.56(m, 1H); 3.95(s, 3H); 3.00(d, J=4.8Hz, 3H); 2.82(s, 3H); 2.69(s, 3H); 1.65(d, J=6.9Hz, 3H) | (M+H)$^+$=435 | A | <1 |
| 304. | 2-(4-Fluoro-phenyl)-5-methoxy-6-(1-methylamino-ethyl)-benzofuran-3-carboxylic acid methylamide | $^1$H NMR in CDCl$_3$: 7.88-7.83(m, 3H); 7.47(s, 1H); 7.33(s, 1H); 7.21-7.16(m, 6H); 5.75(s, 1H); 4.20-4.16(m, 1H); 3.92(s, 3H); 3.47(s, 1H); 2.99(d, J=4.5Hz, 3H); 2.34(s, 3H); 1.44(d, J=6.3Hz, 3H) | (M+H)$^+$=357 | B | >30 |
| 305. | 4-[2-(4-Fluoro-phenyl)-6-(methanesulfonyl-methyl-amino)-3-methylcarbamoyl-benzofuran-5-yloxymethyl]-benzoic acid methyl ester | $^1$H NMR in DMSO: 8.40(brd, 1H, J=4.69); 8.02(d, 2H, J=8.21); 7.93(m, 2H); 7.70(m, 3H); 7.39(t, 2H, J=8.79Hz); 7.34(s, 1H); 5.34(s, 2H); 3.87(s, 3H); 3.22(s, 3H); 2.97(s, 3H); 2.84(d, 3H, J=4.10Hz) | (M+H)$^+$=541 | A | <1 |
| 306. | 2-[2-(4-Fluoro-phenyl)-6-(methanesulfonyl-methyl-amino)-3-methylcarbamoyl-benzofuran-5-yloxymethyl]-benzoic acid methyl ester | $^1$H NMR in DMSO: 8.39(brd, 1H, J=5.28Hz); 8.15(s, 1H); 7.93(m, 2H); 7.82(d, 1H, J=7.62Hz); 7.68(s, 1H); 7.58(t, 1H, J=7.62Hz); 7.37(m, 3H); 5.32(s, 2H); 3.86(s, 3H); 3.20(s, 3H); 2.94(s, 3H); 2.82(d, 3H, J=4.10Hz) | (M+H)$^+$=541 | A | <1 |
| 307. | 6-[(2-Fluoro-ethyl)-methanesulfonyl-amino]-2-(4-fluoro-phenyl)-5-methoxy-benzofuran-3-carboxylic acid methylamide | $^1$H NMR in DMSO: 8.43(m, 1H); 7.93(dd, J=5.3 & 8.8Hz, 2H); 7.62(s, 1H); 7.39(t, J=8.8Hz, 2H); 7.22(s, 1H); 4.54(t, J=5.3Hz, 1H); 4.39(t, J=4.7Hz, 1H); 3.92(m, 4H); 3.84(m, 1H); 3.06(s, 3H); 2.83(d, J=4.7Hz, 3H) | (M+H)$^+$=439 | A | <1 |

TABLE 1-continued

| Example Number | Name | NMR data* | Mass Spec | HCV pol-BB7 IC$_{50}$(μM) A=≦0.5μM B=0.5 to ≦5.0μM C=5.0 to ≦30μM D=>30μM | Replicon (μM) |
|---|---|---|---|---|---|
| 308. | 2-(4-Fluoro-phenyl)-6-[methanesulfonyl-(2,2,2-trifluoro-ethyl)-amino]-5-methoxy-benzofuran-3-carboxylic acid methylamide | $^1$H NMR in DMSO: 8.45(m, 1H); 7.93(dd, J=5.3 & 8.8Hz, 2H); 7.65(s, 1H); 7.39(t, J=8.8Hz, 2H); 7.25(s, 1H); 4.40(m, 2H); 3.94(s, 3H); 3.10(s, 3H); 2.83(d, J=4.7Hz, 3H) | (M+H)$^+$=475 | A | <1 |
| 309. | 2-(4-Fluoro-phenyl)-6-(1-methanesulfonyl-pyrrolidin-2-yl)-5-methoxy-benzofuran-3-carboxylic acid methylamide | $^1$H NMR in CDCl$_3$: 7.84(m, 2H); 7.58(s, 1H); 7.26(s, 1H); 7.18(m, 2H); 5.76(brs, 1H); 5.22(m, 1H); 3.91(s, 3H); 3.75(m, 1H); 3.55(m, 1H); 3.18(m, 1H); 3.00(d, J=4.6Hz, 3H); 2.84(s, 3H); 1.92(m, 2H); 1.84(m, 2H) | M$^+$=446(GC/MS) | A | <1 |
| 310. | 6-(3-Cyclopropyl-5-methoxymethyl-isoxazol-4-yl)-2-(4-fluoro-phenyl)-5-methoxy-benzofuran-3-carboxylic acid methylamide | $^1$H NMR in CDCl$_3$: 7.87(dd, J=8.8 and J=5.1Hz, 2H); 7.44(s, 1H); 7.42(s, 1H); 7.20(apparent t, J=8.8 and 8.4Hz, 2H); 5.81(brs, 1H); 4.40(s, 2H); 3.87(s, 3H); 3.34(s, 3H); 3.01(d, J=4.8Hz, 3H); 1.65(m, 1H); 1.02(m, 2H); 0.88(m, 2H) | (M−H)$^−$=449 | A | <1 |
| 311. | 4-[2-(4-Fluoro-phenyl)-6-(methanesulfonyl-methyl-amino)-3-methylcarbamoyl-benzofuran-5-yloxymethyl]-benzoic acid | $^1$H NMR in DMSO: 8.41(brd, 1H, J=4.10Hz); 7.95(m, 4H); 7.69(s, 1H); 7.58(d, 2H, J=8.21Hz); 7.37(m, 3H); 5.29(s, 2H); 3.21(s, 3H); 2.94(s, 3H); 2.84(d, 3H, J=4.69Hz) | (M+H)$^+$=527 | A | <10 |
| 312. | 3-[2-(4-Fluoro-phenyl)-6-(methanesulfonyl-methyl-amino)-3-methylcarbamoyl-benzofuran-5-yloxymethyl]-benzoic acid | $^1$H NMR in DMSO: 8.41(brd, 1H, J=4.10Hz); 8.14(s, 1H); 7.94(m, 3H); 7.80(d, 1H, J=7.62Hz); 7.69(s, 1H); 7.57(t, 1H, J=8.21Hz); 7.38(m, 3H); 5.33(s, 2H); 3.22(s, 3H); 2.95(s, 3H); 2.84(d, 3H, J=4.10Hz) | (M+H)$^+$=527 | A | <1 |
| 313. | 2-(4-Fluoro-phenyl)-5-methoxy-6-(5-methoxymethyl-isoxazol-3-yl)-benzofuran-3-carboxylic acid methylamide | $^1$H NMR in CDCl$_3$: 8.03(s, 1H); 7.87(dd, J=5.27 & 8.8Hz, 2H); 7.45(s, 1H); 7.20(apparent triplet, J=8.8 & 8.3Hz, 2H); 6.83(s, 1H); 5.80(brs, 1H); 4.61(s, 2H); 3.96(s, 3H); 3.48(s, 3H); 3.00(d, J=4.8Hz, 3H) | (M+H)$^+$=411 | A | <1 |
| 314. | 6-(3,5-Dimethyl-isoxazol-4-yl)-2-(4-fluoro-phenyl)-5-hydroxy-benzofuran-3-carboxylic acid methylamide | $^1$H NMR in CDCl$_3$: 7.90(m, 2H); 7.56(s, 1H); 7.22(m, 3H); 6.04(brs, 1H); 5.83(brs, 1H); 3.00(d, 3H, J=4.69Hz); 2.36(s, 3H); 2.22(s, 3H) | (M+H)$^+$=381 | A | <1 |
| 315. | 2-(4-Fluoro-phenyl)-5-methoxy-6-(5-oxo-pyrrolidin-3-yl)-benzofuran-3-carboxylic acid methylamide | $^1$H NMR in DMSO: 8.36(m, 1H, br); 7.92(dd, 2H); 7.64(s, 1H, br); 7.54(s, 1H); 7.34(dd, 2H); 7.11(s, 1H); 3.89(m, 1H); 3.86(s, 3H); 3.6(m, 1H); 3.21(m, 2H); 2.81(d, 3H); 2.48-2.37(m, 2H) | (M+H)$^+$=383 | A | <10 |
| 316. | 2-(4-Fluoro-phenyl)-6-[methanesulfonyl-(2-trifluoromethoxy-ethyl)-amino]-5-methoxy-benzofuran-3-carboxylic acid methylamide | $^1$H NMR in DMSO: 8.42(m, 1H); 7.94(dd, J=5.9 & 8.8Hz, 2H); 7.57(s, 1H); 7.38(t, J=8.8Hz, 2H); 7.23(s, 1H); 4.11(m, 2H); 3.92(s, 5H); 3.06(s, 3H); 2.84(d, J=4.7Hz, 3H) | (M+H)$^+$=505 | B | <1 |
| 317. | 2-(4-Fluoro-phenyl)-5-methoxy-6-(1H-pyrrol-3-yl)-benzofuran-3-carboxylic acid methylamide | $^1$H NMR in CDCl$_3$: 8.32(m, 1H); 7.89(m, 2H); 7.66(s, 1H); 7.42(m, 1H); 7.33(s, 1H); 7.25(m, 2H); 6.86(m, 1H); 6.67(m, 1H); 5.81(q, 1H); 3.96(s, 3H); 3.01(d, 3H) | (M+H)$^+$=365 | C | <1 |
| 318. | 6-(3,5-Dimethyl-isoxazol-4-yl)-2-(2- | $^1$H NMR in CDCl$_3$: 7.63(s, 1H); 7.54-7.60(m, 1H); | (M+H)$^+$=439.1 | A | >30 |

TABLE 1-continued

| Example Number | Name | NMR data* | Mass Spec | HCV pol-BB7 IC$_{50}$(μM) A=≦0.5μM B=0.5 to ≦5.0μM C=5.0 to ≦30μM D=>30μM | Replicon (μM) |
|---|---|---|---|---|---|
| | ethoxy-4-fluoro-phenyl)-5-methoxy-benzofuran-3-carboxylic acid methylamide | 7.24-7.26(m, 1H); 7.227(s, 1H); 6.80-6.86(t of d, 1H, J=2.34Hz & 8.21Hz); 6.75-6.79(d of d, 1H,); J=2.34 & 11.14Hz); 5.80(brs 1H); 4.05-4.12(q, 2H, J=7.03Hz); 3.87(s, 3H); 2.32(s, 3H); 2.18(s, 3H); 1.37-1.42(t, 3H, J=7.03Hz) | | | |
| 319. | 2-(4-Fluoro-phenyl)-6-(methanesulfonyl-methyl-amino)-5-(thiazol-4-ylmethoxy)-benzofuran-3-carboxylic acid methylamide | $^1$H NMR in DMSO: 9.17(d, 1H, J=1.76Hz); 8.40(brd, 1H, J=4.69Hz); 7.95(m, 2H); 7.86(d, 1H, J=2.34Hz); 7.65(s, 1H); 7.39(m, 3H); 5.39(s, 2H); 3.20(s, 3H); 2.97(s, 3H); 2.85(d, 3H, J=4.69Hz) | (M+H)$^+$=490 | B | <1 |
| 320. | 2-(4-Fluoro-phenyl)-6-(methanesulfonyl-methyl-amino)-5-(2-methyl-thiazol-4-ylmethoxy)-benzofuran-3-carboxylic acid methylamide | $^1$H NMR in DMSO: 8.41(brd, 1H, J=4.10Hz); 7.95(m, 2H), 7.64(s, 1H), 7.60(s, 1H); 7.38(m, 3H); 5.28(s, 2H); 3.20(s, 3H); 3.00(s, 3H); 2.85(d, 3H, J=4.69Hz); 2.68(s, 3H) | (M+H)$^+$=504 | A | <1 |
| 321. | 5-(3-Chloromethyl-[1,2,4]thiadiazol-5-yloxy)-2-(4-fluoro-phenyl)-6-(methanesulfonyl-methyl-amino)-benzofuran-3-carboxylic acid methylamide | $^1$H NMR in DMSO: 8.49(brd, 1H, J=4.69Hz); 8.19(s, 1H); 7.99(m, 2H); 7.90(s, 1H); 7.43(t, 2H, J=8.79Hz); 4.74(s, 2H); 3.16(s, 3H); 3.10(s, 3H); 2.82(d, 3H, J=4.10Hz) | (M+H)$^+$=524.9 | A | <1 |
| 322. | 2-(4-Fluoro-phenyl)-6-{[2-(4-fluoro-phenyl)-2-hydroxy-ethyl]-methanesulfonyl-amino}-5-isopropoxy-benzofuran-3-carboxylic acid methylamide | $^1$H NMR in DMSO: 8.40(d, J=4.4Hz, 1H); 7.90(m, 2H); 7.37(t, J=8.8Hz, 2H); 7.30-7.10(m, 6H); 5.50(m, 1H); 4.78(septet, J=6.1Hz, 1H); 4.50(m, 1H); 3.90(m, 1H); 3.42(m, 1H); 3.00(s, 3H); 2.82(d, J=4.2Hz, 3H); 1.31(d, J=6.1Hz, 6H) | (M+H)$^+$=559 | A | <1 |
| 323. | 2-(4-Fluoro-phenyl)-5-methoxy-6-(2-methyl-2H-[1,2,4]triazol-3-yl)-benzofuran-3-carboxylic acid methylamide | $^1$H NMR in DMSO: 8.46-8.48(d, 1H, J=4.69Hz); 8.01(s, 1H); 7.94-7.99(m, 2H); 7.71(s, 1H); 7.36-7.43(t, 2H, J=8.79Hz); 7.31(s, 1H); 3.89(s, 3H); 3.69(s, 3H); 2.86-2.87(d, 3H, J=4.69Hz) | (M+H)$^+$=381 | A | <1 |
| 324. | 5-(3,5-Dimethyl-isoxazol-4-ylmethoxy)-2-(4-fluoro-phenyl)-6-(methanesulfonyl-methyl-amino)-benzofuran-3-carboxylic acid methylamide | $^1$H NMR in DMSO: 8.45(brd, 1H, J=4.69Hz); 7.94(m, 2H); 7.70(s, 1H); 7.39(m, 3H); 5.05(s, 2H); 3.14(s, 3H); 2.94(s, 3H); 2.85(d, 3H, J=4.10Hz); 2.44(s, 3H); 2.27(s, 3H) | (M+H)$^+$=502 | A | <1 |
| 325. | 2-(4-Fluoro-phenyl)-6-(methanesulfonyl-methyl-amino)-5-(3-methoxy-benzyloxy)-benzofuran-3-carboxylic acid methylamide | $^1$H NMR in DMSO: 8.40(brd, 1H, J=4.10Hz); 7.93(m, 2H); 7.70(s, 1H); 7.42-7.31(m, 4H); 7.12(m, 2H); 6.92(d, 1H, J=8.21Hz); 5.21(s, 2H); 3.77(s, 3H); 3.21(s, 3H); 2.97(s, 3H); 2.84(d, 3H, J=4.10Hz) | (M+H)$^+$=513 | A | <1 |
| 326. | 2-(4-Fluoro-phenyl)-5-hydroxy-6-(isobutyl-methanesulfonyl-amino)-benzofuran-3-carboxylic acid methylamide | $^1$H NMR in DMSO: 10.05(s, 1H); 8.40(d, J=4.4Hz, 1H); 7.93(dd, J=5.3 & 8.8Hz, 2H); 7.48(s, 1H); 7.35(t, J=8.8Hz, 2H); 7.10(s, 1H); 3.40(d, J=7.5Hz, 2H); 2.98(s, 3H); 2.80(d, J=4.4Hz, 3H); 1.50(m, 1H); 0.88(d, J=6.6Hz, 6H) | (M+H)$^+$=435 | B | <30 |
| 327. | 2-(4-Fluoro-phenyl)-6-(methanesulfonyl-methyl-amino)-5-(4-methoxy-benzyloxy)- | $^1$H NMR in DMSO: 8.40(brd, 1H, J=4.69Hz); 7.94(m, 2H); 7.66(s, 1H); 7.47(d, 2H, J=8.79Hz); 7.39(m, 3H); | (M+H)$^+$=513 | A | <1 |

TABLE 1-continued

| Example Number | Name | NMR data* | Mass Spec | HCV pol-BB7 IC$_{50}$(μM) A=≦0.5μM B=0.5 to ≦5.0μM C=5.0 to ≦30μM D=>30μM | Replicon (μM) |
|---|---|---|---|---|---|
| | benzofuran-3-carboxylic acid methylamide | 6.98(d, 2H, J=8.79Hz); 5.15(s, 2H); 3.78(s, 3H); 3.17(s, 3H); 2.90(S, 3H); 2.85(d, 3H, J=4.69Hz) | | | |
| 328. | 2-(4-Fluoro-phenyl)-6-(methanesulfonyl-methyl-amino)-5-(pyridin-4-ylmethoxy)-benzofuran-3-carboxylic acid methylamide | $^1$H NMR in DMSO: 8.62(d, J=5.86Hz); 8.40(brd, 1H, J=4.69Hz); 7.93(m, 2H); 7.74(s, 1H); 7.55(d, 2H, J=5.28Hz); 7.39(t, 2H, J=8.79Hz); 7.31(s, 1H); 5.32(s, 2H); 3.26(s, 3H); 3.02(s, 3H); 2.83(d, 3H, J=4.69Hz) | (M+H)$^+$=484 | A | <1 |
| 329. | 5-(2,2-Dimethyl-4-oxo-4H-benzo[1,3]dioxin-6-ylmethoxy)-2-(4-fluoro-phenyl)-6-(methanesulfonyl-methyl-amino)-benzofuran-3-carboxylic acid methylamide | $^1$H NMR in DMSO: 8.41(brd, 1H, J=4.69Hz); 8.06(s, 1H); 7.94(m, 2H); 7.87(dd, 1H, J=8.21 & 2.34Hz); 7.69(s, 1H); 7.37(m, 3H); 7.19(d, 1H, J=8.79Hz); 5.27(s, 2H); 3.20(s, 3H); 2.95(s, 3H); 2.84(d, 3H, J=4.69Hz); 1.72(s, 6H) | (M+H)$^+$=583 | A | <1 |
| 330. | 6-(Cyclopropylmethyl-methanesulfonyl-amino)-2-(4-fluoro-phenyl)-5-methoxy-benzofuran-3-carboxylic acid methylamide | $^1$H NMR in DMSO: 8.44(m, 1H); 7.94(dd, J=5.9 & 9.4Hz, 2H); 7.62(s, 1H); 7.38(t, J=8.8Hz, 2H); 7.20(s, 1H); 3.90(s, 3H); 3.44(m, 2H); 2.92(s, 3H); 2.84(d, J=4.7Hz, 3H); 0.87(m, 1H); 0.35(d, J=1.7Hz, 2H); 0.05(m, 2H) | (M+H)$^+$=447 | A | <1 |
| 331. | 2-(4-Fluoro-phenyl)-6-(methanesulfonyl-methylcarbamoylmethyl-amino)-5-methoxy-benzofuran-3-carboxylic acid methylamide | $^1$H NMR in DMSO: 8.42(m, 1H); 7.94(dd, J=5.9 & 9.4Hz, 2H); 7.90(s, 1H); 7.83(m, 1H); 7.38(t, J=8.8Hz, 2H); 7.20(s, 1H); 4.17(s, 2H); 3.92(s, 3H); 3.12(s, 3H); 2.84(d, J=4.7Hz, 3H); 2.58(d, J=4.7Hz, 3H) | (M+H)$^+$=464 | A | <1 |
| 332. | 5-Fluoro-2-(4-fluoro-phenyl)-6-methanesulfonylamino-benzofuran-3-carboxylic acid methylamide | $^1$H NMR in CDCl$_3$: 7.89-7.85(m, 2H); 7.87(d, J=6.3Hz, 1H); 7.70(d, J=9.9Hz, 1H); 7.24-7.19(m, 2H); 6.56(s, 1H); 5.74(s, 1H); 3.04(s, 1H); 2.99(d, J=4.8Hz, 3H) | (M+H)$^+$=381 | B | <10 |
| 333. | 6-(Ethyl-methanesulfonyl-amino)-5-fluoro-2-(4-fluoro-phenyl)-benzofuran-3-carboxylic acid methylamide | $^1$H NMR in CDCl$_3$: 7.90-7.86(m, 2H); 7.66(d, J=10.5Hz, 1H); 7.57(d, J=6.0Hz, 1H); 7.24-7.18(m, 2H); 5.74(s, 1H); 3.77(q, J=2.4 & 14.4Hz, 2H); 2.99-2.98(m, 6H); 1.17(t, J=7.5Hz, 3H) | (M+H)$^+$=409 | A | <10 |
| 334. | 2-(4-Fluoro-phenyl)-6-(1-methanesulfonyl-pyrrolidin-3-yl)-5-methoxy-benzofuran-3-carboxylic acid methylamide | $^1$H NMR in CDCl$_3$: 7.85(m, 2H); 7.36(s, 1H); 7.32(s, 1H); 7.20(m, 2H); 5.78(brs, 1H); 3.91(s, 3H); 3.83(m, 2H); 3.60(m, 1H); 3.47(m, 1H); 3.00(d, J=4.8Hz, 3H); 2.87(s, 3H); 2.34(m, 1H); 2.16(m, 1H) | (M+H)$^+$=447 | A | <1 |
| 335. | 5-Ethyl-2-(4-fluoro-phenyl)-6-[methanesulfonyl-(2-methoxy-ethyl)-amino]-benzofuran-3-carboxylic acid methylamide | $^1$H NMR in DMSO: 8.45(m, 1H); 7.94(dd, J=5.3 & 9.4Hz, 2H); 7.78(s, 1H); 7.56(s, 1H); 7.39(t, J=8.8Hz, 2H); 3.32(m, 2H); 3.30(s, 3H); 3.13(s, 3H); 2.84(d, J=4.7Hz, 3H); 2.82(q, J=7.1Hz, 2H); 1.24(t, J=7.1Hz, 3H) | (M+H)$^+$=449 | A | <1 |
| 336. | 2-(4-Fluoro-phenyl)-5-methoxy-6-(3-methoxymethyl-5-methyl-isoxazol-4-yl)-benzofuran-3-carboxylic acid methylamide | $^1$H NMR in CDCl$_3$: 7.87(dd, J=7.0 and 5.1Hz, 2H); 7.41(s, 1H); 7.40(s, 1H); 7.20(t, J=8.8Hz, 2H); 5.81(brs, 1H); 4.45(s, 2H); 3.86(s, 3H); 3.30(s, 3H); 3.00(d, J=4.8Hz, 3H); 2.35(s, 3H) | (M+H)$^+$=425 | A | <1 |

TABLE 1-continued

| Example Number | Name | NMR data* | Mass Spec | HCV pol-BB7 IC$_{50}$(μM) A=≦0.5μM B=0.5 to ≦5.0μM C=5.0 to ≦30μM D=>30μM | Replicon (μM) |
|---|---|---|---|---|---|
| 337. | 5-Ethyl-6-[(2-fluoro-ethyl)-methanesulfonyl-amino]-2-(4-fluoro-phenyl)-benzofuran-3-carboxylic acid methylamide | $^1$H NMR in DMSO: 8.47(m, 1H); 7.94(dd, J=5.3 & 8.8Hz, 2H); 7.84(s, 1H); 7.57(s, 1H); 7.39(t, J=8.8Hz, 2H); 4.65-4.25(m, 2H, F-coupling); 3.98(t, J=4.1Hz, 1H); 3.89(t, J=4.1Hz, 1H); 3.14(s, 3H); 2.84(d, J=4.7Hz, 3H); 2.82(q, J=7.6Hz, 2H) 1.24(t, J=7.6Hz, 3H) | (M+H)$^+$=437 | A | <1 |
| 338. | 2-(4-Fluoro-phenyl)-6-(methanesulfonyl-propyl-amino)-5-propoxy-benzofuran-3-carboxylic acid methylamide | $^1$H NMR in DMSO: 8.40(d, J=4.7Hz, 1H); 7.90(m, 2H); 7.56(s, 1H); 7.36(t, J=8.2Hz, 2H); 7.17(s, 1H); 4.04(t, J=6.5Hz, 2H); 3.53(s, 2H); 2.99(s, 3H); 2.82(d, J=4.7Hz, 3H); 1.80(m, 2H); 1.39(m, 2H); 1.02(t, J=7.6Hz, 3H); 0.85(t, J=4.1Hz, 3H) | (M+H)$^+$=463.1 | A | <1 |
| 339. | 5-Ethyl-2-(4-fluoro-phenyl)-6-(1-hydroxy-1-methyl-ethyl)-benzofuran-3-carboxylic acid methylamide | $^1$H NMR in CDCl$_3$: 7.90(m, 2H); 7.66(s, 1H); 7.65(s, 1H); 7.17(m, 2H); 5.80(brs, 1H); 3.08(q, J=7.5Hz, 2H); 3.02(d, J=4.8Hz, 3H); 1.73(s, 6H); 1.33(t, J=7.5Hz, 3H) | (M+H)$^+$=356.1 | A | <1 |
| 340. | 6-Acetyl-5-ethyl-2-(4-fluoro-phenyl)-benzofuran-3-carboxylic acid methylamide | $^1$H NMR in CDCl$_3$: 7.95(m, 2H); 7.80(s, 1H); 7.69(s, 1H); 7.19(m, 2H); 5.82(brs, 1H); 3.01(d, J=4.8Hz, 3H); 2.62(s, 3H); 2.97(q, J=7.5Hz, 2H); 1.22(t, J=7.5Hz, 3H) | (M+H)$^+$=340.1 | A | <1 |
| 341. | 4-Chloro-6-ethylamino-2-(4-fluoro-phenyl)-5-hydroxy-benzofuran-3-carboxylic acid methylamide | $^1$H NMR in DMSO: 9.82(s, 1H); 8.38(d, J=4.4Hz, 1H); 7.88(dd, J=8.8, 5.3Hz, 2H); 7.35(t, J=8.8Hz, 2H); 6.89(s, 1H); 4.48(t, J=7.0Hz, 1H); 3.37(q, J=7.0Hz, 2H); 2.80(d, J=4.4Hz, 3H); 1.07(t, J=7.0Hz, 3H) | (M+H)$^+$=363 | B | >100 |
| 342. | Methanesulfonic acid 4-chloro-6-ethylamino-2-(4-fluoro-phenyl)-3-methylcarbamoyl-benzofuran-5-yl ester | $^1$H NMR in DMSO: 8.42(d, J=3.7Hz, 1H); 7.90(dd, J=8.8, 5.3Hz, 2H); 7.46(s, 1H); 7.37(t, J=8.8Hz, 2H); 4.96(t, J=6.8Hz, 1H); 3.48(s, 3H); 3.39(pent, J=7.0Hz, 2H); 2.80(d, J=3.7Hz, 3H); 1.10(t, J=7.0Hz, 2H) | (M+H)$^+$=441 | A | <10 |
| 343. | 5-Ethyl-2-(4-fluoro-phenyl)-6-(methanesulfonyl-thiazol-4-ylmethyl-amino)-benzofuran-3-carboxylic acid methylamide | $^1$H NMR in DMSO: 9.06(d, J=1.8Hz, 1H); 8.43(m, 1H); 7.91(dd, J=5.3 & 8.8Hz, 2H); 7.59(s, 1H); 7.45(m, 2H); 7.38(t, J=8.8Hz, 2H); 5.01(d, J=4.9Hz, 1H); 4.83(d, J=4.9Hz, 1H); 3.14(s, 3H); 2.81(d, J=4.7Hz, 3H); 2.65(q, J=7.6Hz, 2H); 1.24(t, J=7.6Hz, 3H) | (M+H)$^+$=488 | A | <1 |
| 344. | 6-(5-Cyclopropyl-3-methoxymethyl-isoxazol-4-yl)-2-(4-fluoro-phenyl)-5-methoxy-benzofuran-3-carboxylic acid methylamide | $^1$H NMR in CDCl$_3$: 7.87(dd, J=8.8 and 5.4Hz, 2H); 7.46(s, 1H); 7.41(s, 1H); 7.20(apparent t, J=8.8 and 8.4Hz, 2H); 5.80(brs, 1H); 4.44(s, 2H); 3.87(s, 3H); 3.28(s, 3H); 3.00(d, J=5.1Hz, 3H); 1.92(m, 1H); 1.13(m, 2H); 0.97(m, 2H) | (M+H)$^+$=451 | A | <1 |
| 345. | 6-(1-Acetyl-pyrrolidin-3-yl)-2-(4-fluoro-phenyl)-5-methoxy-benzofuran-3-carboxylic acid methylamide | $^1$H NMR in CDCl$_3$: 7.85(m, 2H); 7.32(m, 1H); 7.25(m, 3H); 5.77(brs, 1H); 3.92(s, 3H); 3.71-4.12(m, 2H); 3.32-3.70(m, 3H); 2.99(d, J=4.8Hz, 3H); 2.18-2.39(m, 2H); 2.10(s, 3H) | (M+H)$^+$=411 | A | <10 |

TABLE 1-continued

| Example Number | Name | NMR data* | Mass Spec | HCV pol-BB7 IC$_{50}$(μM) A=≦0.5μM B=0.5 to ≦5.0μM C=5.0 to ≦30μM D=>30μM | Replicon (μM) |
|---|---|---|---|---|---|
| 346. | 5-(3,4-Difluoro-benzyloxy)-2-(4-fluoro-phenyl)-6-(methanesulfonyl-methyl-amino)-benzofuran-3-carboxylic acid methylamide | $^1$H NMR in DMSO: 8.39(d, J=4.4Hz, 1H); 7.91(m, 2H); 7.70(s, 1H); 7.55-7.30(m, 6H); 5.21(s, 2H); 3.18(s, 3H); 2.96(s, 3H); 2.82(m, 3H) | (M+H)$^+$=519.0 | A | <1 |
| 347. | 5-(2-Difluoromethoxy-benzyloxy)-2-(4-fluoro-phenyl)-6-(methanesulfonyl-methyl-amino)-benzofuran-3-carboxylic acid methylamide | $^1$H NMR in CDCl$_3$: 7.86(m, 2H); 7.57-7.42(m, 3H); 7.31-7.20(m, 5H); 6.63(t, 1H, J=73.4Hz); 5.74(brs, 1H); 5.24(s, 2H); 3.28(s, 3H); 2.99(d, 3H, J=4.84Hz); 2.81(s, 3H) | (M+H)$^+$=549 | A | <1 |
| 348. | 2-(4-Fluoro-phenyl)-6-(methanesulfonyl-methyl-amino)-5-propoxy-benzofuran-3-carboxylic acid methylamide | $^1$H NMR in DMSO: 8.39(brd, 1H, J=5.86); 7.92(m, 2H); 7.60(s, 1H); 7.36(t, 2H, J=8.79Hz); 7.18(s, 1H); 4.04(t, 2H, J=7.03); 3.20(s, 3H); 3.02(s, 3H); 2.82(d, 3H, J=4.10Hz); 1.82(m, 2H): 1.03(t, 3H, J=7.03Hz) | (M+H)$^+$=435 | A | <1 |
| 349. | 5-Allyloxy-2-(4-fluoro-phenyl)-6-(methanesulfonyl-methyl-amino)-benzofuran-3-carboxylic acid methylamide | $^1$H NMR in DMSO: 8.37(brm, 1H); 7.92(m, 2H); 7.63(s, 1H); 7.36(t, 2H, J=8.79Hz); 7.21(s, 1H); 6.18-6.06(m, 1H); 5.47(m, 1H); 5.30(m, 1H); 4.70(d, 2H, J=4.69Hz); 3.20(s, 3H); 3.02(s, 3H); 2.82(d, 3H, J=4.10Hz) | (M+H)$^+$=433 | A | <1 |
| 350. | 6-(5-Ethoxymethyl-isoxazol-3-yl)-2-(4-fluoro-phenyl)-5-methoxy-benzofuran-3-carboxylic acid methylamide | $^1$H NMR in CDCl$_3$: 8.03(s, 1H); 7.87(dd, J=5.28 & 8.79Hz, 2H); 7.45(s, 1H); 7.20(t, J=8.79Hz, 2H); 6.82(s, 1H); 5.79(brs, 1H); 4.64(s, 2H); 3.96(s, 3H); 3.65(q, J=7.03Hz, 2H); 3.00(d, J=4.84Hz, 3H); 1.276(t, J=7.03, 6.59Hz, 3H) | (M+H)$^+$=425.21 | A | <1 |
| 351. | 5-Cyclopropylmethoxy-2-(4-fluoro-phenyl)-6-(methanesulfonyl-methyl-amino)-benzofuran-3-carboxylic acid methylamide | $^1$H NMR in DMSO: 8.38(d, J=4.4Hz, 1H); 7.92(m, 2H); 7.60(s, 1H); 7.38(t, J=9.2Hz, 2H); 7.16(s, 1H); 3.95(d, J=7.0Hz, 2H); 3.25(s, 3H); 3.08(s, 3H); 2.83(d, J=4.4Hz, 3H); 1.20(m, 1H); 0.62(d, J=7.0Hz, 2H); 0.39(d, J=5.3Hz, 2H) | (M+H)$^+$=447 | A | <1 |
| 352. | 5-(3,5-Dimethoxy-benzyloxy)-2-(4-fluoro-phenyl)-6-(methanesulfonyl-methyl-amino)-benzofuran-3-carboxylic acid methylamide | $^1$H NMR in DMSO: 8.39(brd, 1H, J=4.69); 7.93(m, 2H); 7.71(s, 1H); 7.38(t, 2H, J=8.79); 7.31(s, 1H); 6.72(d, 2H, J=2.34); 6.46(m, 1H); 5.17(s, 2H); 3.75(s, 6H); 3.22(s, 3H); 3.00(s, 3H); 2.83(d, 3H, J=4.69Hz) | (M+H)$^+$=543 | A | <1 |
| 353. | 2-(4-Fluoro-phenyl)-5-(4-methanesulfonyl-benzyloxy)-6-(methanesulfonyl-methyl-amino)-benzofuran-3-carboxylic acid methylamide | $^1$H NMR in DMSO: 8.39(brd, 1H, J=4.40Hz); 7.98-7.89(m, 4H); 7.80(d, 2H, J=8.4Hz); 7.71(s, 1H); 7.37(m, 3H); 5.36(s, 2H); 3.28(s, 3H); 3.22(s, 3H); 2.98(s, 3H); 2.81(d, 3H, J=4.40Hz) | (M−H)$^−$=559 | A | <1 |
| 354. | 2-(4-Fluoro-phenyl)-5-hydroxy-6-[methanesulfonyl-(2-oxo-propyl)-amino]-benzofuran-3-carboxylic acid methylamide | $^1$H NMR in CDCl$_3$: 8.15(s, 1H); 7.93(m, 2H); 7.39(s, 1H); 7.15(t, J=2.5Hz, 2H); 5.79(s, 1H); 4.54(s, 1H); 4.49(s, 1H); 3.34(s, 3H); 3.24(s, 1H); 3.19(s, 3H); 1.79(s, 2H) | (M+H)$^+$=437.22 | B | <10 |
| 355. | 2-(4-Fluoro-phenyl)-6-(methanesulfonyl-methyl-amino)-5-[2-(4-methoxy-phenyl)-2-oxo- | $^1$H NMR in DMSO: 8.36(d, J=4.8Hz, 1H); 8.04(d, J=8.79Hz, 2H); 7.90(m, 2H); 7.60(s, 1H); 7.36(t, J=8.79Hz, | (M+H)$^+$=541 | A | <1 |

TABLE 1-continued

| Example Number | Name | NMR data* | Mass Spec | HCV pol-BB7 IC$_{50}$(μM) A=≤0.5μM B=0.5 to ≤5.0μM C=5.0 to ≤30μM D=>30μM | Replicon (μM) |
|---|---|---|---|---|---|
| | ethoxy]-benzofuran-3-carboxylic acid methylamide | 2H); 7.28(s, 1H); 7.08(d, J=9.35Hz, 2H); 5.67(s, 2H); 3.86(s, 3H); 3.29(s, 3H); 3.07(s, 3H); 2.77(d, J=4.41Hz, 3H) | | | |
| 356. | 5-(3-Cyano-benzyloxy)-2-(4-fluoro-phenyl)-6-(methanesulfonyl-methyl-amino)-benzofuran-3-carboxylic acid methylamide | $^1$H NMR in DMSO: 8.39(brd, 1H, J=4.69Hz); 8.00(s, 1H); 7-94-7.81(m, 3H); 7.72(s, 1H); 7.64(t, 2H, J=7.62Hz); 7.37(t, 2H, J=8.79Hz); 7.30(s, 1H); 5.29(s, 2H); 3.19(s, 3H); 2.97(s, 3H); 2.82(d, 3H, J=4.69Hz) | (M−H)$^-$=506 | A | <1 |
| 357. | 5-(4-Cyano-benzyloxy)-2-(4-fluoro-phenyl)-6-(methanesulfonyl-methyl-amino)-benzofuran-3-carboxylic acid methylamide | $^1$H NMR in DMSO: 8.37(brd, 1H, J=4.84Hz); 7.90(m, 4H); 7.72(m, 3H); 7.37(t, 2H, J=8.79Hz); 7.30(s, 1H); 5.33(s, 2H); 3.21(s, 3H); 2.97(s, 3H); 2.81(d, 3H, J=4.0Hz) | (M+H)$^+$=508 | A | <1 |
| 358. | 2-(4-Fluoro-phenyl)-5-methoxy-6-(2H-[1,2,4]triazol-3-yl)-benzofuran-3-carboxylic acid methylamide | $^1$H NMR in CDCl$_3$: 8.49(s, 1H); 8.05(s, 1H); 7.86-7.91(m, 2H); 7.58(s, 1H); 7.20-7.26(m, 2H); 5.82(brs, 1H); 4.15(s, 3H); 3.00-3.02(d, 3H, J=5.28Hz) | (M+H)$^+$=366 GCMS | A | <1 |
| 359. | 4-{2-[2-[(4-Fluoro-phenyl)-6-(methanesulfonyl-methyl-amino)-3-methylcarbamoyl-benzofuran-5-yloxy]-acetylamino}-benzoic acid ethyl ester | $^1$H NMR in DMSO: 10.37(s, 1H); 8.39(brd, 1H, J=4.84Hz); 7.91(m, 4H); 7.75(d, 2H, J=8.35Hz); 7.70(s, 1H); 7.37(t, 2H, J=8.79Hz); 7.20(s, 1H); 4.93(s, 2H); 4.28(q, 2H, J=7.03Hz); 3.28(s, 3H); 3.14(s, 3H); 2.78(d, 3H, J=4.40Hz); 1.30(t, 3H, J=7.03Hz) | (M−H)$^-$=596 | A | <10 |
| 360. | 2-(4-Fluoro-phenyl)-5-[2-(4-fluoro-phenyl)-2-oxo-ethoxy]-6-(methanesulfonyl-methyl-amino)-benzofuran-3-carboxylic acid methylamide | $^1$H NMR in DMSO: 8.38(brd, 1H, J=5.28Hz); 8.17(m, 2H); 7.90(m, 2H); 7.62(s, 1H); 7.45-7.31(m, 5H); 5.73(s, 2H); 3.29(s, 3H); 3.06(s, 3H); 2.78(d, 3H, J=4.69Hz) | (M−H)$^-$=527 | A | <1 |
| 361. | 6-(Benzyl-methanesulfonyl-amino)-2-(4-fluoro-phenyl)-5-isopropoxy-benzofuran-3-carboxylic acid methylamide | $^1$H NMR in DMSO: 8.38(brd, 1H, J=4.69Hz); 7.86(m, 2H); 7.33(t, 2H, J=8.79Hz); 7.28-7.16(m, 6H); 7.10(s, 1H); 4.80(brm, 3H); 3.11(s, 3H); 2.79(d, 3H, J=4.69Hz); 1.38(d, 6H, J=5.86Hz) | (M+H)$^+$=511 | A | <1 |
| 362. | 4-Chloro-6-(ethyl-methyl-amino)-2-(4-fluoro-phenyl)-5-methoxy-benzofuran-3-carboxylic acid methylamide | $^1$H NMR in DMSO: 8.38(d, J=4.4Hz, 1H); 7.90(m, 2H); 7.36(t, J=8.4Hz, 2H); 7.05(s, 1H); 3.86(s, 3H); 3.09(q, J=7.03Hz, 2H); 2.81(d, J=4.4Hz, 3H); 2.75(s, 3H); 0.93(t, J=7.1Hz, 3H) | (M+H)$^+$=391.0 | A | <10 |
| 363. | 4-Chloro-6-ethylamino-2-(4-fluoro-phenyl)-5-methoxy-benzofuran-3-carboxylic acid methylamide | $^1$H NMR in DMSO: 8.34(d, J=4.8Hz, 1H); 7.86(m, 2H); 7.33(t, J=9.2Hz, 2H); 6.99(s, 1H); 4.67(t, J=6.6Hz, 1H); 3.89(s, 3H); 3.38(q, J=7.04Hz, 2H); 2.80(d, J=4.4Hz, 3H); 1.07(t, J=7.0Hz, 3H) | (M+H)$^+$=377.0 | A | <1 |
| 364. | 6-Ethylamino-2-(4-fluoro-phenyl)-5-hydroxy-benzofuran-3-carboxylic acid methylamide | $^1$H NMR in DMSO: 8.20(d, J=4.7Hz, 1H); 7.88(dd, J=8.8, 5.3Hz, 2H); 7.29(t, J=8.8Hz, 2H); 6.83(s, 1H); 6.66(s, 1H); 4.83(t, J=5.0Hz, 1H); 3.11(m, 2H); 2.79(d, J=4.7Hz, 3H); 1.19(t, J=7.0Hz, 3H) | (M+H)$^+$=329 | B | >30 |
| 365. | 5-(3-Bromo-propoxy)-6-ethylamino-2-(4-fluoro-phenyl)-benzofuran-3-carboxylic acid | $^1$H NMR in DMSO: 8.30(d, J=4.7Hz, 1H); 7.86(dd, J=8.8, 5.3Hz, 2H); 7.30(t, J=8.8Hz, 2H); 6.93(s, 1H); | (M+H)$^+$=499, 451 | A | <1 |

TABLE 1-continued

| Example Number | Name | NMR data* | Mass Spec | HCV pol-BB7 IC$_{50}$(μM) A=≦0.5μM B=0.5 to ≦5.0μM C=5.0 to ≦30μM D=>30μM | Replicon (μM) |
|---|---|---|---|---|---|
|  | methylamide | 6.75(s, 1H); 5.20(t, J=5.0Hz, 1H); 4.14(t, J=4.8Hz, 2H); 3.78(t, J=6.7Hz, 2H); 3.20(m, 2H); 2.81(d, J=4.7Hz, 3H); 2.36(m, 2H); 1.23(t, J=7.0Hz, 3H) |  |  |  |
| 366. | 5-Allyloxy-6-ethylamino-2-(4-fluoro-phenyl)-benzofuran-3-carboxylic acid methylamide | $^1$H NMR in DMSO: 8.20(d, J=4.7Hz, 1H); 7.80(dd, J=8.8, 5.3Hz, 2H); 7.31(t, J=8.8Hz, 2H); 6.93(s, 1H); 6.74(s, 1H); 6.10(m, 1H); 5.50(m, 1H); 5.30(m, 1H); 5.00(t, J=5.0Hz, 1H); 4.60(m, 2H); 3.18(m, 2H); 2.80(d, J=4.7Hz, 2H); 1.20(t, J=7.0Hz, 3H) | (M+H)$^+$=369 | A | <1 |
| 367. | 5-(3-Ethoxy-propoxy)-6-ethylamino-2-(4-fluoro-phenyl)-benzofuran-3-carboxylic acid methylamide | $^1$H NMR in DMSO: 8.20(d, J=4.4Hz, 1H); 7.80(dd, J=8.8, 5.3Hz, 2H); 7.31(t, J=8.8Hz, 2H); 6.90(s, 1H); 6.72(s, 1H); 5.01(t, J=5.7Hz, 1H); 4.07(t, J=6.5Hz, 2H); 3.56(t, J=6.4Hz, 2H); 3.42(q, J=7.0Hz, 2H); 3.20(m, 2H); 2.80(d, J=4.4Hz, 3H); 2.00(t, J=6.5Hz, 2H); 1.20(t, J=7.0Hz, 3H); 1.10(t, J=7.0Hz, 3H) | (M+H)$^+$=415 | A | <1 |
| 368. | 2-[2-(4-Fluoro-phenyl)-5-methoxy-3-methylcarbamoyl-benzofuran-6-yl]-pyrrolidine-1-carboxylic acid amide | $^1$H NMR in CDCl$_3$: 7.83(m, 2H); 7.15(s, 1H); 7.14(s, 1H); 7.10(m, 2H); 5.76(brs, 1H); 5.18(d, J=8.353Hz, 1H); 4.25(s, 2H); 3.93(s, 3H); 3.72(m, 2H); 2.99(d, J=4.836Hz, 3H); 1.89(m, 2H); 1.25(s, 2H) | (M+H)$^+$=412 | A | <1 |
| 369. | 2-(4-Fluoro-phenyl)-6-(methanesulfonyl-methyl-amino)-5-(2-oxo-propoxy)-benzofuran-3-carboxylic acid methylamide | $^1$H NMR in DMSO: 8.38(brd, 1H, J=4.69Hz); 7.90(m, 2H); 7.62(s, 1H); 7.36(t, 2H, J=8.79Hz); 7.12(s, 1H); 4.97(s, 2H); 3.24(s, 3H); 3.04(s, 3H); 2.81(d, 3H, J=4.10Hz); 2.20(s, 3H) | (M−H)$^−$=447 | A | <1 |
| 370. | 2-(4-Fluoro-phenyl)-5-(2-hydroxy-propoxy)-6-(methanesulfonyl-methyl-amino)-benzofuran-3-carboxylic acid methylamide | $^1$H NMR in DMSO: 8.41(brd, 1H, J=4.69Hz); 7.94(m, 2H); 7.60(s, 1H); 7.38(t, 2H, J=8.79Hz); 7.20(s, 1H); 4.87(d, 1H, J=4.69Hz); 4.06(m, 1H); 3.96(m, 2H); 3.24(s, 3H); 3.06(s, 3H); 2.84(d, 3H, J=4.69Hz); 1.22(d, 3H, J=5.86) | (M−H)$^−$=449 | A | <1 |
| 371. | 2-(4-Fluoro-phenyl)-6-(methanesulfonyl-methyl-amino)-5-(1-methyl-1H-tetrazol-5-ylmethoxy)-benzofuran-3-carboxylic acid methylamide | $^1$H NMR in DMSO: 8.44(brd, 1H, J=4.10Hz); 7.94(m, 2H); 7.76(s, 1H); 7.48(s, 1H); 7.40(t, 2H, J=8.79); 5.65(s, 2H); 4.18(s, 3H); 3.18(s, 3H); 3.02(s, 3H); 2.86(d, 3H, J=4.10Hz) | (M+H)$^+$=489 | A | <1 |
| 372. | 2-(4-Fluoro-phenyl)-6-(5-isopropoxymethyl-isoxazol-3-yl)-5-methoxy-benzofuran-3-carboxylic acid methylamide | $^1$H NMR in CDCl$_3$: 7.96(s, 1H); 7.85(dd, J=5.28 & 8.79Hz, 2H); 7.40(s, 1H); 7.18(t, J=8.35& 8.79Hz, 2H); 6.78(s, 1H); 5.98(brs, 1H); 4.64(s, 2H); 3.94(s, 3H); 3.78(septet, J=6.15Hz, 1H); 3.01(d, J=4.83Hz, 3H); 1.25(d, J=6.15Hz, 6H) | (M+H)$^+$=439 | A | <1 |
| 373. | 5-(5-Diethylamino-[1,2,4]thiadiazol-3-ylmethoxy)-2-(4-fluoro-phenyl)-6-(methanesulfonyl-methyl-amino)-benzofuran-3-carboxylic acid methylamide | $^1$H NMR in DMSO: 8.38(brd, 1H, J=4.40Hz); 7.94(m, 2H); 7.61(s, 1H); 7.37(m, 3H); 5.22(s, 2H); 3.47(brm, 4H); 3.28(s, 3H); 3.08(s, 3H); 2.84(d, 3H, J=4.84Hz); 1.18(t, 6H, J=7.03Hz) | (M+H)$^+$=562 | A | <1 |

TABLE 1-continued

| Example Number | Name | NMR data* | Mass Spec | HCV pol-BB7 IC$_{50}$(μM) A=≦0.5μM B=0.5 to ≦5.0μM C=5.0 to ≦30μM D=>30μM | Replicon (μM) |
|---|---|---|---|---|---|
| 374. | 5-[5-(Cyclopropylmethyl-amino)-[1,2,4]thiadiazol-3-ylmethoxy]-2-(4-fluoro-phenyl)-6-(methanesulfonyl-methyl-amino)-benzofuran-3-carboxylic acid methylamide | $^1$H NMR in DMSO: 8.60(brm, 1H); 8.38(brd, 1H, J=4.10Hz); 7.94(m, 2H); 7.61(s, 1H); 7.38(m, 3H); 5.19(brs, 2H); 3.26(s, 3H); 3.18(t, 2H, J=5.86Hz); 3.07(s, 3H); 2.84(d, 3H, J=4.69Hz); 1.10(m, 1H); 0.48(m, 2H); 0.24(m, 2H) | (M+H)$^+$=560 | A | <1 |
| 375. | 6-(2-Amino-1-hydroxy-1-methyl-ethyl)-2-(4-fluoro-phenyl)-5-isopropoxy-benzofuran-3-carboxylic acid methylamide | $^1$H NMR in CDCl$_3$: 7.85(m, 2H); 7.71(s, 1H); 7.19(s, 1H); 7.16(m, 2H); 6.35(brs, 1H); 4.76(m, 1H); 4.60(brs, 2H); 3.48(m, 2H); 2.99(d, J=4.69Hz, 3H); 1.47(s, 3H); 1.40(d, J=5.86Hz, 3H); 1.37(d, J=5.86Hz, 3H) | (M+H)$^+$=401.1 | B | <30 |
| 376. | 6-(1-Amino-1-methyl-ethyl)-2-(4-fluoro-phenyl)-5-isopropoxy-benzofuran-3-carboxylic acid methylamide | $^1$H NMR in CDCl$_3$: 7.84(m, 2H); 7.49(s, 1H); 7.37(s, 1H); 7.26(m, 2H); 5.74(brs, 1H); 4.84(septet, J=6.15Hz, 1H); dd 4.53(brs, 2H); 2.99(d, J=2.64Hz, 3H); 1.67(s, 6H); 1.47(d, J=6.16Hz, 6H) | (M+H)$^+$=386 | A | <1 |
| 377. | 2-[2-(4-Fluoro-phenyl)-5-methoxy-3-methylcarbamoyl-benzofuran-6-yl]-pyrrolidine-1-carboxylic acid methylamide | $^1$H NMR in CDCl$_3$: 7.85(m, 2H); 7.34(s, 1H); 7.30(s, 1H); 7.18(m, 2H); 5.77(s, 1H); 4.03(d, J=4.39Hz, 1H); 3.94(s, 3H); 3.71(m, 2H); 2.99(d, J=1.32Hz, 3H); 2.71(d, J=1.32Hz, 3H); 2.38(m, 1H); 1.86(m, 3H) | (M+H)$^+$=426 | A | <10 |
| 378. | 6-(3,5-Dimethyl-isoxazol-4-yl)-2-(4-fluoro-phenyl)-5-methoxy-benzofuran-3-carboxylic acid ethylamide | $^1$H NMR in DMSO: 8.53(s, 1H); 7.94-7.99(m, 2H); 7.61(s, 1H); 7.37-7.43(t, 2H, J=9.38Hz); 7.22(s, 1H); 3.85(s, 3H) 3.36-3.40(t, 2H, J=5.86Hz); 2.31(s, 3H); 2.12(s, 3H); 1.16-1.20(t, 3H, J=5.28Hz) | (M+H)$^+$=409 | A | <1 |
| 379. | 6-(3,5-Dimethyl-isoxazol-4-yl)-2-(4-fluoro-phenyl)-5-methoxy-benzofuran-3-carboxylic acid isopropylamide | $^1$H NMR in DMSO: 8.42-8.45(d, 1H, J=8.21Hz); 7.93-7.98(m, 2H), 7.59(s, 1H); 7.37-7.42(t, 2H, J=8.79Hz); 7.18(s, 1H); 4.18-4.24(septet, 1H, J=7.03Hz); 3.83(s, 3H); 2.30(s, 3H); 2.11(s, 3H); 1.19-1.21(d, 6H, J=7.03Hz) | (M+H)$^+$=423 | B | >30 |
| 380. | 6-(3,5-Dimethyl-isoxazol-4-yl)-2-(4-fluoro-phenyl)-5-methoxy-benzofuran-3-carboxylic acid cyclopropylamide | $^1$H NMR in DMSO: 8.59-8.61(d, 1H, J=4.10Hz); 7.90-7.94(m, 2H); 7.95(s, 1H); 7.36-7.42(t, 2H, J=8.79Hz); 7.16(s, 1H); 3.83(s, 3H); 2.93-2.99(m, 1H); 2.29(s, 3H); 2.10(s, 3H); 0.71-0.77(m, 2H); 0.54-0.60(m, 2H) | (M+H)$^+$=421 | A | <1 |
| 381. | 2-(4-Fluoro-phenyl)-5-isopropoxy-6-(5-methyl-2-oxo-oxazolidin-5-yl)-benzofuran-3-carboxylic acid methylamide | $^1$H NMR in CDCl$_3$: 7.85(m, 2H); 7.77(s, 1H); 7.35(s, 1H); 7.19(m, 2H); 5.74(brs, 1H); 5.03(brs, 1H); 4.76(m, 1H); 3.78(dd, J=2.2 & 8.4Hz, 2H); 2.97(d, J=5.2Hz, 3H); 1.82(s, 3H); 1.40(d, J=5.2Hz, 3H); 1.37(d, J=5.2Hz, 3H) | (M+H)$^+$=427.1 | A | <1 |
| 382. | [2-(4-Fluoro-phenyl)-6-(methanesulfonyl-methyl-amino)-3-methylcarbamoyl-benzofuran-5-yloxy]-acetic acid tert-butyl ester | $^1$H NMR in DMSO: 8.38(brd, 1H, J=4.69Hz); 7.93(m, 2H); 7.63(s, 1H); 7.38(t, 2H, J=8.79Hz); 7.10(s, 1H); 4.82(s, 2H); 3.26(s, 3H); 3.07(s, 3H); 2.82(d, 3H, J=4.69Hz); 1.46(s, 9H) | (M+H$_2$O)$^+$=524 | A | <1 |
| 383. | 2-(4-Fluoro-phenyl)-5-methoxy-6-(5-methyl- | $^1$H NMR in DMSO: 13.42(s, 1H), 8.44-8.46(d, 1H, | (M+H)$^+$=381 | B | <10 |

TABLE 1-continued

| Example Number | Name | NMR data* | Mass Spec | HCV pol-BB7 IC$_{50}$(μM) A=≦0.5μM B=0.5 to ≦5.0μM C=5.0 to ≦30μM D=>30μM | Replicon (μM) |
|---|---|---|---|---|---|
| | 2H-[1,2,4]triazol-3-yl)-benzofuran-3-carboxylic acid methylamide | J=4.69Hz); 8.25(s, 1H); 7.94-7.99(m, 2H); 7.36-7.42(t, 2H, J=8.79Hz); 7.27(s, 1H); 4.02(s, 3H); 2.85-2.86(d, 3H, J=4.69Hz); 2.34(s, 3H) | | | |
| 384. | 6-(1-Amino-1-methyl-ethyl)-2-(4-fluoro-phenyl)-5-methoxy-benzofuran-3-carboxylic acid methylamide | $^1$H NMR in CDCl$_3$: 7.84(m, 2H); 7.51(s, 1H); 7.32(s, 1H); 7.17(m, 2H); 5.84(brs, 1H); 3.95(s, 3H); 2.97(d, J=4.84Hz, 3H); 2.19(brs, 2H); 1.59(s, 6H) | (M+H—NH$_2$)$^+$=340 | B | <30 |
| 385. | 6-(1-Acetylamino-1-methyl-ethyl)-2-(4-fluoro-phenyl)-5-methoxy-benzofuran-3-carboxylic acid methylamide | $^1$H NMR in CDCl$_3$: 7.84(m, 2H); 7.52(s, 1H); 7.31(s, 1H); 7.15(m, 2H); 6.03(brs, 1H); 5.76(brs, 1H); 3.92(s, 3H); 2.96(d, J=4.84Hz, 3H); 1.92(s, 3H); 1.80(s, 6H) | (M+H—NHAc)$^+$=340 | A | <1 |
| 386. | [2-(4-Fluoro-phenyl)-6-(methanesulfonyl-methyl-amino)-3-methylcarbamoyl-benzofuran-5-yloxy]-acetic acid | $^1$H NMR in DMSO: 8.39(brd, 1H, J=4.69Hz); 7.93(m, 2H); 7.62(s, 1H); 7.38(t, 2H, J=8.79Hz); 7.17(s, 1H); 4.86(s, 2H); 3.26(s, 3H); 3.06(s, 3H); 2.83(d, 3H, J=4.69Hz) | (M−H)$^−$=449 | A | <30 |
| 387. | 6-(2,5-Dimethyl-2H-[1,2,4]triazol-3-yl)-2-(4-fluoro-phenyl)-5-methoxy-benzofuran-3-carboxylic acid methylamide | $^1$H NMR in DMSO: 8.45-8.47(d, 1H, J=4.69Hz); 7.93-7.98(m, 2H); 7.69(s, 1H); 7.36-7.42(t, 2H, J=8.79Hz); 7.29(s, 1H); 3.88(s, 3H); 3.60(s, 3H); 2.85-2.86(d, 3H, J=4.10Hz); 2.28(s, 3H) | (M+H)$^+$=395 | B | <10 |
| 388. | 2-(4-Fluoro-phenyl)-6-(methanesulfonyl-methyl-amino)-5-(thiazol-2-ylmethoxy)-benzofuran-3-carboxylic acid methylamide | $^1$H NMR in DMSO: 8.40(brm, 1H); 7.95(m, 2H); 7.89(d, 1H, J=2.93Hz); 7.82(d, 1H, J=2.93); 7.70(s, 1H); 7.40(m, 3H); 5.60(s, 2H); 3.25(s, 3H); 3.02(s, 3H); 2.85(d, 3H, J=4.69Hz) | (M+H)$^+$=490 | A | <1 |
| 389. | 2-(4-Fluoro-phenyl)-5-methoxy-6-(4-methyl-2,5-dioxo-imidazolidin-4-yl)-benzofuran-3-carboxylic acid methylamide | $^1$H NMR in DMSO: 10.59(brs, 1H); 8.37(m, 1H); 7.96(s, 1H); 7.94(m, 2H); 7.71(s, 1H); 7.39(m, 2H); 7.15(s, 1H); 3.77(s, 3H); 2.82(d, J=4.8Hz, 3H); 1.71(s, 3H) | (M+H)$^+$=412 | A | <10 |
| 390. | 2-(4-Fluoro-phenyl)-6-(1-methanesulfonylamino-1-methyl-ethyl)-5-methoxy-benzofuran-3-carboxylic acid methylamide | $^1$H NMR in CDCl$_3$: 7.84(m, 2H); 7.51(s, 1H); 7.44(s, 1H); 7.19(m, 2H); 5.88(s, 1H); 5.79(brs, 1H); 4.00(s, 3H); 2.98(d, J=4.84Hz, 3H); 2.52(s, 3H); 1.82(s, 6H) | (M+H—NH—SO$_2$Me)$^+$=340 | A | <10 |
| 391. | 5-(6-Bromomethyl-pyridin-2-ylmethoxy)-6-[(6-bromomethyl-pyridin-2-ylmethyl)-methanesulfonyl-amino]-2-(4-fluoro-phenyl)-benzofuran-3-carboxylic acid methylamide | $^1$H NMR in DMSO: 8.38(d, J=4.8Hz, 1H); 7.90(m, 3H); 7.73(t, J=7.1Hz, 1H); 7.64(s, 1H); 7.60(d, J=7.5Hz, 1H); 7.53(d, J=7.5Hz, 1H); 7.48(d, J=7.5Hz, 1H); 7.37(m, 3H); 7.31(s, 1H); 5.33(s, 2H); 4.98(s, 2H); 4.72(s, 2H); 4.61(s, 2H); 3.18(s, 3H); 2.81(d, J=4.8Hz, 3H) | (M+H)$^+$=746 | A | <10 |
| 392. | 2-[2-(4-Fluoro-phenyl)-6-(methanesulfonyl-methyl-amino)-3-methylcarbamoyl-benzofuran-5-yloxymethyl]-thiazole-4-carboxylic acid ethyl ester | $^1$H NMR in DMSO: 8.60(s, 1H); 8.40(brd, 1H, J=4.69Hz); 7.95(m, 2H); 7.73(s, 1H); 7.40(m, 3H); 5.63(s, 2H); 4.32(q, 2H, J=7.03Hz); 3.27(s, 3H); 3.06(s, 3H); 2.84(d, 3H, J=4.69Hz); 1.32(t, 3H, J=7.03) | (M+H)$^+$=562 | A | <1 |
| 393. | 2-[2-(4-Fluoro-phenyl)-6-(methanesulfonyl-methyl-amino)-3-methylcarbamoyl- | $^1$H NMR in DMSO: 8.52(s, 1H); 8.41(brd, 1H, J=4.69Hz); 7.95(m, 2H); 7.73(s, 1H); 7.40(m, 3H); 5.61(s, | (M−H)$^−$=532 | A | >30 |

TABLE 1-continued

| Example Number | Name | NMR data* | Mass Spec | HCV pol-BB7 IC$_{50}$(μM) A=≦0.5μM B=0.5 to ≦5.0μM C=5.0 to ≦30μM D=>30μM | Replicon (μM) |
|---|---|---|---|---|---|
| | benzofuran-5-yloxymethyl]-thiazole-4-carboxylic acid | 2H); 3.26(s, 3H); 3.06(s, 3H); 2.85(d, 3H, J=4.69Hz) | | | |
| 394. | 6-Dimethylamino-2-(4-fluoro-phenyl)-5-methoxy-benzofuran-3-carboxylic acid methylamide | $^1$H NMR in CDCl$_3$: 7.85(dd, J=8.8 & 5.3Hz, 2H); 7.26(s, 1H); 7.17(t, J=8.8Hz, 2H); 7.14(s, 1H); 5.80(brs, 1H); 3.96(s, 3H); 2.98(d, J=4.8Hz, 3H); 2.84(s, 6H) | (M+H)$^+$=343 | A | <1 |
| 395. | 5-Cyanomethoxy-2-(4-fluoro-phenyl)-6-(methanesulfonyl-methyl-amino)-benzofuran-3-carboxylic acid methylamide | $^1$H NMR in DMSO: 8.44(brd, 1H, J=4.10Hz); 7.93(m, 2H); 7.77(s, 1H); 7.41(m, 3H); 5.32(s, 2H); 3.22(s, 3H); 3.08(s, 3H); 2.84(d, 3H, J=4.69Hz) | (M+H)$^+$=432; | A | <1 |
| 396. | 2-(4-Fluoro-phenyl)-6-(methanesulfonyl-methyl-amino)-5-(5-methyl-isoxazol-3-ylmethoxy)-benzofuran-3-carboxylic acid methylamide | $^1$H NMR in DMSO: 8.40(brd, 1H, J=4.69Hz); 7.95(m, 2H); 7.68(s, 1H), 7.38(m, 3H); 6.40(s, 1H); 5.30(s, 2H); 3.21(s, 3H); 3.00(s, 3H); 2.84(d, 3H, J=4.10Hz); 2.44(s, 3H) | (M+H)$^+$=488 | A | <1 |
| 397. | 5-(5-Chloro-[1,2,3]thiadiazol-4-ylmethoxy)-2-(4-fluoro-phenyl)-6-(methanesulfonyl-methyl-amino)-benzofuran-3-carboxylic acid methylamide | $^1$H NMR in DMSO: 8.46(brd, 1H, J=4.10Hz); 7.98(m, 2H); 7.69(s, 1H); 7.51(s, 1H); 7.40(t, 2H, J=8.79Hz); 5.66(s, 2H); 3.17(s, 3H); 2.95(s, 3H); 2.87(d, 3H, J=4.69Hz) | (M+H)$^+$=525 | A | <1 |
| 398. | 2-(4-Fluoro-phenyl)-6-(methanesulfonyl-methyl-amino)-5-(1-methyl-1H-imidazol-2-ylmethoxy)-benzofuran-3-carboxylic acid methylamide | $^1$H NMR in DMSO: 8.42(brd, 1H, J=4.69); 7.98(m, 2H); 7.70(s, 1H); 7.52(s, 1H); 7.39(t, 2H, J=8.79); 7.21(s, 1H); 6.91(s, 1H); 5.27(s, 2H); 3.74(s, 3H); 3.15(s, 3H); 2.94(s, 3H); 2.87(d, 3H, J=4.69Hz) | (M+H)$^+$=487 | A | <1 |
| 399. | 5-(1-Benzyl-1H-imidazol-2-ylmethoxy)-2-(4-fluoro-phenyl)-6-(methanesulfonyl-methyl-amino)-benzofuran-3-carboxylic acid methylamide | $^1$H NMR in DMSO: 8.42(brm, 1H); 7.95(m, 2H); 7.68(s, 1H); 7.51(s, 1H); 7.42-7.20(m, 8H); 7.00(s, 1H); 5.38(s, 2H); 5.25(s, 2H); 3.04(s, 3H); 2.91(s, 3H); 2.86(d, 3H, J=4.10Hz) | (M+H)$^+$=563 | A | *** |
| 400. | 2-(2,4-Difluoro-phenyl)-6-(3,5-dimethyl-isoxazol-4-yl)-5-methoxy-benzofuran-3-carboxylic acid methylamide | $^1$H NMR in DMSO: 8.10-8.12, (d, 1H, J=4.69Hz); 7.78-7.86(q, 1H, J=6.45Hz); 7.61(s, 1H); 7.42-7.49(m, 1H); 7.33(s, 1H); 7.27-7.32(m, 1H); 3.85(s, 3H); 2.77-2.78(d, 3H, J=4.69Hz); 2.29(s, 3H); 2.10(s, 3H) | (M+H)$^+$=413 | A | *** |
| 401. | 6-(3,5-Dimethyl-isoxazol-4-yl)-2-(4-fluoro-phenyl)-5-(thiazol-4-ylmethoxy)-benzofuran-3-carboxylic acid methylamide | $^1$H NMR in DMSO: 9.13(d, 1H, J=1.17Hz); 8.41-8.43(d, 1H, J=4.69Hz); 7.94-7.99(m, 2H); 7.64-7.65(d, 1H, J=1.17Hz); 7.61(s, 1H); 7.45(s, 1H); 7.36-7.42(t, 2H, J=8.79Hz); 5.28(s, 2H); 2.86-2.88(d, 3H, J=4.69Hz); 2.29(s, 3H); 2.11(s, 3H) | (M+H)$^+$=478 | A | <1 |
| 402. | 5-(5-Amino-4H-[1,2,4]triazol-3-ylmethoxy)-2-(4-fluoro-phenyl)-6-(methanesulfonyl-methyl-amino)-benzofuran-3-carboxylic acid methylamide | $^1$H NMR in DMSO: 11.94(brs, 1H); 8.36(brd, 1H, J=4.69Hz); 7.93(m, 2H); 7.57(s, 1H); 7.36(m, 3H); 5.96(brs, 2H); 5.01(s, 2H); 3.19(s, 3H); 2.99(s, 3H); 2.83(d, 3H, J=4.10Hz) | (M+H)$^+$=489 | A | <1 |
| 403. | 5-(4-Chloro-1-methyl-1H-pyrazol-3-ylmethoxy)-2-(4-fluoro- | $^1$H NMR in DMSO: 8.44(brd, 1H, J=4.69Hz); 7.96(m, 3H); 7.62(s, 1H); 7.47(s, | (M+H)$^+$=521 | A | <1 |

TABLE 1-continued

| Example Number | Name | NMR data* | Mass Spec | HCV pol-BB7 IC$_{50}$(μM) A=≦0.5μM B=0.5 to ≦5.0μM C=5.0 to ≦30μM D=>30μM | Replicon (μM) |
|---|---|---|---|---|---|
| | phenyl)-6-(methanesulfonyl-methyl-amino)-benzofuran-3-carboxylic acid methylamide | 1H); 7.38(t, 2H, J=8.79Hz); 5.16(s, 2H); 3.84(s, 3H); 3.16(s, 3H); 2.93(s, 3H); 2.86(d, 3H, J=4.69Hz) | | | |
| 404. | 2-(4-Fluoro-phenyl)-6-(methanesulfonyl-methyl-amino)-5-(2-pyrazol-1-yl-ethoxy)-benzofuran-3-carboxylic acid methylamide | $^1$H NMR in DMSO: 8.42(brm, 1H); 7.97-7.90(m, 3H); 7.56(s, 1H); 7.47(s, 1H); 7.38(t, 2H, J=8.79); 7.23(s, 1H); 6.27(m, 1H); 4.60(brm, 2H); 4.54(brm, 2H); 2.99(s, 3H); 2.84(m, 6H) | (M+H)$^+$=487 | A | <1 |
| 405. | 2-(4-Fluoro-phenyl)-5-(1H-imidazol-2-ylmethoxy)-6-(methanesulfonyl-methyl-amino)-benzofuran-3-carboxylic acid methylamide | $^1$H NMR in DMSO: 12.24(brs, 1H); 8.41(brd, 1H, J=4.10Hz); 7.95(m, 2H); 7.63(s, 1H); 7.47(s, 1H); 7.39(t, 2H, J=8.79Hz); 7.19(s, 1H); 6.95(s, 1H); 5.20(s, 2H); 3.16(s, 3H); 2.91(s, 3H); 2.86(d, 3H, J=4.69Hz) | (M+H)$^+$=473 | A | <1 |
| 406. | 6-(2,5-Dioxo-imidazolidin-4-yl)-2-(4-fluoro-phenyl)-5-methoxy-benzofuran-3-carboxylic acid methylamide | $^1$H NMR in DMSO: 8.38(m, 1H); 8.08(s, 1H); 7.93(m, 2H); 7.56(s, 1H); 7.34(m, 2H); 7.15(s, 1H); 5.29(s, 1H); 3.90(s, 1H); 3.80(s, 3H); 2.82(d, J=3.6Hz, 3H) | (M+H)$^+$=398 | B | <10 |
| 407. | 5-(3,5-Dimethyl-isoxazol-4-yl)-2-(4-fluoro-phenyl)-6-methanesulfonylamino-benzofuran-3-carboxylic acid methylamide | $^1$H NMR in DMSO: 9.18(brs, 1H); 8.37(d, J=2.20Hz, 1H); 7.98-7.93(m, 2H); 7.72(s, 1H); 7.41-7.34(m, 3H); 3.01(s, 3H); 2.79(d, J=4.84Hz, 3H); 2.22(s, 3H); 2.04(s, 3H) | (M−H)$^−$=456.0 | *** | <10 |
| 408. | 2-(4-Fluoro-phenyl)-6-(methanesulfonyl-methyl-amino)-5-(1-thiazol-2-yl-ethoxy)-benzofuran-3-carboxylic acid methylamide | $^1$H NMR in DMSO: 8.33(brd, 1H, J=4.10); 7.92(m, 2H); 7.84(d, 1H, J=2.93Hz); 7.75(d, 1H, J=2.93); 7.66(s, 1H); 7.38(t, 2H, J=8.79Hz); 7.30(s, 1H); 6.03(q, 1H, J=6.45Hz); 3.26(s, 3H); 3.09(s, 3H); 2.82(d, 3H, J=4.69Hz); 1.76(d, 3H, J=6.45) | (M+H)$^+$=504 | *** | <1 |
| 409. | 6-(3,5-Dimethyl-isoxazol-4-yl)-2-(4-fluoro-phenyl)-5-(5-methyl-isoxazol-3-ylmethoxy)-benzofuran-3-carboxylic acid methylamide | $^1$H NMR in DMSO: 8.41(brd, 1H, J=4.69); 7.95(m, 2H); 7.62(s, 1H); 7.40(m, 3H); 6.16(s, 1H); 5.20(s, 2H); 2.86(d, 3H, J=4.69Hz); 2.41(s, 3H); 2.28(s, 3H); 2.10(s, 3H) | (M+H)$^+$=476 | A | <1 |
| 410. | 6-(3,5-Dimethyl-isoxazol-4-yl)-2-(4-fluoro-phenyl)-5-(thiazol-2-ylmethoxy)-benzofuran-3-carboxylic acid methylamide | $^1$H NMR in DMSO: 8.41(brd, 1H, J=4.10Hz); 7.95(m, 2H); 7.83(d, 1H, J=2.34Hz); 7.75(d, 1H, J=2.93Hz); 7.64(s, 1H); 7.46(s, 1H); 7.38(t, 2H, J=8.79Hz); 5.49(s, 2H); 2.86(d, 3H, J=4.10Hz); 2.30(s, 3H); 2.12(s, 3H) | (M+H)$^+$=478 | A | <1 |
| 411. | 6-Acetyl-2-(4-fluoro-phenyl)-benzofuran-3-carboxylic acid methylamide | $^1$H NMR in CD$_3$OD: 8.22(m, 1H); 7.98(m, 3H); 7.76(m, 1H); 7.27(m, 2H); 2.96(s, 3H); 2.67(s, 3H) | (M+H)$^+$=312 | B | *** |
| 412. | 2-(4-Fluoro-phenyl)-5-(2-hydroxy-2-methyl-propoxy)-6-(methanesulfonyl-methyl-amino)-benzofuran-3-carboxylic acid methylamide | $^1$H NMR in DMSO: 8.41(brm, 1H); 7.94(m, 2H); 7.64(s, 1H); 7.38(t, 2H, J=8.79Hz); 7.20(s, 1H); 4.61(s, 1H); 3.86(s, 2H); 3.24(s, 3H); 3.08(s, 3H); 2.83(d, 3H, J=4.69Hz); 1.28(s, 6H) | (M−H)$^−$=463 | A | *** |
| 413. | 5-Diethylcarbamoylmethoxy-2-(4-fluoro-phenyl)-6- | $^1$H NMR in DMSO: 8.42(brd, 1H, J=4.69Hz); 7.93(m, 2H); 7.60(s, 1H); 7.38(t, | (M+H)$^+$=506 | A | *** |

TABLE 1-continued

| Example Number | Name | NMR data* | Mass Spec | HCV pol-BB7 IC$_{50}$(μM) A=≦0.5μM B=0.5 to ≦5.0μM C=5.0 to ≦30μM D=>30μM | Replicon (μM) |
|---|---|---|---|---|---|
| | (methanesulfonyl-methyl-amino)-benzofuran-3-carboxylic acid methylamide | 2H, J=8.79Hz); 7.10(s, 1H); 4.98(s, 2H); 3.36(m, 4H); 3.27(s, 3H); 3.09(s, 3H); 2.81(d, 3H, J=4.69Hz); 1.21(t, 3H, J=7.03Hz); 1.06(t, 3H, J=7.03) | | | |
| 414. | 6-(3,5-Dimethyl-isoxazol-4-yl)-5-ethoxy-2-(4-fluoro-phenyl)-benzofuran-3-carboxylic acid methylamide | $^1$H NMR in DMSO: 8.41-8.42(d, 1H, J=4.69Hz); 7.92-7.97(m, 2H); 7.58(s, 1H); 7.35-7.41(t, 2H, J=8.79Hz); 7.21(s, 1H); 4.05-4.12(q, 2H, J=7.03Hz); 2.84-2.85(d, 3H, J=4.69Hz); 2.30(s, 3H); 2.12(s, 3H); 1.27-1.32(t, 3H, J=7.03Hz) | (M+H)$^+$=409.0 | A | *** |
| 415. | 2-(4-Fluoro-phenyl)-6-(methanesulfonyl-methyl-amino)-5-(thiazol-2-ylcarbamoylmethoxy)-benzofuran-3-carboxylic acid methylamide | $^1$H NMR in DMSO: 12.30(brs, 1H); 8.41(brd, 1H, J=4.69Hz); 7.92(m, 2H); 7.67(s, 1H); 7.51(d, 1H, J=3.52Hz); 7.38(t, 2H, J=8.79Hz); 7.27(d, 1H, J=3.52Hz); 7.18(s, 1H); 5.06(s, 2H); 3.12(m, 6H); 2.79(d, 3H, J=4.69Hz) | (M−H)$^−$=531 | A | <1 |
| 416. | 2-(4-Fluoro-phenyl)-6-(methanesulfonyl-methyl-amino)-5-([1,3,4]thiadiazol-2-ylcarbamoylmethoxy)-benzofuran-3-carboxylic acid methylamide | $^1$H NMR in DMSO: 12.81(brs, 1H), 9.22(s, 1H); 8.42(brm, 1H); 7.92(m, 2H); 7.67(s, 1H); 7.39(t, 2H, J=8.79Hz); 7.18(s, 1H); 5.12(s, 2H); 3.17(s, 3H); 3.10(s, 3H); 2.79(d, 3H, J=4.10Hz) | (M−H)$^−$=532 | A | <1 |
| 417. | 5-[(4,5-Dimethyl-thiazol-2-ylcarbamoyl)-methoxy]-2-(4-fluoro-phenyl)-6-(methanesulfonyl-methyl-amino)-benzofuran-3-carboxylic acid methylamide | $^1$H NMR in DMSO: 12.05(brs, 1H); 8.41(brd, 1H, J=4.10Hz); 7.92(m, 2H); 7.66(s, 1H); 7.39(t, 2H, J=8.79Hz); 7.16(s, 1H); 5.00(s, 2H); 3.28(s, 3H); 3.10(s, 3H); 2.80(d, 3H, J=4.10Hz); 2.24(s, 3H); 2.17(s, 3H) | (M+H)$^+$=561 | A | <1 |
| 418. | 5-Cyclopropyl-2-(4-fluoro-phenyl)-6-methanesulfonylamino-benzofuran-3-carboxylic acid methylamide | $^1$H NMR in DMSO: 9.32(brs, 1H); 8.36(m, 1H); 7.94(dd, J=5.3 & 8.8Hz, 2H); 7.58(s, 1H); 7.36(t, J=8.8Hz, 2H); 7.14(s, 1H); 3.03(s, 3H); 2.83(d, J=4.6Hz, 3H); 2.31(m, 1H); 1.00(m, 2H); 0.68(m, 2H) | (M+H)$^+$=403 | A | <1 |
| 419. | 5-[2-(4-Cyano-piperidin-1-yl)-ethoxy]-6-(3,5-dimethyl-isoxazol-4-yl)-2-(4-fluoro-phenyl)-benzofuran-3-carboxylic acid methylamide | $^1$H NMR in DMSO: 8.41-8.43(d, 1H, J=4.69Hz); 7.93-7.97(m, 2H); 7.58(s, 1H); 7.35-7.41(t, 2H, J=8.79Hz); 7.26(s, 1H); 4.08-4.12(t, 2H, J=5.86Hz); 2.85-2.86(d, 3H, J=4.69Hz); 2.82-2.86(m, 1H); 2.63-2.66(t, 2H, J=5.86Hz); 2.50-2.55(m, 3H); 2.31(s, 3H); 2.26-2.31(m, 1H); 2.14(s, 3H); 1.77-1.84(m, 2H); 1.63-1.70(m, 2H) | (M+H)$^+$=517.1 | A | <1 |
| 420. | 2-(4-Fluoro-phenyl)-6-methanesulfonylamino-5-thiophen-2-yl-benzofuran-3-carboxylic acid methylamide | $^1$H NMR in DMSO: 9.29(s, 1H); 8.48(d, J=4.84Hz, 1H); 8.02-7.97(m, 2H); 7.75(s, 1H); 7.97(s, 1H); 7.64(d, J=5.27Hz, 1H); 7.45-7.37(m, 3H); 7.19-7.16(m, 1H); 2.94(s, 3H); 2.84(d, J=4.40Hz, 3H) | (M−H)$^−$=443 | A | <1 |
| 421. | 2-(4-Fluoro-phenyl)-6-(methanesulfonyl-methyl-amino)-5-methylcarbamoylmethoxy-benzofuran-3-carboxylic acid methylamide | $^1$H NMR in DMSO: 8.40(brd, 1H, J=4.69Hz); 7.93(m, 3H); 7.70(s, 1H); 7.39(t, 2H, J=8.79Hz); 7.16(s, 1H); 4.66(s, 2H); 3.25(s, 3H); 3.13(s, 3H); 2.83(d, 3H, J=4.69Hz); 2.68(d, 3H, J=4.69Hz) | (M+H)$^+$=464 | A | <1 |
| 422. | 2-(4-Fluoro-phenyl)-5-(1-hydroxymethyl-cyclopropylmethoxy)-6- | $^1$H NMR in DMSO: 8.53(d, J=4.8Hz, 1H); 8.07(dd, J=8.8, 5.3Hz, 2H); 7.72(s, 2H); | (M−H)$^−$=545 | B | <10 |

TABLE 1-continued

| Example Number | Name | NMR data* | Mass Spec | HCV pol-BB7 IC$_{50}$(µM) A=≦0.5µM B=0.5 to ≦5.0µM C=5.0 to ≦30µM D=>30µM | Replicon (µM) |
|---|---|---|---|---|---|
| | [(1-hydroxymethyl-cyclopropylmethyl)-methanesulfonyl-amino]-benzofuran-3-carboxylic acid methylamide | 7.52(t, J=8.8Hz, 2H); 4.50(brd, 1H); 4.15(t, J=9.3Hz, 1H); 4.07(d, J=9.9Hz, 1H); 3.60(m, 2H); 3.50(m, 1H); 3.30(d, J=11.0Hz, 1H); 3.17(s, 3H); 2.94(d, J=4.8Hz, 3H); 0.75(s, 4H) | | | |
| 423. | 6-Diethylamino-5-ethoxy-2-(4-fluoro-phenyl)-benzofuran-3-carboxylic acid methylamide | $^1$H NMR in CDCl$_3$: 7.85(dd, J=8.8, 5.3Hz, 2H); 7.30(s, 1H); 7.77(t, J=8.8Hz, 2H); 6.67(s, 1H); 5.75(brs, 1H); 4.10(q, J=7.0Hz, 2H); 3.20(q, J=7.0Hz, 4H); 1.40(t, J=7.0Hz, 6H); 1.30(t, J=7.0Hz, 3H) | (M+H)$^+$=385 | A | <1 |
| 424. | 5-Carbamoylmethoxy-2-(4-fluoro-phenyl)-6-(methanesulfonyl-methyl-amino)-benzofuran-3-carboxylic acid methylamide | $^1$H NMR in DMSO: 8.41(brd, 1H, J=4.69Hz); 7.93(m, 2H), 7.72(s, 1H), 7.40(m, 4H); 7.15(s, 1H); 4.64(s, 2H); 3.26(s, 3H); 3.13(s, 3H); 2.84(d, 3H, J=4.69Hz) | (M−H)$^−$=448 | A | <1 |
| 425. | 5-[2-(3,5-Dimethyl-pyrazol-1-yl)-ethoxy]-2-(4-fluoro-phenyl)-6-(methanesulfonyl-methyl-amino)-benzofuran-3-carboxylic acid methylamide | $^1$H NMR in DMSO: 8.41(brd, 1H, J=4.69Hz); 7.94(m, 2H); 7.60(s, 1H); 7.38(t, 2H, J=8.79Hz); 7.22(s, 1H); 5.81(s, 1H); 4.44(brd, 2H, J=4.69Hz); 4.40(brd, 2H, J=4.69Hz); 3.06(s, 3H); 2.89(s, 3H); 2.84(d, 3H, J=4.69Hz); 2.28(s, 3H); 2.08(s, 3H) | (M+H)$^+$=515 | A | <1 |
| 426. | 2-(4-Fluoro-phenyl)-5-furan-2-yl-6-methanesulfonylamino-benzofuran-3-carboxylic acid methylamide | $^1$H NMR in DMSO: 9.34(s, 1H); 8.50(d, J=4.40Hz, 2H); 7.99-7.96(m, 2H); 7.91(s, 1H); 7.82(s, 1H); 7.74(s, 1H); 7.40(t, J=8.79Hz, 2H); 7.09(d, J=3.52Hz, 1H); 6.65(s, 1H); 3.04(s, 3H); 2.85(d, J=4.40Hz, 3H) | (M−H)$^−$=427.0 | A | <1 |
| 427. | 6-(3,5-Dimethyl-isoxazol-4-yl)-2-(4-fluoro-phenyl)-5-(1-methyl-1H-tetrazol-5-ylmethoxy)-benzofuran-3-carboxylic acid methylamide | $^1$H NMR in DMSO: 8.44-8.45(d, 1H, J=4.69Hz); 7.93-7.97(m, 2H); 7.63(s, 1H); 7.53(s, 1H); 7.36-7.42(t, 2H, J=8.79Hz); 5.56(s, 2H); 3.93(s, 3H); 2.86-2.88(d, 3H, J=4.69Hz); 2.24(s, 3H); 2.07(s, 3H) | (M+H)$^+$=477 | A | <1 |
| 428. | 5-Cyclopropylmethoxy-6-(3,5-dimethyl-isoxazol-4-yl)-2-(4-fluoro-phenyl)-benzofuran-3-carboxylic acid methylamide | $^1$H NMR in DMSO: 8.39-8.41(d, 1H, J=4.69Hz); 7.91-7.96(m, 2H); 7.58(s, 1H); 7.35-7.41(t, 2H, J=8.79Hz); 7.18(s, 1H); 3.86-3.88(d, 2H, J=7.03Hz); 2.83-2.85(d, 3H, J=4.69Hz); 2.32(s, 3H); 2.15(s, 3H); 1.12-1.20(m, 1H); 0.51-0.57(m, 2H); 0.26-0.31(m, 2H) | (M+H)$^+$=435 | A | <1 |
| 429. | 6-(3,5-Dimethyl-isoxazol-4-yl)-5-(3,5-dimethyl-isoxazol-4-ylmethoxy)-2-(4-fluoro-phenyl)-benzofuran-3-carboxylic acid methylamide | $^1$H NMR in DMSO: 8.43-8.45(d, 1H, J=4.69Hz); 7.92-7.96(m, 2H); 7.59(s, 1H); 7.44(s, 1H); 7.36-7.41(t, 2H, J=8.79Hz); 4.97(s, 2H); 2.86-2.87(d, 3H, J=4.69Hz); 2.28(s, 3H); 2.21(s, 3H); 2.03(s, 3H); 1.97(s, 3H) | (M+H)$^+$=490 | A | <1 |
| 430. | 2-(4-Fluoro-phenyl)-5-methoxy-6-(5-methyl-[1,3,4]oxadiazol-2-yl)-benzofuran-3-carboxylic acid methylamide | $^1$H NMR in CDCl$_3$: 8.05(s, 1H); 7.92-7.87(m, 2H); 7.52(s, 1H); 7.27-7.23(m, 2H); 5.80(s, 1H); 4.03(s, 3H); 3.02(d, J=4.5Hz, 3H); 2.65(s, 3H) | (M+H)$^+$=381 | A | <10 |
| 431. | 6-(3-Cyano-4-hydroxy-2-oxo-2,5-dihydro-pyrrol-1-ylmethyl)-2-(4-fluoro-phenyl)-5-methoxy- | $^1$H NMR in DMSO: 8.36-8.34(m, 1H); 7.94-7.89(m, 2H); 7.36-7.28(m, 3H); 7.10(s, 1H); 4.47(s, 2H); | (M+H)$^+$=436 | A | *** |

TABLE 1-continued

| Example Number | Name | NMR data* | Mass Spec | HCV pol-BB7 IC$_{50}$(μM) A=≦0.5μM B=0.5 to ≦5.0μM C=5.0 to ≦30μM D=>30μM | Replicon (μM) |
|---|---|---|---|---|---|
| | benzofuran-3-carboxylic acid methylamide | 3.85(s, 2H); 2.81(d, J=4.2Hz, 3H) | | | |
| 432. | 4-Chloro-6-[ethyl-(2-methoxy-acetyl)-amino]-2-(4-fluoro-phenyl)-5-methoxy-benzofuran-3-carboxylic acid methylamide | $^1$H NMR in CDCl$_3$: 7.90(dd, J=8.3, 5.3Hz, 2H); 7.40(s, 1H); 7.20(t, J=8.3Hz, 2H); 5.90(brs, 1H); 3.91(s, 3H); 3.80-3.70(m, 2H); 3.62(s, 2H); 3.30(s, 3H); 2.98(d, J=4.4Hz, 3H); 1.10(t, J=7.0Hz, 3H) | (M+H)$^+$=343 | B | <10 |
| 433. | 6-(3,5-Dimethyl-isoxazol-4-yl)-2-(4-fluoro-phenyl)-5-(2-morpholin-4-yl-ethoxy)-benzofuran-3-carboxylic acid methylamide | $^1$H NMR in DMSO: 8.41-8.42(d, 1H, J=4.69Hz); 7.93-7.97(m, 2H); 7.58(s, 1H); 7.35-7.41(t, 2H, J=8.79Hz); 7.26(s, 1H); 4.11-4.14(t, 2H, J=5.28Hz); 3.52-3.55(t, 4H, J=4.10Hz); 2.84-2.86(d, 3H, J-4.69Hz); 2.61-2.65(t, 2H, J=5.86Hz); 2.36-2.40(t, 4H, J=4.10Hz); 2.31(s, 3H); 2.15(s, 3H) | (M+H)$^+$=494 | A | *** |
| 434. | 6-(3,5-Dimethyl-isoxazol-4-yl)-2-(4-fluoro-phenyl)-5-(3-piperidin-1-yl-propoxy)-benzofuran-3-carboxylic acid methylamide | $^1$H NMR in DMSO: 8.42-8.44(d, 1H, J=4.69Hz); 7.92-7.97(m, 2H); 7.58(s, 1H); 7.35-7.41(t, 2H, J=8.79Hz); 7.22(s, 1H); 4.01-4.06(t, 2H, J=6.45Hz); 2.84-2.85(d, 3H, J=4.69Hz); 2.28(s, 3H); 2.25-2.28(m, 4H); 2.11(s, 3H); 1.91(s, 2H); 1.75-1.84(m, 2H); 1.36-1.48(m, 4H); 0.84-0.86(m, 2H) | (M+H)$^+$=506.1 | B | *** |
| 435. | 2-(4-Fluoro-phenyl)-5-(thiazol-4-ylmethoxy)-benzofuran-3-carboxylic acid methylamide | $^1$H NMR in DMSO: 9.12(s, 1H); 8.34(d, J=4.0Hz, 1H); 7.92(m, 2H); 7.79(s, 1H); 7.57(d, J=8.8Hz, 1H); 7.34(t, J=8.3Hz, 2H); 7.23(s, 1H); 7.07(m, 1H); 5.25(s, 2H); 2.82(d, J=3.5Hz, 3H) | (M+H)$^+$=383.0 | B | >30 |
| 436. | 2-(4-Fluoro-phenyl)-6-(2-hydroxy-acetyl)-5-methoxy-benzofuran-3-carboxylic acid methylamide | $^1$H NMR in CDCl$_3$: 8.20(s, 1H); 7.87(m, 2H); 7.45(s, 1H); 7.22(m, 2H); 5.77(brs, 1H); 4.82(s, 2H); 4.01(s, 3H); 3.75(brs, 1H); 3.00(d, J=4.8Hz, 3H) | (M+H)$^+$=358.1 | A | <10 |
| 437. | 5-Cyclopropyl-2-(4-fluoro-phenyl)-6-(methanesulfonyl-methyl-amino)-benzofuran-3-carboxylic acid methylamide | $^1$H NMR in DMSO: 8.39(d, J=4.40Hz, 1H); 7.95-7.90(m, 2H); 7.81(s, 1H); 7.39-7.33(m, 2H); 7.13(s, 1H); 3.22(s, 3H); 3.14(s, 3H); 2.82(d, J=4.40Hz, 3H); 2.33-2.24(m, 1H); 0.96(d, J=8.35Hz, 2H); 0.79-0.63(m, 2H) | (M+H)$^+$=417 | A | <1 |
| 438. | 2-(4-Fluoro-phenyl)-5-hydroxy-6-[(2-hydroxy-propyl)-methanesulfonyl-amino]-benzofuran-3-carboxylic acid methylamide | $^1$H NMR in DMSO: 9.97(s, 1H); 8.40(brd, 1H, J=4.10Hz); 7.92(m, 2H); 7.55(s, 1H); 7.35(t, 2H, J=8.79Hz); 7.09(s, 1H); 4.72(brs, 1H); 3.58-3.40(m, 3H); 3.01(s, 3H); 2.80(d, 3H, J=4.69Hz); 1.03(d, 3H, J=5.86Hz) | (M−H)$^−$=435 | A | *** |
| 439. | 2-(4-Fluoro-phenyl)-6-[(2-hydroxy-propyl)-methanesulfonyl-amino]-5-methoxy-benzofuran-3-carboxylic acid methylamide | $^1$H NMR in DMSO: 8.41(brd, 1H, J=5.28Hz); 7.92(m, 2H); 7.66(s, 1H); 7.36(t, 2H, J=8.79Hz); 7.18(s, 1H); 4.66(brs, 1H); 3.89(s, 3H); 3.56(brm, 3H); 3.00(s, 3H); 2.82(d, 3H, J=4.69Hz); 1.03(d, 3H, J=5.28Hz) | (M−H)$^−$=449 | A | *** |
| 440. | 6-(1-Acetyl-pyrrolidin-2-yl)-5-ethyl-2-(4-fluoro-phenyl)-benzofuran-3-carboxylic acid | $^1$H NMR in CDCl$_3$: (mixture of two enantiomers) 7.90(m, 2H); 7.68(s, 1H); 7.21(s, 1H); 7.15(m, 2H); | (M+H)$^+$=409.1 | A | *** |

TABLE 1-continued

| Example Number | Name | NMR data* | Mass Spec | HCV pol-BB7 IC$_{50}$(μM) A=≦0.5μM B=0.5 to ≦5.0μM C=5.0 to ≦30μM D=>30μM | Replicon (μM) |
|---|---|---|---|---|---|
| | methylamide | 5.80(brs, 1H); 5.20(dd, J=2.1Hz, J=8.4Hz, 1H); 3.85(m, 1H); 3.65(m, 1H); 3.20-3.40(1H); 3.01(d, J=5.2Hz, 3H); 2.70-2.90, 2H); 2.30-2.50, 1H); 1.80-2.10, 2H); 1.82(s, 3H); 1.34(t, J=7.5Hz, 3H) | | | |
| 441. | 2-(4-Fluoro-phenyl)-6-methanesulfonylamino-5-(tetrahydro-furan-2-yl)-benzofuran-3-carboxylic acid methylamide | $^1$H NMR in DMSO: 9.15(s, 1H); 8.44(d, J=4.40Hz, 1H); 7.94-7.89(m, 2H); 7.62(d, J=4.40Hz, 2H); 7.39-7.34(m, 2H); 5.21(t, J=7.47Hz, 1H); 4.06-4.03(m, 1H); 3.82-3.80(m, 1H); 3.08(s, 3H); 2.82(d, J=4.40Hz, 3H); 2.45-2.41(m, 1H); 1.98-1.94(m, 2H); 1.65(m, 1H) | (M−H)$^-$=431.0 | A | <1 |
| 442. | 2-(4-Fluoro-phenyl)-5-methoxy-6-(tetrahydro-furan-3-yl)-benzofuran-3-carboxylic acid methylamide | $^1$H NMR in DMSO: 8.34-8.36(d, 1H, J=4.69Hz); 7.90-7.95(m, 2H); 7.53(s, 1H); 7.33-7.39(t, 2H, J=8.79Hz); 7.10(s, 1H); 4.00-4.06(t, 1H, J=7.62Hz); 3.90-3.97(m, 1H); 3.89(s, 3H); 3.68-3.85(m, 2H); 3.56-3.61(t, 1H, J=7.62Hz); 2.83-2.84(d, 3H, J=4.69Hz); 2.21-2.31(m, 1H); 1.95-2.06(m, 1H) | (M+H)$^+$=370.0 | A | <1 |
| 443. | 2-(4-Fluoro-phenyl)-6-(methanesulfonyl-methoxymethyl-amino)-5-propoxy-benzofuran-3-carboxylic acid methylamide | $^1$H NMR in DMSO: 8.40(d, J=4.2Hz, 1H); 7.94(dd, J=8.8, 5.3Hz, 2H); 7.65(s, 1H); 7.36(t, J=8.8Hz, 2H); 7.19(s, 1H); 5.94(brs, 2H); 4.03(t, J=7.0Hz, 2H); 3.32(s, 3H); 3.08(s, 3H); 2.81(d, J=4.2Hz, 3H); 1.80(sextet, J=7.0Hz, 2H); 1.01(t, J=7.0Hz, 3H) | (M+H)$^+$=465 | A | <1 |
| 444. | 2-(4-Fluoro-phenyl)-5-hydroxy-6-(methanesulfonyl-methoxymethyl-amino)-benzofuran-3-carboxylic acid methylamide | $^1$H NMR in DMSO: 10.08(s, 1H); 8.40(d, J=4.4Hz, 1H); 7.92(dd, J=8.8, 5.7Hz, 2H); 7.53(s, 1H); 7.35(t, J=8.8Hz, 2H); 7.12(s, 1H); 4.92(brs, 2H); 3.31(s, 3H); 3.08(s, 3H); 2.80(d, J=4.8Hz, 3H) | (M−H)$^-$=421 | A | <10 |
| 445. | 2-(4-Fluoro-phenyl)-6-methanesulfonylamino-5-propoxy-benzofuran-3-carboxylic acid methylamide | $^1$H NMR in CDCl$_3$: 7.82(dd, J=8.8 & 6.3Hz, 2H); 7.73(s, 1H); 7.41(s, 1H); 7.18(t, J=8.8Hz, 2H); 6.92(s, 1H); 5.77(brs, 1H); 4.07(t, J=6.6Hz, 2H); 2.98(d, J=9.8Hz, 3H); 2.95(s, 3H); 1.85(sextet, J=7.0Hz, 2H); 1.06(t, J=7.0Hz, 3H) | (M+H)$^+$=421 | A | <1 |
| 446. | 5-(4-Cyano-benzyloxy)-2-(4-fluoro-phenyl)-6-(methanesulfonyl-methoxymethyl-amino)-benzofuran-3-carboxylic acid methylamide | $^1$H NMR in DMSO: 8.40(d, J=4.6Hz, 1H); 7.93(dd, J=8.8, 5.3Hz, 2H); 7.88(d, J=8.2Hz, 2H); 7.75(s, 1H); 7.71(d, J=8.2Hz, 2H); 7.37(t, J=8.8Hz, 2H); 7.31(s, 1H); 5.33(s, 2H); 4.94(brs, 2H); 3.31(s, 3H); 3.04(s, 3H); 2.81(d, J=4.6Hz, 3H) | (M−H)$^-$=536 | A | <1 |
| 447. | 5-(3-Cyano-benzyloxy)-2-(4-fluoro-phenyl)-6-(methanesulfonyl-methoxymethyl-amino)-benzofuran-3-carboxylic acid methylamide | $^1$H NMR in DMSO: 8.40(d, J=4.4Hz, 1H); 8.00(s, 1H); 7.90-7.80(m, 4H); 7.75(s, 1H); 7.62(t, J=8.0Hz, 1H); 7.39(t, J=8.0Hz, 2H); 7.31(s, 1H); 5.28(s, 2H); 4.92(brs, 2H); 3.31(s, 3H); 3.04(s, 3H); 2.82(d, J=4.4Hz, 3H) | (M+H)$^+$=536 | A | <1 |
| 448. | 6-(1-Cyclopropanecarbonyl-pyrrolidin-2-yl)-2-(4- | $^1$H NMR in CDCl$_3$: 7.84(m, 2H); 7.34(s, 1H); 7.18-7.23(m, 3H); 5.74(brs, 1H); | (M+H)$^+$=465 | A | *** |

TABLE 1-continued

| Example Number | Name | NMR data* | Mass Spec | HCV pol-BB7 IC$_{50}$(μM) A=≦0.5μM B=0.5 to ≦5.0μM C=5.0 to ≦30μM D=>30μM | Replicon (μM) |
|---|---|---|---|---|---|
| | fluoro-phenyl)-5-isopropoxy-benzofuran-3-carboxylic acid methylamide | 5.50(d, J=7.47Hz, 1H); 4.73(septet, J=5.72Hz, 1H); 3.85(m, 1H); 3.82(m, 1H); 2.99(d, J=4.84Hz, 3H); 2.22-2.43(m, 1H); 1.92-2.00(m, 2H); 1.79-1.80(m, 2H); 1.40(m, 6H); 0.85-1.01(m, 4H) | | | |
| 449. | 2-(4-Fluoro-phenyl)-5-methoxy-6-[1,3,4]oxadiazol-2-yl-benzofuran-3-carboxylic acid methylamide | $^1$H NMR in CDCl$_3$: 8.51(s, 1H); 8.11(s, 1H); 7.91-7.87(m, 2H); 7.54(s, 1H); 7.26-7.20(m, 2H); 5.80(s, 1H); 4.04(s, 3H); 2.99(d, J=5.4Hz, 3H) | (M+H)$^+$=368 | A | *** |
| 450. | 2-(4-Fluoro-phenyl)-6-(methanesulfonyl-methyl-amino)-5-thiophen-2-yl-benzofuran-3-carboxylic acid methylamide | $^1$H NMR in DMSO: 8.48(m, 1H); 7.98-7.96(m, 3H); 7.83(m, 1H); 7.61-7.60(m, 1H); 7.42-7.36(m, 3H); 7.13(m, 1H); 3.16(s, 3H); 3.08(s, 3H); 2.66(d, J=3.96Hz, 3H) | (M+H)$^+$=458.9 | A | *** |
| 451. | 2-(4-Fluoro-phenyl)-6-{[2-(4-fluoro-phenyl)-2-hydroxy-ethyl]-methanesulfonyl-amino}-5-hydroxy-benzofuran-3-carboxylic acid methylamide | $^1$H NMR in DMSO: 10.03(brs, 1H); 8.42(brd, 1H, J=4.69Hz); 7.94(m, 2H); 7.38(t, 2H, J=8.79Hz); 7.32(m, 3H); 7.13(m, 3H); 5.58(m, 1H); 4.62(m, 1H); 3.70(brm, 2H); 3.01(s, 3H); 2.82(d, 3H, J=4.10Hz) | (M−H)$^−$=515 | A | *** |
| 452. | 5-Methoxy-2-phenyl-benzofuran-3-carboxylic acid methylamide | *** | *** | A | <10 |
| 453. | 5-Hydroxy-2-phenyl-benzofuran-3-carboxylic acid methylamide | *** | *** | C | *** |

*All $^1$H NMR and $^{13}$C NMR spectra were acquired on a Varian Mercury VX 300 Spectrometer and referenced to tetramethylsilane (TMS) unless indicated otherwise. Chemical shifts and coupling constants are reported in parts per million (ppm) and Hertz (Hz) respectively. Multiplicities indicated are: s = singlet, d = doublet, t = triplet, q = quartet, m = multiplet dd = doublet of doublets, and br indicates a broad signal.
** Mass Spectroscopy data is expressed as a mass to charge ratio (m/z) for either (M+H) or (M−H) molecular ion.
*** Indicates that data was not collected.

Table 2 lists examples of pharmaceutically acceptable salts of select compounds listed in Table 1.

TABLE 2

| Example Number | Name | NMR Data* |
|---|---|---|
| 454. | 2-(4-Fluoro-phenyl)-5-isopropoxy-6-methanesulfonylamino-benzofuran-3-carboxylic acid methylamide, potassium salt | $^1$HNMR in DMSO 8.18-8.15(brm, 1H); 7.87-7.81(m, 2H); 7.28-7.22(m, 2H); 6.77(s, 1H); 4.57(septet, J=6.45Hz, 1H); 2.78(d, J=4.7Hz, 3H); 2.55(s, 3H); 1.18(d, J=5.86Hz, 6H) |
| 455. | 2-(4-Fluoro-phenyl)-5-isopropoxy-6-methanesulfonylamino-benzofuran-3-carboxylic acid methylamide, sodium salt | $^1$H NMR in DMSO 8.18-8.15(br m, 1H); 7.87-7.81(m, 2H); 7.28-7.22(m, 2H); 6.77(s, 1H); 4.57(septet, J=6.45Hz, 1H); 2.78(d, J=4.7Hz, 3H); 2.55(s, 3H); 1.18(d, J=5.86Hz, 6H) |
| 456. | 2-(4-Fluoro-phenyl)-6-methanesulfonylamino-5-methoxy-benzofuran-3-carboxylic acid methylamide, potassium salt | *** |
| 457. | 2-(4-Fluoro-phenyl)-6-methanesulfonylamino-5-methoxy-benzofuran-3-carboxylic acid methylamide, sodium salt | *** |
| 458. | 2-(4-Fluoro-phenyl)-5-isopropoxy-6-(propane-2-sulfonylamino)-benzofuran-3-carboxylic acid methylamide, potassium salt | *** |
| 459. | 2-(4-Fluoro-phenyl)-5-isopropoxy-6-(propane-2-sulfonylamino)-benzofuran-3-carboxylic acid methylamide, sodium salt | *** |

TABLE 2-continued

| Example Number | Name | NMR Data* |
|---|---|---|
| 460. | 2-(4-Fluoro-phenyl)-5-isopropoxy-6-methanesulfonylamino-benzofuran-3-carboxylic acid isopropylamide, potassium salt | *** |
| 461. | 2-(4-Fluoro-phenyl)-5-isopropoxy-6-methanesulfonylamino-benzofuran-3-carboxylic acid isopropylamide, sodium salt | *** |
| 462. | 2-(4-Fluoro-phenyl)-5-isopropoxy-6-methanesulfonylamino-benzofuran-3-carboxylic acid ethylamide, potassium salt | *** |
| 463. | 2-(4-Fluoro-phenyl)-5-isopropoxy-6-methanesulfonylamino-benzofuran-3-carboxylic acid ethylamide, sodium salt | *** |

*All $^1$H NMR and $^{13}$C NMR spectra were acquired on a Varian Mercury VX 300 Spectrometer and referenced to tetramethylsilane (TMS) unless indicated otherwise. Chemical shifts and coupling constants are reported in parts per million (ppm) and Hertz (Hz) respectively. Multiplicities indicated are: s = singlet, d = doublet, t = triplet, q = quartet, m = multiplet dd = doublet of doublets, and br indicates a broad signal.
*** Indicates that data was not collected.

EXAMPLE 464

Inhibition of Viral RNA Replication

Antiviral activity of representative compounds of the invention was first evaluated in a human liver-derived cell line (Huh-7-Clone A) containing the HCV replicon (BB7 sequence) (See Lohmann et al. *Science*. 1999, 285:110-3; Blight K J et al., *Science*. 2000, 290:1972-4; Pietschmann, T. et al., *J. Virol*. 2001, 73:1252-1264; and Lohmann, V. et al., *J. Virol*. 2001, 75:1437-1449). The HCV replicon is a subgenomic viral RNA that expresses the HCV proteins required for its own replication. These proteins include non-structural proteins NS3, NS4A, NS4B, NS5A and NS5B. The replicon also contains a foreign gene encoding a drug-selectable marker (neomycin phosphotransferase) to allow for G418 (neomycin) selection of cells that contain the replicon.

An ELISA (enzyme-linked immunosorbant assay) was used to determine the effect of compounds within the scope of the invention on the amount of HCV NS5A protein produced after a 72-hour incubation of the replicon-containing cells in the presence of varying concentrations of compound. COSTAR® 96-well cell culture plates were used but other known cell culture plates may be used. After incubation, media is removed from wells and the cells are fixed to the assay plate using 0.05% glutaraldehyde. The glutaraldehyde is then washed off using phosphate-buffered saline (PBS) following a 1 hour incubation and cells are blocked for non-specific antibody binding using for example SUPERBLOCK® reagent (blocking buffer) in PBS. The blocking agent is rinsed from the cells with PBS after 1 hour at 37° C. and primary monoclonal antibody is added to each well containing compound. Primary antibody is incubated for 1 hour at 37° C. and rinsed 3 times with PBS containing 0.02% TWEEN-20™ before addition of Horseradish Peroxidase (HRP) conjugated secondary antibody. HRP is incubated for 1 hour at 37° C. and rinsed several times, first with PBS/TWEEN-20™ followed by PBS alone. To quantify peroxidase activity, 3,3',5,5'-tetramethylbenzidine (TMB) substrate is added to the plate and after 30 minutes, the plates are read in an ELISA plate reader at an OD of 650 nm. Compound dose response was measured in an 8-point dose curve diluted serially to determine the inhibitory concentration at 50% ($EC_{50}$ value). Representative compounds of the invention showed a dose-dependent inhibition of intracellular NS5A levels. Ranges of 50% effective concentrations ($EC_{50}$s) for representative compounds within the scope of this invention are listed in Table 1. Preferred compounds have 50% effective concentrations at about 30 µM or less, more preferred compounds have 50% effective concentrations at about 5 µM or less, and most preferred compounds have 50% effective concentrations at about 0.5 µM or less.

EXAMPLE 465

Inhibition of Viral RNA-dependent RNA polymerase (RdRp)

The HCV NS5B-directed RdRp activity was established and characterized in a standard in vitro biochemical assay using a purified HCV NS5B protein derived from the consensus sequence of a patient infected with HCV genotype 1b virus (BB7). (See Blight K J et al., *Science*. 2000, 290:1972-4). The NS5B consensus sequence was cloned and expressed in *E. coli* as a histidine tagged (GSHHHHHH) fusion protein, of which the carboxyl terminal 21 amino acids were removed to enhance its solubility.

In addition to evaluating their activity in the replicon assay, representative compounds within the scope of the present invention, as shown in examples 1-453 of Table 1, were also evaluated for antiviral activity using this assay. A measure of the inhibitory activity of compounds of the invention may be expressed as $IC_{50}$ values. $IC_{50}$ values represent the concentration of the compound at which 50% of the RdRp activity is inhibited. The results of the assay for inhibition of RdRp activity of HCV, NS5B proteins for a substantial majority of the compounds tested revealed $IC_{50}$ values ranging from <0.5 to about 30 µM. These low concentrations of test compounds required to achieve 50% inhibition of the RdRp activity indicate that the compounds of the invention are effective at inhibiting RNA synthesis by viral RdRp enzymes.

Although the present invention has been described and exemplified in terms of certain preferred embodiments, other embodiments will be apparent to those skilled in the art. The invention is, therefore, not limited to the particular embodiments described and exemplified, but is capable of modification or variation without departing from the spirit of the invention, the full scope of which is delineated by the appended claims.

What is claimed is:

1. A compound having the formula:

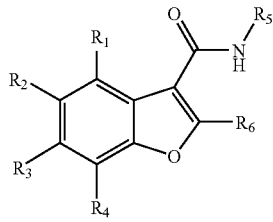

wherein:
R₁ represents a radical selected from the group consisting of hydrogen, alkyl, halogen, and cyano;
R₂ represents a heterocyclic-substituted alkyl radical, a heterocyclic-substituted alkoxy radical and a substituted or unsubstituted heterocyclic radical;
R₃ represents a radical selected from the group consisting of hydrogen, a substituted or unsubstituted alkyl radical, a substituted or unsubstituted alkoxy group, alkenyl, halogen, hydroxy, polyfluoroalkyl, polyfluoroalkoxy, formyl, carboxyl, alkylcarbonyl, alkoxycarbonyl, hydroxyalkylcarbonyl, amino, a substituted or unsubstituted monoalkylamino, dialkylamino, cyano, amido, alkoxyamido, a substituted or unsubstituted heteroarylamino, acetylsulfonylamino, ureido, carboxamide, sulfonamide, a substituted sulfonamide, a substituted or unsubstituted heterocyclosulfonyl, alkylthio, alkylsulfinyl, alkylsulfonyl, alkylsulfonic acid, a substituted or unsubstituted heterocyclic radical, and —O(CH₂)—C(=O)—R₇;
R₄ represents a radical selected from the group consisting of hydrogen, alkyl, halogen, and alkoxy;
R₅ represents a radical selected from the group consisting of an alkyl (C₁-C₆) group, cycloalkyl, and cycloalkylalkyl;
R₆ represents a radical selected from the group consisting of a substituted or unsubstituted aryl group and a substituted or unsubstituted heteroaryl group;
R₇ represents a radical selected from the group consisting of dialkylamino, a substituted or unsubstituted arylamino, a substituted or unsubstituted heteroarylamino, and a substituted or unsubstituted aryl group,
said monoalkylamino substituents being one or more radical(s) independently selected from the group consisting of cycloalkyl, hydroxy, alkoxy, and a substituted or unsubstituted heterocyclic radical;
said arylamino substituents and said heteroarylamino substituents being one or more radical(s) independently selected from an alkyl group and an alkoxycarbonyl;
said sulfonamide substituents being one or more radical(s) independently selected from the group consisting of alkenyl, cycloalkyl, alkoxy, hydroxy, halogen, polyfluoroalkyl, polyfluoroalkoxy, carboxyl, alkylcarbonyl, alkoxycarbonyl, carboxamide, a substituted or unsubstituted aryl group, and a substituted or unsubstituted heterocyclic radical;
said heterocyclosulfonyl substituents being one or more radical(s) independently selected from the group consisting of alkoxy and hydroxy;
said alkyl radical substituents and said alkoxy group substituents being one or more radical(s) independently selected from the group consisting of alkenyl, amino, monoalkylamino, dialkylamino, alkoxy, cycloalkyl, hydroxy, carboxyl, halogen, cyano, polyfluoroalkyl, polyfluoroalkoxy, sulfonamide, carboxamide, alkylsulfonyl, alkylcarbonyl, alkoxycarbonyl, mercapto, 2,2-dimethyl-4-oxo-4H-benzo[1,3]dioxinyl, a substituted or unsubstituted aryl group, and a substituted or unsubstituted heterocyclic radical;
said heterocyclic radical substituents being one or more radical(s) independently selected from the group consisting of alkyl, amino, amido, monoalkylamino, cycloalkyl-alkylamino, dialkylamino, alkoxy, alkoxyalkyl, hydroxy, hydroxyalkyl, cycloalkyl, cycloalkylalkyl, carboxyl, carboxamide, halogen, haloalkyl, cyano, polyfluoroalkyl, polyfluoroalkoxy, alkylsulfonyl, alkylcarbonyl, cycloalkylcarbonyl, alkoxycarbonyl, mercapto, oxo, a substituted or unsubstituted aryl group, arylalkyl, and a substituted or unsubstituted heteroaryl group;
said heteroaryl group substituents being one or more radical(s) independently selected from the group consisting of alkyl, amino, alkoxy, alkoxyalkyl, hydroxy, hydroxyalkyl, cycloalkyl, carboxyl, carboxamide, halogen, polyfluoroalkyl, polyfluoroalkoxy, alkylsulfonyl, mercapto, and oxo;
said aryl group substituents being one or more radical(s) independently selected from the group consisting of alkyl, acetylenyl, alkoxy, hydroxy, halogen, polyfluoroalkyl, polyfluoroalkoxy, cyano, amino, monoalkylamino, dialkylamino, aminoalkyl, alkoxyalkoxy, amido, amidoalkyl, carboxyl, alkylsulfonyl, alkylcarbonyl, alkoxycarbonyl, mercapto, and a heterocyclic radical; and pharmaceutically acceptable salts thereof.

2. A compound having the formula:

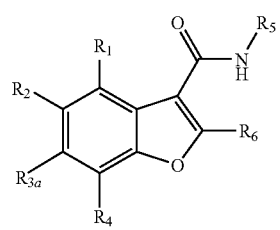

wherein:
R₁ represents a radical selected from the group consisting of hydrogen, alkyl, halogen, and cyano;
R₂ represents a radical selected from the group consisting of hydrogen, a substituted or unsubstituted alkyl radical, a substituted or unsubstituted alkoxy group, hydroxy, cycloalkyl, cycloalkyloxy, polyfluoroalkyl, polyfluoroalkoxy, halogen, amino, monoalkylamino, dialkylamino, cyano, a substituted or unsubstituted benzyloxy group, and a substituted or unsubstituted heterocyclic radical;
R₃ₐ represents a radical selected from the group consisting of a substituted or unsubstituted heteroarylamino, a substituted or unsubstituted heterocyclosulfonyl, and a substituted or unsubstituted heterocyclic radical;
R₄ represents a radical selected from the group consisting of hydrogen, alkyl, halogen, and alkoxy;
R₅ represents a radical selected from the group consisting of an alkyl (C₁-C₆) group, cycloalkyl, and cycloalkylalkyl;

R₆ represents a radical selected from the group consisting of a substituted or unsubstituted aryl group and a substituted or unsubstituted heteroaryl group;

R₇ represents a radical selected from the group consisting of dialkylamino, a substituted or unsubstituted arylamino, a substituted or unsubstituted heteroarylamino, and a substituted or unsubstituted aryl group, said arylamino substituents and said heteroarylamino substituents being one or more radical(s) independently selected from an alkyl group and an alkoxycarbonyl;

said heterocyclosulfonyl substituents being one or more radical(s) independently selected from the group consisting of alkoxy and hydroxy;

said alkyl radical substituents and said alkoxy group substituents being one or more radical(s) independently selected from the group consisting of alkenyl, amino, monoalkylamino, dialkylamino, alkoxy, cycloalkyl, hydroxy, carboxyl, halogen, cyano, polyfluoroalkyl, polyfluoroalkoxy, sulfonamide, carboxamide, alkylsulfonyl, alkylcarbonyl, alkoxycarbonyl, mercapto, 2,2-dimethyl-4-oxo-4H-benzo[1,3]dioxinyl, a substituted or unsubstituted aryl group, and a substituted or unsubstituted heterocyclic radical;

said heterocyclic radical substituents being one or more radical(s) independently selected from the group consisting of alkyl, amino, amido, monoalkylamino, cycloalkyl-alkylamino, dialkylamino, alkoxy, alkoxyalkyl, hydroxy, hydroxyalkyl, cycloalkyl, cycloalkylalkyl, carboxyl, carboxamide, halogen, haloalkyl, cyano, polyfluoroalkyl, polyfluoroalkoxy, alkylsulfonyl, alkylcarbonyl, cycloalkylcarbonyl, alkoxycarbonyl, mercapto, oxo, a substituted or unsubstituted aryl group, arylalkyl, and a substituted or unsubstituted heteroaryl group;

said heteroaryl group substituents being one or more radical(s) independently selected from the group consisting of alkyl, amino, alkoxy, alkoxyalkyl, hydroxy, hydroxyalkyl, cycloalkyl, carboxyl, carboxamide, halogen, polyfluoroalkyl, polyfluoroalkoxy, alkylsulfonyl, mercapto, and oxo;

said benzyloxy group substituents being one or more radical(s) independently selected from the group consisting of alkyl, alkoxy, polyfluoroalkyl, polyfluoroalkoxy, hydroxy, carboxyl, alkoxycarbonyl, halogen, cyano, alkylsulfonyl, and phenyl;

said aryl group substituents being one or more radical(s) independently selected from the group consisting of alkyl, acetylenyl, alkoxy, hydroxy, halogen, polyfluoroalkyl, polyfluoroalkoxy, cyano, amino, monoalkylamino, dialkylamino, aminoalkyl, alkoxyalkyl, amido, amidoalkyl, carboxyl, alkylsulfonyl, alkylcarbonyl, alkoxycarbonyl, mercapto, and a heterocyclic radical; and pharmaceutically acceptable salts thereof.

3. A compound having the formula:

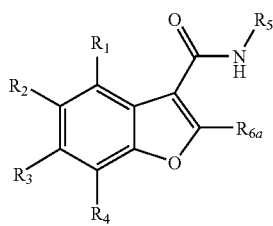

Ib wherein:

R₁ represents a radical selected from the group consisting of hydrogen, alkyl, halogen, and cyano;

R₂ represents a radical selected from the group consisting of hydrogen, a substituted or unsubstituted alkyl radical, a substituted or unsubstituted alkoxy group, hydroxy, cycloalkyl, cycloalkyloxy, polyfluoroalkyl, polyfluoroalkoxy, halogen, amino, monoalkylamino, dialkylamino, cyano, a substituted or unsubstituted benzyloxy group, and a substituted or unsubstituted heterocyclic radical;

R₃ represents a radical selected from the group consisting of hydrogen, a substituted or unsubstituted alkyl radical, a substituted or unsubstituted alkoxy group, alkenyl, halogen, hydroxy, polyfluoroalkyl, polyfluoroalkoxy, formyl, carboxyl, alkylcarbonyl, alkoxycarbonyl, hydroxyalkylcarbonyl, amino, a substituted or unsubstituted monoalkylamino, dialkylamino, cyano, amido, alkoxyamido, a substituted or unsubstituted heteroarylamino, acetylsulfonylamino, ureido, carboxamide, sulfonamide, a substituted sulfonamide, a substituted or unsubstituted heterocyclosulfonyl, alkylthio, alkylsulfinyl, alkylsulfonyl, alkylsulfonic acid, a substituted or unsubstituted heterocyclic radical, and —O(CH₂)—C(=O)—R₇;

R₄ represents a radical selected from the group consisting of hydrogen, alkyl, halogen, and alkoxy;

R₅ represents a radical selected from the group consisting of an alkyl (C₁-C₆) group, cycloalkyl, and cycloalkylalkyl;

R₆ₐ represents a substituted or unsubstituted heteroaryl group;

R₇ represents a radical selected from the group consisting of dialkylamino, a substituted or unsubstituted arylamino, a substituted or unsubstituted heteroarylamino, and a substituted or unsubstituted aryl group, said monoalkylamino substituents being one or more radical(s) independently selected from the group consisting of cycloalkyl, hydroxy, alkoxy, and a substituted or unsubstituted heterocyclic radical;

said arylamino substituents and said heteroarylamino substituents being one or more radical(s) independently selected from an alkyl group and an alkoxycarbonyl;

said sulfonamide substituents being one or more radical(s) independently selected from the group consisting of alkenyl, cycloalkyl, alkoxy, hydroxy, halogen, polyfluoroalkyl, polyfluoroalkoxy, carboxyl, alkylcarbonyl, alkoxycarbonyl, carboxamide, a substituted or unsubstituted aryl group, and a substituted or unsubstituted heterocyclic radical;

said heterocyclosulfonyl substituents being one or more radical(s) independently selected from the group consisting of alkoxy and hydroxy;

said alkyl radical substituents and said alkoxy group substituents being one or more radical(s) independently selected from the group consisting of alkenyl, amino, monoalkylamino, dialkylamino, alkoxy, cycloalkyl, hydroxy, carboxyl, halogen, cyano, polyfluoroalkyl, polyfluoroalkoxy, sulfonamide, carboxamide, alkylsulfonyl, alkylcarbonyl, alkoxycarbonyl, mercapto, 2,2-dimethyl-4-oxo-4H-benzo[1,3]dioxinyl, a substituted or unsubstituted aryl group, and a substituted or unsubstituted heterocyclic radical;

said heterocyclic radical substituents being one or more radical(s) independently selected from the group consisting of alkyl, amino, amido, monoalkylamino, cycloalkyl-alkylamino, dialkylamino, alkoxy, alkoxyalkyl, hydroxy, hydroxyalkyl, cycloalkyl, cycloalkylalkyl, carboxyl, carboxamide, halogen, haloalkyl, cyano, polyfluoroalkyl, polyfluoroalkoxy, alkylsulfonyl, alkylcarbonyl, cycloalkylcarbonyl, alkoxycarbonyl, mercapto, oxo, a substituted or unsubstituted aryl group, arylalkyl, and a substituted or unsubstituted heteroaryl group;

said heteroaryl group substituents being one or more radical(s) independently selected from the group consisting of alkyl, amino, alkoxy, alkoxyalkyl, hydroxy, hydroxyalkyl, cycloalkyl, carboxyl, carboxamide, halogen, polyfluoroalkyl, polyfluoroalkoxy, alkylsulfonyl, mercapto, and oxo;

said benzyloxy group substituents being one or more radical(s) independently selected from the group consisting of alkyl, alkoxy, polyfluoroalkyl, polyfluoroalkoxy, hydroxy, carboxyl, alkoxycarbonyl, halogen, cyano, alkylsulfonyl, and phenyl;

said aryl group substituents being one or more radical(s) independently selected from the group consisting of alkyl, acetylenyl, alkoxy, hydroxy, halogen, polyfluoroalkyl, polyfluoroalkoxy, cyano, amino, monoalkylamino, dialkylamino, aminoalkyl, alkoxyalkoxy, amido, amidoalkyl, carboxyl, alkylsulfonyl, alkylcarbonyl, alkoxycarbonyl, mercapto, and a heterocyclic radical; and pharmaceutically acceptable salts thereof.

4. The compound according to claim 1, wherein $R_5$ is methyl.

5. A compound having the formula:

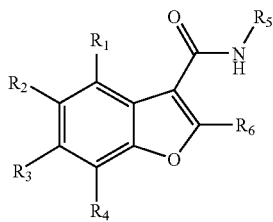

wherein:

$R_1$ represents a radical selected from the group consisting of hydrogen, methyl, and chloro;

$R_2$ represents a radical selected from the group consisting of 2,2-dimethyl-4-oxo-4H-benzo[1,3]dioxin-5-ylmethoxy, 2,2-dimethyl-4-oxo-4H-benzo[1,3]dioxin-7-ylmethoxy, 2,2-dimethyl-4-oxo-4H-benzo[1,3]dioxin-6-ylmethoxy, 3-chloromethyl-[1,2,4]thiadiazol-5-yloxy, 5-chloro-[1,2,4]thiadiazol-3-ylmethoxy, 5-chloro-[1,2,3]thiadiazol-4-ylmethoxy, 5-p-tolyl-[1,3,4]oxadiazol-2-ylmethoxy, 5-(3,5-dimethyl-isoxazol-4-yl)-[1,2,4]oxadiazol-3-ylmethoxy, 5-(cyclopropylmethyl-amino)-[1,2,4]thiadiazol-3-ylmethoxy, 5-tert-butyl-[1,2,4]oxadiazol-3-ylmethoxy, 5-(4-methoxy-phenyl)-[1,2,4]oxadiazol-3-ylmethoxy, 5-diethylamino-[1,2,4]thiadiazol-3-ylmethoxy, [1,3,4]thiadiazol-2-ylcarbamoylmethoxy, 3,5-dimethyl-isoxazol-4-yl, isoxazol-3-ylmethoxy, 3,5-dimethyl-isoxazol-4-ylmethoxy, 5-methyl-isoxazol-3-ylmethoxy, thiazol-2-ylmethoxy, thiazol-4-ylmethoxy, 2-methyl-thiazol-4-ylmethoxy, 1-thiazol-2-yl-ethoxy, thiazol-2-ylcarbamoylmethoxy, (4,5-dimethyl-thiazol-2-ylcarbamoyl)-methoxy, 4-chloro-1-methyl-1H-pyrazol-3-ylmethoxy, 2-pyrazol-1-yl-ethoxy, 2-(3,5-dimethyl-pyrazol-1-yl)ethoxy, 4-ethoxycarbonyl-thiazol-2-ylmethoxy, 4-carboxy-thiazol-2-ylmethoxy, 5-amino-4H-[1,2,4]triazol-3-ylmethoxy, thiophen-2-yl, furan-2-yl, 2-morpholin-4-yl-ethoxy, 3-piperidin-1-yl-propoxy, tetrahydro-furan-2-yl, 1-methyl-1H-tetrazol-5-ylmethoxy, 1-methyl-1H-imidazol-2-ylmethoxy, 1-benzyl-1H-imidazol-2-ylmethoxy, 3H-imidazol-4-ylmethoxy, pyridine-4-ylmethoxy, 6-bromomethyl-pyridin-2-ylmethoxy, and 2-(4-cyano-piperidin-1-yl)-ethoxy;

$R_3$ represents a radical selected from the group consisting of hydrogen, methyl, methoxy, hydroxy, hydroxymethyl, 1-hydroxy-ethyl, 1-hydroxy-2-methyl-propyl, 1-hydroxy-1-methyl-ethyl, formyl, ureido, vinyl, bromo, chloro, cyano, acetyl, 2-hydroxy-acetyl, carboxy, azetidin-1-yl, carboxylic acid amide, amino, methylamino, dimethylamino, ethylamino, diethylamino, isopropylamino, tert-butylamino, ethyl-methyl-amino, 2-methoxy-ethylamino, cyclopropylmethyl-amino, 2,3-dihydroxy-propylamino, 1-methylamino-ethyl, dimethylaminomethyl, 1-amino-1-methyl-ethyl, 2-amino-1-hydroxy-1-methyl-ethyl, acetylamino, 1-acetylamino-1-methyl-ethyl, (2-methoxy-ethyl)-methyl-amino, ethyl-(2-methoxyacetyl)-amino, 3-chloro-propane-1-sulfonylamino, methanesulfonylamino, ethyl-methanesulfonyl-amino, isopropyl-methanesulfonyl-amino, isobutyl-methanesulfonyl-amino, cyclobutyl-methanesulfonyl-amino, cyclopentyl-methanesulfonyl-amino, cyclopropylmethyl-methanesulfonyl-amino, (2-hydroxy-ethyl)-methanesulfonyl-amino, (2-hydroxy-propyl)methanesulfonyl-amino, (2-fluoro-ethyl)-methanesulfonyl-amino, 2-(4-fluoro-phenyl)-2-hydroxy-ethyl]-methanesulfonyl-amino, (1-hydroxymethyl-cyclopropylmethyl)-methanesulfonyl-amino, (4-carboxy-benzyl)-methanesulfonyl-amino, allyl-methanesulfonyl-amino, acetyl-methanesulfonyl-amino, benzyl-methanesulfonyl-amino, carboxymethyl-methanesulfonyl-amino, methanesulfonylaminomethyl, 1-methanesulfonylamino-1-methyl-ethyl, methanesulfonyl-methyl-amino, 1-(methanesulfonyl-methyl-amino)-ethyl, methanesulfonyl-propyl-amino, methanesulfonyl-(2-methoxy-ethyl)-amino, methanesulfonyl-(2,2,2-trifluoro-ethyl)-amino, methanesulfonyl-(2-oxo-propyl)-amino, methanesulfonyl-(2-trifluoromethoxy-ethyl)-amino, methanesulfonyl-(4-methoxy-benzyl)-amino, methanesulfonyl-(4-methoxycarbonyl-benzyl)-amino, methanesulfonyl-methoxymethyl-amino, methanesulfonyl-methylcarbamoylmethyl-amino, (methanesulfonyl-methyl-amino)-methyl, sulfamoyl, methylsulfamoyl, dimethylsulfamoyl, ethylsulfamoyl, cyclopropylsulfamoyl, cyclobutylsulfamoyl, 3-methanesulfonyl-phenyl, 4-methanesulfonyl-phenyl, benzyloxy, 1H-pyrazol-4-yl, 2H-pyrazol-3-yl, 1-methyl-1H-pyrazol-3-yl, 2-methyl-2H-pyrazol-3-yl, 5-methyl-1H-pyrazol-4-yl, 5-methyl-2H-pyrazol-3-yl, 1,5-dimethyl-1H-pyrazol-3-yl, 2,5-dimethyl-2H-pyrazol-3-yl, 2,5-dimethyl-2H-pyrazol-3-ylamino, 3,5-dimethyl-1H-pyrazol-4-yl, 1,3,5-trimethyl-1H-pyrazol-4-yl, isoxazol-3-yl, 5-methyl-isoxazol-3-yl, 3-cyclopropyl-isoxazol-5-yl, 5-cyclopropyl-isoxazol-3-yl, 3,5-dimethyl-isoxazol-4-yl, 3,5-dimethyl-isoxazol-4-ylamino, 5-methoxymethyl-isoxazol-3-yl, 5-ethoxymethyl-isoxazol-3-yl, 5-isopropoxymethyl-isoxazol-3-yl, 5-hydroxymethyl-isoxazol-3-yl, 4-(2-hydroxy-ethyl)-isoxazol-3-yl, 3-methoxymethyl-5-methyl-isoxazol-4-yl, 5-methoxymethyl-3-methyl-isoxazol-4-yl, 5-cyclopropyl-3-methoxymethyl-isoxazol-4-yl, 3-cyclopropyl-5-methoxymethyl-isoxazol-4-yl, (3,5-dimethyl-isoxazol-4- ylmethyl)-methanesulfonyl-amino, 3-metho-xymethyl-isoxazol-5-yl), 3-methyl-isoxazol-5-yl, methanesulfonyl-(5-methyl-isoxazol-3-ylmethyl)-amino, thiazol-2-yl, thiazol-5-yl, methanesulfonyl-thiazol-2-ylmethyl-amino, methanesulfonyl-thiazol-4-ylmethyl-amino, methanesulfonyl-(2-methyl-thiazol-4-ylmethyl)-amino, (4-carboxy-thiazol-2-ylmethyl)-methanesulfonyl-amino, (4-ethoxycarbonyl-thiazol-2-ylmethyl)-methanesulfonyl-amino, pyridin-3-yl, pyridin-4-yl, pyridin-4-ylamino, 6-fluoro-pyridin-3-yl, methanesulfonyl-pyridin-4-ylmethyl-amino, (6-bromomethyl-pyridin-2-ylmethyl)-methanesulfonyl-amino, pyrrolidin-1-yl, pyrrolidin-2-yl, pyrrolidine-1-sulfonyl, 3-hydroxy-pyrrolidin-1-yl, 3-hydroxy-pyrrolidine-1-sulfonyl, 5-oxo-pyrrolidin-3-yl, 1-acetyl-pyrrolidin-2-yl, 1-acetyl-pyrrolidin-3-yl, 1-carbamoylpyrrolidin-2-yl, 1-methylcarbamoyl-pyrrolidin-2-yl, 4-methylcarbamoyl-5-oxo-pyrrolidin-3-yl, 1-cyclopropanecarbonyl-pyrrolidin-2-yl, 1-methanesulfonyl-pyrrolidin-2-yl, 1-methanesulfonyl-pyrrolidin-3-yl, 3-amino-pyrrolidin-1-yl, 3-methanesulfonyl-pyrrolidin-1-yl, 1H-pyrrol-2-yl, 1H-pyrrol-3-yl, 3-cyano-4-hydroxy-2-oxo-2,5-dihydro-pyrrol-1-ylmethyl, furan-2-yl, furan-3-yl, (furan-3-ylmethyl)-amino, tetrahydro-furan-3-yl, (tetrahydro-furan-2-ylmethyl)-amino, [1,3,4]oxadiazol-2-yl, [1,2,4]oxadiazol-3-yl, 5-methyl-[1,2,4]oxadiazol-3-yl, 5-methyl-[1,3,4]oxadiazol-2-yl, 5-trifluoromethyl-[1,2,4]oxadiazol-3-yl, morpholin-4-yl, 2,6-dimethyl-morpholin-4-yl, 2-morpholin-4-yl-ethylamino, morpholine-4-sulfonyl, methanesulfonyl-(2-morpholin-4-yl-ethyl)-amino, thiomorpholin-4-yl, thiomorpholine-4-sulfonyl, 1-oxo-thiomorpholin-4-yl, 1,1-dioxido-isothiazolidin-2-yl, 2-oxo-oxazolidin-5-yl, 5-methyl-2-oxo-oxazolidin-5-yl, oxazol-5-yl, 1H-imidazol-4-yl, 1H-imidazol-2-yl, 2,5-dioxo-imidazolidin-4-yl, 4-methyl-2,5-dioxo-imidazolidin-4-yl, pyrimidin-5-yl, 2,5-dimethyl-2H-[1,2,4]triazol-3-yl, 2-methyl-2H-[1,2,4]triazol-3-yl, 4H-[1,2,4]triazol-3-yl, 5-methyl-2H-[1,2,4]triazol-3-yl, 1H-tetrazol-5-yl, 1-methyl-1H-tetrazol-5-ylmethoxy, methanesulfonyl-(1-methyl-1H-tetrazol-5-ylmethyl)-amino, piperidin-1-yl, 4-fluoro-piperidin-1-yl, 4,4-difluoro-piperidin-1-yl, 3-hydroxy-piperidin-1-yl, 4-hydroxy-piperidin-1-yl, 4-hydroxy-piperidine-1-sulfonyl, 4-carbamoyl-piperazin-1-yl, 4-methyl-piperazin-1-yl, and 5-chloro-[1,2,4]thiadiazol-3-ylmethyl;

$R_4$ represents a radical selected from the group consisting of hydrogen and methyl;

$R_5$ represents a radical selected from the group consisting of methyl, ethyl, isopropyl, and cyclopropyl; and $R_6$ represents a radical selected from the group consisting of phenyl, 4-methyl-phenyl, 4-ethyl-phenyl, 4-methoxy-phenyl, 4-hydroxy-phenyl, 4-bromo-phenyl, 2-chloro-phenyl, 2-fluoro-phenyl, 4-fluoro-phenyl, 2,4-difluoro-phenyl, 3,4-difluoro-phenyl, 4-bromo-3-fluoro-phenyl, 3-chloro-4-fluoro-phenyl, 4-chloro-3-fluoro-phenyl, 2,4,5-trifluoro-phenyl, 3-fluoro-4-methyl-phenyl, 4-fluoro-3-methyl-phenyl, 4-fluoro-3-hydroxy-phenyl, 2-ethoxy-4-fluoro-phenyl, 3-trifluoromethyl-phenyl, 4-trifluoromethyl-phenyl, 4-cyano-phenyl, 4-amino-phenyl, 4-(acetylamino-methyl)-phenyl, 4-morpholin-4-yl-phenyl, 4-pyrrolidin-1-yl-phenyl, furan-2-yl, furan-3-yl, 3-methyl-furan-2-yl, thiophen-2-yl, 5-chloro-thiophen-2-yl, pyridin-4-yl, and pyridin-3-yl; and the pharmaceutically acceptable salts thereof.

6. The compound according to claim 1, selected from the group consisting of:

2-(4-fluoro-phenyl)-6-(methanesulfonyl-methyl-amino)-5-(2-morpholin-4-yl-ethoxy)-benzofuran-3-carboxylic acid methylamide;

2-(4-fluoro-phenyl)-5-(2-methyl-thiazol-4-ylmethoxy)-6-morpholin-4-yl-benzofuran-3-carboxylic acid methylamide;

5-[5-(3,5-dimethyl-isoxazol-4-yl)-[1,2,4]oxadiazol-3-ylmethoxy]-2-(4-fluoro-phenyl)-6-morpholin-4-yl-benzofuran-3-carboxylic acid methylamide;

5-(5-tert-butyl-[1,2,4]oxadiazol-3-ylmethoxy)-2-(4-fluoro-phenyl)-6-morpholin-4-yl-benzofuran-3-carboxylic acid methylamide;

5-(5-chloro-[1,2,4]thiadiazol-3-ylmethoxy)-2-(4-fluoro-phenyl)-6-morpholin-4-yl-benzofuran-3-carboxylic acid methylamide;

2-(4-fluoro-phenyl)-6-morpholin-4-yl-5-(5-p-tolyl-[1,3,4]oxadiazol-2-ylmethoxy)-benzofuran-3-carboxylic acid methylamide;

2-(4-fluoro-phenyl)-5-(1-methyl-1H-tetrazol-5-ylmethoxy)-6-morpholin-4-yl-benzofuran-3-carboxylic acid methylamide;

2-(4-fluoro-phenyl)-5-[5-(4-methoxy-phenyl)-[1,2,4]oxadiazol-3-ylmethoxy]-6-morpholin-4-yl-benzofuran-3-carboxylic acid methylamide;

5-(1-benzyl-1H-imidazol-2-ylmethoxy)-2-(4-fluoro-phenyl)-6-morpholin-4-yl-benzofuran-3-carboxylic acid methylamide;

5-(3,5-dimethyl-isoxazol-4-ylmethoxy)-2-(4-fluoro-phenyl)-6-morpholin-4-yl-benzofuran-3-carboxylic acid methylamide;

2-(4-fluoro-phenyl)-5-(5-methyl-isoxazol-3-ylmethoxy)-6-morpholin-4-yl-benzofuran-3-carboxylic acid methylamide;

2-(4-fluoro-phenyl)-5-(3H-imidazol-4-ylmethoxy)-6-morpholin-4-yl-benzofuran-3-carboxylic acid methylamide;

5-(4-chloro-1-methyl-1H-pyrazol-3-ylmethoxy)-2-(4-fluoro-phenyl)-6-morpholin-4-yl-benzofuran-3-carboxylic acid methylamide;

2-(4-fluoro-phenyl)-6-morpholin-4-yl-5-(1-thiazol-2-yl-ethoxy)-benzofuran-3-carboxylic acid methylamide;

5-(2,2-dimethyl-4-oxo-4H-benzo[1,3]dioxin-5-ylmethoxy)-2-(4-fluoro-phenyl)-6-morpholin-4-yl-benzofuran-3-carboxylic acid methylamide;

5-(2,2-dimethyl-4-oxo-4H-benzo[1,3]dioxin-5-ylmethoxy)-6-(ethyl-methanesulfonyl-amino)-2-(4-fluoro-phenyl)-benzofuran-3-carboxylic acid methylamide;

5-(2,2-dimethyl-4-oxo-4H-benzo[1,3]dioxin-7-ylmethoxy)-2-(4-fluoro-phenyl)-6-(methanesulfonyl-methyl-amino)-benzofuran-3-carboxylic acid methylamide;

2-(4-fluoro-phenyl)-6-(methanesulfonyl-methyl-amino)-5-(thiazol-4-ylmethoxy)-benzofuran-3-carboxylic acid methylamide;

2-(4-fluoro-phenyl)-6-(methanesulfonyl-methyl-amino)-5-(2-methyl-thiazol-4-ylmethoxy)-benzofuran-3-carboxylic acid methylamide;

5-(3-chloromethyl-[1,2,4]thiadiazol-5-yloxy)-2-(4-fluoro-phenyl)-6-(methanesulfonyl-methylamino)-benzofuran-3-carboxylic acid methylamide;

5-(3,5-dimethyl-isoxazol-4-ylmethoxy)-2-(4-fluoro-phenyl)-6-(methanesulfonyl-methyl-amino)-benzofuran-3-carboxylic acid methylamide;

2-(4-fluoro-phenyl)-6-(methanesulfonyl-methyl-amino)-5-(pyridin-4-ylmethoxy)-benzofuran-3-carboxylic acid methylamide;

5-(2,2-dimethyl-4-oxo-4H-benzo[1,3]dioxin-6-yl-methoxy)-2-(4-fluoro-phenyl)-6-(methanesulfonyl-methyl-amino)-benzofuran-3-carboxylic acid methylamide;

2-(4-fluoro-phenyl)-6-(methanesulfonyl-methyl-amino)-5-(1-methyl-1H-tetrazol-5-ylmethoxy)-benzofuran-3-carboxylic acid methylamide;

5-(5-diethylamino-[1,2,4]thiadiazol-3-ylmethoxy)-2-(4-fluoro-phenyl)-6-(methanesulfonyl-methyl-amino)-benzofuran-3-carboxylic acid methylamide;

5-[5-(cyclopropylmethyl-amino)-[1,2,4]thiadiazol-3-yl-methoxy]-2-(4-fluoro-phenyl)-6-(methanesulfonyl-methyl-amino)-benzofuran-3-carboxylic acid methylamide;

2-(4-fluoro-phenyl)-6-(methanesulfonyl-methyl-amino)-5-(thiazol-2-ylmethoxy)-benzofuran-3-carboxylic acid methylamide;

5-(6-bromomethyl-pyridin-2-ylmethoxy)-6-[(6-bromom-ethyl-pyridin-2-ylmethyl)-methanesulfonyl-amino]-2-(4-fluoro-phenyl)-benzofuran-3-carboxylic acid methylamide;

2-[2-(4-fluoro-phenyl)-6-(methanesulfonyl-methyl-amino)-3-methylcarbamoyl-benzofuran-5-yloxymethyl]-thiazole-4-carboxylic acid ethyl ester;

2-[2-(4-fluoro-phenyl)-6-(methanesulfonyl-methyl-amino)-3-methylcarbamoyl-benzofuran-5-yloxymethyl]-thiazole-4-carboxylic acid;

2-(4-fluoro-phenyl)-6-(methanesulfonyl-methyl-amino)-5-(5-methyl-isoxazol-3-ylmethoxy)-benzofuran-3-carboxylic acid methylamide;

5-(5-chloro-[1,2,3]thiadiazol-4-ylmethoxy)-2-(4-fluoro-phenyl)-6-(methanesulfonyl-methylamino)-benzofuran-3-carboxylic acid methylamide;

2-(4-fluoro-phenyl)-6-(methanesulfonyl-methyl-amino)-5-(1-methyl-1H-imidazol-2-ylmethoxy)-benzofuran-3-carboxylic acid methylamide;

5-(1-benzyl-1H-imidazol-2-ylmethoxy)-2-(4-fluoro-phenyl)-6-(methanesulfonyl-methyl-amino)-benzofuran-3-carboxylic acid methylamide;

6-(3,5-dimethyl-isoxazol-4-yl)-2-(4-fluoro-phenyl)-5-(thiazol-4-ylmethoxy)-benzofuran-3-carboxylic acid methylamide;

5-(5-amino-4H-[1,2,4]triazol-3-ylmethoxy)-2-(4-fluoro-phenyl)-6-(methanesulfonyl-methylamino)-benzofuran-3-carboxylic acid methylamide;

5-(4-chloro-1-methyl-1H-pyrazol-3-ylmethoxy)-2-(4-fluoro-phenyl)-6-(methanesulfonyl-methylamino)-benzofuran-3-carboxylic acid methylamide;

2-(4-fluoro-phenyl)-6-(methanesulfonyl-methyl-amino)-5-(2-pyrazol-1-yl-ethoxy)-benzofuran-3-carboxylic acid methylamide;

2-(4-fluoro-phenyl)-5-(1H-imidazol-2-ylmethoxy)-6-(methanesulfonyl-methyl-amino)-benzofuran-3-carboxylic acid methylamide;

5-(3,5-dimethyl-isoxazol-4-yl)-2-(4-fluoro-phenyl)-6-methanesulfonylamino-benzofuran-3-carboxylic acid methylamide;

2-(4-fluoro-phenyl)-6-(methanesulfonyl-methyl-amino)-5-(1-thiazol-2-yl-ethoxy)-benzofuran-3-carboxylic acid methylamide;

6-(3,5-dimethyl-isoxazol-4-yl)-2-(4-fluoro-phenyl)-5-(5-methyl-isoxazol-3-ylmethoxy)-benzofuran-3-carboxylic acid methylamide;

6-(3,5-dimethyl-isoxazol-4-yl)-2-(4-fluoro-phenyl)-5-(thiazol-2-ylmethoxy)-benzofuran-3-carboxylic acid methylamide;

2-(4-fluoro-phenyl)-6-(methanesulfonyl-methyl-amino)-5-(thiazol-2-ylcarbamoylmethoxy)-benzofuran-3-carboxylic acid methylamide;

2-(4-fluoro-phenyl)-6-(methanesulfonyl-methyl-amino)-5-([1,3,4]thiadiazol-2-ylcarbamoylmethoxy)-benzofuran-3-carboxylic acid methylamide;

5-[(4,5-dimethyl-thiazol-2-ylcarbamoyl)-methoxy]-2-(4-fluoro-phenyl)-6-(methanesulfonyl-methyl-amino)-benzofuran-3-carboxylic acid methylamide;

5-[2-(4-cyano-piperidin-1-yl)-ethoxy]-6-(3,5-dimethyl-isoxazol-4-yl)-2-(4-fluoro-phenyl)-benzofuran-3-carboxylic acid methylamide;

2-(4-fluoro-phenyl)-6-methanesulfonylamino-5-thiophen-2-yl-benzofuran-3-carboxylic acid methylamide;

5-[2-(3,5-dimethyl-pyrazol-1-yl)-ethoxy]-2-(4-fluoro-phenyl)-6-(methanesulfonyl-methylamino)-benzofuran-3-carboxylic acid methylamide;

2-(4-fluoro-phenyl)-5-furan-2-yl-6-methanesulfonylamino-benzofuran-3-carboxylic acid methylamide;

6-(3,5-dimethyl-isoxazol-4-yl)-2-(4-fluoro-phenyl)-5-(1-methyl-1H-tetrazol-5-ylmethoxy)-benzofuran-3-carboxylic acid methylamide;

6-(3,5-dimethyl-isoxazol-4-yl)-5-(3,5-dimethyl-isoxazol-4-ylmethoxy)-2-(4-fluoro-phenyl)-benzofuran-3-carboxylic acid methylamide;

6-(3,5-dimethyl-isoxazol-4-yl)-2-(4-fluoro-phenyl)-5-(2-morpholin-4-yl-ethoxy)-benzofuran-3-carboxylic acid methylamide;

6-(3,5-dimethyl-isoxazol-4-yl)-2-(4-fluoro-phenyl)-5-(3-piperidin-1-yl-propoxy)-benzofuran-3-carboxylic acid methylamide;

2-(4-fluoro-phenyl)-5-(thiazol-4-ylmethoxy)-benzofuran-3-carboxylic acid methylamide;

2-(4-fluoro-phenyl)-6-methanesulfonylamino-5-(tetrahydro-furan-2-yl)-benzofuran-3-carboxylic acid methylamide;

2-(4-fluoro-phenyl)-6-(methanesulfonyl-methyl-amino)-5-thiophen-2-yl-benzofuran-3-carboxylic acid methylamide;

and pharmaceutically acceptable salts thereof.

7. The compound according to claim 2, selected from the group consisting of: 2-(4-fluoro-phenyl)-5-methoxy-6-morpholin-4-yl-benzofuran-3-carboxylic acid methylamide; 2-(4-fluoro-phenyl)-5-isopropoxy-6-morpholin-4-yl-benzofuran-3-carboxylic acid methylamide; 5-benzyloxy-2-(4-fluoro-phenyl)-6-morpholin-4-yl-benzofuran-3-carboxylic acid methylamide; 2-(4-fluoro-phenyl)-6-[(furan-3-ylmethyl)-amino]-5-isopropoxy-benzofuran-3-carboxylic acid methylamide; 6-(3,5-dimethyl-isoxazol-4-yl)-2-(4-fluoro-phenyl)-5-methoxy-benzofuran-3-carboxylic acid methylamide; 6-(3,5-dimethyl-isoxazol-4-yl)-2-(4-fluoro-phenyl)-5-(3-hydroxy-propoxy)benzofuran-3-carboxylic acid methylamide; 2-(4-fluoro-phenyl)-6-[4-(2-hydroxy-ethyl)-isoxazol-3-yl]-5-methoxy-benzofuran-3-carboxylic acid methylamide; and pharmaceutically acceptable salts thereof.

8. The compound according to claim 1, 2 or 3 in the form of a pharmaceutically acceptable salt.

9. The compound according to claim 8, wherein the pharmaceutically acceptable salt is selected from hydrochloric, sulfuric, acetic, lactic, sodium, potassium, piperidine, or ammonium.

10. The compound according to claim 9, wherein in the pharmaceutically acceptable salt is a potassium salt or a sodium salt.

11. A composition for treatment of viral infections, said composition comprising a compound as claimed in claim 1, in an amount effective to attenuate viral infectivity, and a pharmaceutically acceptable carrier medium.

12. The composition according to claim 11, wherein said compound is selected from the group consisting of:

- 2-(4-fluoro-phenyl)-6-(methanesulfonyl-methyl-amino)-5-(2-morpholin-4-yl-ethoxy)-benzofuran-3-carboxylic acid methylamide;
- 2-(4-fluoro-phenyl)-5-(2-methyl-thiazol-4-ylmethoxy)-6-morpholin-4-yl-benzofuran-3-carboxylic acid methylamide;
- 5-[5-(3,5-dimethyl-isoxazol-4-yl)-[1,2,4]oxadiazol-3-ylmethoxy]-2-(4-fluoro-phenyl)-6-morpholin-4-yl-benzofuran-3-carboxylic acid methylamide;
- 5-(5-tert-butyl-[1,2,4]oxadiazol-3-ylmethoxy)-2-(4-fluoro-phenyl)-6-morpholin-4-yl-benzofuran-3-carboxylic acid methylamide;
- 5-(5-chloro-[1,2,4]thiadiazol-3-ylmethoxy)-2-(4-fluoro-phenyl)-6-morpholin-4-yl-benzofuran-3-carboxylic acid methylamide;
- 2-(4-fluoro-phenyl)-6-morpholin-4-yl-5-(5-p-tolyl-[1,3,4]oxadiazol-2-ylmethoxy)-benzofuran-3-carboxylic acid methylamide;
- 2-(4-fluoro-phenyl)-5-(1-methyl-1H-tetrazol-5-ylmethoxy)-6-morpholin-4-yl-benzofuran-3-carboxylic acid methylamide;
- 2-(4-fluoro-phenyl)-5-[5-(4-methoxy-phenyl)-[1,2,4]oxadiazol-3-ylmethoxy]-6-morpholin-4-yl-benzofuran-3-carboxylic acid methylamide;
- 5-(1-benzyl-1H-imidazol-2-ylmethoxy)-2-(4-fluoro-phenyl)-6-morpholin-4-yl-benzofuran-3-carboxylic acid methylamide;
- 5-(3,5-dimethyl-isoxazol-4-ylmethoxy)-2-(4-fluoro-phenyl)-6-morpholin-4-yl-benzofuran-3-carboxylic acid methylamide;
- 2-(4-fluoro-phenyl)-5-(5-methyl-isoxazol-3-ylmethoxy)-6-morpholin-4-yl-benzofuran-3-carboxylic acid methylamide;
- 2-(4-fluoro-phenyl)-5-(3H-imidazol-4-ylmethoxy)-6-morpholin-4-yl-benzofuran-3-carboxylic acid methylamide;
- 5-(4-chloro-1-methyl-1H-pyrazol-3-ylmethoxy)-2-(4-fluoro-phenyl)-6-morpholin-4-yl-benzofuran-3-carboxylic acid methylamide;
- 2-(4-fluoro-phenyl)-6-morpholin-4-yl-5-(1-thiazol-2-yl-ethoxy)-benzofuran-3-carboxylic acid methylamide;
- 5-(2,2-dimethyl-4-oxo-4H-benzo[1,3]dioxin-5-ylmethoxy)-2-(4-fluoro-phenyl)-6-morpholin-4-yl-benzofuran-3-carboxylic acid methylamide;
- 5-(2,2-dimethyl-4-oxo-4H-benzo[1,3]dioxin-5-ylmethoxy)-6-(ethyl-methanesulfonyl-amino)-2-(4-fluoro-phenyl)-benzofuran-3-carboxylic acid methylamide;
- 5-(2,2-dimethyl-4-oxo-4H-benzo[1,3]dioxin-7-ylmethoxy)-2-(4-fluoro-phenyl)-6-(methanesulfonyl-methyl-amino)-benzofuran-3-carboxylic acid methylamide;
- 2-(4-fluoro-phenyl)-6-(methanesulfonyl-methyl-amino)-5-(thiazol-4-ylmethoxy)-benzofuran-3-carboxylic acid methylamide;
- 2-(4-fluoro-phenyl)-6-(methanesulfonyl-methyl-amino)-5-(2-methyl-thiazol-4-ylmethoxy)-benzofuran-3-carboxylic acid methylamide;
- 5-(3-chloromethyl-[1,2,4]thiadiazol-5-yloxy)-2-(4-fluoro-phenyl)-6-(methanesulfonyl-methylamino)-benzofuran-3-carboxylic acid methylamide;
- 5-(3,5-dimethyl-isoxazol-4-ylmethoxy)-2-(4-fluoro-phenyl)-6-(methanesulfonyl-methyl-amino)-benzofuran-3-carboxylic acid methylamide;
- 2-(4-fluoro-phenyl)-6-(methanesulfonyl-methyl-amino)-5-(pyridin-4-ylmethoxy)-benzofuran-3-carboxylic acid methylamide;
- 5-(2,2-dimethyl-4-oxo-4H-benzo[1,3]dioxin-6-ylmethoxy)-2-(4-fluoro-phenyl)-6-(methanesulfonyl-methyl-amino)-benzofuran-3-carboxylic acid methylamide;
- 2-(4-fluoro-phenyl)-6-(methanesulfonyl-methyl-amino)-5-(1-methyl-1H-tetrazol-5-ylmethoxy)-benzofuran-3-carboxylic acid methylamide;
- 5-(5-diethylamino-[1,2,4]thiadiazol-3-ylmethoxy)-2-(4-fluoro-phenyl)-6-(methanesulfonyl-methyl-amino)-benzofuran-3-carboxylic acid methylamide;
- 5-[5-(cyclopropylmethyl-amino)-[1,2,4]thiadiazol-3-ylmethoxy]-2-(4-fluoro-phenyl)-6-(methanesulfonyl-methyl-amino)-benzofuran-3-carboxylic acid methylamide;
- 2-(4-fluoro-phenyl)-6-(methanesulfonyl-methyl-amino)-5-(thiazol-2-ylmethoxy)-benzofuran-3-carboxylic acid methylamide;
- 5-(6-bromomethyl-pyridin-2-ylmethoxy)-6-[(6-bromomethyl-pyridin-2-ylmethyl)-methanesulfonyl-amino]-2-(4-fluoro-phenyl)-benzofuran-3-carboxylic acid methylamide;
- 2-[2-(4-fluoro-phenyl)-6-(methanesulfonyl-methyl-amino)-3-methylcarbamoyl-benzofuran-5-yloxymethyl]-thiazole-4-carboxylic acid ethyl ester;
- 2-[2-(4-fluoro-phenyl)-6-(methanesulfonyl-methyl-amino)-3-methylcarbamoyl-benzofuran-5-yloxymethyl]-thiazole-4-carboxylic acid;
- 2-(4-fluoro-phenyl)-6-(methanesulfonyl-methyl-amino)-5-(5-methyl-isoxazol-3-ylmethoxy)-benzofuran-3-carboxylic acid methylamide;
- 5-(5-chloro-[1,2,3]thiadiazol-4-ylmethoxy)-2-(4-fluoro-phenyl)-6-(methanesulfonyl-methyl-amino)-benzofuran-3-carboxylic acid methylamide;
- 2-(4-fluoro-phenyl)-6-(methanesulfonyl-methyl-amino)-5-(1-methyl-1H-imidazol-2-ylmethoxy)-benzofuran-3-carboxylic acid methylamide;
- 5-(1-benzyl-1H-imidazol-2-ylmethoxy)-2-(4-fluoro-phenyl)-6-(methanesulfonyl-methyl-amino)-benzofuran-3-carboxylic acid methylamide;
- 6-(3,5-dimethyl-isoxazol-4-yl)-2-(4-fluoro-phenyl)-5-(thiazol-4-ylmethoxy)-benzofuran-3-carboxylic acid methylamide;
- 5-(5-amino-4H-[1,2,4]triazol-3-ylmethoxy)-2-(4-fluoro-phenyl)-6-(methanesulfonyl-methyl-amino)-benzofuran-3-carboxylic acid methylamide;
- 5-(4-chloro-1-methyl-1H-pyrazol-3-ylmethoxy)-2-(4-fluoro-phenyl)-6-(methanesulfonyl-methyl-amino)-benzofuran-3-carboxylic acid methylamide;
- 2-(4-fluoro-phenyl)-6-(methanesulfonyl-methyl-amino)-5-(2-pyrazol-1-yl-ethoxy)-benzofuran-3-carboxylic acid methylamide;
- 2-(4-fluoro-phenyl)-5-(1H-imidazol-2-ylmethoxy)-6-(methanesulfonyl-methyl-amino)-benzofuran-3-carboxylic acid methylamide;
- 5-(3,5-dimethyl-isoxazol-4-yl)-2-(4-fluoro-phenyl)-6-methanesulfonylamino-benzofuran-3-carboxylic acid methylamide;

2-(4-fluoro-phenyl)-6-(methanesulfonyl-methyl-amino)-
5-(1-thiazol-2-yl-ethoxy)-benzofuran-3-carboxylic
acid methylamide;
6-(3,5-dimethyl-isoxazol-4-yl)-2-(4-fluoro-phenyl)-5-(5-
methyl-isoxazol-3-ylmethoxy)-benzofuran-3-carboxylic acid methylamide;
6-(3,5-dimethyl-isoxazol-4-yl)-2-(4-fluoro-phenyl)-5-
(thiazol-2-ylmethoxy)-benzofuran-3-carboxylic acid methylamide;
2-(4-fluoro-phenyl)-6-(methanesulfonyl-methyl-amino)-
5-(thiazol-2-ylcarbamoylmethoxy)-benzofuran-3-carboxylic acid methylamide;
2-(4-fluoro-phenyl)-6-(methanesulfonyl-methyl-amino)-
5-([1,3,4]thiadiazol-2-ylcarbamoylmethoxy)-benzofuran-3-carboxylic acid methylamide;
5-[(4,5-dimethyl-thiazol-2-ylcarbamoyl)-methoxy]-2-(4-
fluoro-phenyl)-6-(methanesulfonyl-methyl-amino)-
benzofuran-3-carboxylic acid methylamide;
5-[2-(4-cyano-piperidin-1-yl)-ethoxy]-6-(3,5-dimethyl-
isoxazol-4-yl)-2-(4-fluoro-phenyl)-benzofuran-3-carboxylic acid methylamide;
2-(4-fluoro-phenyl)-6-methanesulfonylamino-5-
thiophen-2-yl-benzofuran-3-carboxylic acid methylamide;
5-[2-(3,5-dimethyl-pyrazol-1-yl)-ethoxy]-2-(4-fluoro-
phenyl)-6-(methanesulfonyl-methyl-amino)-benzofuran-3-carboxylic acid methylamide;
2-(4-fluoro-phenyl)-5-furan-2-yl-6-methanesulfonylamino-benzofuran-3-carboxylic acid methylamide;
6-(3,5-dimethyl-isoxazol-4-yl)-2-(4-fluoro-phenyl)-5-(1-
methyl-1H-tetrazol-5-ylmethoxy)-benzofuran-3-carboxylic acid methylamide;
6-(3,5-dimethyl-isoxazol-4-yl)-5-(3,5-dimethyl-isoxazol-
4-ylmethoxy)-2-(4-fluoro-phenyl)-benzofuran-3-carboxylic acid methylamide;
6-(3,5-dimethyl-isoxazol-4-yl)-2-(4-fluoro-phenyl)-5-(2-
morpholin-4-yl-ethoxy)-benzofuran-3-carboxylic acid methylamide;
6-(3,5-dimethyl-isoxazol-4-yl)-2-(4-fluoro-phenyl)-5-(3-
piperidin-1-yl-propoxy)-benzofuran-3-carboxylic acid methylamide;
2-(4-fluoro-phenyl)-5-(thiazol-4-ylmethoxy)-benzofuran-3-carboxylic acid methylamide;
2-(4-fluoro-phenyl)-6-methanesulfonylamino-5-(tetrahydro-furan-2-yl)-benzofuran-3-carboxylic acid methylamide;
2-(4-fluoro-phenyl)-6-(methanesulfonyl-methyl-amino)-
5-thiophen-2-yl-benzofuran-3-carboxylic acid methylamide;
and pharmaceutically acceptable salts thereof.

13. A method for or treatment of hepatitis C infections and diseases associated with such infections in a living host having said infections, said method comprising administering to said living host a therapeutically effective amount of a compound according to claim 1.

14. The method according to claim 13, wherein said living host is a mammal.

15. The method according to claim 13, wherein said living host is a human.

16. The method according to claim 15, wherein the compound is administered orally.

17. The method according to claim 16, wherein the compound is administered orally at a dose range of about 0.05 to about 100 mg/kg.

18. The method according to claim 13, wherein the compound is administered from 1 to 4 times daily.

19. The method according to claim 13, wherein the compound is administered in combination, either concurrently or sequentially, with at least one other biologically active agent.

20. The method according to claim 19, wherein said other biologically active agent is selected from the group consisting of interferon, pegylated interferon, ribavirin, protease inhibitors, polymerase inhibitors, small interfering RNA compounds, anti-sense compounds, nucleotide analogs, nucleoside analogs, immunoglobulins, immunomodulators, hepatoprotectants, anti-inflammatory agents, antibiotics, antivirals, and anti-infective compounds.

21. The method according to claim 13, wherein the compound is selected from the group consisting of:
2-(4-fluoro-phenyl)-6-(methanesulfonyl-methyl-amino)-
5-(2-morpholin-4-yl-ethoxy)benzofuran-3-carboxylic acid methylamide;
2-(4-fluoro-phenyl)-5-(2-methyl-thiazol-4-ylmethoxy)-6-
morpholin-4-yl-benzofuran-3-carboxylic acid methylamide;
5-[5-(3,5-dimethyl-isoxazol-4-yl)-[1,2,4]oxadiazol-3-yl-
methoxy]-2-(4-fluoro-phenyl)-6-morpholin-4-yl-benzofuran-3-carboxylic acid methylamide;
5-(5-tert-butyl-[1,2,4]oxadiazol-3-ylmethoxy)-2-(4-
fluoro-phenyl)-6-morpholin-4-yl-benzofuran-3-carboxylic acid methylamide;
5-(5-chloro-[1,2,4]thiadiazol-3-ylmethoxy)-2-(4-fluoro-
phenyl)-6-morpholin-4-yl-benzofuran-3-carboxylic acid methylamide;
2-(4-fluoro-phenyl)-6-morpholin-4-yl-5-(5-p-tolyl-[1,3,
4]oxadiazol-2-ylmethoxy)-benzofuran-3-carboxylic acid methylamide;
2-(4-fluoro-phenyl)-5-(1-methyl-1H-tetrazol-5-yl-
methoxy)-6-morpholin-4-yl-benzofuran-3-carboxylic acid methylamide;
2-(4-fluoro-phenyl)-5-[5-(4-methoxy-phenyl)-[1,2,4]oxadiazol-3-ylmethoxy]-6-morpholin-4-yl-benzofuran-3-carboxylic acid methylamide;
5-(1-benzyl-1H-imidazol-2-ylmethoxy)-2-(4-fluoro-phenyl)-6-morpholin-4-yl-benzofuran-3-carboxylic acid methylamide;
5-(3,5-dimethyl-isoxazol-4-ylmethoxy)-2-(4-fluoro-phenyl)-6-morpholin-4-yl-benzofuran-3-carboxylic acid methylamide;
2-(4-fluoro-phenyl)-5-(5-methyl-isoxazol-3-ylmethoxy)-
6-morpholin-4-yl-benzofuran-3-carboxylic acid methylamide;
2-(4-fluoro-phenyl)-5-(3H-imidazol-4-ylmethoxy)-6-
morpholin-4-yl-benzofuran-3-carboxylic acid methylamide;
5-(4-chloro-1-methyl-1H-pyrazol-3-ylmethoxy)-2-(4-
fluoro-phenyl)-6-morpholin-4-yl-benzofuran-3-carboxylic acid methylamide;
2-(4-fluoro-phenyl)-6-morpholin-4-yl-5-(1-thiazol-2-yl-
ethoxy)-benzofuran-3-carboxylic acid methylamide;
5-(2,2-dimethyl-4-oxo-4H-benzo[1,3]dioxin-5-yl-
methoxy)-2-(4-fluoro-phenyl)-6-morpholin-4-yl-benzofuran-3-carboxylic acid methylamide;
5-(2,2-dimethyl-4-oxo-4H-benzo[1,3]dioxin-5-yl-
methoxy)-6-(ethyl-methanesulfonyl-amino)-2-(4-
fluoro-phenyl)-benzofuran-3-carboxylic acid methylamide;
5-(2,2-dimethyl-4-oxo-4H-benzo[1,3]dioxin-7-yl-
methoxy)-2-(4-fluoro-phenyl)-6-(methanesulfonyl-methyl-amino)-benzofuran-3-carboxylic acid methylamide;

2-(4-fluoro-phenyl)-6-(methanesulfonyl-methyl-amino)-5-(thiazol-4-ylmethoxy)-benzofuran-3-carboxylic acid methylamide;
2-(4-fluoro-phenyl)-6-(methanesulfonyl-methyl-amino)-5-(2-methyl-thiazol-4-ylmethoxy)-benzofuran-3-carboxylic acid methylamide;
5-(3-chloromethyl-[1,2,4]thiadiazol-5-yloxy)-2-(4-fluoro-phenyl)-6-(methanesulfonyl-methyl-amino)-benzofuran-3-carboxylic acid methylamide;
5-(3,5-dimethyl-isoxazol-4-ylmethoxy)-2-(4-fluoro-phenyl)-6-(methanesulfonyl-methyl-amino)-benzofuran-3-carboxylic acid methylamide;
2-(4-fluoro-phenyl)-6-(methanesulfonyl-methyl-amino)-5-(pyridin-4-ylmethoxy)-benzofuran-3-carboxylic acid methylamide;
5-(2,2-dimethyl-4-oxo-4H-benzo[1,3]dioxin-6-ylmethoxy)-2-(4-fluoro-phenyl)-6-(methanesulfonyl-methyl-amino)-benzofuran-3-carboxylic acid methylamide;
2-(4-fluoro-phenyl)-6-(methanesulfonyl-methyl-amino)-5-(1-methyl-1H-tetrazol-5-ylmethoxy)-benzofuran-3-carboxylic acid methylamide;
5-(5-diethylamino-[1,2,4]thiadiazol-3-ylmethoxy)-2-(4-fluoro-phenyl)-6-(methanesulfonyl-methyl-amino)-benzofuran-3-carboxylic acid methylamide;
5-[5-(cyclopropylmethyl-amino)-[1,2,4]thiadiazol-3-ylmethoxy]-2-(4-fluoro-phenyl)-6-(methanesulfonyl-methyl-amino)-benzofuran-3-carboxylic acid methylamide;
2-(4-fluoro-phenyl)-6-(methanesulfonyl-methyl-amino)-5-(thiazol-2-ylmethoxy)-benzofuran-3-carboxylic acid methylamide;
5-(6-bromomethyl-pyridin-2-ylmethoxy)-6-[(6-bromomethyl-pyridin-2-ylmethyl)-methanesulfonyl-amino]-2-(4-fluoro-phenyl)-benzofuran-3-carboxylic acid methylamide;
2-[2-(4-fluoro-phenyl)-6-(methanesulfonyl-methyl-amino)-3-methylcarbamoyl-benzofuran-5-yloxymethyl]-thiazole-4-carboxylic acid ethyl ester;
2-[2-(4-fluoro-phenyl)-6-(methanesulfonyl-methyl-amino)-3-methylcarbamoyl-benzofuran-5-yloxymethyl]-thiazole-4-carboxylic acid;
2-(4-fluoro-phenyl)-6-(methanesulfonyl-methyl-amino)-5-(5-methyl-isoxazol-3-ylmethoxy)-benzofuran-3-carboxylic acid methylamide;
5-(5-chloro-[1,2,3]thiadiazol-4-ylmethoxy)-2-(4-fluoro-phenyl)-6-(methanesulfonyl-methyl-amino)-benzofuran-3-carboxylic acid methylamide;
2-(4-fluoro-phenyl)-6-(methanesulfonyl-methyl-amino)-5-(1-methyl-1H-imidazol-2-ylmethoxy)-benzofuran-3-carboxylic acid methylamide;
5-(1-benzyl-1H-imidazol-2-ylmethoxy)-2-(4-fluoro-phenyl)-6-(methanesulfonyl-methyl-amino)-benzofuran-3-carboxylic acid methylamide;
6-(3,5-dimethyl-isoxazol-4-yl)-2-(4-fluoro-phenyl)-5-(thiazol-4-ylmethoxy)-benzofuran-3-carboxylic acid methylamide;
5-(5-amino-4H-[1,2,4]triazol-3-ylmethoxy)-2-(4-fluoro-phenyl)-6-(methanesulfonyl-methyl-amino)-benzofuran-3-carboxylic acid methylamide;
5-(4-chloro-1-methyl-1H-pyrazol-3-ylmethoxy)-2-(4-fluoro-phenyl)-6-(methanesulfonyl-methyl-amino)-benzofuran-3-carboxylic acid methylamide;
2-(4-fluoro-phenyl)-6-(methanesulfonyl-methyl-amino)-5-(2-pyrazol-1-yl-ethoxy)-benzofuran-3-carboxylic acid methylamide;
2-(4-fluoro-phenyl)-5-(1H-imidazol-2-ylmethoxy)-6-(methanesulfonyl-methyl-amino)-benzofuran-3-carboxylic acid methylamide;
5-(3,5-dimethyl-isoxazol-4-yl)-2-(4-fluoro-phenyl)-6-methanesulfonylamino-benzofuran-3-carboxylic acid methylamide;
2-(4-fluoro-phenyl)-6-(methanesulfonyl-methyl-amino)-5-(1-thiazol-2-yl-ethoxy)-benzofuran-3-carboxylic acid methylamide;
6-(3,5-dimethyl-isoxazol-4-yl)-2-(4-fluoro-phenyl)-5-(5-methyl-isoxazol-3-ylmethoxy)-benzofuran-3-carboxylic acid methylamide;
6-(3,5-dimethyl-isoxazol-4-yl)-2-(4-fluoro-phenyl)-5-(thiazol-2-ylmethoxy)-benzofuran-3-carboxylic acid methylamide;
2-(4-fluoro-phenyl)-6-(methanesulfonyl-methyl-amino)-5-(thiazol-2-ylcarbamoylmethoxy)-benzofuran-3-carboxylic acid methylamide;
2-(4-fluoro-phenyl)-6-(methanesulfonyl-methyl-amino)-5-([1,3,4]thiadiazol-2-ylcarbamoylmethoxy)-benzofuran-3-carboxylic acid methylamide;
5-[(4,5-dimethyl-thiazol-2-ylcarbamoyl)-methoxy]-2-(4-fluoro-phenyl)-6-(methanesulfonyl-methyl-amino)-benzofuran-3-carboxylic acid methylamide;
5-[2-(4-cyano-piperidin-1-yl)-ethoxy]-6-(3,5-dimethyl-isoxazol-4-yl)-2-(4-fluoro-phenyl)-benzofuran-3-carboxylic acid methylamide;
2-(4-fluoro-phenyl)-6-methanesulfonylamino-5-thiophen-2-yl-benzofuran-3-carboxylic acid methylamide;
5-[2-(3,5-dimethyl-pyrazol-1-yl)-ethoxy]-2-(4-fluoro-phenyl)-6-(methanesulfonyl-methyl-amino)-benzofuran-3-carboxylic acid methylamide;
2-(4-fluoro-phenyl)-5-furan-2-yl-6-methanesulfonylamino-benzofuran-3-carboxylic acid methylamide;
6-(3,5-dimethyl-isoxazol-4-yl)-2-(4-fluoro-phenyl)-5-(1-methyl-1H-tetrazol-5-ylmethoxy)-benzofuran-3-carboxylic acid methylamide;
6-(3,5-dimethyl-isoxazol-4-yl)-5-(3,5-dimethyl-isoxazol-4-ylmethoxy)-2-(4-fluoro-phenyl)-benzofuran-3-carboxylic acid methylamide;
6-(3,5-dimethyl-isoxazol-4-yl)-2-(4-fluoro-phenyl)-5-(2-morpholin-4-yl-ethoxy)-benzofuran-3-carboxylic acid methylamide;
6-(3,5-dimethyl-isoxazol-4-yl)-2-(4-fluoro-phenyl)-5-(3-piperidin-1-yl-propoxy)-benzofuran-3-carboxylic acid methylamide;
2-(4-fluoro-phenyl)-5-(thiazol-4-ylmethoxy)-benzofuran-3-carboxylic acid methylamide;
2-(4-fluoro-phenyl)-6-methanesulfonylamino-5-(tetrahydro-furan-2-yl)-benzofuran-3-carboxylic acid methylamide;
2-(4-fluoro-phenyl)-6-(methanesulfonyl-methyl-amino)-5-thiophen-2-yl-benzofuran-3-carboxylic acid methylamide;
and pharmaceutically acceptable salts thereof.

22. The compound according to claim 2, selected from the group consisting of:
2-(4-fluoro-phenyl)-5-isopropoxy-6-pyrrolidin-1-yl-benzofuran-3-carboxylic acid methylamide;
6-(3-amino-pyrrolidin-1-yl)-2-(4-fluoro-phenyl)-5-isopropoxy-2,3-dihydro-benzofuran-3-carboxylic acid methylamide;
2-(4-fluoro-phenyl)-5-isopropoxy-6-morpholin-4-yl-benzofuran-3-carboxylic acid methylamide;
6-(3,5-dimethyl-isoxazol-4-yl)-2-(4-fluoro-phenyl)-5-methoxy-benzofuran-3-carboxylic acid methylamide;

2-(4-fluoro-phenyl)-5-(4-methoxy-benzyloxy)-6-morpholin-4-yl-benzofuran-3-carboxylic acid methylamide;
2-(4-fluoro-phenyl)-6-morpholin-4-yl-5-(thiazol-2-yl-methoxy)-benzofuran-3-carboxylic acid methylamide;
2-(4-fluoro-phenyl)-6-morpholin-4-yl-5-(thiazol-4-yl-methoxy)-benzofuran-3-carboxylic acid methylamide;
2-(4-fluoro-phenyl)-5-isopropoxy-6-(methanesulfonyl-thiazol-4-ylmethyl-amino)-benzofuran-3-carboxylic acid methylamide;
2-(4-fluoro-phenyl)-6-(5-hydroxymethyl-isoxazol-3-yl)-5-isopropoxy-benzofuran-3-carboxylic acid methylamide;
2-(4-fluoro-phenyl)-6-(5-hydroxymethyl-isoxazol-3-yl)-5-methoxy-benzofuran-3-carboxylic acid methylamide;
2-(4-fluoro-phenyl)-6-[4-(2-hydroxy-ethyl)-isoxazol-3-yl]-5-methoxy-benzofuran-3-carboxylic acid methylamide;
6-(1-acetyl-pyrrolidin-2-yl)-2-(4-fluoro-phenyl)-5-methoxy-benzofuran-3-carboxylic acid methylamide;
2-(4-fluoro-phenyl)-5-methoxy-6-(2-oxo-oxazolidin-5-yl)-benzofuran-3-carboxylic acid methylamide;
2-(4-fluoro-phenyl)-5-methoxy-6-(5-methyl-[1,2,4]oxadiazol-3-yl)-benzofuran-3-carboxylic acid methylamide;
6-(3,5-dimethyl-isoxazol-4-yl)-2-(4-fluoro-phenyl)-5-(3-hydroxy-propoxy)-benzofuran-3-carboxylic acid methylamide;
2-(4-fluoro-phenyl)-5-isopropoxy-6-(2-morpholin-4-yl-ethylamino)-benzofuran-3-carboxylic acid methylamide;
2-(4-fluoro-phenyl)-5-isopropoxy-6-piperidin-1-yl-benzofuran-3-carboxylic acid methylamide;
2-(4-fluoro-phenyl)-5-methoxy-6-morpholin-4-yl-benzofuran-3-carboxylic acid methylamide;
2-(4-fluoro-phenyl)-5-isopropoxy-6-(3-methanesulfonyl-pyrrolidin-1-yl)-benzofuran-3-carboxylic acid methylamide;
6-azetidin-1-yl-2-(4-fluoro-phenyl)-5-isopropoxy-benzofuran-3-carboxylic acid methylamide;
2-(4-fluoro-phenyl)-6-(3-hydroxy-pyrrolidin-1-yl)-5-isopropoxy-benzofuran-3-carboxylic acid methylamide;
2-(4-fluoro-phenyl)-6-[(furan-3-ylmethyl)-amino]-5-isopropoxy-benzofuran-3-carboxylic acid methylamide;
2-(4-fluoro-phenyl)-5-methoxy-6-pyrrolidin-1-yl-benzofuran-3-carboxylic acid methylamide;
5-benzyloxy-2-(4-fluoro-phenyl)-6-morpholin-4-yl-benzofuran-3-carboxylic acid methylamide;
2-(4-fluoro-phenyl)-5-isopropoxy-6-[(tetrahydro-furan-2-ylmethyl)-amino]-benzofuran-3-carboxylic acid methylamide;
2-(4-fluoro-phenyl)-5-hydroxy-6-morpholin-4-yl-benzofuran-3-carboxylic acid methylamide;
5-cyclopropylmethoxy-2-(4-fluoro-phenyl)-6-morpholin-4-yl-benzofuran-3-carboxylic acid methylamide;
6-(2,5-dimethyl-2H-pyrazol-3-ylamino)-2-(4-fluoro-phenyl)-5-isopropoxy-benzofuran-3-carboxylic acid methylamide;
2-(4-fluoro-phenyl)-6-morpholin-4-yl-5-(pyridin-4-yl-methoxy)-benzofuran-3-carboxylic acid methylamide;
2-(4-fluoro-phenyl)-5-isopropoxy-6-(pyridin-4-ylamino)-benzofuran-3-carboxylic acid methylamide;
2-(4-fluoro-phenyl)-5-isopropoxy-6-(4-methyl-piperazin-1-yl)-benzofuran-3-carboxylic acid methylamide;
6-(1,1-dioxido-isothiazolidin-2-yl)-2-(4-fluoro-phenyl)-5-isopropoxy-benzofuran-3-carboxylic acid methylamide;
6-(2,6-dimethyl-morpholin-4-yl)-2-(4-fluoro-phenyl)-5-isopropoxy-benzofuran-3-carboxylic acid methylamide;
2-(4-fluoro-phenyl)-5-isopropoxy-6-(1H-tetrazol-5-yl)-benzofuran-3-carboxylic acid methylamide;
2-(4-fluoro-phenyl)-6-(4-hydroxy-piperidin-1-yl)-5-isopropoxy-benzofuran-3-carboxylic acid methylamide;
2-(4-fluoro-phenyl)-6-(3-hydroxy-piperidin-1-yl)-5-isopropoxy-benzofuran-3-carboxylic acid methylamide;
2-(4-fluoro-phenyl)-5-isopropoxy-6-(morpholine-4-sulfonyl)-benzofuran-3-carboxylic acid methylamide;
2-(4-fluoro-phenyl)-5-isopropoxy-6-pyrimidin-5-yl-benzofuran-3-carboxylic acid methylamide;
2-(4-fluoro-phenyl)-6-furan-2-yl-5-isopropoxy-benzofuran-3-carboxylic acid methylamide;
2-(4-fluoro-phenyl)-6-furan-3-yl-5-isopropoxy-benzofuran-3-carboxylic acid methylamide;
2-(4-fluoro-phenyl)-5-isopropoxy-6-pyridin-3-yl-benzofuran-3-carboxylic acid methylamide;
2-(4-fluoro-phenyl)-5-isopropoxy-6-(pyrrolidine-1-sulfonyl)-benzofuran-3-carboxylic acid methylamide;
6-(3,5-dimethyl-isoxazol-4-yl)-2-(4-fluoro-phenyl)-5-isopropoxy-benzofuran-3-carboxylic acid methylamide;
2-(4-fluoro-phenyl)-6-(6-fluoro-pyridin-3-yl)-5-isopropoxy-benzofuran-3-carboxylic acid methylamide;
5-ethoxy-2-(4-fluoro-phenyl)-6-morpholin-4-yl-benzofuran-3-carboxylic acid methylamide;
5-(4-fluoro-benzyloxy)-2-(4-fluoro-phenyl)-6-morpholin-4-yl-benzofuran-3-carboxylic acid methylamide;
2-(4-fluoro-phenyl)-5-isopropoxy-6-oxazol-5-yl-benzofuran-3-carboxylic acid methylamide;
2-(4-fluoro-phenyl)-6-(4-hydroxy-pipendine-1-sulfonyl)-5-isopropoxy-benzofuran-3-carboxylic acid methylamide;
6-(4,4-difluoro-piperidin-1-yl)-2-(4-fluoro-phenyl)-5-isopropoxy-benzofuran-3-carboxylic acid methylamide;
2-(4-difluoro-phenyl)-6-(4-fluoro-piperidin-1-yl)-5-isopropoxy-benzofuran-3-carboxylic acid methylamide;
5-difluoromethoxy-2-(4-fluoro-phenyl)-6-morpholin-4-yl-benzofuran-3-carboxylic acid methylamide;
5-cyclopentyloxy-2-(4-fluoro-phenyl)-6-morpholin-4-yl-benzofuran-3-carboxylic acid methylamide;
2-(4-fluoro-phenyl)-5-isopropoxy-6-(thiomorpholine-4-sulfonyl)-benzofuran-3-carboxylic acid methylamide;
2-(4-fluoro-phenyl)-6-(3-hydroxy-pyrrolidine-1-sulfonyl)-5-isopropoxy-benzofuran-3-carboxylic acid methylamide;
2-(4-fluoro-phenyl)-5-isopropoxy-6-pyridin-4-yl-benzofuran-3-carboxylic acid methylamide;
5-(2-chloro-ethoxy)-2-(4-fluoro-phenyl)-6-morpholin-4-yl-benzofuran-3-carboxylic acid methylamide;
2-(4-fluoro-phenyl)-5-isopropoxy-6-(5-trifluoromethyl-[1,2,4]oxadiazol-3-yl)-benzofuran-3-carboxylic acid methylamide;
2-(4-fluoro-phenyl)-5-isopropoxy-6-thiomorpholin-4-yl-benzofuran-3-carboxylic acid methylamide;
2-(4-fluoro-phenyl)-5-isopropoxy-6-(1-oxo-thiomorpholin-4-yl)-benzofuran-3-carboxylic acid methylamide;
2-(4-fluoro-phenyl)-5-isopropoxy-6-[methanesulfonyl-(2-morpholin-4-yl-ethyl)-amino]-benzofuran-3-carboxylic acid methylamide;

2-(4-fluoro-phenyl)-5-isopropoxy-6-(5-methyl-[1,2,4] oxadiazol-3-yl)-benzofuran-3-carboxylic acid methylamide;
2-(4-fluoro-phenyl)-5-isopropoxy-6-[1,2,4]oxadiazol-3-yl-benzofuran-3-carboxylic acid methylamide;
2-(4-fluoro-phenyl)-5-(3-methoxy-benzyloxy)-6-morpholin-4-yl-benzofuran-3-carboxylic acid methylamide;
2-(4-fluoro-phenyl)-5-methoxy-6-(1-methyl-1H-tetrazol-5-ylmethoxy)-benzofuran-3-carboxylic acid methylamide;
2-(4-fluoro-phenyl)-5-[1-(4-fluoro-phenyl)-ethoxy]-6-morpholin-4-yl-benzofuran-3-carboxylic acid methylamide;
5-(4-cyano-benzyloxy)-2-(4-fluoro-phenyl)-6-morpholin-4-yl-benzofuran-3-carboxylic acid methylamide;
2-(4-fluoro-phenyl)-6-morpholin-4-yl-5-(2-oxo-propoxy)-benzofuran-3-carboxylic acid methylamide;
2-(4-fluoro-phenyl)-5-isopropoxy-6-thiazol-2-yl-benzofuran-3-carboxylic acid methylamide;
2-(4-fluoro-phenyl)-5-isopropoxy-6-(1H-pyrrol-2-yl)-benzofuran-3-carboxylic acid methylamide;
2-(4-fluoro-phenyl)-5-isopropoxy-6-morpholin-4-ylmethyl-benzofuran-3-carboxylic acid methylamide;
2-(4-fluoro-phenyl)-5-(2-methoxy-ethoxy)-6-morpholin-4-yl-benzofuran-3-carboxylic acid methylamide;
2-(4-fluoro-phenyl)-5-isopropoxy-6-thiazol-5-yl-benzofuran-3-carboxylic acid methylamide;
5-(cyano-methyl-methoxy)-2-(4-fluoro-phenyl)-6-morpholin-4-yl-benzofuran-3-carboxylic acid methylamide;
2-(4-fluoro-phenyl)-5-isopropoxy-6-(2H-pyrazol-3-yl)-benzofuran-3-carboxylic acid methylamide;
2-(4-fluoro-phenyl)-5-isopropoxy-6-(2-methyl-2H1-pyrazol-3-yl)-benzofuran-3-carboxylic acid methylamide;
2-(4-fluoro-phenyl)-5-isopropoxy-6-(1-methyl-1H-pyrazol-3-yl)-benzofuran-3-carboxylic acid methylamide;
2-(4-fluoro-phenyl)-5-isopropoxy-6-(3-methyl-isoxazol-5-yl)-benzofuran-3-carboxylic acid methylamide;
6-[(5-chloro-[1,2,4]thiadiazol-3-ylmethyl)-methanesulfonyl-amino]-2-(4-fluoro-phenyl)-5-isopropoxy-benzofuran-3-carboxylic acid methylamide;
6-(3,5-dimethyl-isoxazol-4-ylamino)-2-(4-fluoro-phenyl)-5-isopropoxy-benzofuran-3-carboxylic acid methylamide;
2-(4-fluoro-phenyl)-5-methoxy-6-pyridin-3-yl-benzofuran-3-carboxylic acid methylamide;
2-(4-fluoro-phenyl)-5-isopropoxy-6-(1H-pyrazoL-4-yl)-benzofuran-3-carboxylic acid methylamide;
6-(3-cyclopropyl-isoxazol-5-yl)-2-(4-fluoro-phenyl)-5-isopropoxy-benzofuran-3-carboxylic acid methylamide;
2-(4-fluoro-phenyl)-5-isopropoxy-6-(3-methoxymethyl-isoxazol-5-yl)-benzofuran-3-carboxylic acid methylamide;
2-(4-fluoro-phenyl)-6-(1H-imidazol-2-yl)-5-isopropoxy-benzofuran-3-carboxylic acid methylamide;
6-(2,5-dimethyl-2H-pyrazol-3-yl)-2-(4-fluoro-phenyl)-5-isopropoxy-benzofuran-3-carboxylic acid methylamide;
6-(3,5-dimethyl-1H-pyrazol-4-yl)-2-(4-fluoro-phenyl)-5-isopropoxy-benzofuran-3-carboxylic acid methylamide;
2-(4-fluoro-phenyl)-5-isopropoxy-6-(5-methyl-2H-pyrazol-3-yl)-benzofuran-3-carboxylic acid methylamide;
6-(1,5-dimethyl-1H-pyrazol-3-yl)-2-(4-fluoro-phenyl)-5-isopropoxy-benzofuran-3-carboxylic acid methylamide;
2-(4-fluoro-phenyl)-5-(2-hydroxy-2-methyl-propoxy)-6-morpholin-4-yl-benzofuran-3-carboxylic acid methylamide;
2-(4-fluoro-phenyl)-5-(2-hydroxy-2-methyl-butoxy)-6-morpholin-4-yl-benzofuran-3-carboxylic acid methylamide;
2-(4-fluoro-phenyl)-5-(2-hydroxy-propoxy)-6-morpholin-4-yl-benzofuran-3-carboxylic acid methylamide;
6-(3,5-dimethyl-1H-pyrazol-4-yl)-2-(4-fluoro-phenyl)-5-methoxy-benzofuran-3-carboxylic acid methylamide;
2-(4-fluoro-phenyl)-5-isopropoxy-6-(5-methyl-1H-pyrazol-4-yl)-benzofuran-3-carboxylic acid methylamide;
4-[2-(4-fluoro-phenyl)-3-methylcarbamoyl-6-morpholin-4-yl-benzofuran-5-yloxymethyl]-benzoic acid methyl ester;
3-[2-(4-fluoro-phenyl)-3-methylcarbamoyl-6-morpholin-4-yl-benzofuran-5-yloxymethyl]-benzoic acid methyl ester;
2-(4-fluoro-phenyl)-5-isopropoxy-6-(1,3,5-trimethyl-1H-pyrazol-4-yl)-benzofuran-3-carboxylic acid methylamide;
2-(4-fluoro-phenyl)-5-isopropoxy-6-pyrrolidin-2-yl-benzofuran-3-carboxylic acid methylamide;
4-[2-(4-fluoro-phenyl)-3-methylcarbamoyl-6-morpholin-4-yl-benzofuran-5-yloxymethyl]-benzoic acid;
3-[2-(4-fluoro-phenyl)-3-methylcarbamoyl-6-morpholin-4-yl-benzofuran-5-yloxymethyl]-benzoic acid;
2-(4-fluoro-phenyl)-5-isopropoxy-6-[methanesulfonyl-(1-methyl-1H-tetrazol-5-ylmethyl)-amino]-benzofuran-3-carboxylic acid methylamide;
2-(4-fluoro-phenyl)-5-isopropoxy-6-[methanesulfonyl-(2-methyl-thiazol-4-ylmethyl)-amino]-benzofuran-3-carboxylic acid methylamide;
2-(4-fluoro-phenyl)-5-isopropoxy-6-(5-methoxymethyl-isoxazol-3-yl)-benzofuran-3-carboxylic acid methylamide;
6-(5-cyclopropyl-isoxazol-3-yl)-2-(4-fluoro-phenyl)-5-isopropoxy-benzofuran-3-carboxylic acid methylamide;
2-(4-fluoro-phenyl)-5-isopropoxy-6-(1-methanesulfonyl-pyrrolidin-2-yl)-benzofuran-3-carboxylic acid methylamide;
4-[2-(4-fluoro-phenyl)-5-methoxy-3-methylcarbamoyl-benzofuran-6-yl]-2-oxo-pyrrolidine-3-carboxylic acid methylamide;
2-(4-fluoro-phenyl)-5-isopropoxy-6-(4H-[1,2,4]triazol-3-yl)-benzofuran-3-carboxylic acid methylamide;
2-(4-fluoro-phenyl)-5-methoxy-6-(5-methoxymethyl-3-methyl-isoxazol-4-yl)-benzofuran-3-carboxylic acid methylamide;
2-(4-fluoro-phenyl)-5-isopropoxy-6-[methanesulfonyl-(5-methyl-isoxazol-3-ylmethyl)-amino]-benzofuran-3-carboxylic acid methylamide;
2-(4-fluoro-phenyl)-5-isopropoxy-6-(5-methyl-isoxazol-3-yl)-benzofuran-3-carboxylic acid methylamide;
6-[(3,5-dimethyl-isoxazol-4-ylmethyl)-methanesulfonyi-amino]-2-(4-fluoro-phenyl)-5-isopropoxy-benzofuran-3-carboxylic acid methylamide;
2-(4-fluoro-phenyl)-5-isopropoxy-6-(methanesulfonyl-thiazol-2-ylmethyl-amino)-benzofuran-3-carboxylic acid methylamide;
2-({[2-(4-fluoro-phenyl)-5-isopropoxy-3-methylcarbamoyl-benzofuran-6-yl]-methanesulfonyl-amino }-methyl)-thiazole-4-carboxylic acid ethyl ester;

6-[(3,5-dimethy-isoxazol-4ylmethy)-methanesulfonyl-amino]-2-(4-fluoro-phenyl)-5-methoxy-benzofuran-3-carboxylic acid methylamide;

2-(4-fluoro-phenyl)-6-(methanesulfonyl-thiazol-4-ylmethyl-amino)-5-methoxy-benzofuran-3 -carboxylic acid methylamide;

2-({[2-(4-fluoro-phenyl)-5-isopropoxy-3-methylcarbamoyl-benzofuran-6-yl]-methanesulfonyl-amino}-methyl)-thiazole-4-carboxylic acid;

2-(4-fluoro-phenyl)-6-(1H-imidazol-4-yl)-5-methoxy-benzofuran-3-carboxylic acid methylamide;

2-(4-fluoro-phenyl)-6-(1H-imidazol-2-yl)-5-methoxy-benzofuran-3-carboxylic acid methylamide;

2-(4-fluoro-phenyl)-6-(methanesulfonyl-pyridin-4-ylmethyl-amino)-5-methoxy-benzofuran-3-carboxylic acid methylamide;

2-(4-fluoro-phenyl)-6-(1-methanesulfonyl-pyrrolidin-2-yl-5-methoxy-benzofuran-3-carboxylic acid methylamide;

6-(3-cyclopropyl-5-methoxymethyl-isoxazol-4-yl)-2-(4-fluoro-phenyl)-5-methoxy-benzofuran-3-carboxylic acid methylamide;

2-(4-fluoro-phenyl)-5-methoxy-6-(5-methoxymethyl-isoxazol-3-yl)-benzofuran-3-carboxylic acid methylamide;

6-(3,5-dimethyl-isoxazol-4-yl)-2-(4-fluoro-phenyl)-5-hydroxy-benzofuran-3-carboxylic acid methylamide;

2-(4-fluoro-phenyl)-5-methoxy-6-(5-oxo-pyrrolidin-3-yl)-benzofuran-3-carboxylic acid methylamide;

2-(4-fluoro-phenyl)-5-methoxy-6-(1H-pyrrol-3-yl)-benzofuran-3-carboxylic acid methylamide;

6-(3,5-dimethyl-isoxazol-4-yl)-2-(2-ethoxy-4-fluoro-phenyl)-5-methoxy-benzofuran-3-carboxylic acid methylamide;

2-(4-fluoro-phenyl)-5-methoxy-6-(2-methyl-2H-[1,2,4]triazol-3-yl)-benzofuran-3-carboxylic acid methylamide;

2-(4-fluoro-phenyl)-6-(1-methanesulfonyl-pyrrolidin-3-yl)-5-methoxy-benzofuran-3-carboxylic acid methylamide;

2-(4-fluoro-phenyl)-5-methoxy-6-(3-methoxymethyl-5-methyl-isoxazol-4-yl)-benzofuran-3-carboxylic acid methylamide;

5-ethyl-2-(4-fluoro-phenyl)-6-(methanesulfonyl-thiazol-4-ylmethyl-amino)-benzofuran-3-carboxylic acid methylamide;

6-(5-cyclopropyl-3-methoxymethyl-isoxazol-4-yl)-2-(4-fluoro-phenyl)-5-methoxy-benzofuran-3-carboxylic acid methylamide;

6-(1-acetyl-pyrrolidin-3-yl)-2-(4-fluoro-phenyl)-5-methoxy-benzofuran-3-carboxylic acid methylamide;

6-(5-ethoxymethyl-isoxazol-3-yl)-2-(4-fluoro-phenyl)-5-methoxy-benzofuran-3-carboxylic acid methylamide;

2-(4-fluoro-phenyl)-5-methoxy-6-(2H-[1,2,4]triazol-3-yl)-benzofuran-3-carboxylic acid methylamide;

2-[2-(4-fluoro-phenyl)-5-methoxy-3-methylcarbamoyl-benzofuran-6-yl]-pyrrolidine-1-carboxylic acid amide;

2-(4-fluoro-phenyl)-6-(5-isopropoxymethyl-isoxazol-3-yl)-5-methoxy-benzofuran-3-carboxylic acid methylamide;

2-[2-(4-fluoro-phenyl)-5-methoxy-3-methylcarbamoyl-benzofuran-6-yl]-pyrrolidine-1-carboxylic acid methylamide;

6-(3,5-dimethyl-isoxazol-4-yl)-2-(4-fluoro-phenyl)-5-methoxy-benzofuran-3-carboxylic acid ethylamide;

6-(3,5-dimethyl-isoxazol-4-yl)-2-(4-fluoro-phenyl)-5-methoxy-benzofuran-3-carboxylic acid isopropylamide;

6-(3,5-dimethyl-isoxazol-4-yl)-2-(4-fluoro-phenyl)-5-methoxy-benzofuran-3-carboxylic acid cyclopropylamide;

2-(4-fluoro-phenyl)-5-isopropoxy-6-(5-methyl-2-oxo-oxazolidin-5-yl)-benzofuran-3-carboxylic acid methylamide;

2-(4-fluoro-phenyl)-5-methoxy-6-(5-methyl-2H-[1,2,4]triazol-3-yl)-benzofuran-3-carboxylic acid methylamide;

6-(2,5-dimethyl-2H-[1,2,4]triazol-3-yl)-2-(4-fluoro-phenyl)-5-methoxy-benzofuran-3-carboxylic acid methylamide;

2-(4-fluoro-phenyl)-5-methoxy-6-(4-methyl-2,5-dioxo-imidazolidin-4-yl)-benzofuran-3-carboxylic acid methylamide;

2-(2,4-difluoro-phenyl)-6-(3,5-dimethyl-isoxazol-4-yl)-5-methoxy-benzofuran-3-carboxylic acid methylamide;

6-(2,5-dioxo-imidazolidin-4-yl)-2-(4-fluoro-phenyl)-5-methoxy-benzofuran-3-carboxylic acid methylamide;

6-(3,5-dimethyl-isoxazol-4-yl)-5-ethoxy-2-(4-fluoro-phenyl)-benzofuran-3-carboxylic acid methylamide;

5-cyclopropylmethoxy-6-(3,5-dimethyl-isoxazol-4-yl)-2-(4-fluoro-phenyl)-benzofuran-3-carboxylic acid methylamide;

2-(4-fluoro-phenyl)-5-methoxy-6-(5-methyl-[1,3,4]oxadiazol-2-yl)-benzofuran-3-carboxylic acid methylamide;

6-(3-cyano-4-hydroxy-2-oxo-2,5-dihydro-pyrrol-1-ylmethyl)-2-(4-fluoro-phenyl)-5-methoxy-benzofuran-3-carboxylic acid methylamide;

6-(1-acetyl-pyrrolidin-2-yl)-5-ethyl-2-(4-fluoro-phenyl)-benzofuran-3-carboxylic acid methylamide;

2-(4-fluoro-phenyl)-5-methoxy-6-(tetrahydro-furan-3-yl)-benzofuran-3-carboxylic acid methylamide;

6-(1-cyclopropanecarbonyl-pyrrolidin-2-yl)-2-(4-fluoro-phenyl)-5-isopropoxy-benzorfuran-3-carboxylic acid methylamide;

2-(4-fluoro-phenyl)-5-methoxy-6-[1,3,4]oxadiazol-2-yl-benzofuran-3-carboxylic acid methylamide; and pharmaceutically acceptable salts thereof.

23. A composition for or treatment of viral infections, said composition comprising a compound as claimed in claim 2, in an amount effective to attenuate viral infectivity, and a pharmaceutically acceptable carrier medium.

24. The composition according to claim 23, wherein said compound is selected from the group consisting of:

2-(4-fluoro-phenyl)-5-isopropoxy-6-pyrrolidin-1-yl-benzofuran-3-carboxylic acid methylamide;

6-(3-amino-pyrrolidin-1-yl)-2-(4-fluoro-phenyl)-5-isopropoxy-2,3-dihydro-benzofuran-3-carboxylic acid methylamide;

2-(4-fluoro-phenyl)-5-isopropoxy-6-morpholin-4-yl-benzofuran-3-carboxylic acid methylamide;

6-(3,5-dimethyl-isoxazol-4-yl)-2-(4-fluoro-phenyl)-5-methoxy-benzofuran-3-carboxylic acid methylamide;

2-(4-fluoro-phenyl)-5-(4-methoxy-benzyloxy)-6-morpholin-4-yl-benzofuran-3-carboxylic acid methylamide;

2-(4-fluoro-phenyl)-6-morpholin-4-yl-5-(thiazol-2-ylmethoxy)-benzofuran-3-carboxylic acid methylamide;

2-(4-fluoro-phenyl)-6-morpholin-4-yl-5-(thiazol-4-ylmethoxy)-benzofuran-3-carboxylic acid methylamide;

2-(4-fluoro-phenyl)-5-isopropoxy-6-(methanesulfonyl-thiazol-4-ylmethyl-amino)-benzofuran-3-carboxylic acid methylamide;
2-(4-fluoro-phenyl)-6-(5-hydroxymethyl-isoxazol-3-yl)-5-isopropoxy-benzofuran-3-carboxylic acid methylamide;
2-(4-fluoro-phenyl)-6-(5-hydroxymethyl-isoxazol-3-yl)-5-methoxy-benzofuran-3-carboxylic acid methylamide;
2-(4-fluoro-phenyl)-6-[4-(2-hydroxy-ethyl)-isoxazol-3-yl]-5-methoxy-benzofuran-3-carboxylic acid methylamide;
6-(1-acetyl-pyrrolidin-2-yl)-2-(4-fluoro-phenyl)-5-methoxy-benzofuran-3-carboxylic acid methylamide;
2-(4-fluoro-phenyl)-5-methoxy-6-(2-oxo-oxazolidin-5-yl)-benzofuran-3-carboxylic acid methylamide;
2-(4-fluoro-phenyl)-5-methoxy-6-(5-methyl-[1,2,4]oxadiazol-3-yl)-benzofuran-3-carboxylic acid methylamide;
6-(3,5-dimethyl-isoxazol-4-yl)-2-(4-fluoro-phenyl)-5-(3-hydroxy-propoxy)-benzofuran-3-carboxylic acid methylamide;
2-(4-fluoro-phenyl)-5-isopropoxy-6-(2-morpholin-4-yl-ethylamino)-benzofuran-3-carboxylic acid methylamide;
2-(4-fluoro-phenyl)-5-isopropoxy-6-piperidin-1-yl-benzofuran-3-carboxylic acid methylamide;
2-(4-fluoro-phenyl)-5-methoxy-6-morpholin-4-yl-benzofuran-3-carboxylic acid methylamide;
2-(4-fluoro-phenyl)-5-isopropoxy-6-(3-methanesulfonyl-pyrrolidin-1-yl)-benzofuran-3-carboxylic acid methylamide;
6-azetidin-1-yl-2-(4-fluoro-phenyl)-5-isopropoxy-benzofuran-3-carboxylic acid methylamide;
2-(4-fluoro-phenyl)-6-(3-hydroxy-pyrrolidin-1-yl)-5-isopropoxy-benzofuran-3-carboxylic acid methylamide;
2-(4-fluoro-phenyl)-6-[(furan-3-ylmethyl)-amino]-5-isopropoxy-benzofuran-3-carboxylic acid methylamide;
2-(4-fluoro-phenyl)-5-methoxy-6-pyrrolidin-1-yl-benzofuran-3-carboxylic acid methylamide;
5-benzyloxy-2-(4-fluoro-phenyl)-6-morpholin-4-yl-benzofuran-3-carboxylic acid methylamide;
2-(4-fluoro-phenyl)-5-isopropoxy-6-[(tetrahydro-furan-2-ylmethyl)-amino]-benzofuran-3-carboxylic acid methylamide;
2-(4-fluoro-phenyl)-5-hydroxy-6-morpholin-4-yl-benzofuran-3-carboxylic acid methylamide;
5-cyclopropylmethoxy-2-(4-fluoro-phenyl)-6-morpholin-4-yl-benzofuran-3-carboxylic acid methylamide;
6-(2,5-dimethyl-2H-pyrazol-3-ylamino)-2-(4-fluoro-phenyl)-5-isopropoxy-benzofuran-3-arboxylic acid methylamide;
2-(4-fluoro-phenyl)-6-morpholin-4-yl-5-(pyridin-4-ylmethoxy)-benzofuran-3-carboxylic acid methylamide;
2-(4-fluoro-phenyl)-5-isopropoxy-6-(pyridin-4-ylamino)-benzofuran-3-carboxylic acid methylamide;
2-(4-fluoro-phenyl)-5-isopropoxy-6-(4-methyl-piperazin-1-yl)-benzofuran-3-carboxylic acid methylamide;
6-(1,1-dioxido-isothiazolidin-2-yl)-2-(4-fluoro-phenyl)-5-isopropoxy-benzofuran-3-carboxylic acid methylamide;
6-(2,6-dimethyl-morpholin-4-yl)-2-(4-fluoro-phenyl)-5-isopropoxy-benzofuran-3-carboxylic acid methylamide;
2-(4-fluoro-phenyl)-5-isopropoxy-6-(1H-tetrazol-5-yl)-benzofuran-3-carboxylic acid methylamide;
2-(4-fluoro-phenyl)-6-(4-hydroxy-pipendin-1-yl)-5-isopropoxy-benzofuran-3-carboxylic acid methylamide;
2-(4-fluoro-phenyl)-6-(3-hydroxy-piperidin-1-yl)-5-isopropoxy-benzofuran-3-carboxylic acid methylamide;
2-(4-fluoro-phenyl)-5-isopropoxy-6-(morpholine-4-sulfonyl)-benzofuran-3-carboxylic acid methylamide;
2-(4-fluoro-phenyl)-5-isopropoxy-6-pyrimidin-5-yl-benzofuran-3-carboxylic acid methylamide;
2-(4-fluoro-phenyl)-6-furan-2-yl-5-isopropoxy-benzofuran-3-carboxylic acid methylamide;
2-(4-fluoro-phenyl)-6-furan-3-yl-5-isopropoxy-benzofuran-3-carboxylic acid methylamide;
2-(4-fluoro-phenyl)-5-isopropoxy-6-pyridin-3-yl-benzofuran-3-carboxylic acid methylamide;
2-(4-fluoro-phenyl)-5-isopropoxy-6-(pyrrolidine-1-sulfonyl)-benzofuran-3-carboxylic acid methylamide;
6-(3,5-dimethyl-isoxazol-4-yl)-2-(4-fluoro-phenyl)-5-isopropoxy-benzofuran-3-carboxylic acid methylamide;
2-(4-fluoro-phenyl)-6-(6-fluoro-pyridin-3-yl)-5-isopropoxy-benzofuran-3-carboxylic acid methylamide;
5-ethoxy-2-(4-fluoro-phenyl)-6-morpholin-4-yl-benzofuran-3-carboxylic acid methylamide;
5-(4-fluoro-benzyloxy)-2-(4-fluoro-phenyl)-6-morpholin-4-yl-benzofuran-3-carboxylic acid methylamide;
2-(4-fluoro-phenyl)-5-isopropoxy-6-oxazol-5-yl-benzofuran-3-carboxylic acid methylamide;
2-(4-fluoro-phenyl)-6-(4-hydroxy-piperidine-1-sulfonyl)-5-isopropoxy-benzofuran-3-carboxylic acid methylamide;
6-(4,4-difluoro-piperidin-1-yl)-2-(4-fluoro-phenyl)-5-isopropoxy-benzofuran-3-carboxylic acid methylamide;
2-(4-difluoro-phenyl)-6-(4-fluoro-piperidin-1-yl)-5-isopropoxy-benzofuran-3-carboxylic acid methylamide;
5-difluoromethoxy-2-(4-fluoro-phenyl)-6-morpholin-4-yl-benzofuran-3-carboxylic acid methylamide;
5-cyclopentyloxy-2-(4-fluoro-phenyl)-6-morpholin-4-yl-benzofuran-3-carboxylic acid methylamide;
2-(4-fluoro-phenyl)-5-isopropoxy-6-(thiomorpholine-4-sulfonyl)-benzofuran-3-carboxylic acid methylamide;
2-(4-fluoro-phenyl)-6-(3-hydroxy-pyrrolidine-1-sulfonyl)-5-isopropoxy-benzofuran-3-carboxylic acid methylamide;
2-(4-fluoro-phenyl)-5-isopropoxy-6-pyridin-4-yl-benzofuran-3-carboxylic acid methylamide;
5-(2-chloro-ethoxy)-2-(4-fluoro-phenyl)-6-morpholin-4-yl-benzofuran-3-carboxylic acid methylamide;
2-(4-fluoro-phenyl)-5-isopropoxy-6-(5-trifluoromethyl-[1,2,4]oxadiazol-3-yl)-benzofuran-3-carboxylic acid methylamide;
2-(4-fluoro-phenyl)-5-isopropoxy-6-thiomorpholin-4-yl-benzofuran-3-carboxylic acid methylamide;
2-(4-fluoro-phenyl)-5-isopropoxy-6-(1-oxo-thiomorpholin-4-yl)-benzofuran-3-carboxylic acid methylamide;
2-(4-fluoro-phenyl)-5-isopropoxy-6-[methanesulfonyl-(2-morpholin-4-yl-ethyl)-amino]-benzofuran-3-carboxylic acid methylamide;
2-(4-fluoro-phenyl)-5-isopropoxy-6-(5-methyl-[1,2,4]oxadiazol-3-yl)-benzofuran-3-carboxylic acid methylamide;
2-(4-fluoro-phenyl)-5-isopropoxy-6-[1,2,4]oxadiazol-3-yl-benzofuran-3-carboxylic acid methylamide;
2-(4-fluoro-phenyl)-5-(3-methoxy-benzyloxy)-6-morpholin-4-yl-benzofuran-3-carboxylic acid methylamide;

2-(4-fluoro-phenyl)-5-methoxy-6-(1-methyl-1H-tetrazol-5-ylmethoxy)-benzofuran-3-carboxylic acid methylamide;

2-(4-fluoro-phenyl)-5-[1-(4-fluoro-phenyl)-ethoxy]-6-morpholin-4-yl-benzofuran-3-carboxylic acid methylamide;

5-(4-cyano-benzyloxy)-2-(4-fluoro-phenyl)-6-morpholin-4-yl-benzofuran-3-carboxylic acid methylamide;

2-(4-fluoro-phenyl)-6-morpholin-4-yl-5-(2-oxo-propoxy)-benzofuran-3-carboxylic acid methylamide;

2-(4-fluoro-phenyl)-5-isopropoxy-6-thiazol-2-yl-benzofuran-3-carboxylic acid methylamide;

2-(4-fluoro-phenyl)-5-isopropoxy-6-(1H-pyrrol-2-yl)-benzofuran-3-carboxylic acid methylamide;

2-(4-fluoro-phenyl)-5-isopropoxy-6-morpholin-4-ylmethyl-benzofuran-3-carboxylic acid methylamide;

2-(4-fluoro-phenyl)-5-(2-methoxy-ethoxy)-6-morpholin-4-yl-benzofuran-3-carboxylic acid methylamide;

2-(4-fluoro-phenyl)-5-isopropoxy-6-thiazol-5-yl-benzofuran-3-carboxylic acid methylamide;

5-(cyano-methyl-methoxy)-2-(4-fluoro-phenyl)-6-morpholin-4-yl-benzofuran-3-carboxylic acid methylamide;

2-(4-fluoro-phenyl)-5-isopropoxy-6-(2H-pyrazol-3-yl)-benzofuran-3-carboxylic acid methylamide;

2-(4-fluoro-phenyl)-5-isopropoxy-6-(2-methyl-2H-pyrazol-3-yl)-benzofuran-3-carboxylic acid methylamide;

2-(4-fluoro-phenyl)-5-isopropoxy-6-(1-methyl-1H-pyrazol-3-yl)-benzofuran-3-carboxylic acid methylamide;

2-(4-fluoro-phenyl)-5-isopropoxy-6-(3-methyl-isoxazol-5-yl)-benzofuran-3-carboxylic acid methylamide;

6-[(5-chloro-[,2,4]thiadiazol-3-ylmethyl)-methanesulfonyl-amino]-2-(4-fluoro-phenyl)-5-isopropoxy-benzofuran-3-carboxylic acid methylamide;

6-(3,5-dimethyl-isoxazol-4-ylamino)-2-(4-fluoro-phenyl)-5-isopropoxy-benzofuran-3-carboxylic acid methylamide;

2-(4-fluoro-phenyl)-5-methoxy-6-pyridin-3-yl-benzofuran-3-carboxylic acid methylamide;

2-(4-fluoro-phenyl)-5-isopropoxy-6-(1H-pyrazol-4-yl)-benzofuran-3-carboxylic acid methylamide;

6-(3-cyclopropyl-isoxazol-5-yl)-2-(4-fluoro-phenyl)-5-isopropoxy-benzofuran-3-carboxylic acid methylamide;

2-(4-fluoro-phenyl)-5-isopropoxy-6-(3-methoxymethyl-isoxazol-5-yl)-benzofuran-3-carboxylic acid methylamide;

2-(4-fluoro-phenyl)-6-(1H-imidazol-2-yl)-5-isopropoxy-benzofuran-3-carboxylic acid methylamide;

6-(2,5-dimethyl-2H-pyrazol-3-yl)-2-(4-fluoro-phenyl)-5-isopropoxy-benzofuran-3-carboxylic acid methylamide;

6-(3,5-dimethyl-1H-pyrazol-4-yl)-2-(4-fluoro-phenyl)-5-isopropoxy-benzofuran-3-carboxylic acid methylamide;

2-(4-fluoro-phenyl)-5-isopropoxy-6-(5-methyl-2H-pyrazol-3-yl)-benzofuran-3-carboxylic acid methylamide;

6-(1,5-dimethyl-1H-pyrazol-3-yl)-2-(4-fluoro-phenyl)-5-isopropoxy-benzofuran-3-carboxylic acid methylamide;

2-(4-fluoro-phenyl)-5-(2-hydroxy-2-methyl-propoxy)-6-morpholin-4-yl-benzofuran-3-carboxylic acid methylamide;

2-(4-fluoro-phenyl)-5-(2-hydroxy-2-methyl-butoxy)-6-morpholin-4-yl-benzofuran-3-carboxylic acid methylamide;

2-(4-fluoro-phenyl)-5-(2-hydroxy-propoxy)-6-morpholin-4-yl-benzofuran-3-carboxylic acid methylamide;

6-(3,5-dimethyl-1H-pyrazol-4-yl)-2-(4-fluoro-phenyl)-5-methoxy-benzofuran-3-carboxylic acid methylamide;

2-(4-fluoro-phenyl)-5-isopropoxy-6-(5-methyl-1H-pyrazol-4-yl)-benzofuran-3-carboxylic acid methylamide;

4-[2-(4-fluoro-phenyl)-3-methylcarbamoyl-6-morpholin-4-yl-benzofuran-5-yloxymethyl]-benzoic acid methyl ester;

3-[2-(4-fluoro-phenyl)-3-methylcarbamoyl-6-morpholin-4-yl-benzofuran-5-yloxymethyl]-benzoic acid methyl ester;

2-(4-fluoro-phenyl)-5-isopropoxy-6-(1,3,5-trimethyl-1H-pyrazol-4-yl)-benzofuran-3-carboxylic acid methylamide;

2-(4-fluoro-phenyl)-5-isopropoxy-6-pyrrolidin-2-yl-benzofuran-3-carboxylic acid methylamide;

4-[2-(4-fluoro-phenyl)-3-methylcarbamoyl-6-morpholin-4-yl-benzofuran-5-yloxymethyl]-benzoic acid;

3-[2-(4-fluoro-phenyl)-3-methylcarbamoyl-6-morpholin-4-yl-benzofuran-5-yloxymethyl]-benzoic acid;

2-(4-fluoro-phenyl)-5-isopropoxy-6-[methanesulfonyl-(1-methyl-1H-tetrazol-5-ylmethyl)-amino]-benzofuran-3-carboxylic acid methylamide;

2-(4-fluoro-phenyl)-5-isopropoxy-6-[methanesulfonyl-(2-methyl-thiazol-4-ylmethyl)-amino]-benzofuran-3-carboxylic acid methylamide;

2-(4-fluoro-phenyl)-5-isopropoxy-6-(5-methoxymethyl-isoxazol-3-yl)-benzofuran-3-carboxylic acid methylamide;

6-(5-cyclopropyl-isoxazol-3-yl)-2-(4-fluoro-phenyl)-5-isopropoxy-benzofuran-3-carboxylic acid methylamide;

2-(4-fluoro-phenyl)-5-isopropoxy-6-(1-methanesulfonyl-pyrrolidin-2-yl)-benzofuran-3-carboxylic acid methylamide;

4-[2-(4-fluoro-phenyl)-5-methoxy-3-methylcarbamoyl-benzofuran-6-yl]-2-oxo-pyrrolidine-3-carboxylic acid methylamide;

2-(4-fluoro-phenyl)-5-isopropoxy-6-(4H-[1,2,4]triazol-3-yl)-benzofuran-3-carboxylic acid methylamide;

2-(4-fluoro-phenyl)-5-methoxy-6-(5-methoxymethyl-3-methyl-isoxazol-4-yl)-benzofuran-3-carboxylic acid methylamide;

2-(4-fluoro-phenyl)-5-isopropoxy-6-[methanesulfonyl-(5-methyl-isoxazol-3-ylmethyl)-amino]-benzofuran-3-carboxylic acid methylamide;

2-(4-fluoro-phenyl)-5-isopropoxy-6-(5-methyl-isoxazol-3-yl)-benzofuran-3-carboxylic acid methylamide;

6-[(3,5-dimethyl-isoxazol-4-ylmethyl)-methanesulfonyl-amino]-2-(4-fluoro-phenyl)-5-isopropoxy-benzofuran-3-carboxylic acid methylamide;

2-(4-fluoro-phenyl)-5-isopropoxy-6-(methanesulfonyl-thiazol-2-ylmethyl-amino)-benzofuran-3-carboxylic acid methylamide;

2-({[2-(4-fluoro-phenyl)-5-isopropoxy-3-methylcarbamoyl-benzofuran-6-yl]-methanesulfonyl-amino}-methyl)-thiazole-4-carboxylic acid ethyl ester;

6-[(3,5-dimethyl-isoxazol-4-ylmethyl)-methanesulfonyl-amino]-2-(4-fluoro-phenyl)-5-methoxy-benzofuran-3-carboxylic acid methylamide;

2-(4-fluoro-phenyl)-6-(methanesulfonyl-thiazol-4-ylmethyl-amino)-5-methoxy-benzofuran-3-carboxylic acid methylamide;

2-({[2-(4-fluoro-phenyl)-5-isopropoxy-3-methylcarbamoyl-benzofuran-6-yl]-methanesulfonyl-amino }-methyl)-thiazole-4-carboxylic acid;

2-(4-fluoro-phenyl)-6-(1H-imidazol-4-yl)-5-methoxy-benzofuran-3-carboxylic acid methylamide;
2-(4-fluoro-phenyl)-6-(1H-imidazol-2-yl)-5-methoxy-benzofuran-3-carboxylic acid methylamide;
2-(4-fluoro-phenyl)-6-(methanesulfonyl-pyridin-4-ylmethyl-amino)-5-methoxy-benzofuran-3-carboxylic acid methylamide;
2-(4-fluoro-phenyl)-6-(1-methanesulfonyl-pyrrolidin-2-yl)-5-methoxy-benzofuran-3-carboxylic acid methylamide;
6(3-cyclopropyl-5-methoxymethyl-isoxazol-4-yl)-2-(4-fluoro-phenyl)-5-methoxy-benzofuran-3-carboxylic acid methylamide;
2-(4-fluoro-phenyl)-5-methoxy-6-(5-methoxymethyl-isoxazol-3-yl)-benzofuran-3-carboxylic acid methylamide;
6-(3,5-dimethyl-isoxazol-4-yl)-2-(4-fluoro-phenyl)-5-hydroxy-benzofuran-3-carboxylic acid methylamide;
2-(4-fluoro-phenyl)-5-methoxy-6-(5-oxo-pyrrolidin-3-yl)-benzofuran-3-carboxylic acid methylamide;
2-(4-fluoro-phenyl)-5-methoxy-6-(1H-pyrrol-3-yl)-benzofuran-3-carboxylic acid methylamide;
6-(3,5-dimethyl-isoxazol-4-yl)-2-(2-ethoxy-4-fluoro-phenyl)-5-methoxy-benzofuran-3-carboxylic acid methylamide;
2-(4-fluoro-phenyl)-5-methoxy-6-(2-methyl-2H-[1,2,4]triazol-3-yl)-benzofuran-3-carboxylic acid methylamide;
2-(4-fluoro-phenyl)-6-(1-methanesulfonyl-pyrrolidin-3-yl)-5-methoxy-benzofuran-3-carboxylic acid methylamide;
2-(4-fluoro-phenyl)-5-methoxy-6-(3-methoxymethyl-5-methyl-isoxazol-4-yl)-benzofuran-3-carboxylic acid methylamide;
5-ethyl-2-(4-fluoro-phenyl)-6-(methanesulfonyl-thiazol-4-ylmethyl-amino)-benzofuran-3-carboxylic acid methylamide;
6-(5-cyclopropyl-3-methoxymethyl-isoxazol-4-yl)-2-(4-fluoro-phenyl)-5-methoxy-benzofuran-3-carboxylic acid methylamide;
6-(1-acetyl-pyrrolidin-3-yl)-2-(4-fluoro-phenyl)-5-methoxy-benzofuran-3-carboxylic acid methylamide;
6-(5-ethoxymethyl-isoxazol-3-yl)-2-(4-fluoro-phenyl)-5-methoxy-benzofuran-3-carboxylic acid methylamide;
2-(4-fluoro-phenyl)-5-methoxy-6-(2H-[1,2,4]triazol-3-yl)-benzofuran-3-carboxylic acid methylamide;
2-[2-(4-fluoro-phenyl)-5-methoxy-3-methylcarbamoyl-benzofuran-6-yl]-pyrrolidine-1-carboxylic acid amide;
2-(4-fluoro-phenyl)-6-(5-isopropoxymethyl-isoxazol-3-yl)-5-methoxy-benzofuran-3-carboxylic acid methylamide;
2-[2-(4-fluoro-phenyl)-5-methoxy-3-methylcarbamoyl-benzofuran-6-yl]-pyrrolidine-1-carboxylic acid methylamide;
6-(3,5-dimethyl-isoxazol-4-yl)-2-(4-fluoro-phenyl)-5-methoxy-benzofuran-3-carboxylic acid ethylamide;
6-(3,5-dimethyl-isoxazol-4-yl)-2-(4-fluoro-phenyl)-5-methoxy-benzofuran-3-carboxylic acid isopropylamide;
6-(3,5-dimethyl-isoxazol-4-yl)-2-(4-fluoro-phenyl)-5-methoxy-benzofuran-3-carboxylic acid cyclopropylamide;
2-(4-fluoro-phenyl)-5-isopropoxy-6-(5-methyl-2-oxo-oxazolidin-5-yl)-benzofuran-3-carboxylic acid methylamide;
2-(4-fluoro-phenyl)-5-methoxy-6-(5-methyl-2H-[1,2,4]triazol-3-yl)-benzofuran-3-carboxylic acid methylamide;
6-(2,5-dimethyl-2H-[1,2,4]triazol-3-yl)-2-(4-fluoro-phenyl)-5-methoxy-benzofuran-3-carboxylic acid methylamide;
2-(4-fluoro-phenyl)-5-methoxy-6-(4-methyl-2,5-dioxo-imidazolidin-4-yl)-benzofuran-3-carboxylic acid methylamide;
2-(2,4-difluoro-phenyl)-6-(3,5-dimethyl-isoxazol-4-yl)-5-methoxy-benzofuran-3-carboxylic acid methylamide;
6-(2,5-dioxo-imidazolidin-4-yl)-2-(4-fluoro-phenyl)-5-methoxy-benzofuran-3-carboxylic acid methylamide;
6-(3,5-dimethyl-isoxazol-4-yl)-5-ethoxy-2-(4-fluoro-phenyl)-benzofuran-3-carboxylic acid methylamide;
5-cyclopropylmethoxy-6-(3,5-dimethyl-isoxazol-4-yl)-2-(4-fluoro-phenyl)-benzofuran-3-carboxylic acid methylamide;
2-(4-fluoro-phenyl)-5-methoxy-6-(5-methyl-[1,3,4]oxadiazol-2-yl)-benzofuran-3-carboxylic acid methylamide;
6-(3-cyano-4-hydroxy-2-oxo-2,5-dihydro-pyrrol-1-ylmethyl)-2-(4-fluoro-phenyl)-5-methoxy-benzofuran-3-carboxylic acid methylamide;
6-(1-acetyl-pyrrolidin-2-yl)-5-ethyl-2-(4-fluoro-phenyl)-benzofuran-3-carboxylic acid methylamide;
2-(4-fluoro-phenyl)-5-methoxy-6-(tetrahydro-furan-3-yl)-benzofuran-3-carboxylic acid methylamide;
6-(1-cyclopropanecarbonyl-pyrrolidin-2-yl)-2-(4-fluoro-phenyl)-5-isopropoxy-benzofuran-3 -carboxylic acid methylamide;
2-(4-fluoro-phenyl)-5-methoxy-6-[1,3,4]oxadiazol-2-yl-benzofuran-3-carboxylic acid methylamide; and pharmaceutically acceptable salts thereof.

25. The compound according to claim 3, selected from the group consisting of:
2-furan-3-yl-5-methoxy-benzofuran-3-carboxylic acid methylamide;
2-furan-2-yl-5-methoxy-benzofuran-3-carboxylic acid methylamide;
2-(5-chloro-thiophen-2-yl)-5-methoxy-benzofuran-3-carboxylic acid methylamide;
2-(5-chloro-thiophen-2-yl)-5-ethoxy-benzofuran-3-carboxylic acid methylamide;
5-methoxy-2-thiophen-2-yl-benzofuran-3-carboxylic acid methylamide;
5-chloro-2-pyridin-3-yl-benzofuran-3-carboxylic acid methylamide;
5-methoxy-2-(4-morpholin-4-yl-phenyl)-benzofuran-3-carboxylic acid methylamide;
5-isopropoxy-2-(4-pyrrolidin-1-yl-phenyl)-benzofuran-3-carboxylic acuid methylamide;
5-fluoro-2-pyridin-4-yl-benzofuran-3-carboxylic acid methylamide;
5-methoxy-2-pyridin-4-yl-benzofuran-3-carboxylic acid methylamide;
5-isopropoxy-2-(3-methyl-furan-2-yl)-benzofuran-3-carboxylic acid methylamide; and the pharmaceutically acceptable salts thereof.

26. A composition for or treatment of viral infections, said composition comprising a compound as claimed in claim 3, in an amount effective to attenuate viral infectivity, and a pharmaceuticall acceptable carrier medium.

27. The composition according to claim 23, wherein the compound is selected from the group consisting of: 2-(4-fluoro-phenyl)-5-methoxy-6-morpholin-4-yl-benzofuran-3- carboxylic acid methylamide; 2-(4-fluoro-phenyl)-5-isopropoxy-6-morpholin-4-yl-benzofuran-3-carboxylic acid methylamide; 5-benzyloxy-2-(4-fluoro-phenyl)-6-morpholin-4-yl-benzofuran-3-carboxylic acid methylamide; 2-(4-fluoro-phenyl)-6-[(furan-3-ylmethyl)-amino]-5-isopropoxy-benzofuran-3-carboxylic acid methylamide; 6-(3,5-dimethyl-isoxazol-4-yl)-2-(4-fluoro-phenyl)-5-methoxy-benzofuran-3-carboxylic acid methylamide; 6-(3,5-dimethyl-isoxazol-4-yl)-2-(4-fluoro-phenyl)-5-(3-hydroxypropoxy)-benzofuran-3-carboxylic acid methylamide; 2-(4-fluoro-phenyl)-6-[4-(2-hydroxy-ethyl)-isoxazol-3-yl]-5-methoxy-benzofuran-3-carboxylic acid methylamide; and pharmaceutically acceptable salts thereof.

28. A composition according to claim 11, 23 or 26 further comprising at least one supplemental agent selected from the group of interferon, pegylated interferon, ribavirin, protease inhibitors, polymerase inhibitors, small interfering RNA compounds, anti-sense compounds, nucleotide analogs, nucleoside analogs, immunoglobulins, immunomodulators, hepatoprotectants, anti-inflammatory agents, antibiotics, antivirals, and anti-infective compounds.

29. The composition according to claim 26, wherein said compound is selected from the group consisting of:
    2-furan-3-yl-5-methoxy-benzofuran-3-carboxylic acid methylamide;
    2-furan-2-yl-5-methoxy-benzofuran-3-carboxylic acid methylamide;
    2-(5-chloro-thiophen-2-yl)-5-methoxy-benzofuran-3-carboxylic acid methylamide;
    2-(5-chloro-thiophen-2-yl)-5-ethoxy-benzofuran-3-carboxylic acid methylamide;
    5-methoxy-2-thiophen-2-yl-benzofuran-3-carboxylic acid methylamide;
    5-chloro-2-pyridin-3-yl-benzofuran-3-carboxylic acid methylamide;
    5-methoxy-2-(4-morpholin-4-yl-phenyl)-benzofuran-3-carboxylic acid methylamide;
    5-isopropoxy-2-(4-pyrrolidin-1-yl-phenyl)-benzofuran-3-carboxylic acuid methylamide;
    5-fluoro-2-pyridin-4-yl-benzofuran-3-carboxylic acid methylamide;
    5-methoxy-2-pyridin-4-yl-benzofuran-3-carboxylic acid methylamide;
    5-isopropoxy-2-(3-methyl-furan-2-yl)-benzofuran-3-carboxylic acid methylamide; and the pharmaceutically acceptable salts thereof.

30. A method for or treatment of hepatitis C infections and diseases associated with such infections in a living host having said infections, said method comprising administering to said living host a therapeutically effective amount of a compound according to claim 2.

31. The method according to claim 30, wherein said living host is a mammal.

32. The method according to claim 30, wherein said living host is a human.

33. The method according to claim 32, wherein the compound is administered orally.

34. The method according to claim 33, wherein the compound is administered orally at a dose range of about 0.05 to about 100 mg/kg.

35. The method according to claim 30, wherein the compound is administered from 1 to 4 times daily.

36. The method according to claim 30, wherein the compound is administered in combination, either concurrently or sequentially, with at least one other biologically active agent.

37. The method according to claim 36, wherein said other biologically active agent is selected from the group consisting of interferon, pegylated interferon, ribavirin, protease inhibitors, polymerase inhibitors, small interfering RNA compounds, anti-sense compounds, nucleotide analogs, nucleoside analogs, immunoglobulins, immunomodulators, hepatoprotectants, anti-inflammatory agents, antibiotics, antivirals, and anti-infective compounds.

38. The method according to claim 30, wherein the compound is selected from the group consisting of:
    2-(4-fluoro-phenyl)-5-isopropoxy-6-pyrrolidin-1-yl-benzofuran-3-carboxylic acid methylamide;
    6-(3-amino-pyrrolidin-1-yl)-2-(4-fluoro-phenyl)-5-isopropoxy-2,3-dihydro-benzofuran-3-carboxylic acid methylamide;
    2-(4-fluoro-phenyl)-5-isopropoxy-6-morpholin-4-yl-benzofuran-3-carboxylic acid methylamide;
    6-(3,5-dimethyl-isoxazol-4-yl)-2-(4-fluoro-phenyl)-5-methoxy-benzofuran-3-carboxylic acid methylamide;
    2-(4-fluoro-phenyl)-5-(4-methoxy-benzyloxy)-6-morpholin-4-yl-benzofuran-3-carboxylic acid methylamide;
    2-(4-fluoro-phenyl)-6-morpholin-4-yl-5-(thiazol-2-ylmethoxy)-benzofuran-3-carboxylic acid methylamide;
    2-(4-fluoro-phenyl)-6-morpholin-4-yl-5-(thiazol-4-ylmethoxy)-benzofuran-3-carboxylic acid methylamide;
    2-(4-fluoro-phenyl)-5-isopropoxy-6-(methanesulfonyl-thiazol-4-ylmethyl-amino)-benzofuran-3-carboxylic acid methylamide;
    2-(4-fluoro-phenyl)-6-(5-hydroxymethyl-isoxazol-3-yl)-5-isopropoxy-benzofuran-3-carboxylic acid methylamide;
    2-(4-fluoro-phenyl)-6-(5-hydroxymethyl-isoxazol-3-yl)-5-methoxy-benzofuran-3-carboxylic acid methylamide;
    2-(4-fluoro-phenyl)-6-[4-(2-hydroxy-ethyl)-isoxazol-3-yl]-5-methoxy-benzofuran-3-carboxylic acid methylamide;
    6-(1-acetyl-pyrrolidin-2-yl)-2-(4-fluoro-phenyl)-5-methoxy-benzofuran-3-carboxylic acid methylamide;
    2-(4-fluoro-phenyl)-5-methoxy-6-(2-oxo-oxazolidin-5-yl)-benzofuran-3-carboxylic acid methylamide;
    2-(4-fluoro-phenyl)-5-methoxy-6-(5-methyl-[1,2,4]oxadiazol-3-yl)-benzofuran-3-carboxylic acid methylamide;
    6-(3,5-dimethyl-isoxazol-4-yl)-2-(4-fluoro-phenyl)-5-(3-hydroxy-propoxy)-benzofuran-3-carboxylic acid methylamide;
    2-(4-fluoro-phenyl)-5-isopropoxy-6-(2-morpholin-4-yl-ethylamino)-benzofuran-3-carboxylic acid methylamide;
    2-(4-fluoro-phenyl)-5-isopropoxy-6-piperidin-1-yl-benzofuran-3-carboxylic acid methylamide;
    2-(4-fluoro-phenyl)-5-methoxy-6-morpholin-4-yl-benzofuran-3-carboxylic acid methylamide;
    2-(4-fluoro-phenyl)-5-isopropoxy-6-(3-methanesulfonyl-pyrrolidin-1-yl)-benzofuran-3-carboxylic acid methylamide;
    6-azetidin-1-yl-2-(4-fluoro-phenyl)-5-isopropoxy-benzofuran-3-carboxylic acid methylamide;
    2-(4-fluoro-phenyl)-6-(3-hydroxy-pyrrolidin-1-yl)-isopropoxy-benzofuran-3-carboxylic acid methylamide;
    2-(4-fluoro-phenyl)-6-[(furan-3-ylmethyl)-amino]-5-isopropoxy-benzofuran-3-carboxylic acid methylamide;
    2-(4-fluoro-phenyl)-5-methoxy-6-pyrrolidin-1-yl-benzofuran-3-carboxylic acid methylamide;
    5-benzyloxy-2-(4-fluoro-phenyl)-6-morpholin-4-yl-benzofuran-3-carboxylic acid methylamide;

2-(4-fluoro-phenyl)-5-isopropoxy-6-[(tetrahydro-furan-2-ylmethyl)-amino]-benzofuran-3-carboxylic acid methylamide;
2-(4-fluoro-phenyl)-5-hydroxy-6-morpholin-4-yl-benzofuran-3-carboxylic acid methylamide;
5-cyclopropylmethoxy-2-(4-fluoro-phenyl)-6-morpholin-4-yl-benzofuran-3-carboxylic acid methylamide;
6-(2,5-dimethyl-2H-pyrazol-3-ylamino)-2-(4-fluoro-phenyl)-5-isopropoxy-benzofuran-3-carboxylic acid methylamide;
2-(4-fluoro-phenyl)-6-morpholin-4-yl-5-(pyridin-4-ylmethoxy)-benzofuran-3-carboxylic acid methylamide;
2-(4-fluoro-phenyl)-5-isopropoxy-6-(pyridin-4-ylamino)-benzofuran-3-carboxylic acid methylamide;
2-(4-fluoro-phenyl)-5-isopropoxy-6-(4-methyl-piperazin-1-yl)-benzofuran-3-carboxylic acid methylamide;
6-(1,1-dioxido-isothiazolidin-2-yl)-2-(4-fluoro-phenyl)-5-isopropoxy-benzofuran-3-carboxylic acid methylamide;
6-(2,6-dimethyl-morpholin-4-yl)-2-(4-fluoro-phenyl)-5-isopropoxy-benzofuran-3-carboxylic acid methylamide;
2-(4-fluoro-phenyl)-5-isopropoxy-6-(1H-tetrazol-5-yl)-benzofuran-3-carboxylic acid methylamide;
2-(4-fluoro-phenyl)-6-(4-hydroxy-piperidin-1-yl)-5-isopropoxy-benzofuran-3-carboxylic acid methylamide;
2-(4-fluoro-phenyl)-6-(3-hydroxy-piperidin-1-yl)-5-isopropoxy-benzofuran-3-carboxylic acid methylamide;
2-(4-fluoro-phenyl)-5-isopropoxy-6-(morpholine-4-sulfonyl)-benzofuran-3-carboxylic acid methylamide;
2-(4-fluoro-phenyl)-5-isopropoxy-6-pyrimidin-5-yl-benzofuran-3-carboxylic acid methylamide;
2-(4-fluoro-phenyl)-6-furan-2-yl-5-isopropoxy-benzofuran-3-carboxylic acid methylamide;
2-(4-fluoro-phenyl)-6-furan-3-yl-5-isopropoxy-benzofuran-3-carboxylic acid methylamide;
2-(4-fluoro-phenyl)-5-isopropoxy-6-pyridin-3yl benzofuran-3-carboxylic acid methylamide;
2-(4-fluoro-phenyl)-5-isopropoxy-6-(pyrrolidine-1-sulfonyl)-benzofuran-3-carboxylic acid methylamide;
6-(3,5-dimethyl-isoxazol-4-yl)-2-(4-fluoro-phenyl)-5-isopropoxy-benzofuran-3-carboxylic acid methylamide;
2-(4-fluoro-phenyl)-6-(6-fluoro-pyridin-3-yl)-5-isopropoxy-benzofuran-3-carboxylic acid methylamide;
5-ethoxy-2-(4-fluoro-phenyl)-6-morpholin-4-yl-benzofuran-3-carboxylic acid methylamide;
5-(4-fluoro-benzyloxy)-2-(4-fluoro-phenyl)-6-morpholin-4-yl-benzofuran-3-carboxylic acid methylamide;
2-(4-fluoro-phenyl)-5-isopropoxy-6-oxazol-5-yl-benzofuran-3-carboxylic acid methylamide;
2-(4-fluoro-phenyl)-6-(4-hydroxy-piperidine-1-sulfonyl)-5-isopropoxy-benzofuran-3-carboxylic acid methylamide;
6-(4,4-difluoro-piperidin-1-yl)-2-(4-fluoro-phenyl)-5-isopropoxy-benzofuran-3-carboxylic acid methylamide;
2-(4-difluoro-phenyl)-6-(4-fluoro-piperidin-1-yl)-5-isopropoxy-benzofuran-3-carboxylic acid methylamide;
5-difluoromethoxy-2-(4-fluoro-phenyl)-6-morpholin-4-yl-benzofuran-3-carboxylic acid methylamide;
5-cyclopentyloxy-2-(4-fluoro-phenyl)-6-morpholin-4-yl-benzofuran-3-carboxylic acid methylamide;
2-(4-fluoro-phenyl)-5-isopropoxy-6-(thiomorpholine-4-sulfonyl)-benzofuran-3-carboxylic acid methylamide;
2-(4-fluoro-phenyl)-6-(3-hydroxy-pyrrolidine-1-sulfonyl)-isopropoxy-benzofuran-3-carboxylic acid methylamide;
2-(4-fluoro-phenyl)-5-isopropoxy-6-pyridin-4-yl-benzofuran-3-carboxylic acid methylamide;
5-(2-chloro-ethoxy)-2-(4-fluoro-phenyl)-6-morpholin-4-yl-benzofuran-3-carboxylic acid methylamide;
2-(4-fluoro-phenyl)-5-isopropoxy-6-(5-trifluoromethyl-[1,2,4]oxadiazol-3-yl)-benzofuran-3-carboxylic acid methylamide;
2-(4-fluoro-phenyl)-5-isopropoxy-6-thiomorpholin-4-yl-benzofuran-3-carboxylic acid methylamide;
2-(4-fluoro-phenyl)-5-isopropoxy-6-(1-oxo-thiomorpholin-4-yl)-benzofuran-3-carboxylic acid methylamide;
2-(4-fluoro-phenyl)-5-isopropoxy-6-[methanesulfonyl-(2-morpholin-4-yl-ethyl)-amino]-benzofuran-3-carboxylic acid methylamide;
2-(4-fluoro-phenyl)-5-isopropoxy-6-(5-methyl-[1,2,4]oxadiazol-3-yl)-benzofuran-3-carboxylic acid methylamide;
2-(4-fluoro-phenyl)-5-isopropoxy-6-[1,2,4]oxadiazol-3-yl-benzofuran-3-carboxylic acid methylamide;
2-(4-fluoro-phenyl)-5-(3-methoxy-benzyloxy)-6-morpholin-4-yl-benzofuran-3-carboxylic acid methylamide;
2-(4-fluoro-phenyl)-5-methoxy-6-(1-methyl-1H-tetrazol-5-ylmethoxy)-benzofuran-3-carboxylic acid methylamide;
2-(4-fluoro-phenyl)-5-[1-(4-fluoro-phenyl)-ethoxy]-6-morpholin-4-yl-benzofuran-3-carboxylic acid methylamide;
5-(4-cyano-benzyloxy)-2-(4-fluoro-phenyl)-6-morpholin-4-yl-benzofuran-3-carboxylic acid methylamide;
2-(4-fluoro-phenyl)-6-morpholin-4-yl-5-(2-oxo-propoxy)-benzofuran-3-carboxylic acid methylamide;
2-(4-fluoro-phenyl)-5-isopropoxy-6-thiazol-2-yl-benzofuran-3-carboxylic acid methylamide;
2-(4-fluoro-phenyl)-5-isopropoxy-6-(1H-pyrrol-2-yl)-benzofuran-3-carboxylic acid methylamide;
2-(4-fluoro-phenyl)-5-isopropoxy-6-morpholin-4-ylmethyl-benzofuran-3-carboxylic acid methylamide;
2-(4-fluoro-phenyl)-5-(2-methoxy-ethoxy)-6-morpholin-4-yl-benzofuran-3-carboxylic acid methylamide;
2-(4-fluoro-phenyl)-5-isopropoxy-6-thiazol-5-yl-benzofuran-3-carboxylic acid methylamide;
5-(cyano-methyl-methoxy)-2-(4-fluoro-phenyl)-6-morpholin-4-yl-benzofuran-3-carboxylic acid methylamide;
2-(4-fluoro-phenyl)-5-isopropoxy-6-(2H-pyrazol-3-yl)-benzofuran-3-carboxylic acid methylamide;
2-(4-fluoro-phenyl)-5-isopropoxy-6-(2-methyl-2H-pyrazol-3-yl)-benzofuran-3-carboxylic acid methylamide;
2-(4-fluoro-phenyl)-5-isopropoxy-6-(1-methyl-1H-pyrazol-3-yl)-benzofuran-3-carboxylic acid methylamide;
2-(4-fluoro-phenyl)-5-isopropoxy-6-(3-methyl-isoxazol-5-yl)-benzofuran-3-carboxylic acid methylamide;
6-[(5-chloro-[1,2,4]thiadiazol-3-ylmethyl)-methanesulfonyl-amino]-2-(4-fluoro-phenyl)-5-isopropoxy-benzofuran-3-carboxylic acid methylamide;
6-(3,5-dimethyl-isoxazol-4-ylamino)-2-(4-fluoro-phenyl)-5-isopropoxy-benzofuran-3-carboxylic acid methylamide;
2-(4-fluoro-phenyl)-5-methoxy-6-pyridin-3-yl-benzofuran-3-carboxylic acid methylamide;
2-(4-fluoro-phenyl)-5-isopropoxy-6-(1H-pyrazol-4-yl)-benzofuran-3-carboxylic acid methylamide;
6-(3-cyclopropyl-isoxazol-5-yl)-2-(4-fluoro-phenyl)-5-isopropoxy-benzofuran-3-carboxylic acid methylamide;

2-(4-fluoro-phenyl)-5-isopropoxy-6-(3-methoxymethyl-isoxazol-5-yl)-benzofuran-3-carboxylic acid methylamide;

2-(4-fluoro-phenyl)-6-(1H-imidazol-2-yl)-5-isopropoxy-benzofuran-3-carboxylic acid methylamide;

6-(2,5-dimethyl-2H-pyrazol-3-yl)-2-(4-fluoro-phenyl)-5-isopropoxy-benzofuran-3-carboxylic acid methylamide;

6-(3,5-dimethyl-1H-pyrazol-4-yl)-2-(4-fluoro-phenyl)-5-isopropoxy-benzofuran-3-carboxylic acid methylamide;

2-(4-fluoro-phenyl)-5-isopropoxy-6-(5-methyl-2H-pyrazol-3-yl)-benzofuran-3-carboxylic acid methylamide;

6-(1,5-dimethyl-1H-pyrazol-3-yl)-2-(4-fluoro-phenyl)-5-isopropoxy-benzofuran-3-carboxylic acid methylamide;

2-(4-fluoro-phenyl)-5-(2-hydroxy-2-methyl-propoxy)-6-morpholin-4-yl-benzofuran-3-carboxylic acid methylamide;

2-(4-fluoro-phenyl)-5-(2-hydroxy-2-methyl-butoxy)-6-morpholin-4-yl-benzofuran-3-carboxylic acid methylamide;

2-(4-fluoro-phenyl)-5-(2-hydroxy-propoxy)-6-morpholin-4-yl-benzofuran-3-carboxylic acid methylamide;

6-(3,5-dimethyl-1H-pyrazol-4-yl)-2-(4-fluoro-phenyl)-5-methoxy-benzofuran-3-carboxylic acid methylamide;

2(4-fluoro-phenyl)-5-isopropoxy-6-(5-methyl-1H-pyrazol-4-yl)-benzofuran-3-carboxylic acid methylamide;

4-[2-(4-fluoro-phenyl)-3-methylcarbamoyl-6-morpholin-4-yl-benzofuran-5-yloxymethyl]-benzoic acid methyl ester;

3 [2-(4-fluoro-phenyl)-3-methylcarbamoyl-6-morpholin-4-yl-benzofuran-5-yloxymethyl]-benzoic acid methyl ester;

2-(4-fluoro-phenyl)-5-isopropoxy-6-(1,3,5-trimethyl-1H-pyrazol-4-yl)-benzofuran-3-carboxylic acid methylamide;

2-(4-fluoro-phenyl)-5-isopropoxy-6-pyrrolidin-2-yl-benzofuran-3-carboxylic acid methylamide;

4-[2-(4-fluoro-phenyl)-3-methylcarbamoyl-6-morpholin-4-yl-benzofuran-5-yloxymethyl]-benzoic acid;

3-[2-(4-fluoro-phenyl)-3-methylcarbamoyl-6-morpholin-4-yl-benzofuran-5-yloxymethyl]-benzoic acid;

2-(4-fluoro-phenyl)-5-isopropoxy-6-[methanesulfonyl-(1-methyl-1H-tetrazol-5-ylmethyl)-amino]-benzofuran-3-carboxylic acid methylamide;

2-(4-fluoro-phenyl)-5-isopropoxy-6-[methanesulfonyl-(2-methyl-thiazol-4-ylmethyl)-amino]-benzofuran-3-carboxylic acid methylamide;

2-(4-fluoro-phenyl)-5-isopropoxy-6-(5-methoxymethyl-isoxazol-3-yl)-benzofuran-3-carboxylic acid methylamide;

6-(5-cyclopropyl-isoxazol-3-yl)-2-(4-fluoro-phenyl)-5-isopropoxy-benzofuran-3-carboxylic acid methylamide;

2-(4-fluoro-phenyl)-5-isopropoxy-6-(1-methanesulfonyl-pyrrolidin-2-yl)-benzofuran-3-carboxylic acid methylamide;

4-[2-(4-fluoro-phenyl)-5-methoxy-3-methylcarbamoyl-benzofuran-6-yl]-2-oxo-pyrrolidine-3-carboxylic acid methylamide;

2-(4-fluoro-phenyl)-5-isopropoxy-6-(4H-[1,2,4]triazol-3-yl)-benzofuran-3-carboxylic acid methylamide;

2-(4-fluoro-phenyl)-5-methoxy-6-(5-methoxymethyl-3-methyl-isoxazol-4-yl)-benzofuran-3-carboxylic acid methylamide;

2-(4-fluoro-phenyl)-5-isopropoxy-6-[methanesulfonyl-(5-methyl-isoxazol-3-ylmethyl)-amino]-benzofuran-3-carboxylic acid methylamide;

2-(4-fluoro-phenyl)-5-isopropoxy-6-(5-methyl-isoxazol-3-yl)-benzofuran-3-carboxylic acid methylamide;

6-[(3,5-dimethyl-isoxazol-4-ylmethyl)-methanesulfonyl-amino]-2-(4-fluoro-phenyl)-5-isopropoxy-benzofuran-3-carboxylic acid methylamide;

2-(4-fluoro-phenyl)-5-isopropoxy-6-(methanesulfonyl-thiazol-2-ylmethyl-amino)-benzofuran-3-carboxylic acid methylamide;

2-({[2-(4-fluoro-phenyl)-5-isopropoxy-3-methylcarbamoyl-benzofuran-6-yl]-methanesulfonyl-amino}-methyl)-thiazole-4-carboxylic acid ethyl ester;

6-[(3,5-dimethyl-isoxazol-4-ylmethyl)-methanesulfonyl-amino]-2-(4-fluoro-phenyl)-5-methoxy-benzofuran-3-carboxylic acid methylamide;

2-(4-fluoro-phenyl)-6-(methanesulfonyl-thiazol-4-ylmethyl-amino)-5-methoxy-benzofuran-3-carboxylic acid methylamide;

2-({[2-(4-fluoro-phenyl)-5-isopropoxy-3-methylcarbamoyl-benzofuran-6-yl]-methanesulfonyl-amino}-methyl)-thiazole-4-carboxylic acid;

2-(4-fluoro-phenyl)-6-(1H-imidazol-4-yl)-5-methoxy-benzofuran-3-carboxylic acid methylamide;

2-(4-fluoro-phenyl)-6-(1H-imidazol-2-yl)-5-methoxy-benzofuran-3-carboxylic acid methylamide;

2-(4-fluoro-phenyl)-6-(methanesulfonyl-pyridin-4-ylmethyl-amino)-5-methoxy-benzofuran-3-carboxylic acid methylamide;

2-(4-fluoro-phenyl)-6-(1-methanesulfonyl-pyrrolidin-2-yl)-5-methoxy-benzofuran-3-carboxylic acid methylamide;

6-(3-cyclopropyl-5-methoxymethyl-isoxazol-4-yl)-2-(4-fluoro-phenyl)-5-methoxy-benzofuran-3-carboxylic acid methylamide;

2-(4-fluoro-phenyl)-5-methoxy-6-(5-methoxymethyl-isoxazol-3-yl)-benzofuran-3-carboxylic acid methylamide;

6-(3,5-dimethyl-isoxazol-4-yl)-2-(4-fluoro-phenyl)-5-hydroxy-benzofuran-3-carboxylic acid methylamide;

2-(4-fluoro-phenyl)-5-methoxy-6-(5-oxo-pyrrolidin-3-yl)-benzofuran-3-carboxylic acid methylamide;

2-(4-fluoro-phenyl)-5-methoxy-6-(1H-pyrrol-3-yl)-benzofuran-3-carboxylic acid methylamide;

6-(3,5-dimethyl-isoxazol-4-yl)-2-(2-ethoxy-4-fluoro-phenyl)-5-methoxy-benzofuran-3-carboxylic acid methylamide;

2-(4-fluoro-phenyl)-5-methoxy-6-(2-methyl-2H-1,2,4]triazol-3-yl)-benzofuran-3-carboxylic acid methylamide;

2-(4-fluoro-phenyl)-6-(1-methanesulfonyl-pyrrolidin-3-yl)-5-methoxy-benzofuran-3-carboxylic acid methylamide;

2-(4-fluoro-phenyl)-5-methoxy-6-(3-methoxymethyl-5-methyl-isoxazol-4-yl)-benzofuran-3-carboxylic acid methylamide;

5-ethyl-2-(4-fluoro-phenyl)-6-(methanesulfonyl-thiazol-4-ylmethyl-amino)-benzofuran-3-carboxylic acid methylamide;

6-(5-cyclopropyl-3-methoxymethyl-isoxazol-4-yl)-2-(4-fluoro-phenyl)-5-methoxy-benzofuran-3-carboxylic acid methylamide;

6-(1-acetyl-pyrrolidin-3-yl)-2-(4-fluoro-phenyl)-5-methoxy-benzofuran-3-carboxylic acid methylamide;

6-(5-ethoxymethyl-isoxazol-3-yl)-2-(4-fluoro-phenyl)-5-methoxy-benzofuran-3-carboxylic acid methylamide;

2-(4-fluoro-phenyl)-5-methoxy-6-(2H-[1,2,4]triazol-3-yl)-benzofuran-3-carboxylic acid methylamide;
2-[2-(4-fluoro-phenyl)-5-methoxy-3-methylcarbamoyl-benzofuran-6-yl]-pyrrolidine-1-carboxylic acid amide;
2-(4-fluoro-phenyl)-6-(5-isopropoxymethyl-isoxazol-3-yl)-5-methoxy-benzofuran-3-carboxylic acid methylamide;
2-[2-(4-fluoro-phenyl)-5-methoxy-3-methylcarbamoyl-benzofuran-6-yl]-pyrrolidine-1-carboxylic acid methylamide;
6-(3,5-dimethyl-isoxazol-4-yl)-2-(4-fluoro-phenyl)-5-methoxy-benzofuran-3-carboxylic acid ethylamide;
6-(3,5-dimethyl-isoxazol-4-yl)-2-(4-fluoro-phenyl)-5-methoxy-benzofuran-3-carboxylic acid isopropylamide;
6-(3,5-dimethyl-isoxazol-4-yl)-2-(4-fluoro-phenyl)-5-methoxy-benzofuran-3-carboxylic acid cyclopropylamide;
2-(4-fluoro-phenyl)-5-isopropoxy-6-(5-methyl-2-oxo-oxazolidin-5-yl)-benzofuran-3-carboxylic acid methylamide;
2-(4-fluoro-phenyl)-5-methoxy-6-(5-methyl-2H-[1,2,4]triazol-3-yl)-benzofuran-3-carboxylic acid methylamide;
6-(2,5-dimethyl-2H-[1,2,4]triazol-3-yl)-2-(4-fluoro-phenyl)-5-methoxy-benzofuran-3-carboxylic acid methylamide;
2-(4-fluoro-phenyl)-5-methoxy-6-(4-methyl-2,5-dioxo-imidazolidin-4-yl)-benzofuran-3-carboxylic acid methylamide;
2-(2,4-difluoro-phenyl)-6-(3,5-dimethyl-isoxazol-4-yl)-5-methoxy-benzofuran-3-carboxylic acid methylamide;
6-(2,5-dioxo-imidazolidin-4-yl)-2-(4-fluoro-phenyl)-5-methoxy-benzofuran-3-carboxylic acid methylamide;
6-(3,5-dimethyl-isoxazol-4-yl)-5-ethoxy-2-(4-fluoro-phenyl)-benzofuran-3-carboxylic acid methylamide;
5-cyclopropylmethoxy-6-(3,5-dimethyl-isoxazol-4-yl)-2-(4-fluoro-phenyl)-benzofuran-3-carboxylic acid methylamide;
2-(4-fluoro-phenyl)-5-methoxy-6-(5-methyl-[1,3,4]oxadiazol-2-yl)-benzofuran-3-carboxylic acid methylamide;
6-(3-cyano-4-hydroxy-2-oxo-2,5-dihydro-pyrrol-1-ylmethyl)-2-(4-fluoro-phenyl)-5-methoxy-benzofuran-3-carboxylic acid methylamide;
6-(1-acetyl-pyrrolidin-2-yl)-5-ethyl-2-(4-fluoro-phenyl)-benzofuran-3-carboxylic acid methylamide;
2-(4-fluoro-phenyl)-5-methoxy-6-(tetrahydro-furan-3-yl)-benzofuran-3-carboxylic acid methylamide;
6-(1-cyclopropanecarbonyl-pyrrolidin-2-yl)-2-(4-fluoro-phenyl)-5-isopropoxy-benzofuran-3-carboxylic acid methylamide;
2-(4-fluoro-phenyl)-5-methoxy-6-[1,3,4]oxadiazol-2-yl-benzofuran-3-carboxylic acid methylamide; and pharmaceutically acceptable salts thereof.

39. A method for or treatment of hepatitis C infections and diseases associated with such infections in a living host having said infections, said method comprising administering to said living host a therapeutically effective amount of a compound according to claim 3.

40. The method according to claim 39, wherein said living host is a mammal.

41. The method according to claim 39, wherein said living host is a human.

42. The method according to claim 41, wherein the compound is administered orally.

43. The method according to claim 42, wherein the compound is administered orally at a dose range of about 0.05 to about 100 mg/kg.

44. The method according to claim 39, wherein the compound is administered from 1 to 4 times daily.

45. The method according to claim 39, wherein the compound is administered in combination, either concurrently or sequentially, with at least one other biologically active agent.

46. The method according to claim 45, wherein said other biologically active agent is selected from the group consisting of interferon, pegylated interferon, ribavirin, protease inhibitors, polymerase inhibitors, small interfering RNA compounds, anti-sense compounds, nucleotide analogs, nucleoside analogs, immunoglobulins, immunomodulators, hepatoprotectants, anti-inflammatory agents, antibiotics, antivirals, and anti-infective compounds.

47. The method according to claim 39, wherein the compound is selected from the group consisting of:
2-furan-3-yl-5-methoxy-benzofuran-3-carboxylic acid methylamide;
2-furan-2-yl-5-methoxy-benzofuran-3-carboxylic acid methylamide;
2-(5-chloro-thiophen-2-yl)-5-methoxy-benzofuran-3-carboxylic acid methylamide;
2-(5-chloro-thiophen-2-yl)-5-ethoxy-benzofuran-3-carboxylic acid methylamide;
5-methoxy-2-thiophen-2-yl-benzofuran-3-carboxylic acid methylamide;
5-chloro-2-pyridin-3-yl-benzofuran-3-carboxylic acid methylamide;
5-methoxy-2-(4-morpholin-4-yl-phenyl)-benzofuran-3-carboxylic acid methylaniide;
5-isopropoxy-2-(4-pyrrolidin-1-yl-phenyl)-benzofuran-3-carboxylic acuid methylamide;
5-fluoro-2-pyridin-4-yl-benzofuran-3-carboxylic acid methylamide;
5-methoxy-2-pyridin-4-yl-benzofuran-3-carboxylic acid methylamide;
5-isopropoxy-2-(3-methyl-furan-2-yl)-benzofuran-3-carboxylic acid methylamide; and the pharmaceutically acceptable salts thereof.

48. A compound having the formula:

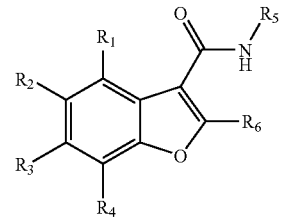

wherein:
R$_1$ represents a radical selected from the group consisting of hydrogen, alkyl, halogen, and cyano;
R$_2$ represents a radical selected from the group consisting of hydrogen, a substituted or unsubstituted alkyl radical, a substituted or unsubstituted alkoxy group, hydroxy, cycloalkyl, cycloalkyloxy, polyfluoroalkyl, polyfluoroalkoxy, halogen, amino, monoalkylamino, dialkylamino, cyano, a substituted or unsubstituted benzyloxy group, and a substituted or unsubstituted heterocyclic radical;

R₃ represents a radical selected from the group consisting of hydrogen, a substituted or unsubstituted alkyl radical, a substituted or unsubstituted alkoxy group, alkenyl, halogen, hydroxy, polyfluoroalkyl, polyfluoroalkoxy, formyl, carboxyl, alkylcarbonyl, alkoxycarbonyl, hydroxyalkylcarbonyl, amino, a substituted or unsubstituted monoalkylamino, dialkylamino, cyano, amido, alkoxyamido, a substituted or unsubstituted heteroarylamino, acetylsulfonylamino, ureido, carboxamide, sulfonamide, a substituted sulfonamide, a substituted or unsubstituted heterocyclosulfonyl, alkylthio, alkylsulfinyl, alkylsulfonyl, alkylsulfonic acid, a substituted or unsubstituted heterocyclic radical, and —O(CH₂)—C(=O)—R₇;

R₄ represents a radical selected from the group consisting of hydrogen, alkyl, halogen, and alkoxy;

R₅ represents a radical selected from the group consisting of an alkyl (C₁-C₆) group, cycloalkyl, and cycloalkylalkyl;

R₆ represents a radical selected from the group consisting of a substituted or unsubstituted aryl group and a substituted or unsubstituted heteroaryl group;

R₇ represents a substituted or unsubstituted heteroarylamino radical, said monoalkylamino substituents being one or more radical(s) independently selected from the group consisting of cycloalkyl, hydroxy, alkoxy, and a substituted or unsubstituted heterocyclic radical;

said arylamino substituents and said heteroarylamino substituents being one or more radical(s) independently selected from an alkyl group and an alkoxycarbonyl;

said sulfonamide substituents being one or more radical(s) independently selected from the group consisting of alkenyl, cycloalkyl, alkoxy, hydroxy, halogen, polyfluoroalkyl, polyfluoroalkoxy, carboxyl, alkylcarbonyl, alkoxycarbonyl, carboxamide, a substituted or unsubstituted aryl group, and a substituted or unsubstituted heterocyclic radical;

said heterocyclosulfonyl substituents being one or more radical(s) independently selected from the group consisting of alkoxy and hydroxy;

said alkyl radical substituents and said alkoxy group substituents being one or more radical(s) independently selected from the group consisting of alkenyl, amino, monoalkylamino, dialkylamino, alkoxy, cycloalkyl, hydroxy, carboxyl, halogen, cyano, polyfluoroalkyl, polyfluoroalkoxy, sulfonamide, carboxamide, alkylsulfonyl, alkylcarbonyl, alkoxycarbonyl, mercapto, 2,2-dimethyl-4-oxo-4H-benzo[1,3]dioxinyl, a substituted or unsubstituted aryl group, and a substituted or unsubstituted heterocyclic radical;

said heterocyclic radical substituents being one or more radical(s) independently selected from the group consisting of alkyl, amino, amido, monoalkylamino, cycloalkyl-alkylamino, dialkylamino, alkoxy, alkoxyalkyl, hydroxy, hydroxyalkyl, cycloalkyl, cycloalkylalkyl, carboxyl, carboxamide, halogen, haloalkyl, cyano, polyfluoroalkyl, polyfluoroalkoxy, alkylsulfonyl, alkylcarbonyl, cycloalkylcarbonyl, alkoxycarbonyl, mercapto, oxo, a substituted or unsubstituted aryl group, arylalkyl, and a substituted or unsubstituted heteroaryl group;

said heteroaryl group substituents being one or more radical(s) independently selected from the group consisting of alkyl, amino, alkoxy, alkoxyalkyl, hydroxy, hydroxyalkyl, cycloalkyl, carboxyl, carboxamide, halogen, polyfluoroalkyl, polyfluoroalkoxy, alkylsulfonyl, mercapto, and oxo;

said benzyloxy group substituents being one or more radical(s) independently selected from the group consisting of alkyl, alkoxy, polyfluoroalkyl, polyfluoroalkoxy, hydroxy, carboxyl, alkoxycarbonyl, halogen, cyano, alkylsulfonyl, and phenyl;

said aryl group substituents being one or more radical(s) independently selected from the group consisting of alkyl, acetylenyl, alkoxy, hydroxy, halogen, polyfluoroalkyl, polyfluoroalkoxy, cyano, amino, monoalkylamino, dialkylamino, aminoalkyl, alkoxyalkoxy, amido, amidoalkyl, carboxyl, alkylsulfonyl, alkylcarbonyl, alkoxycarbonyl, mercapto, and a heterocyclic radical; and pharmaceutically acceptable salts thereof.

49. A compound having the formula:

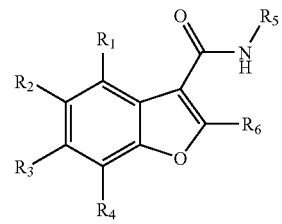

wherein:

R₁ represents a radical selected from the group consisting of hydrogen, methyl, and chloro;

R₂ represents a radical selected from the group consisting of hydrogen, methyl, ethyl, isopropyl, t-butyl, cyclopropyl, hydroxy, hydroxymethyl, methoxymethyl, methoxy, trifluoromethoxy, difluoromethoxy, cyclopropylmethoxy, carboxymethoxy, cyanomethoxy, cyanomethyl-methoxy, 1-hydroxymethyl-cyclopropylmethoxy, carbamoylmethoxy, methylcarbamoylmethoxy, diethylcarbamoylmethoxy, (4-ethoxycarbonyl-phenylcarbamoyl)-methoxy, tert-butoxycarbonylmethoxy, ethoxy, 2-methoxy-ethoxy, 2-chloro-ethoxy, 2-carboxyethoxy, 2,2,2-trifluoroethoxy, 1-(4-fluoro-phenyl)-ethoxy, 2-(4-fluoro-phenyl)-2-oxo-ethoxy, 2-(4-methoxy-phenyl)-2-oxo-ethoxy, propoxy, isopropoxy, 2-oxo-propoxy, 2-hydroxy-propoxy, 3-hydroxy-propoxy, 2-hydroxy-2-methyl-propoxy, 3-bromo-propoxy, 3-ethoxy-propoxy, butoxy, 2-hydroxy-2-methyl-butoxy, cyclopentyloxy, allyloxy, cyano, chloro, fluoro, methanesulfonic acid, benzyloxy, 2-phenylbenzyloxy, 2-difluoromethoxy-benzyloxy, 3-methoxy-benzyloxy, 3-methoxycarbonyl-benzyloxy, 3-carboxy-benzyloxy, 3-cyano-benzyloxy, 4-methoxy-benzyloxy, 4-fluoro-benzyloxy, 4-cyano-benzyloxy, 4-methoxycarbonyl-benzyloxy, 4-carboxy-benzyloxy, 4-carboxy-3-hydroxy-benzyloxy, 4-methanesulfonyl-benzyloxy, 3,4-difluoro-benzyloxy, 3,5-dimethoxy-benzyloxy, 2,2-dimethyl-4-oxo-4H-benzo[1,3]dioxin-5-ylmethoxy, 2,2-dimethyl-4-oxo-4H-benzo[1,3]dioxin-7-ylmethoxy, 2,2-dimethyl-4-oxo-4H-benzo[1,3]dioxin-6-ylmethoxy, 3-chloromethyl-[1,2,4]thiadiazol-5-yloxy, 5-chloro-[1,2,4]thiadiazol-3-ylmethoxy, 5-chloro-[1,2,3]thiadiazol-4-ylmethoxy, 5-p-tolyl-[1,3,4]oxadiazol-2-ylmethoxy, 5-(3,5-dimethyl-isoxazol-4-yl)-[1,2,4]oxadiazol-3-ylmethoxy, 5-(cyclopropylmethyl-amino)-[1,2,4]thiadiazol-3-ylmethoxy, 5-tert-butyl-[1,2,4]oxadiazol-3-ylmethoxy, 5-(4-methoxy-phenyl)-[1,2,4]oxadiazol-3-ylmethoxy, 5-diethylamino-[1,2,4]thiadiazol-3-ylmethoxy, [1,3,4]thiadiazol-2-ylcarbamoylmethoxy, 3,5-dimethyl-isoxazol-4-yl, isoxazol-3-ylmethoxy, 3,5-dimethyl-isoxazol-4-ylmethoxy, 5-methyl-isoxazol-3-ylmethoxy, thiazol-2-ylmethoxy, thiazol-4-ylmethoxy, 2-methyl-thiazol-4-ylmethoxy, 1-thiazol-2-yl-ethoxy, thiazol-2-ylcarbamoylmethoxy, (4,5-dimethyl-thiazol-2-ylcarbamoyl)-methoxy, 4-chloro-1-methyl-i H-pyrazol-3-ylmethoxy, 2-pyrazol-1-yl-ethoxy, 2-(3,5-dimethyl-pyrazol-1-yl)-ethoxy, 4-ethoxycarbonyl-thiazol-2-ylmethoxy, 4-carboxy-thiazol-2-ylmethoxy, 5-amino-4H-[1,2,4]triazol-3-ylmethoxy, thiophen-2-yl, furan-2-yl, 2-morpholin-4-yl-ethoxy, 3-piperidin-1-yl-propoxy, tetrahydro-furan-2-yl, 1-methyl-1H-tetrazol-5-ylmethoxy, 1-methyl-1H-imidazol-2-ylmethoxy, 1-benzyl-1H-imidazol-2-ylmethoxy, 3H-imidazol-4-ylmethoxy, pyridine-4-yl-methoxy, 6-bromomethyl-pyridin-2-ylmethoxy, and 2-(4-cyano-piperidin-1-yl)-ethoxy;

$R_3$ represents a radical selected from the group consisting of hydrogen, methyl, methoxy, hydroxy, hydroxymethyl, 1-hydroxy-ethyl, 1-hydroxy-2-methyl-propyl, 1-hydroxy-1-methyl-ethyl, formyl, ureido, vinyl, bromo, chloro, cyano, acetyl, 2-hydroxy-acetyl, carboxy, azetidin-1-yl, carboxylic acid amide, amino, methylamino, dimethylamino, ethylamino, diethylamino, isopropylamino, tert-butylamino, ethyl-methyl-amino, 2-methoxy-ethylamino, cyclopropylmethyl-amino, 2,3-dihydroxy-propylamino, 1-methylamino-ethyl, dimethylaminomethyl, 1-amino-1-methyl-ethyl, 2-amino-1-hydroxy-1-methyl-ethyl, acetylamino, 1-acetylamino-1-methyl-ethyl, (2-methoxy-ethyl)-methyl-amino, ethyl-(2-methoxy-acetyl)-amino, 3-chloro-propane-1-sulfonylamino, methanesulfonylamino, ethyl-methanesulfonyl-amino, isopropyl-methanesulfonyl-amino, isobutyl-methanesulfonyl-amino, cyclobutyl-methanesulfonyl-amino, cyclopentyl-methanesulfonyl-amino, cyclopropylmethyl-methanesulfonyl-amino, (2-hydroxy-ethyl)-methanesulfonyl-amino, (2-hydroxy-propyl)-methanesulfonyl-amino, (2-fluoro-ethyl)-methanesulfonyl-amino, 2-(4-fluoro-phenyl)-2-hydroxy-ethyl]-methanesulfonyl-amino, (1-hydroxymethyl-cyclopropylmethyl)-methanesulfonyl-amino, (4-carboxy-benzyl)-methanesulfonyl-amino, allyl-methanesulfonyl amino, acetyl-methanesulfonyl-amino, benzyl-methanesulfonyl-amino, carboxymethyl-methanesulfonyl-amino, methanesulfonylamino-methyl, 1-methanesulfonylamino-1-methyl-ethyl, methanesulfonyl-methyl-amino, 1-(methanesulfonyl-methyl-amino)-ethyl, methanesulfonyl-propyl-amino, methanesulfonyl-(2-methoxy-ethyl)-amino, methanesulfonyl-(2,2,2-trifluoro-ethyl)-amino, methanesulfonyl-(2-oxo-propyl)-amino, methanesulfonyl-(2-trifluoromethoxy-ethyl)-amino, methanesulfonyl-(4-methoxy-benzyl)-amino, methanesulfonyl-(4-methoxycarbonyl-benzyl)-amino, methanesulfonyl-methoxymethyl-amino, methanesulfonyl-methylcarbamoylmethyl-amino, (methanesulfonyl-methyl-amino)-methyl, sulfamoyl, methylsulfamoyl, dimethylsulfamoyl, ethylsulfamoyl, cyclopropylsulfamoyl, cyclobutylsulfamoyl, 3-methanesulfonyl-phenyl, 4-methanesulfonyl-phenyl, benzyloxy, 1H-pyrazol-4-yl, 2H-pyrazol-3-yl, 1-methyl-1H-pyrazol-3-yl, 2-methyl-2H-pyrazol-3-yl, 5-methyl-1H-pyrazol-4-yl, 5-methyl-2H-pyrazol-3-yl, 1,5-dimethyl-1H-pyrazol-3-yl, 2,5-dimethyl-2H-pyrazol-3-yl, 2,5-dimethyl-2H-pyrazol-3-ylamino, 3,5-dimethyl-1H-pyrazol-4-yl, 1,3,5-trimethyl-1H-pyrazol-4-yl, isoxazol-3-yl, 5-methyl-isoxazol-3-yl, 3-cyclopropyl-isoxazol-5-yl, 5-cyclopropyl-isoxazol-3-yl, 3,5-dimethyl-isoxazol-4-yl, 3,5-dimethyl-isoxazol-4-ylamino, 5-methoxymethyl-isoxazol-3-yl, 5-ethoxymethyl-isoxazol-3-yl, 5-isopropoxymethyl-isoxazol-3-yl, 5-hydroxymethyl-isoxazol-3-yl, 4-(2-hydroxy-ethyl)-isoxazol-3-yl, 3-methoxymethyl-5-methyl-isoxazol-4-yl, 5-methoxymethyl-3-methyl-isoxazol-4-yl, 5-cyclopropyl-3-methoxymethyl-isoxazol-4-yl, 3-cyclopropyl-5-methoxymethyl-isoxazol-4-yl, (3,5-dimethyl-isoxazol-4-ylmethyl)-methanesulfonyl-amino, 3-metho-xymethyl-isoxazol-5-yl), 3-methyl-isoxazol-5-yl, methanesulfonyl-(5-methyl-isoxazol-3-ylmethyl)-amino, thiazol-2-yl, thiazol-5-yl, methanesulfonyl-thiazol-2-ylmethyl-amino, methanesulfonyl-thiazol-4-ylmethyl-amino, methanesulfonyl-(2-methyl-thiazol-4-ylmethyl)-amino, (4-carboxy-thiazol-2-ylmethyl)-methanesulfonyl-amino, (4-ethoxycarbonyl-thiazol-2-ylmethyl)-methanesulfonyl-amino, pyridin-3-yl, pyridin-4-yl, pyridin-4-ylamino, 6-fluoro-pyridin-3-yl, methanesulfonyl-pyridin-4-ylmethyl-amino, (6-bromomethyl-pyridin-2-ylmethyl)-methanesulfonyl-amino, pyrrolidin-1-yl, pyrrolidin-2-yl, pyrrolidine-1-sulfonyl, 3-hydroxy-pyrrolidin-1-yl, 3-hydroxy-pyrrolidine-1-sulfonyl, 5-oxo-pyrrolidin-3-yl, 1-acetyl-pyrrolidin-2-yl, 1-acetyl-pyrrolidin-3-yl, 1-carbamoyl-pyrrolidin-2-yl, 1-methylcarbamoyl-pyrrolidin-2-yl, 4-methylcarbamoyl-5-oxo-pyrrolidin-3-yl, 1-cyclopropanecarbonyl-pyrrolidin-2-yl, 1-methanesulfonyl-pyrrolidin-2-yl, 1-methanesulfonyl-pyrrolidin-3-yl, 3-amino-pyrrolidin-1-yl, 3-methanesulfonyl-pyrrolidin-1-yl, 1H-pyrrol-2-yl, 1H-pyrrol-3-yl, 3-cyano-4-hydroxy-2-oxo-2,5-dihydro-pyrrol-1-ylmethyl, furan-2-yl, furan-3-yl, (furan-3-ylmethyl)-amino, tetrahydro-furan-3-yl, (tetrahydro-furan-2-ylmethyl)-amino, [1,3,4]oxadiazol-2-yl, [1,2,4]oxadiazol-3-yl, 5-methyl-[1,2,4]oxadiazol-3-yl, 5-methyl-[1,3,4]oxadiazol-2-yl, 5-trifluoromethyl-[1,2,4]oxadiazol-3-yl, morpholin-4-yl, 2,6-dimethyl-morpholin-4-yl, 2-morpholin-4-yl-ethylamino, morpholine-4-sulfonyl, methanesulfonyl-(2-morpholin-4-yl-ethyl)-amino, thiomorpholin-4-yl, thiomorpholine-4-sulfonyl, 1-oxo-thiomorpholin-4-yl, 1,1-dioxido-isothiazolidin-2-yl, 2-oxo-oxazolidin-5-yl, 5-methyl-2-oxo-oxazolidin-5-yl, oxazol-5-yl, 1H-imidazol-4-yl, 1H-imidazol-2-yl, 2,5-dioxo-imidazolidin-4-yl, 4-methyl-2,5-dioxo-imidazolidin-4-yl, pyrimidin-5-yl, 2,5-dimethyl-2H-[1,2,4]triazol-3-yl, 2-methyl-2H-[1,2,4]triazol-3-yl, 4H-[1,2,4]triazol-3-yl, 5-methyl-2H-[1,2,4]triazol-3-yl, 1H-tetrazol-5-yl, 1-methyl-1H-tetrazol-5-ylmethoxy, methanesulfonyl-(1-methyl-1H-tetrazol-5-ylmethyl)-amino, piperidin-1-yl, 4-fluoro-piperidin-1-yl, 4,4-difluoro-piperidin-1-yl, 3-hydroxy-piperidin-1-yl, 4-hydroxy-piperidin-1-yl, 4-hydroxy-piperidine-1-sulfonyl, 4-carbamoyl-piperazin-1-yl, 4-methyl-piperazin-1-yl, and 5-chloro-[1,2,4]thiadiazol-3-ylmethyl;

$R_4$ represents a radical selected from the group consisting of hydrogen and methyl;

$R_5$ represents a radical selected from the group consisting of methyl, ethyl, isopropyl, and cyclopropyl; and $R_6$ represents a radical selected from the group consisting of 4-morpholin-4-yl-phenyl, 4-pyrrolidin-1-yl-phenyl, furan-2-yl, furan-3-yl, 3-methyl-furan-2-yl, thiophen-2-yl, 5-chloro-thiophen-2-yl, pyridin-4-yl, and pyridin-3-yl; and the pharmaceutically acceptable salts thereof.

* * * * *